United States Patent
Yen et al.

(10) Patent No.: US 10,844,043 B2
(45) Date of Patent: Nov. 24, 2020

(54) HETEROAROMATIC COMPOUND AND ORGANIC ELECTROLUMINESCENCE DEVICE USING THE SAME

(71) Applicants: Feng-Wen Yen, Taipei (TW); Li-Chieh Chuang, Nantou (TW)

(72) Inventors: Feng-Wen Yen, Taipei (TW); Li-Chieh Chuang, Nantou (TW)

( * ) Notice: Subject to any disclaimer, the term of this patent is extended or adjusted under 35 U.S.C. 154(b) by 218 days.

(21) Appl. No.: 15/961,833

(22) Filed: Apr. 24, 2018

(65) Prior Publication Data

US 2019/0322641 A1 Oct. 24, 2019

(51) Int. Cl.

| | | |
|---|---|---|
| *C07D 401/10* | (2006.01) | |
| *C07D 413/10* | (2006.01) | |
| *C07D 417/10* | (2006.01) | |
| *C07D 403/10* | (2006.01) | |
| *C07D 421/10* | (2006.01) | |
| *C07D 221/18* | (2006.01) | |
| *C07D 517/04* | (2006.01) | |
| *C07D 513/04* | (2006.01) | |
| *C07D 495/04* | (2006.01) | |
| *C07D 491/04* | (2006.01) | |
| *C07D 471/04* | (2006.01) | |
| *C09K 11/06* | (2006.01) | |
| *H01L 51/00* | (2006.01) | |
| *H01L 51/50* | (2006.01) | |

(52) U.S. Cl.
CPC ......... *C07D 401/10* (2013.01); *C07D 221/18* (2013.01); *C07D 403/10* (2013.01); *C07D 413/10* (2013.01); *C07D 417/10* (2013.01); *C07D 421/10* (2013.01); *C07D 471/04* (2013.01); *C07D 491/04* (2013.01); *C07D 495/04* (2013.01); *C07D 513/04* (2013.01); *C07D 517/04* (2013.01); *C09K 11/06* (2013.01); *H01L 51/0072* (2013.01); *H01L 51/5012* (2013.01); *C09K 2211/104* (2013.01); *C09K 2211/1033* (2013.01); *C09K 2211/1037* (2013.01); *C09K 2211/1044* (2013.01); *C09K 2211/1059* (2013.01); *C09K 2211/1096* (2013.01)

(58) Field of Classification Search
CPC .. C07D 401/10; C07D 403/10; C07D 413/10; C07D 417/10; C07D 421/10; C07D 471/04; C07D 491/04; C07D 498/04; C07D 513/04; C07D 517/04; C07D 221/18
See application file for complete search history.

(56) References Cited

U.S. PATENT DOCUMENTS 9,698,351 B2 7/2017 Yen
2015/0249218 A1 9/2015 Yokoyama et al.

FOREIGN PATENT DOCUMENTS

| CN | 106831749 A | * | 6/2017 |
| CN | 106188026 B | * | 3/2019 |
| KR | 20130069439 A | * | 6/2013 |

OTHER PUBLICATIONS

SciFinder Search, Apr. 20, 2020.*

* cited by examiner

*Primary Examiner* — Vu A Nguyen

(57) ABSTRACT

A heteroaromatic compound which can be used as the fluorescent guest material in the light emitting layer of the organic electroluminescence device is disclosed. The organic electroluminescence device employing the heteroaromatic compound of the present invention can operate under reduced driving voltage, increase current efficiency, and prolong half-life time.

10 Claims, 1 Drawing Sheet

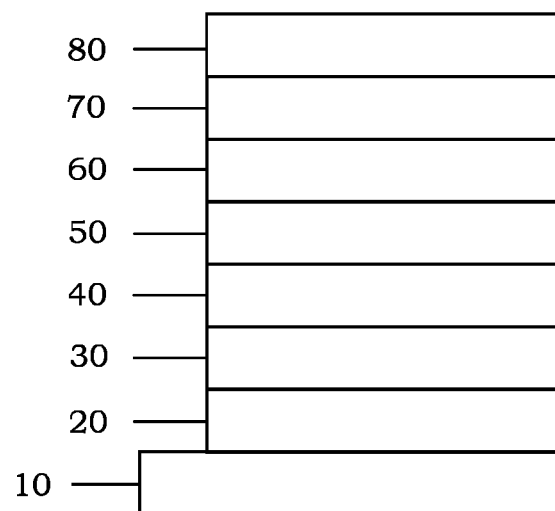

HETEROAROMATIC COMPOUND AND ORGANIC ELECTROLUMINESCENCE DEVICE USING THE SAME

FIELD OF INVENTION

The present invention relates to a heteroaromatic compound and, more particularly, to an organic electroluminescence device using the heteroaromatic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer (HIL), hole transporting layer (HTL), emitting layer (EML), electron transporting layer (ETL), and electron injection layer (EIL). The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

For full-colored displays using organic EL devices, the organic materials used in the organic EL devices are still unsatisfactory in half-life time, driving voltage, and current efficiency. Therefore, there is still a need for an organic compound that can lower the driving voltage, increase the current efficiency, and prolong the half-life time for the organic EL device.

SUMMARY OF THE INVENTION

Accordingly, an object of the present invention is to provide a novel heteroaromatic compound, which can be used as a fluorescent guest material in the emitting layer of the organic EL device to improve the power consumption, current efficiency, and life time of the device.

Another object of the invention is to provide a heteroaromatic compound and an organic EL device using the same, which can operate under reduced voltage and exhibit higher current efficiency and longer half-life time.

According to the present invention, a heteroaromatic compound which can be used in organic EL devices is disclosed. The heteroaromatic compound is represented by the following formula (1):

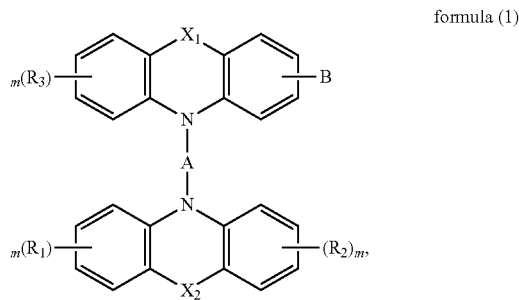

formula (1)

wherein $X_1$ is a divalent bridge selected from the group consisting of O, S, Se, $CR_4R_5$, $NR_6$, and $SiR_7R_8$; $X_2$ is absent or a divalent bridge selected from the group consisting of O, S, Se, $CR_9R_{10}$, $NR_{11}$, and $SiR_{12}R_{13}$; A represents a substituted or unsubstituted fused ring hydrocarbon unit with two to nine rings; m is an integer of 0 to 4; B represents formula (2) below:

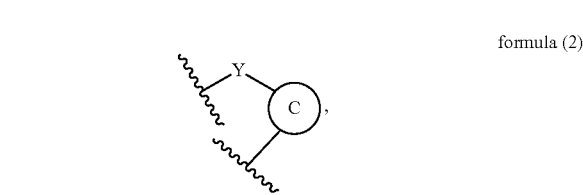

formula (2)

wherein ring C represents a phenyl ring or a fused ring hydrocarbon unit with two to five rings; Y represents a divalent bridge selected from the group consisting of O, S, Se, $CR_{14}R_{15}$, $NR_{16}$, and $SiR_{17}R_{18}$; when $X_2$ is absent, $R_1$ and $R_2$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, a substituted or unsubstituted arylamine group having 6 to 60 carbon atoms, or fused with the connected phenyl group to form a naphthyl group, a dibenzofuranyl group, or a dibenzothiophenyl group; when $X_2$ is a divalent bridge selected from the group consisting of O, S, Se, $CR_9R_{10}$, $NR_{11}$, and $SiR_{12}R_{13}$, $R_1$ and $R_2$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, or a substituted or unsubstituted arylamine group having 6 to 60 carbon atoms; and $R_3$ to $R_{18}$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, or a substituted or unsubstituted arylamine group having 6 to 60 carbon atoms.

The present invention further discloses an organic electroluminescence device. The organic electroluminescence device comprises a pair of electrodes composed of a cathode and an anode, and a light emitting layer between the pair of electrodes. The light emitting layer comprises the heteroaromatic compound of formula (1).

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the heteroaromatic compound and organic EL device using the heteroaromatic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a heteroaromatic compound which can be used as the fluorescent guest material of the light emitting layer in the organic EL device is disclosed. The heteroaromatic compound is represented by the following formula (1):

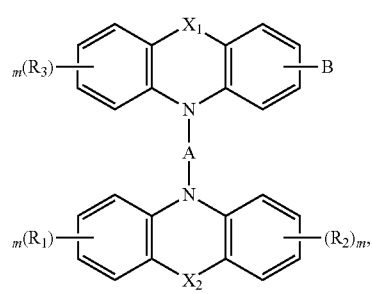

formula (1)

wherein $X_1$ is a divalent bridge selected from the group consisting of O, S, Se, $CR_4R_5$, $NR_6$, and $SiR_7R_8$; $X_2$ is absent or a divalent bridge selected from the group consisting of O, S, Se, $CR_9R_{10}$, $NR_{11}$, and $SiR_{12}R_{13}$; A represents a substituted or unsubstituted fused ring hydrocarbon unit with two to nine rings; m is an integer of 0 to 4; B represents formula (2) below:

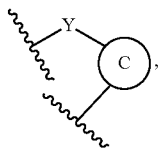

formula (2)

wherein ring C represents a phenyl ring or a fused ring hydrocarbon unit with two to five rings; Y represents a divalent bridge selected from the group consisting of O, S, Se, $CR_{14}R_{15}$, $NR_{16}$, and $SiR_{17}R_{18}$; when $X_2$ is absent, $R_1$ and $R_2$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, a substituted or unsubstituted arylamine group having 6 to 60 carbon atoms, or fused with the connected phenyl group to form a naphthyl group, a dibenzofuranyl group, or a dibenzothiophenyl group; when $X_2$ is a divalent bridge selected from the group consisting of O, S, Se, $CR_9R_{10}$, $NR_{11}$, and $SiR_{12}R_{13}$, $R_1$ and $R_2$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, or a substituted or unsubstituted arylamine group having 6 to 60 carbon atoms; and $R_3$ to $R_{18}$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, or a substituted or unsubstituted arylamine group having 6 to 60 carbon atoms.

In some embodiments, A represents a substituted or unsubstituted naphthyl group, a substituted or unsubstituted phenanthrenyl group, a substituted or unsubstituted anthracenyl group, a substituted or unsubstituted pyrenyl group, a substituted or unsubstituted chrysenyl group, a substituted or unsubstituted triphenylenyl group, a substituted or unsubstituted perylenyl group, a substituted or unsubstituted tetraphenylenyl group, or a substituted or unsubstituted 7,14-diphenylacenaphtho[1,2-k]fluoranthene group.

In some embodiments, A represents one of the following formulas:

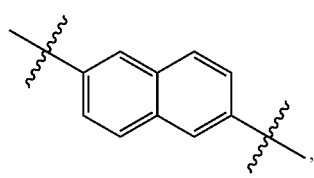

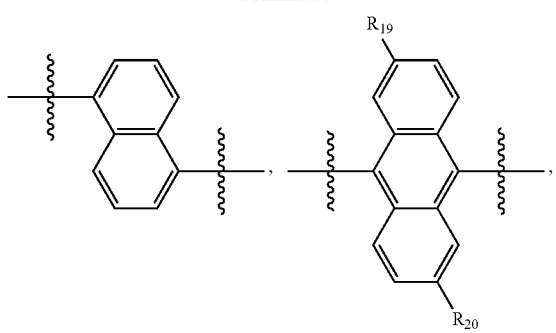

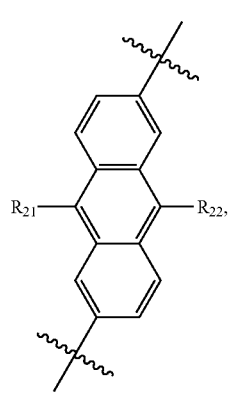

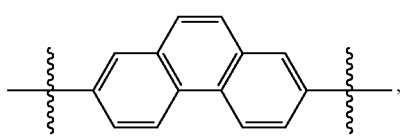

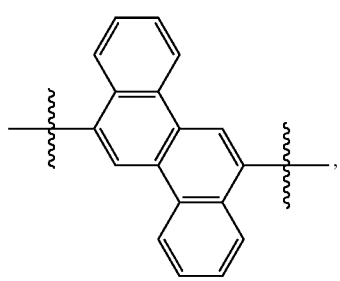

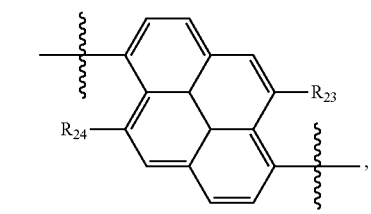

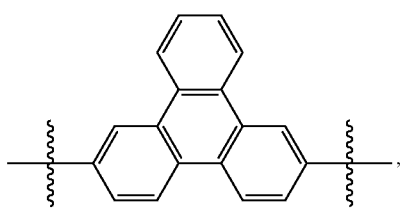

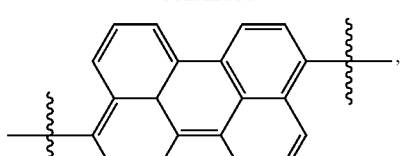

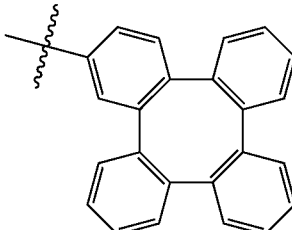

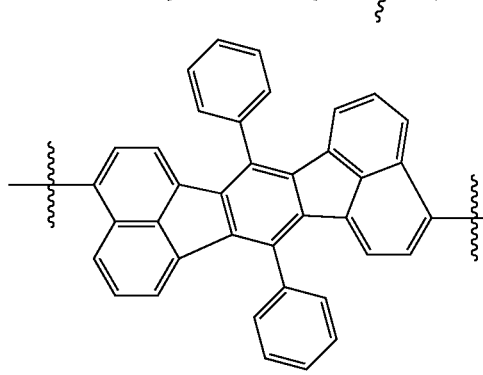

wherein $R_{19}$ to $R_{24}$ are independently a hydrogen atom, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms, or a substituted or unsubstituted arylamine group having 6 to 30 carbon atoms.

In some embodiments, the heteroaromatic compound is represented by one of the following formula (3) to formula (13):

formula (3)

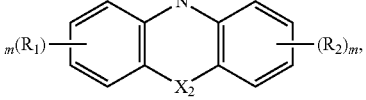

formula (4)
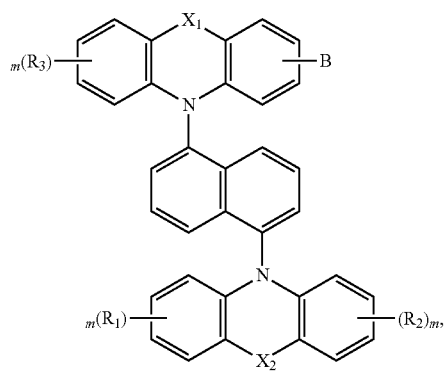
formula (5)
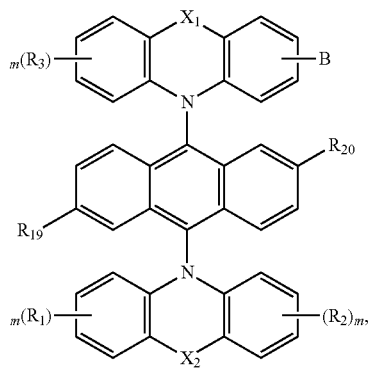
formula (6)
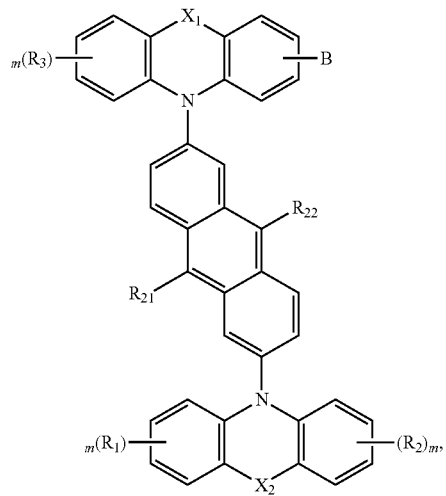
formula (7)
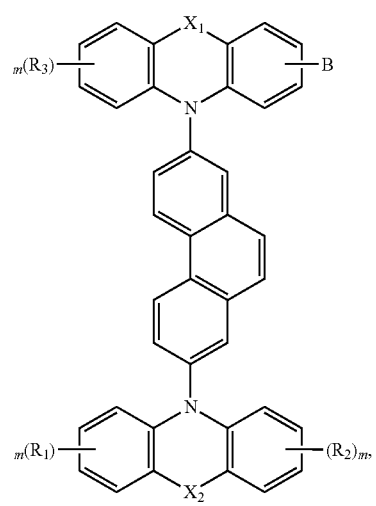
formula (8)
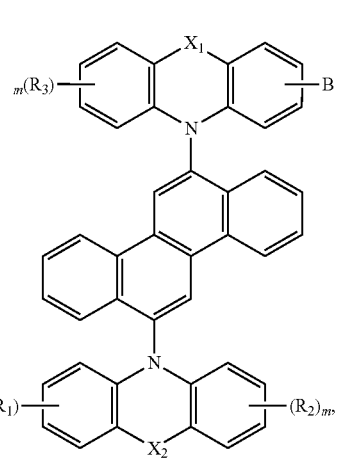
formula (9)
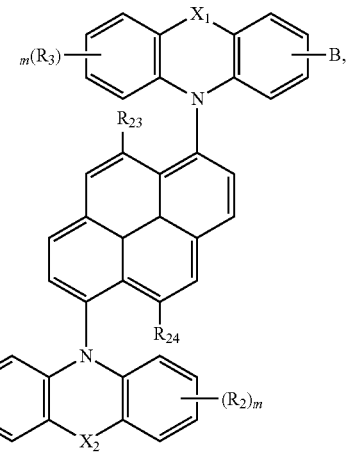

formula (10)
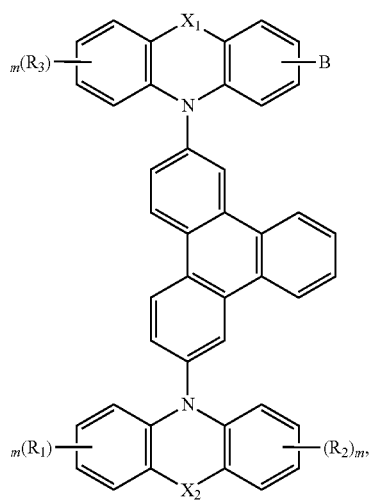
formula (11)
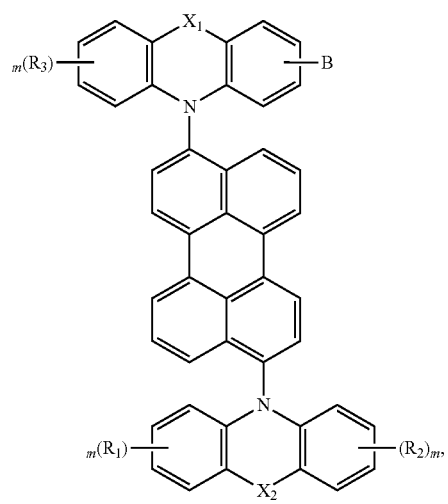
formula (12)
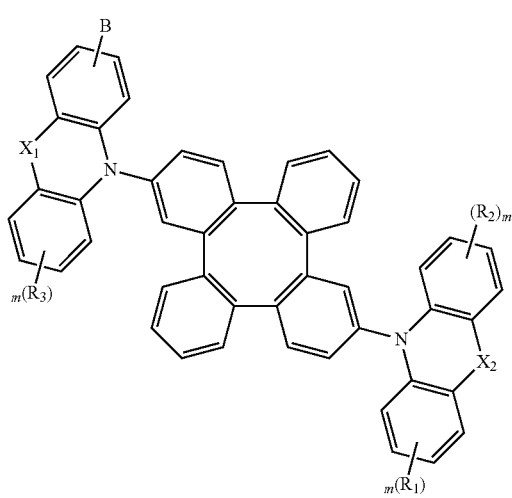
formula (13)
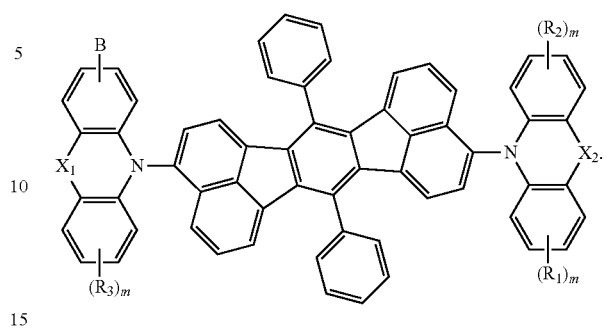
Preferably, the heteroaromatic compound is one of the following compounds:
Compound 1
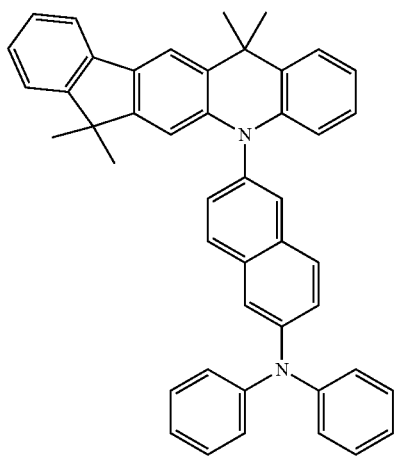
Compound 2
Compound 3
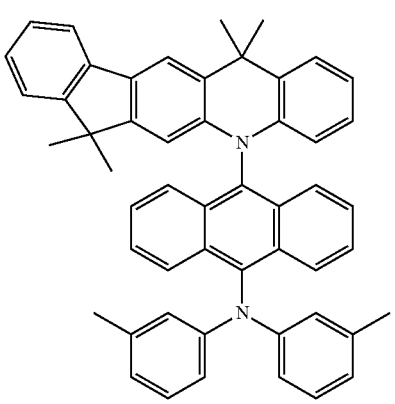

Compound 4
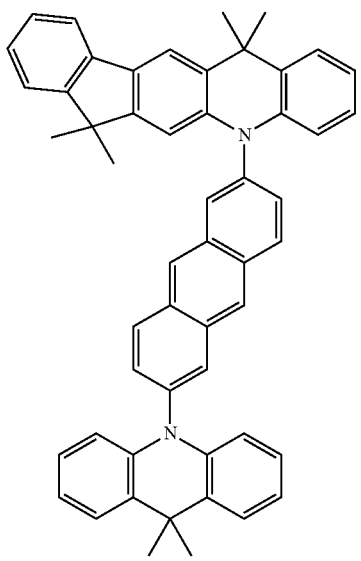
Compound 5
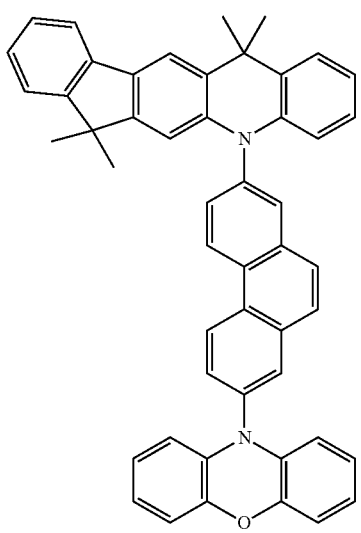
Compound 6
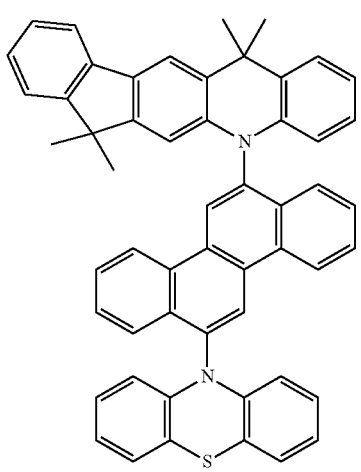
Compound 7
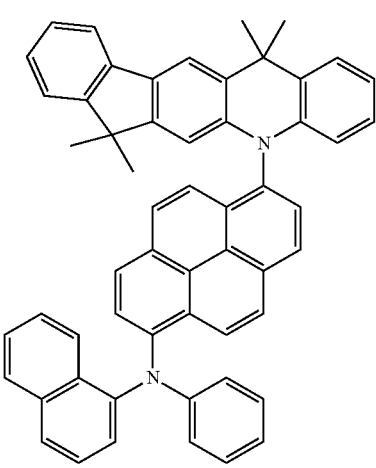
Compound 8
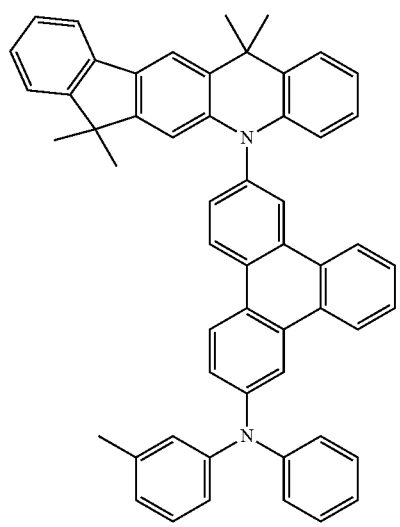
Compound 9
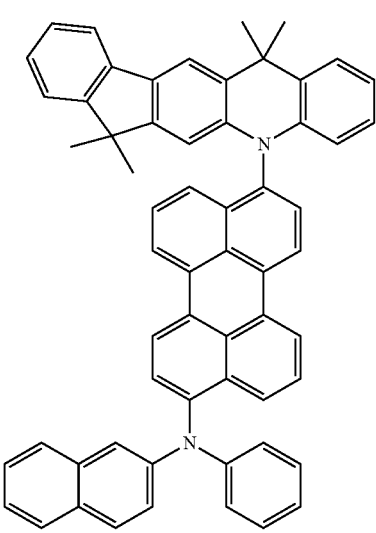

Compound 10
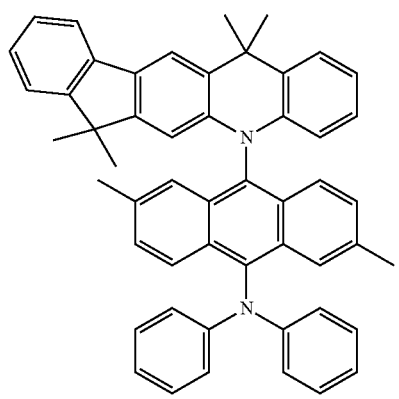
Compound 11
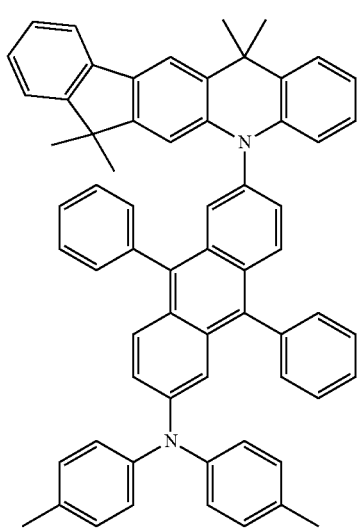
Compound 12
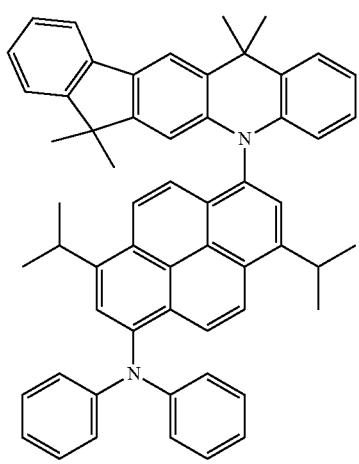
Compound 13
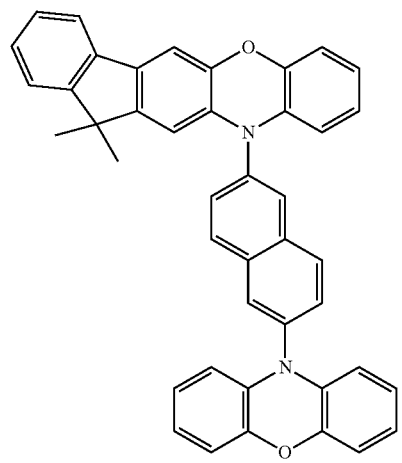
Compound 14
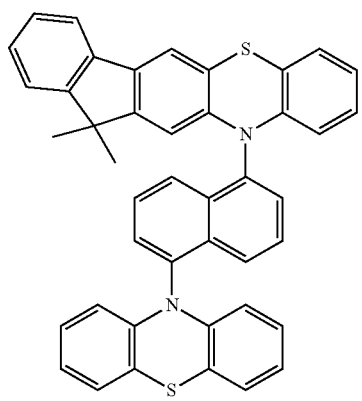
Compound 15
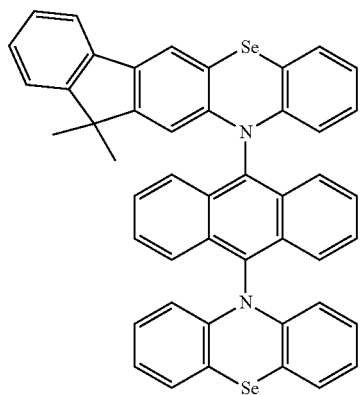

Compound 16
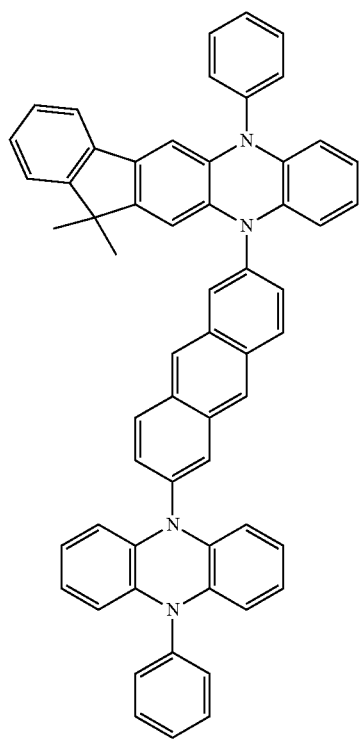
Compound 17
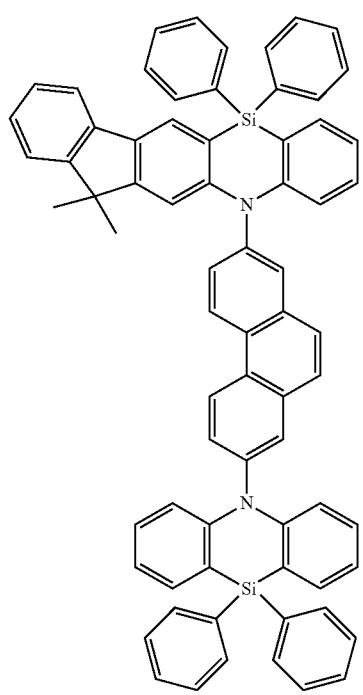
Compound 18
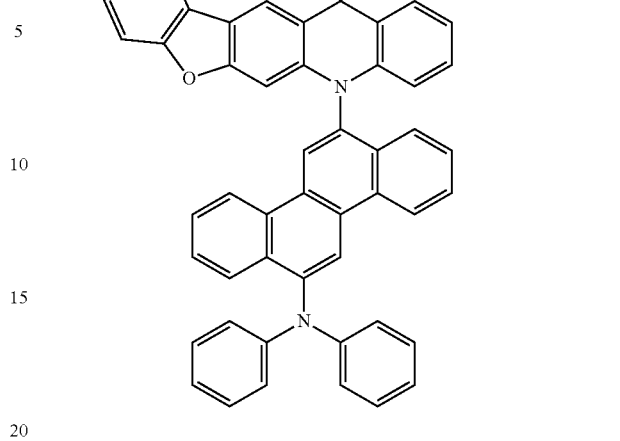
Compound 19
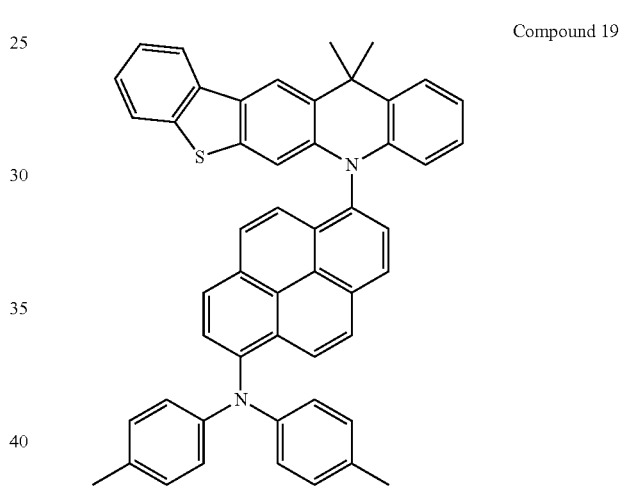
Compound 20
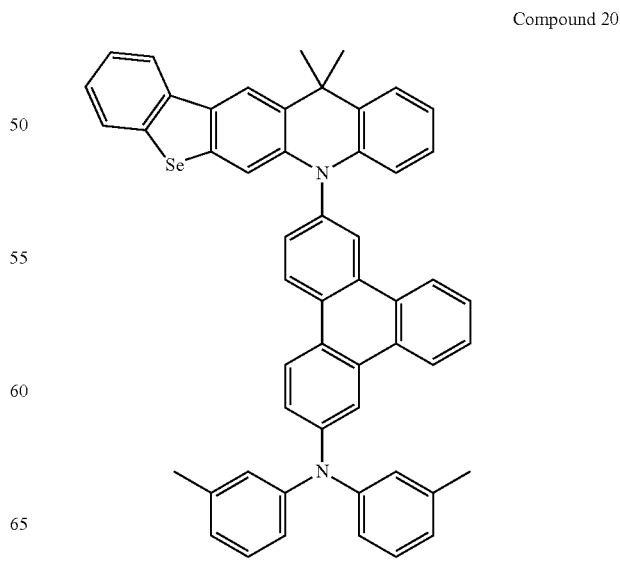

Compound 21
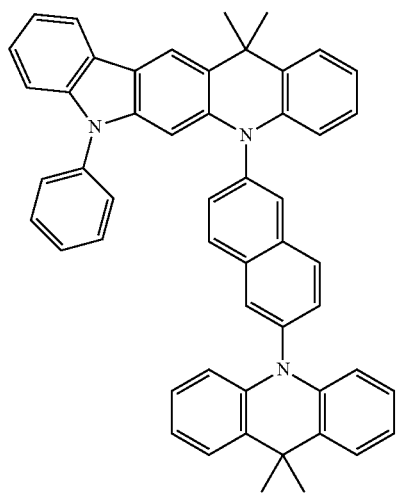
Compound 22
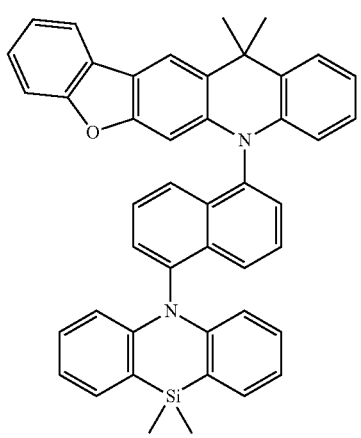
Compound 23
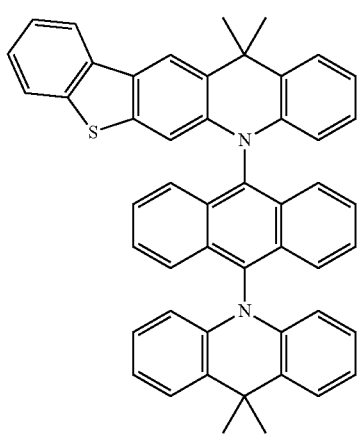
Compound 24
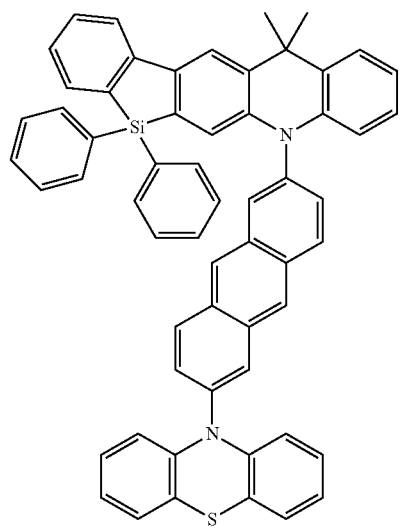
Compound 25
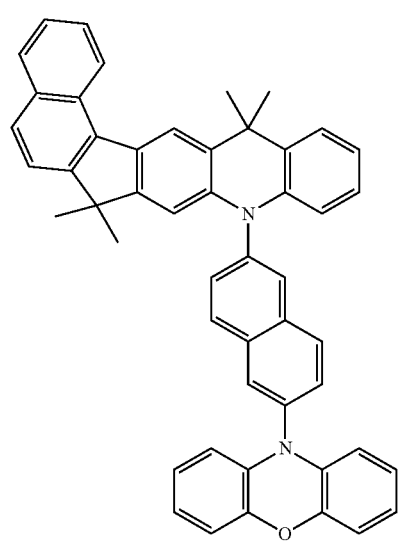
Compound 26
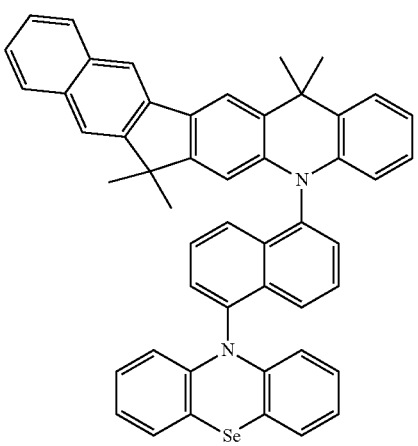

Compound 27
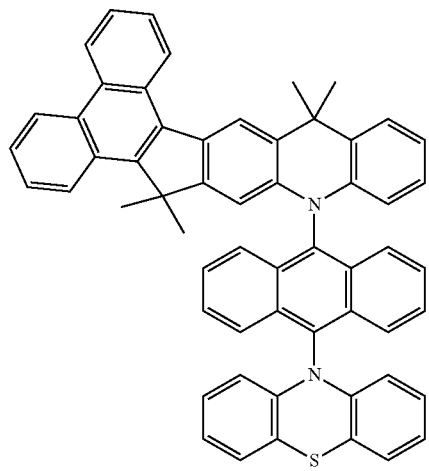
Compound 28
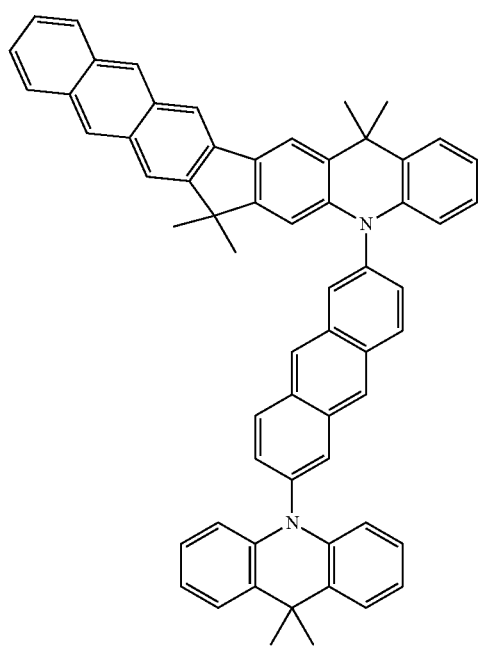
Compound 29
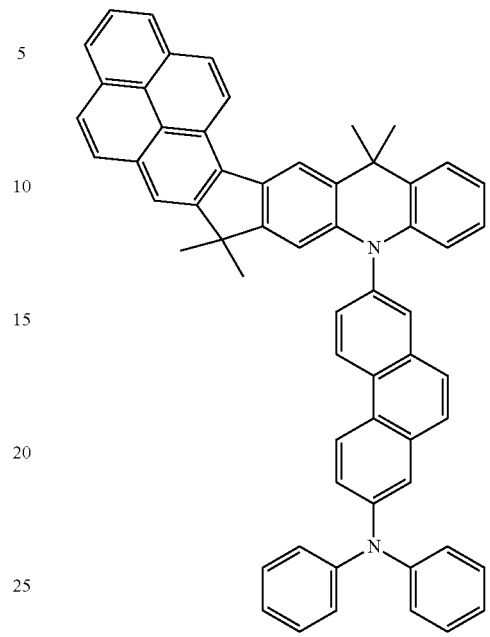
Compound 30
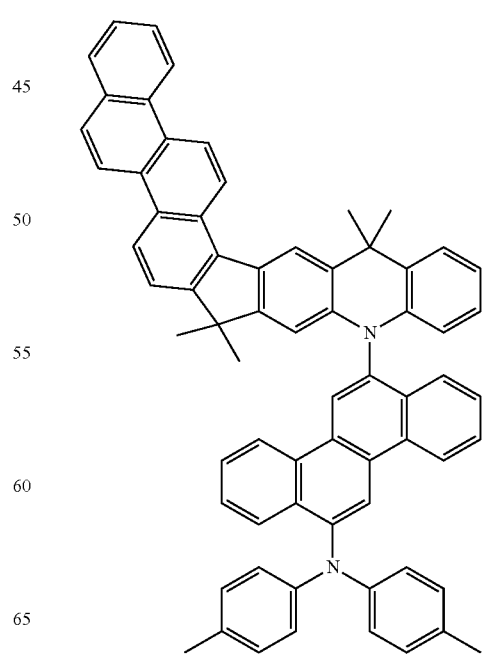

Compound 31
Compound 33
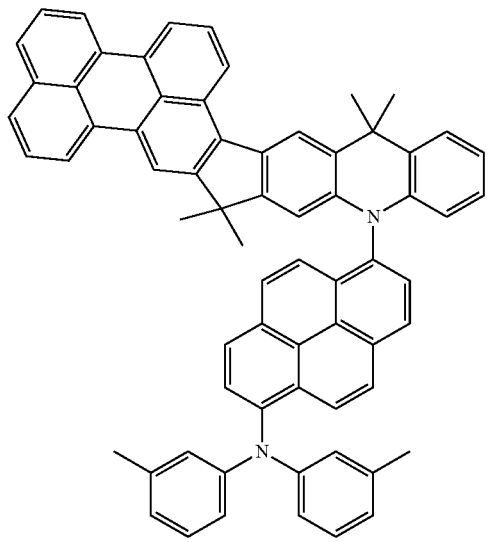
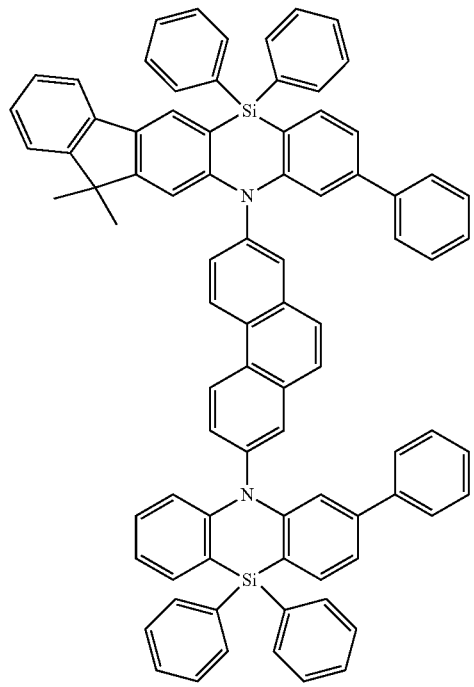
Compound 32
Compound 34

Compound 35
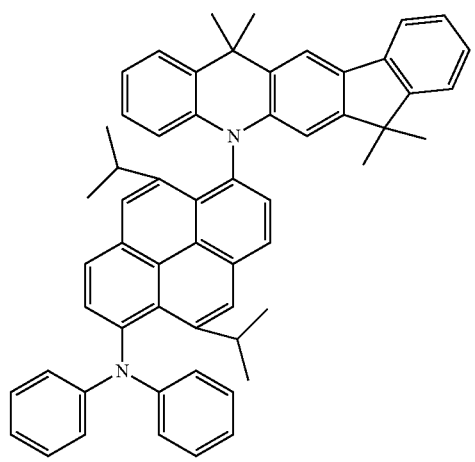
Compound 36
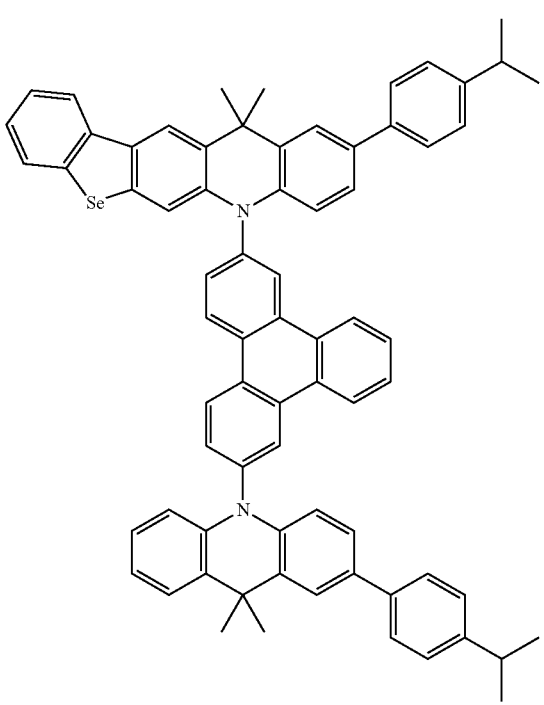
Compound 37
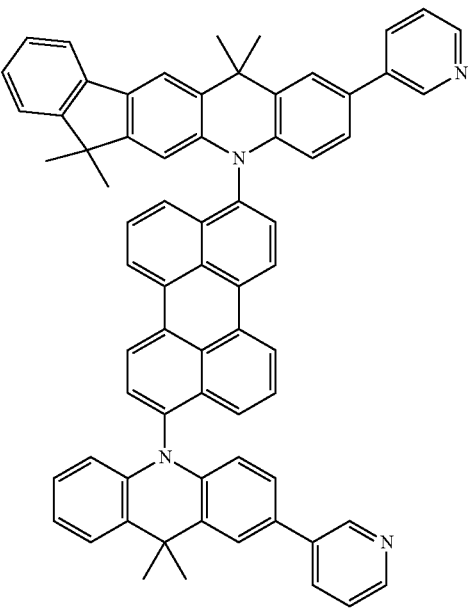
Compound 38
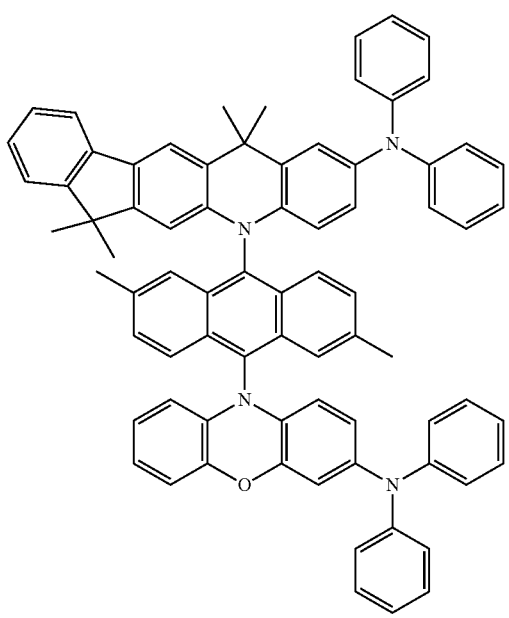

Compound 39
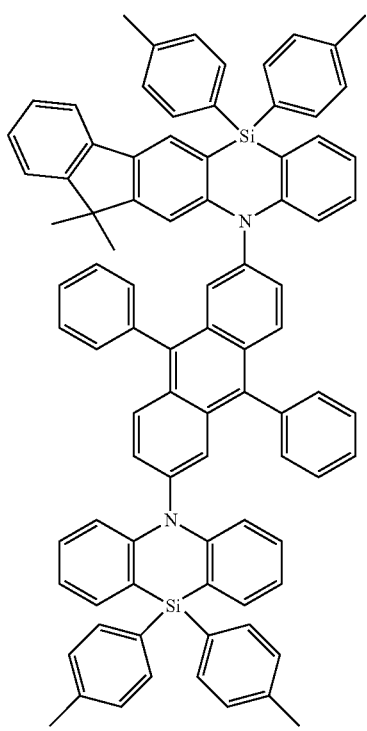
Compound 40
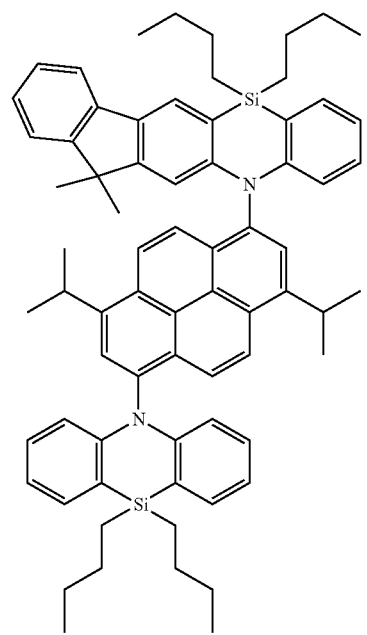
Compound 41
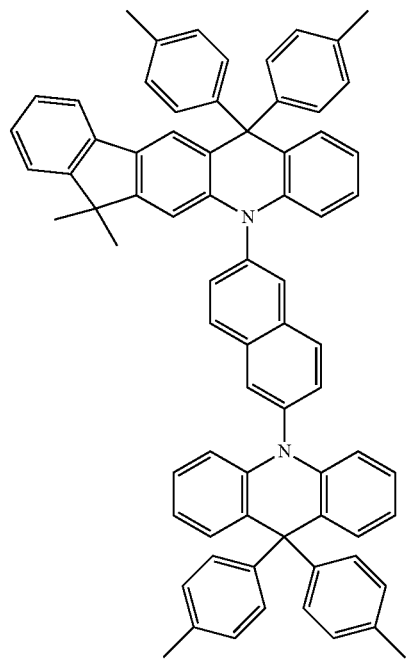
Compound 42
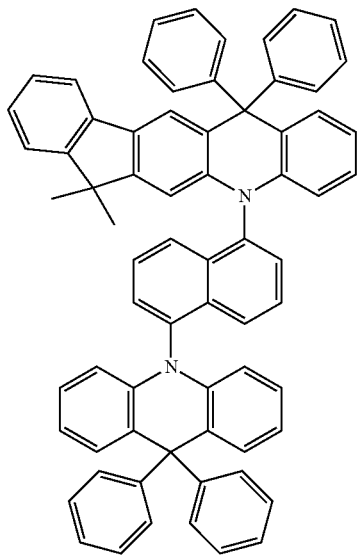

Compound 43
Compound 44
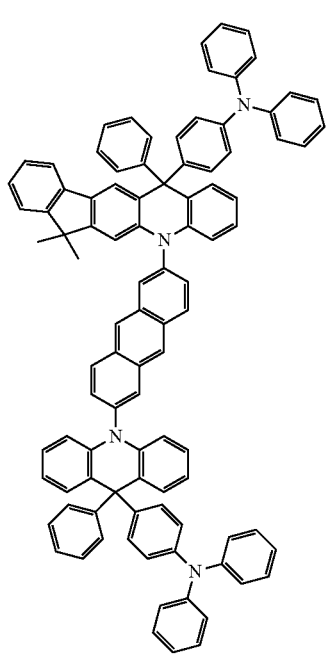
Compound 45
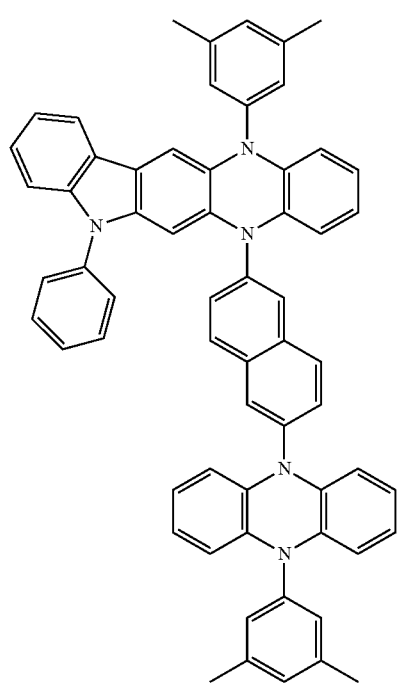
Compound 46
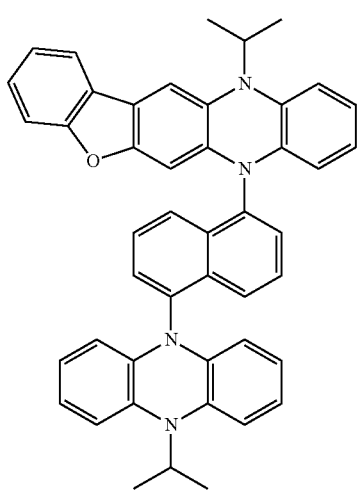

Compound 47
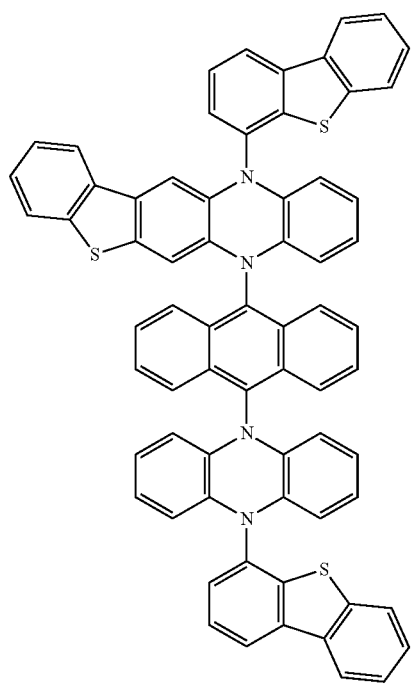
Compound 48
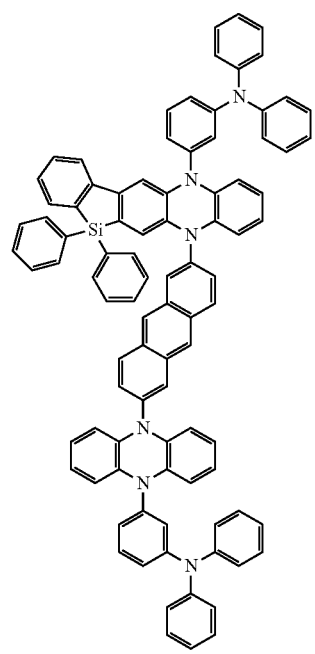
Compound 49
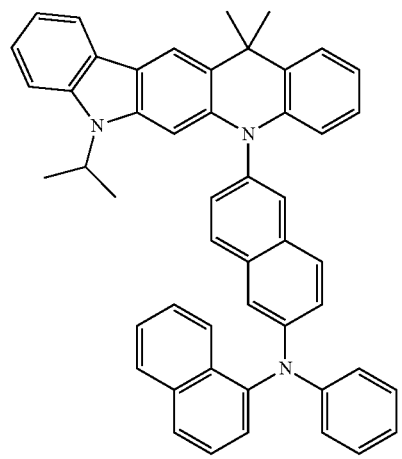
Compound 50
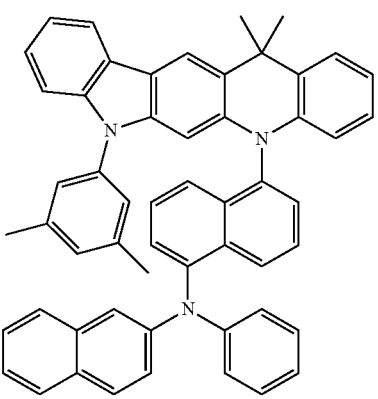
Compound 51
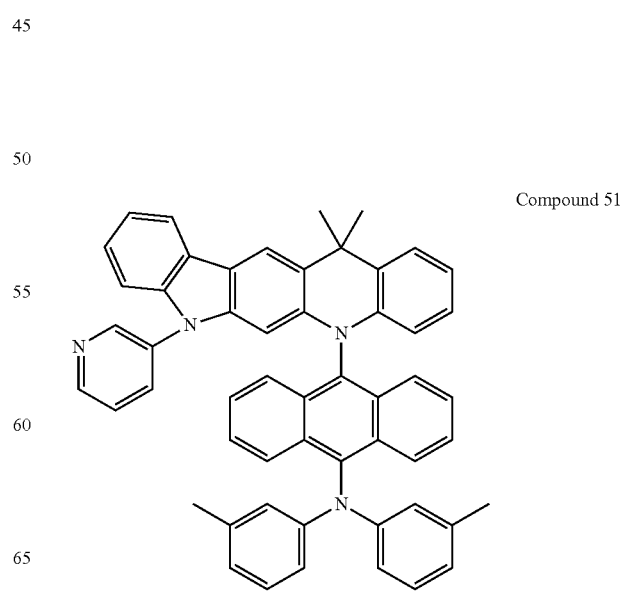

-continued
Compound 52
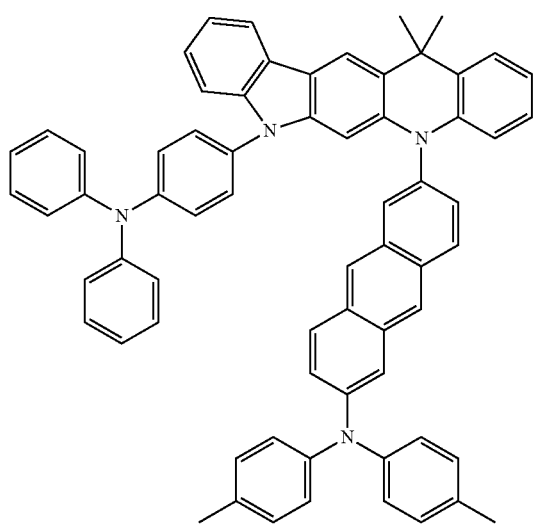
Compound 53
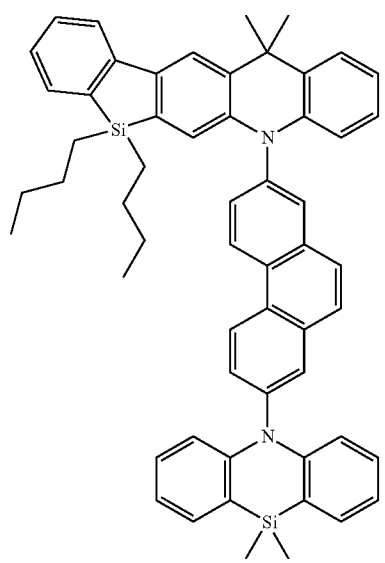
Compound 54
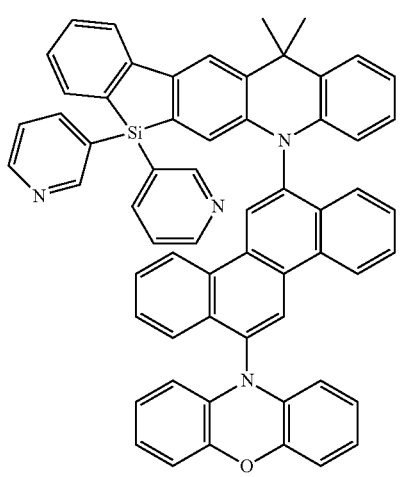
Compound 55
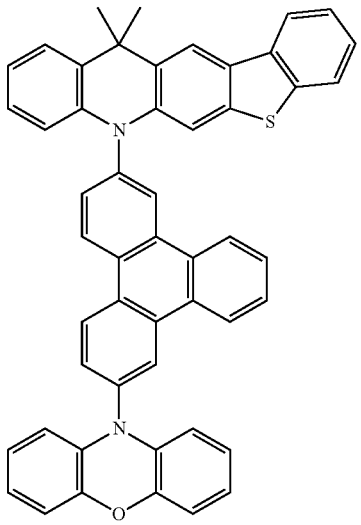
Compound 56
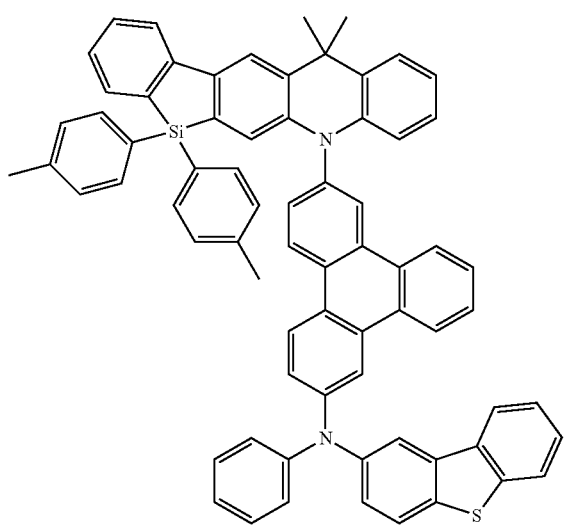
Compound 57
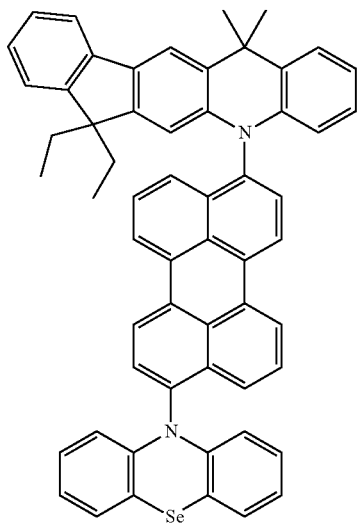

Compound 58
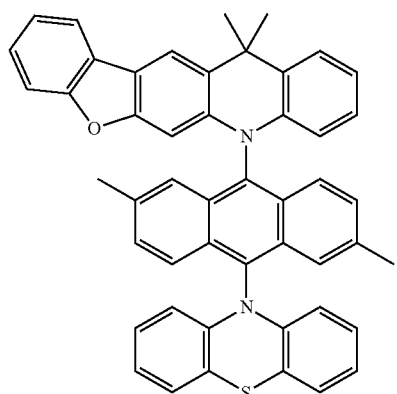
Compound 59
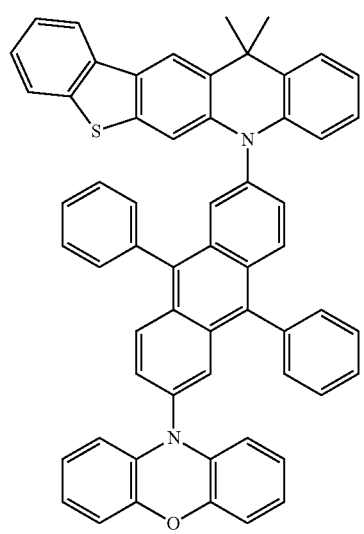
Compound 60
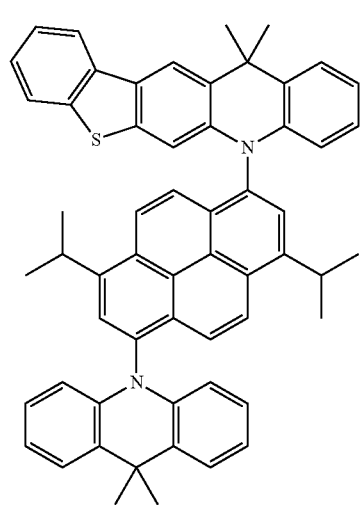
Compound 61
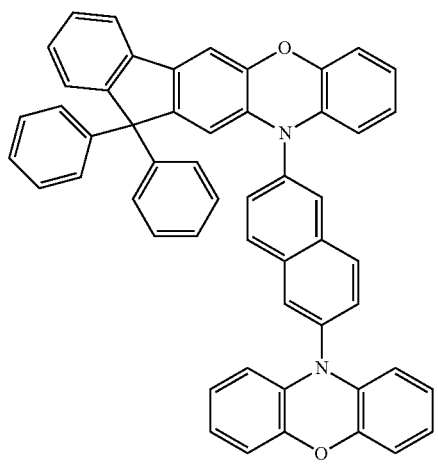
Compound 62
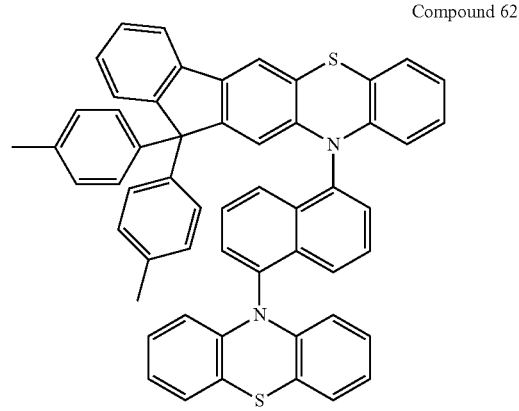
Compound 63
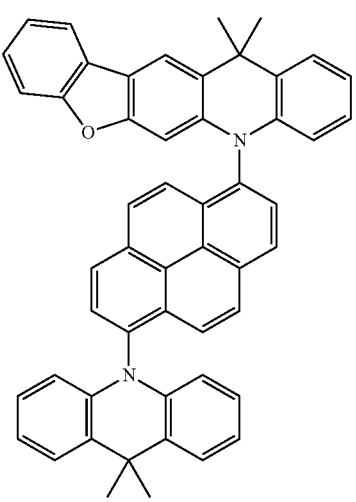

Compound 64
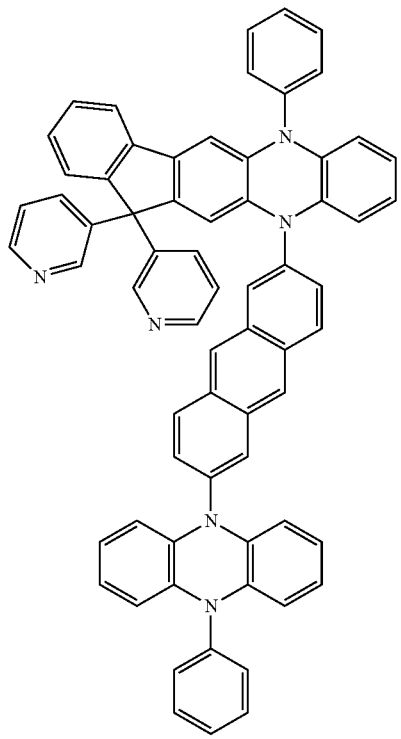
Compound 65
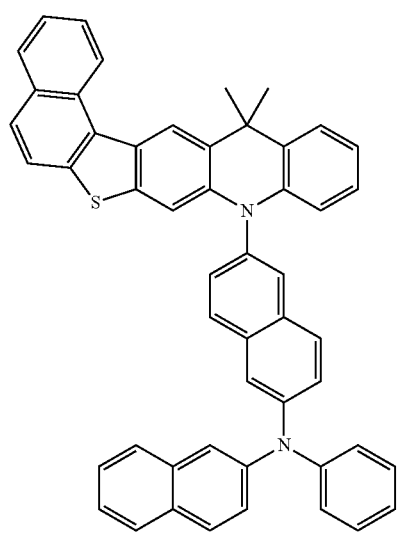
Compound 66
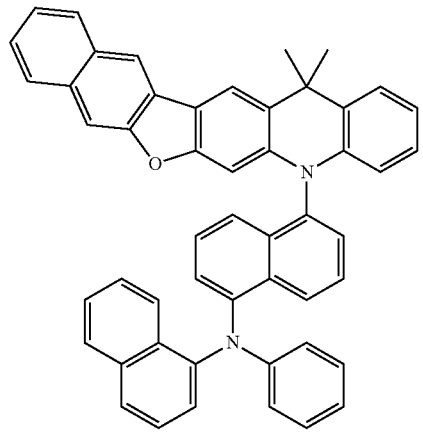
Compound 67
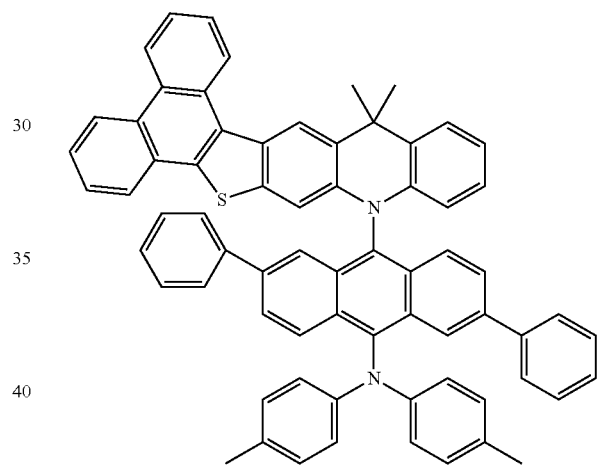
Compound 68
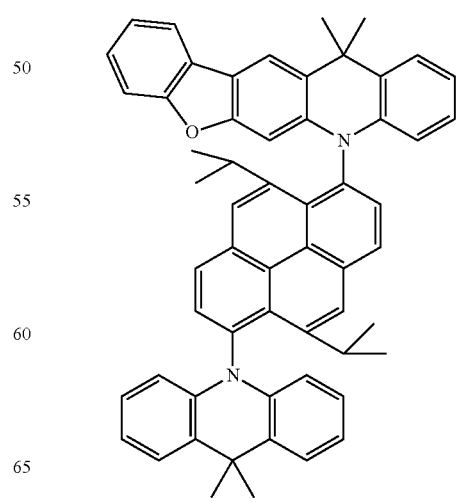

Compound 69
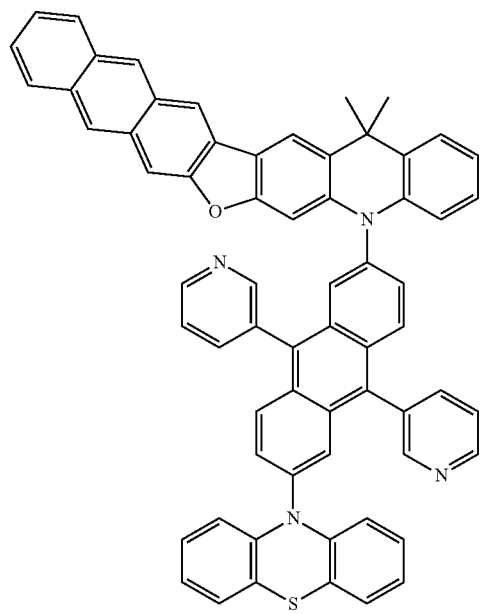
Compound 70
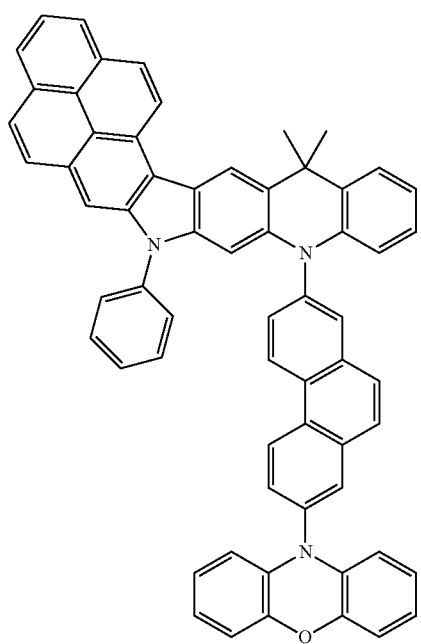
Compound 71
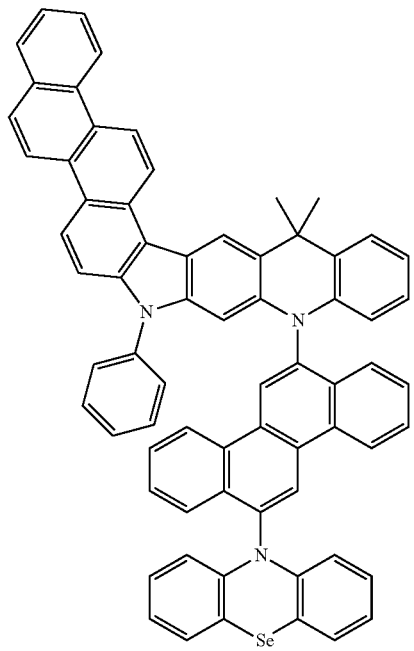
Compound 72
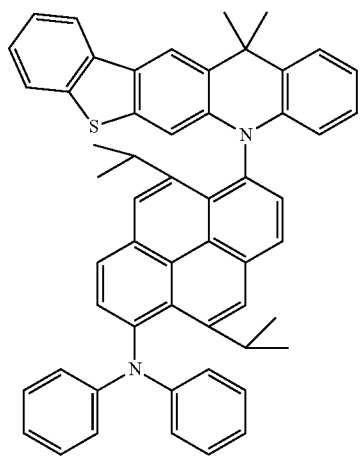

Compound 73
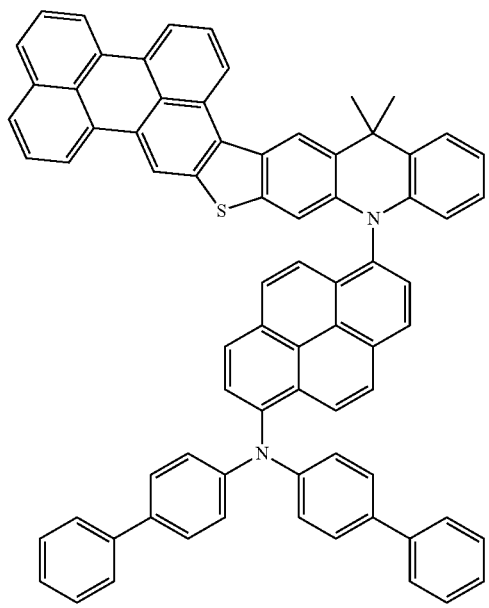
Compound 75
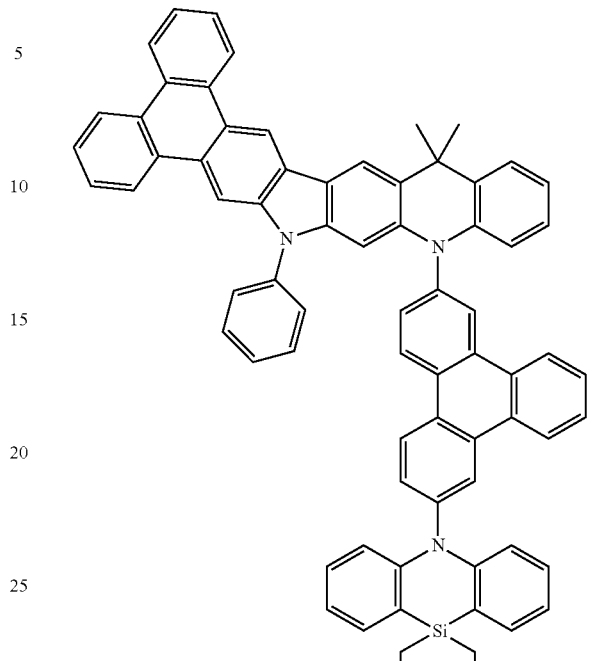
Compound 74
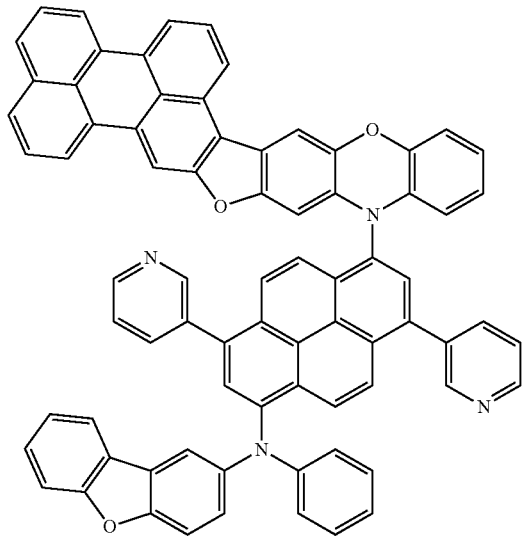
Compound 76
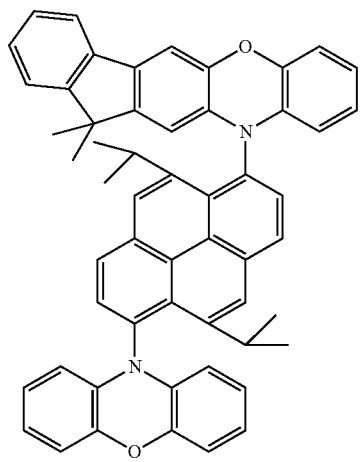

Compound 77
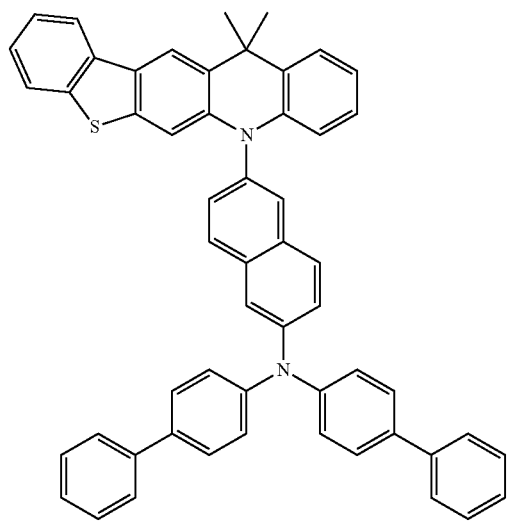
Compound 80
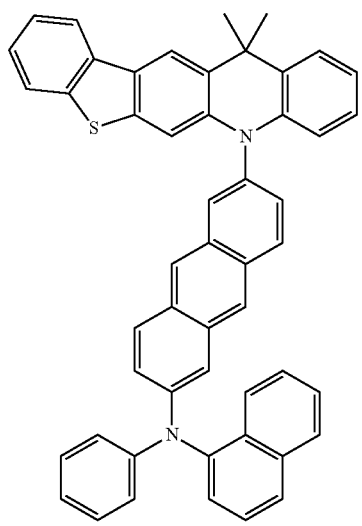
Compound 78
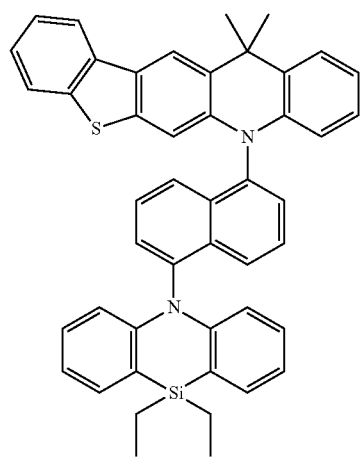
Compound 81
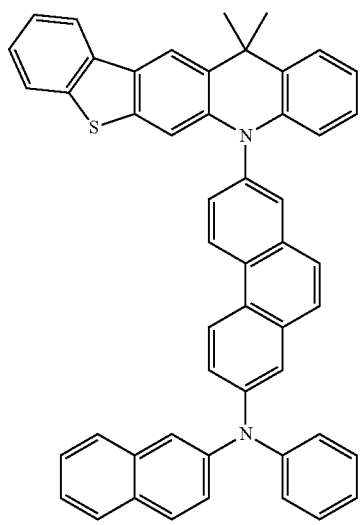
Compound 79
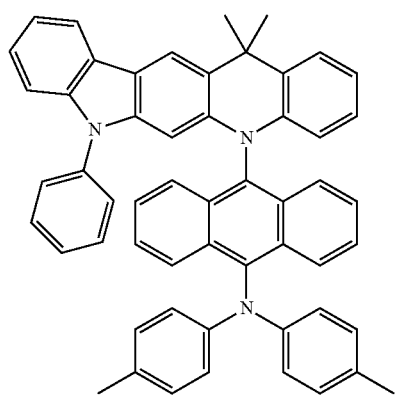
Compound 82
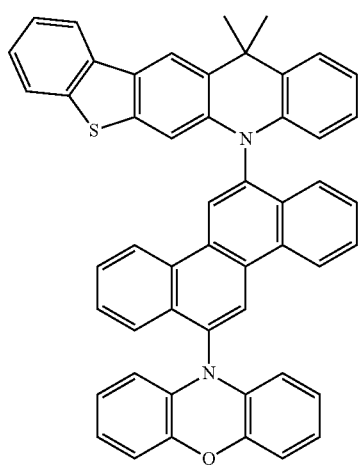

Compound 83
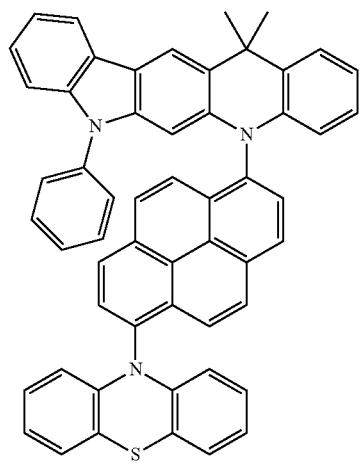
Compound 84
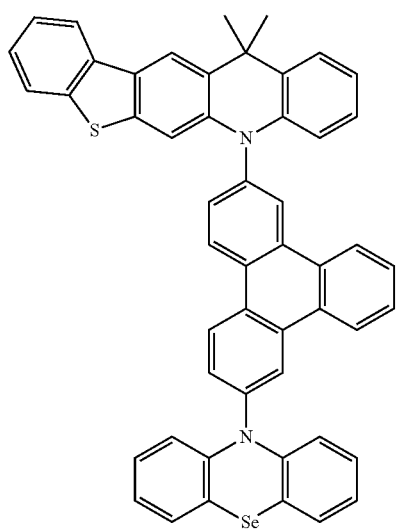
Compound 85
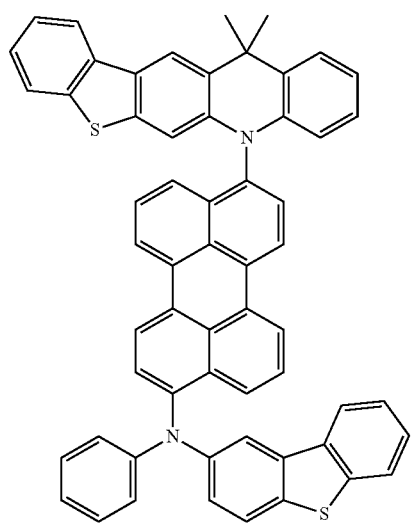
Compound 86
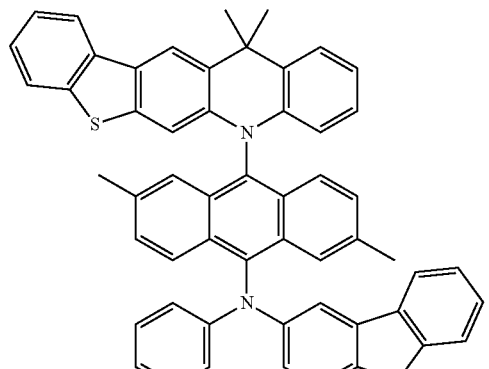
Compound 87
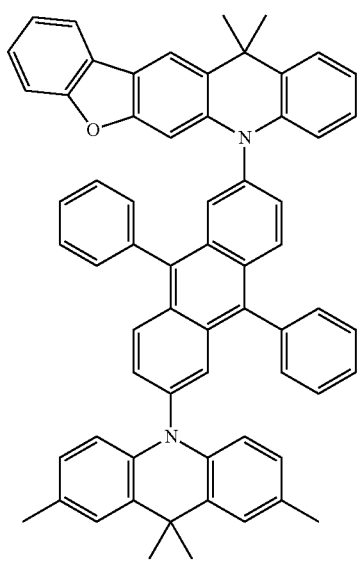 [SMILES: CC1(C)c2ccccc2N(c2ccc3c(-c4ccccc4)c4cc(N5c6ccccc6Oc6ccccc65)ccc4c(-c4ccccc4)c3c2)c2cc3sc4ccccc4c3cc21]
Compound 88
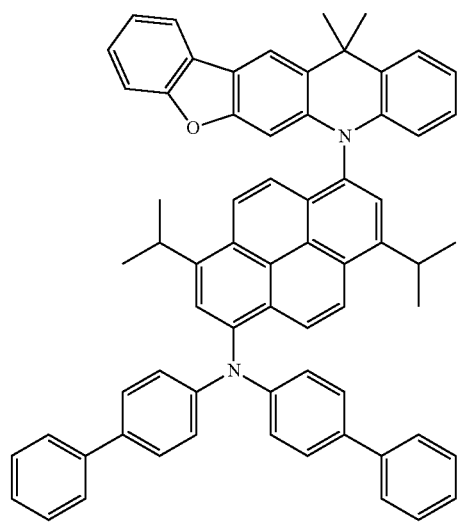

Compound 89
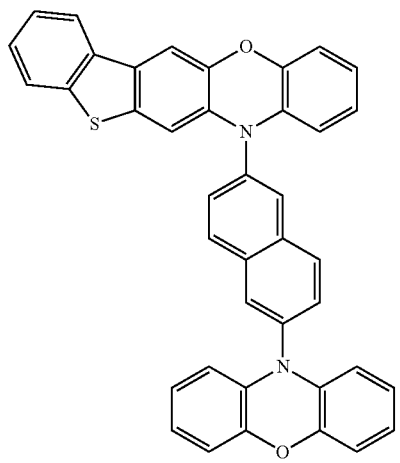
Compound 90
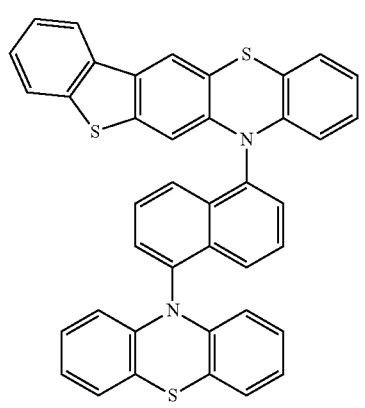
Compound 91
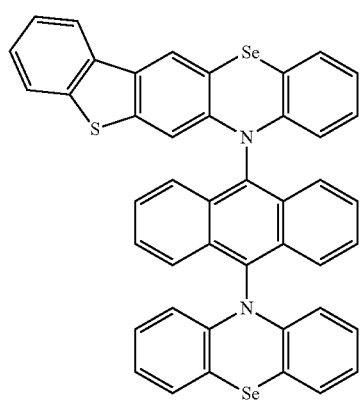
Compound 92
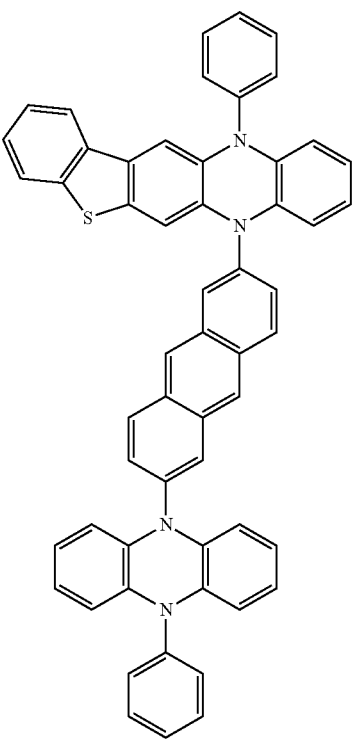
Compound 93
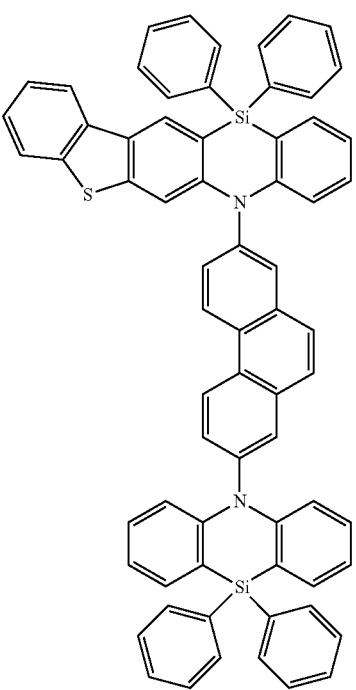

Compound 94
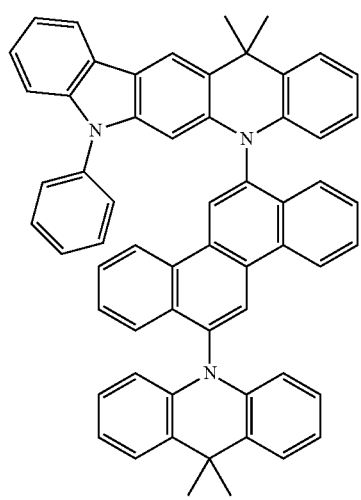
Compound 95
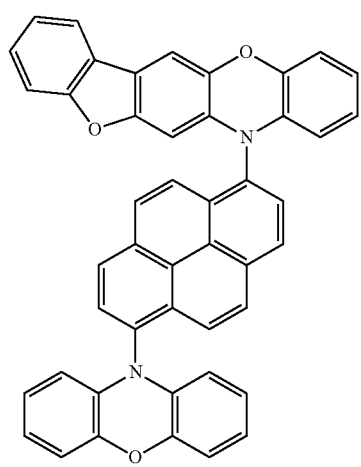
Compound 96
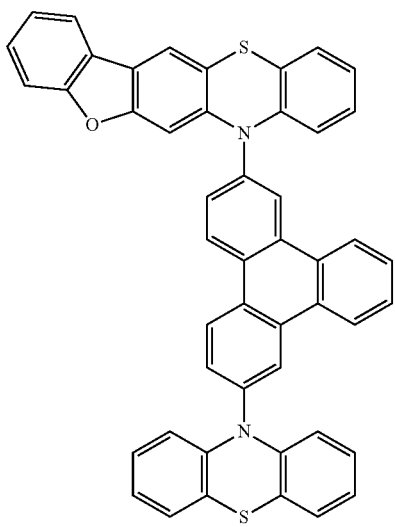
Compound 97
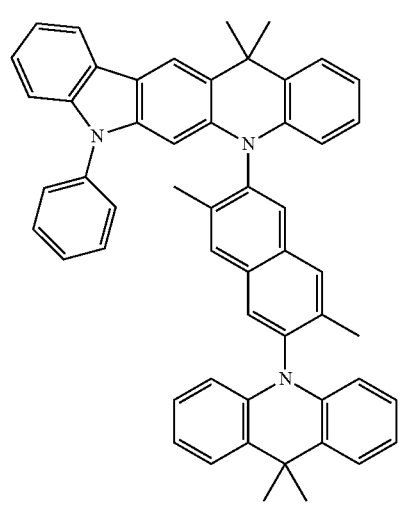
Compound 98
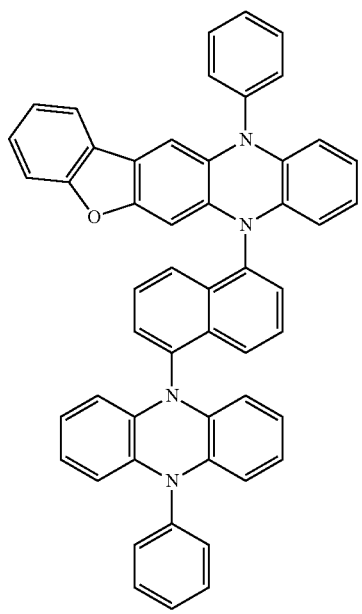
Compound 99
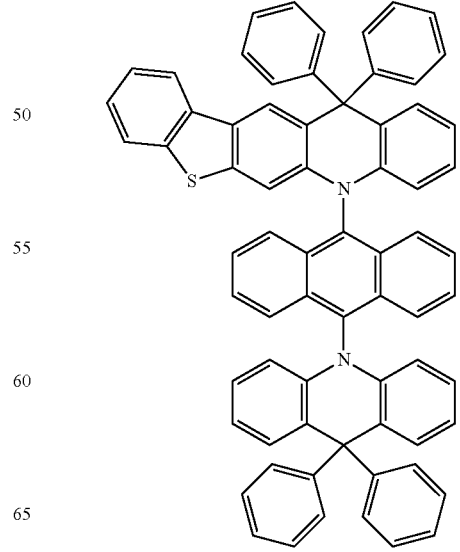

Compound 100
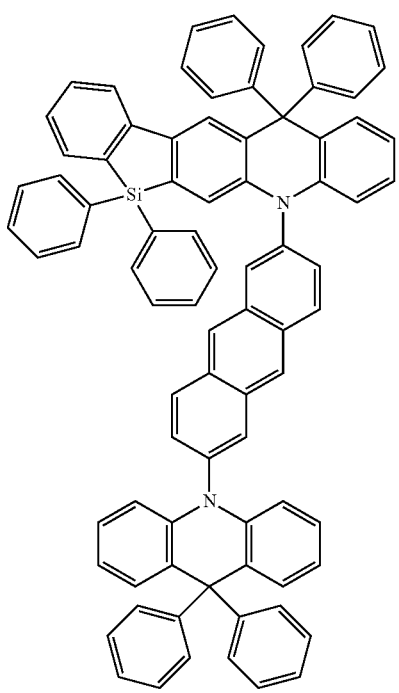
Compound 101
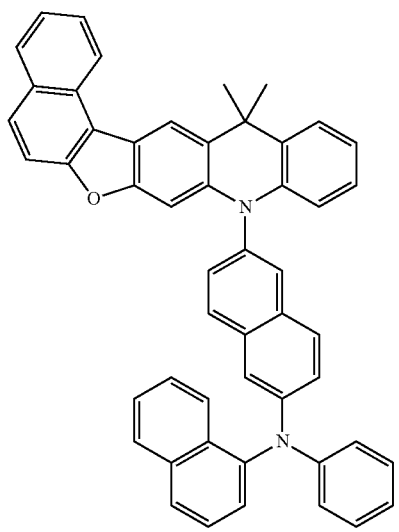
Compound 102
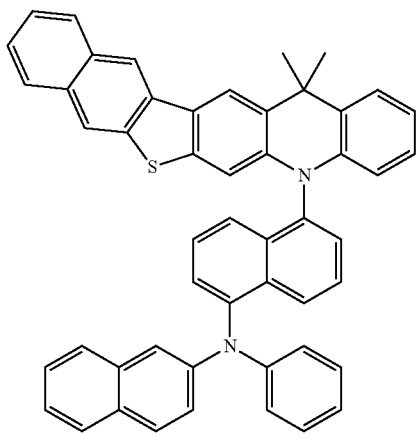
Compound 103
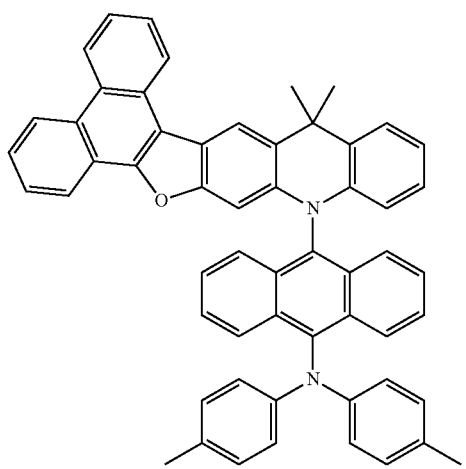
Compound 104
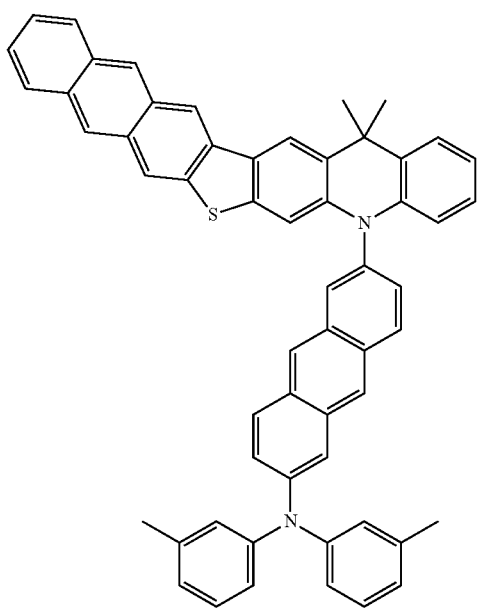

Compound 105
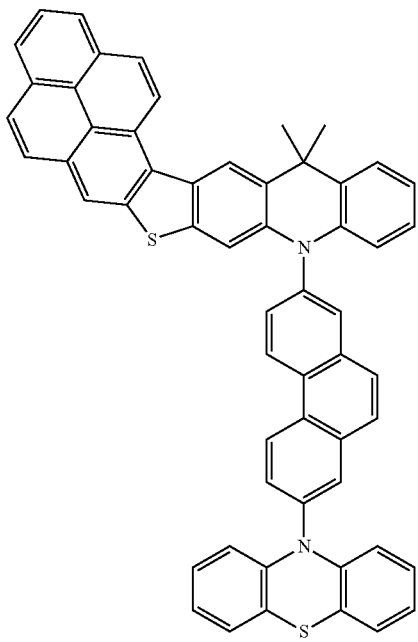
Compound 106
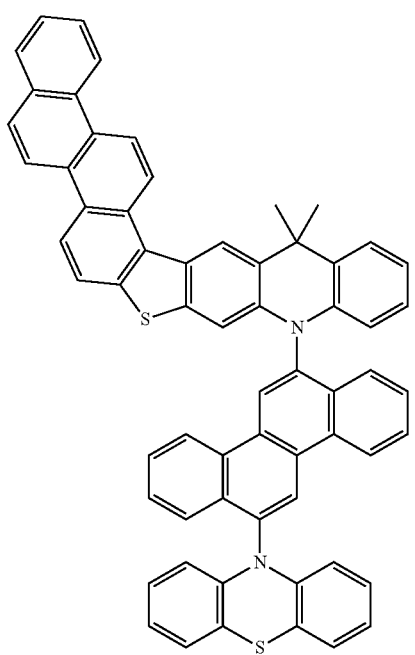
Compound 107
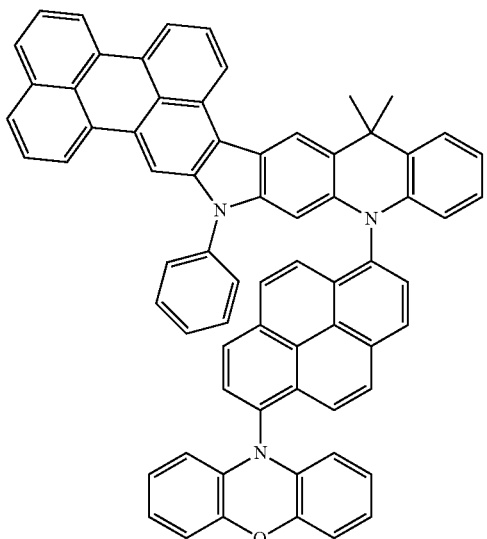
Compound 108
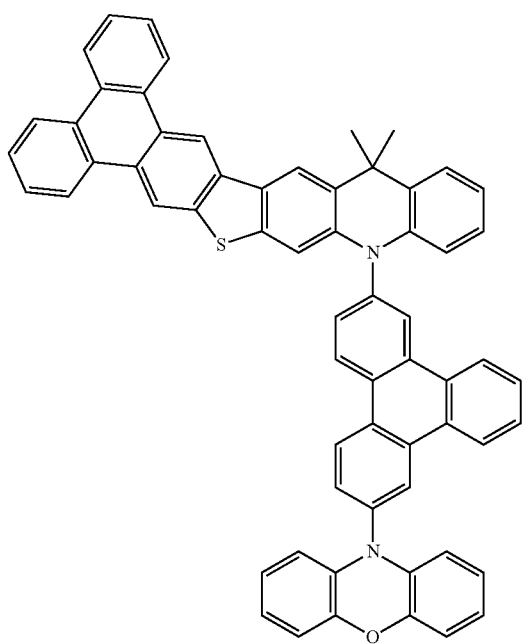

Compound 109
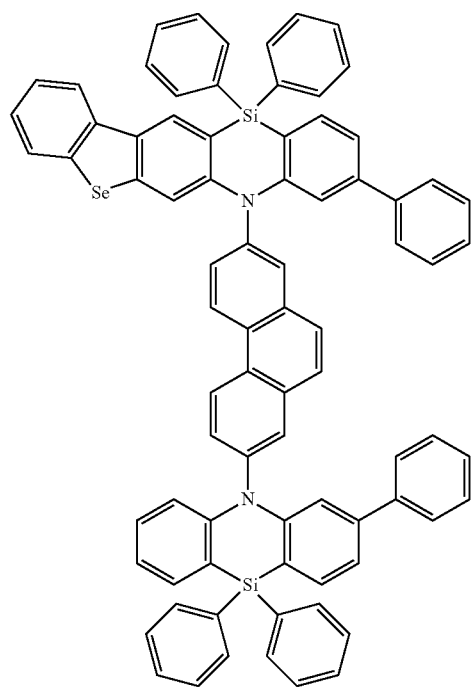
Compound 110
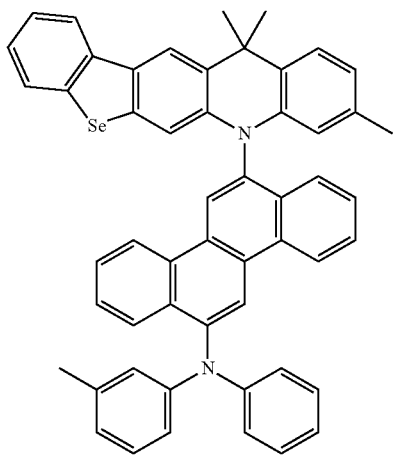
Compound 111
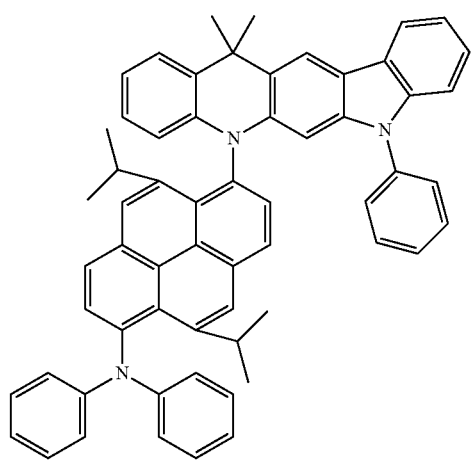
Compound 112
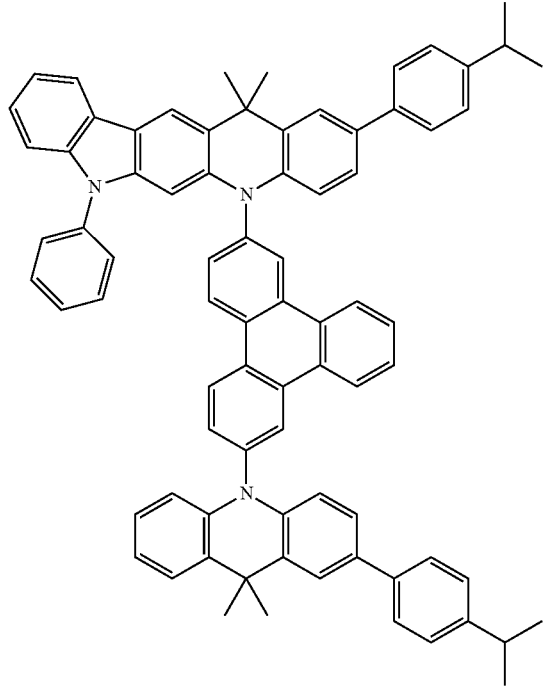
Compound 113
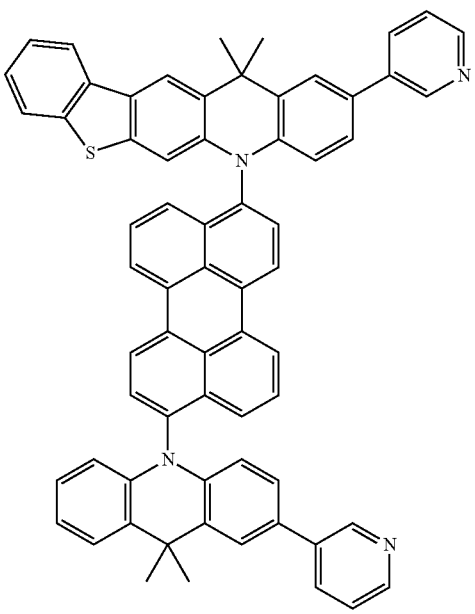

Compound 114
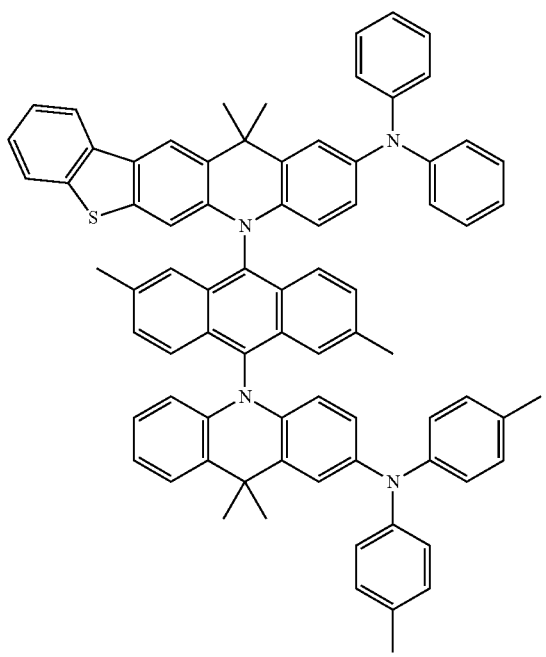
Compound 115
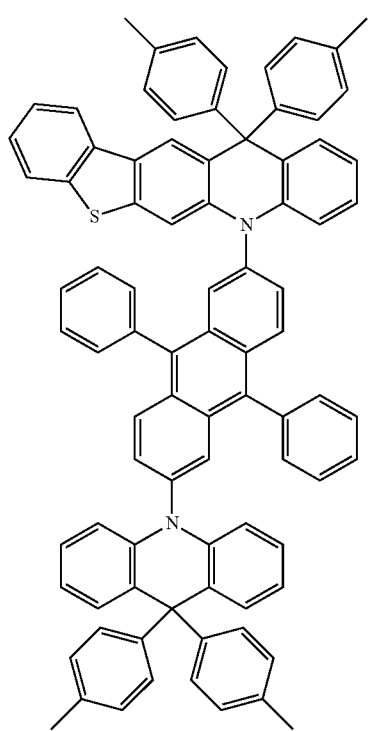
Compound 116
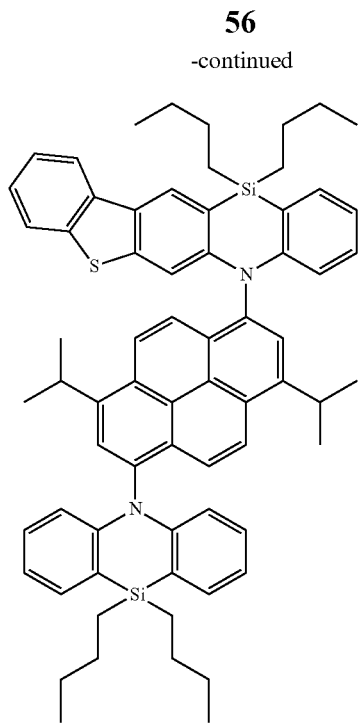
Compound 117
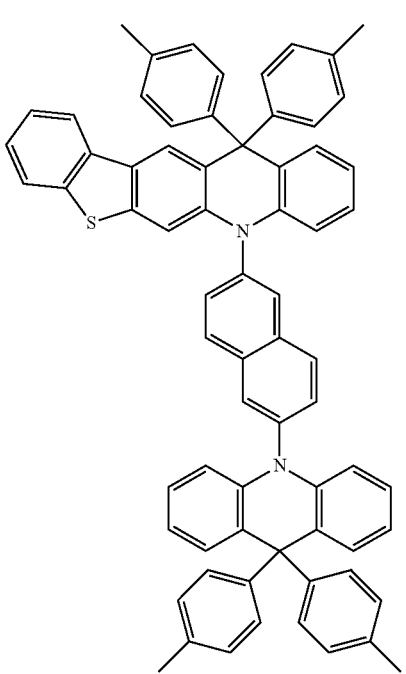

Compound 118
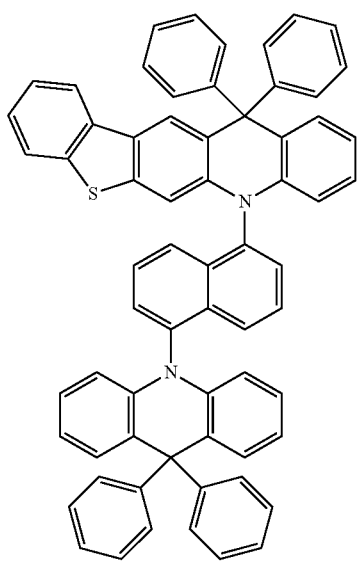
Compound 119
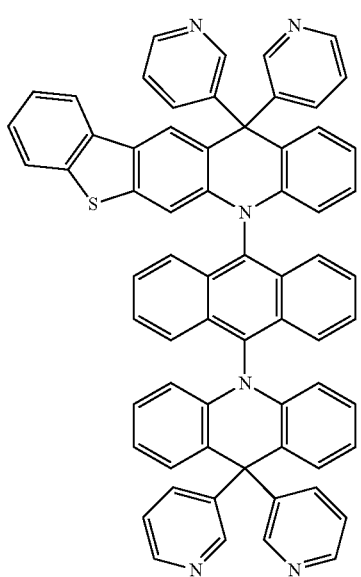
Compound 120
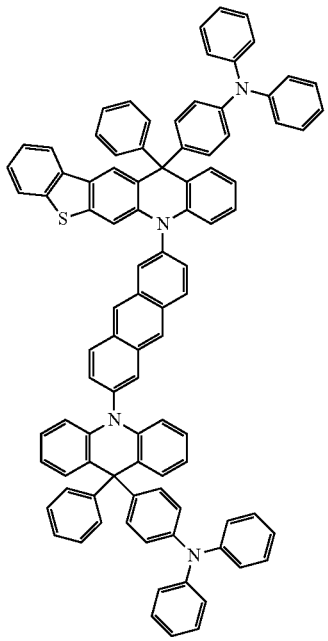
Compound 121
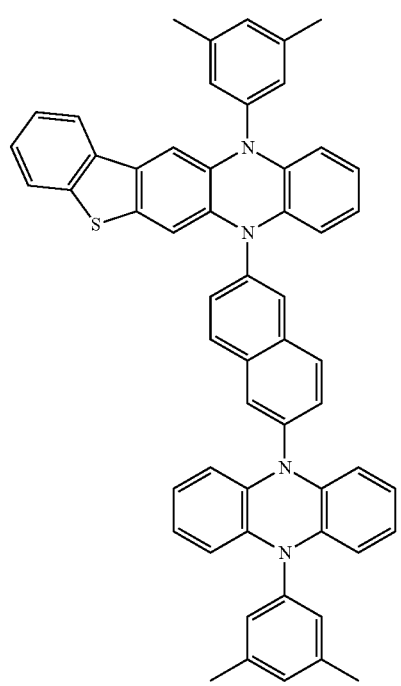

Compound 122
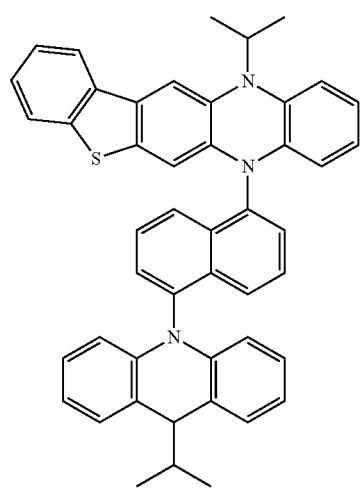
Compound 123
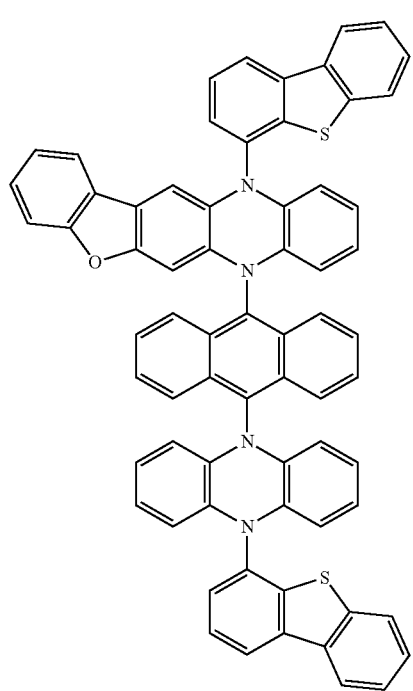
Compound 124
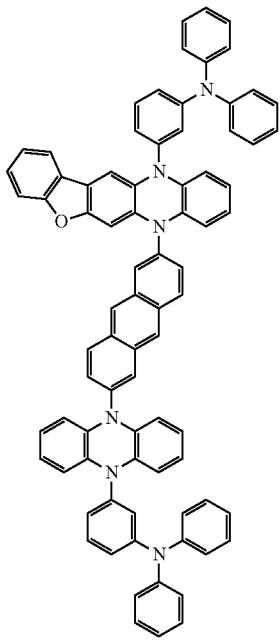
Compound 125
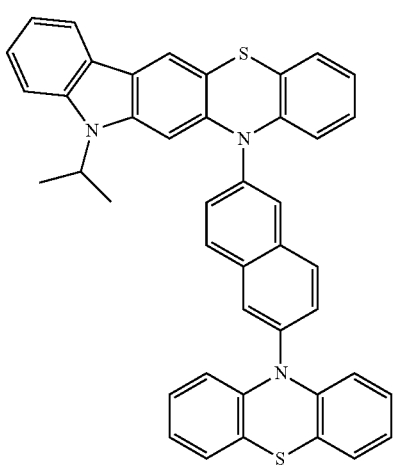
Compound 126
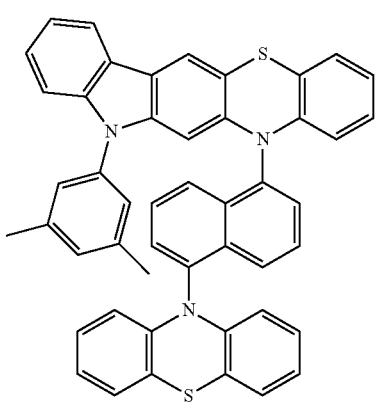

Compound 127
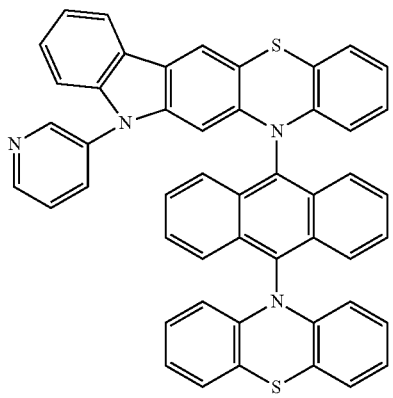
Compound 128
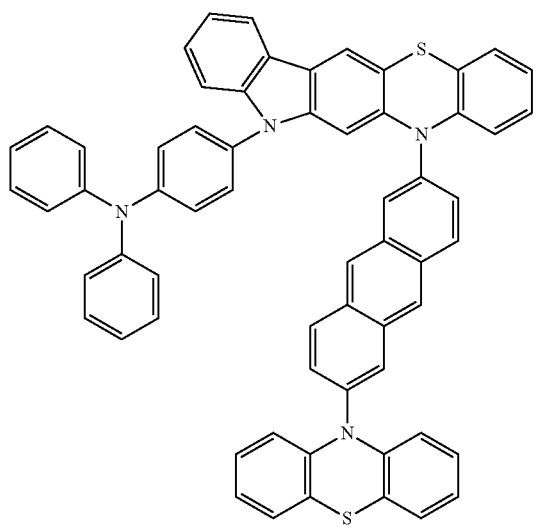
Compound 129
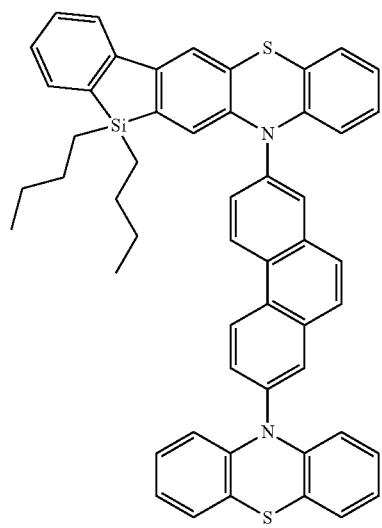
Compound 130
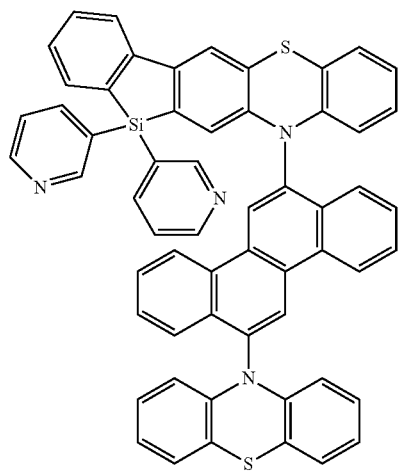
Compound 131
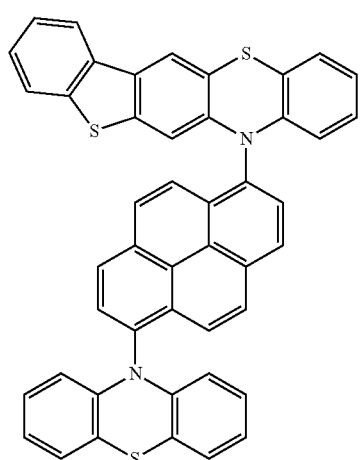
Compound 132
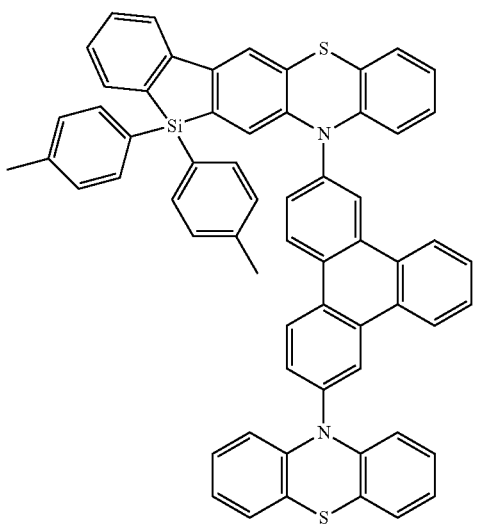

Compound 133
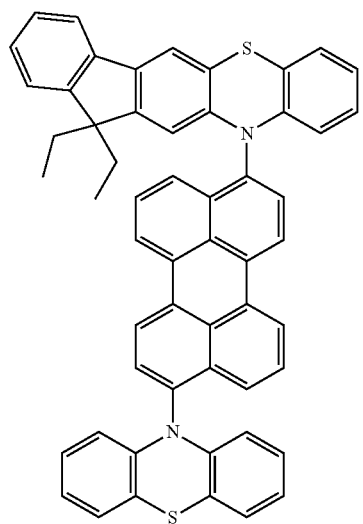
Compound 134
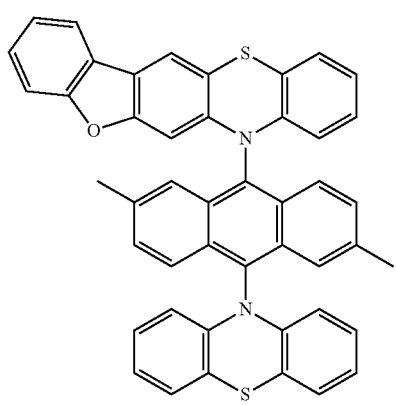
Compound 135
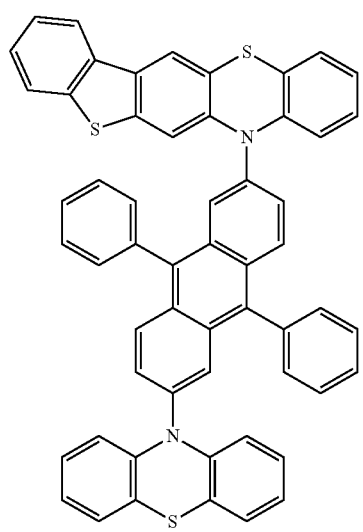
Compound 136
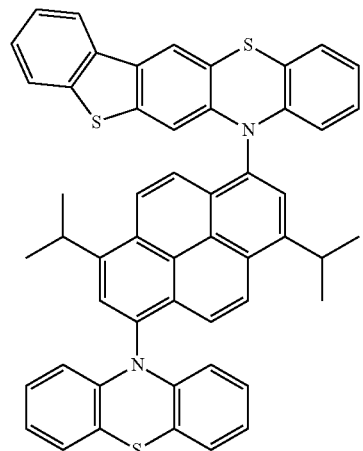
Compound 137
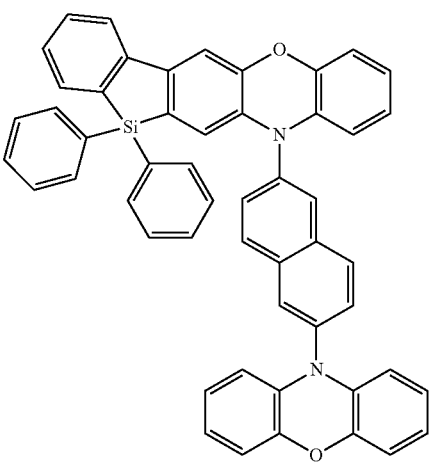
Compound 138
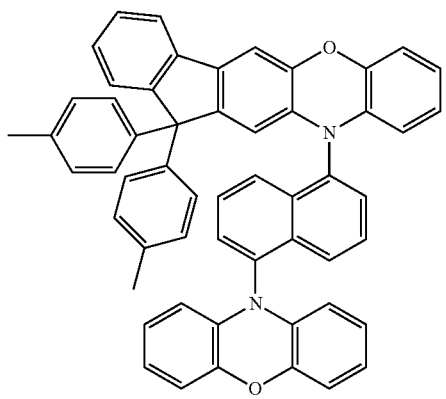

Compound 139
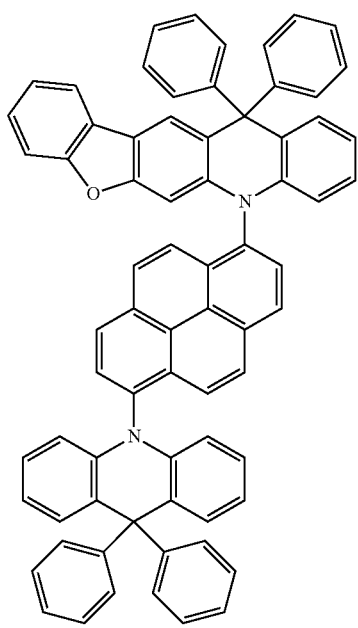
Compound 140
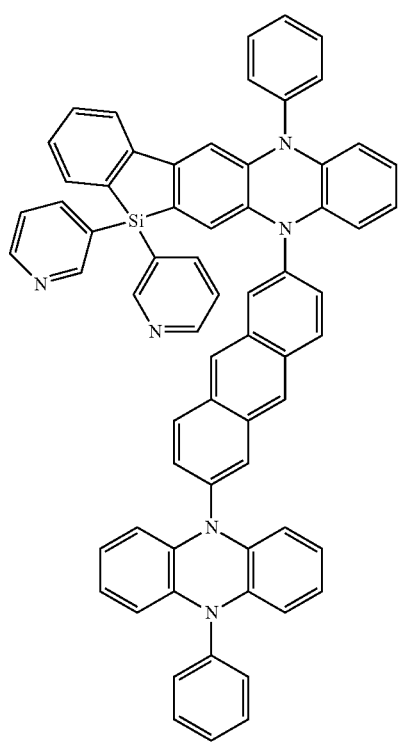
Compound 141
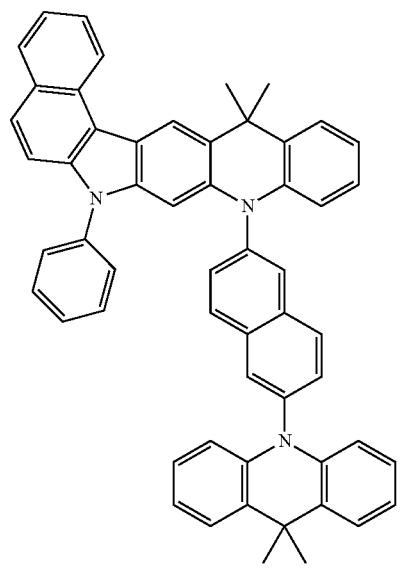
Compound 142
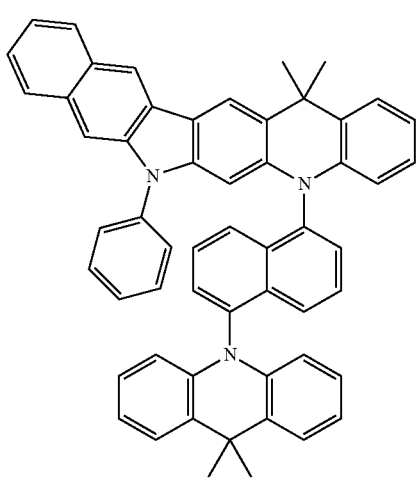
Compound 143
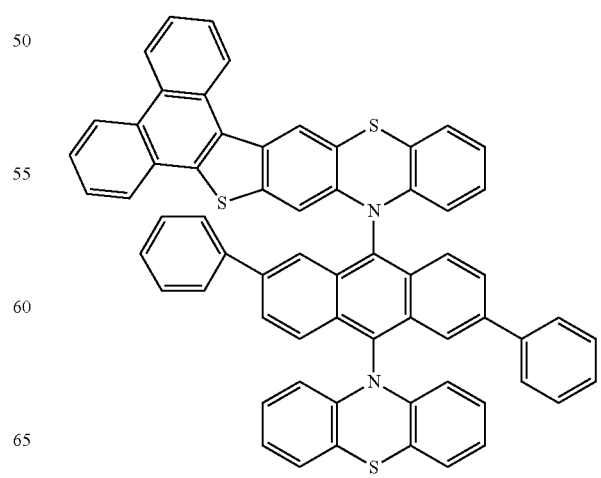

Compound 144
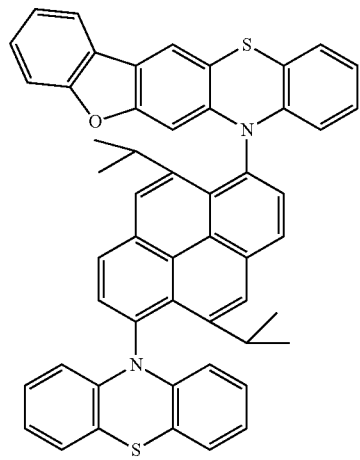
Compound 146
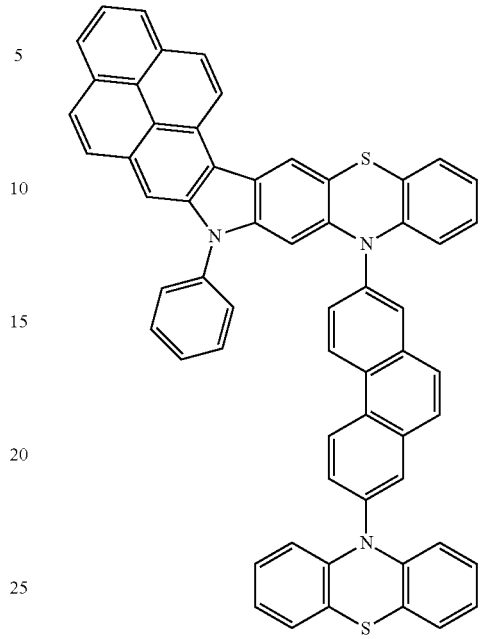
Compound 145
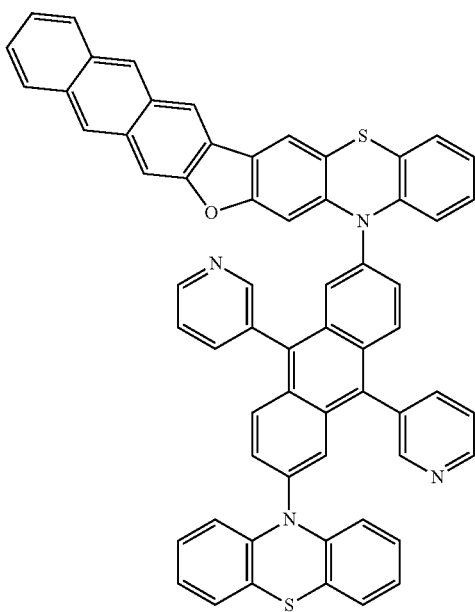
Compound 147
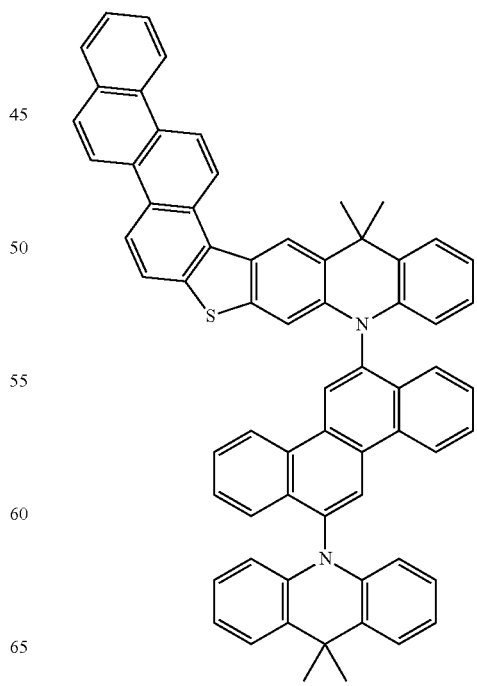

Compound 148
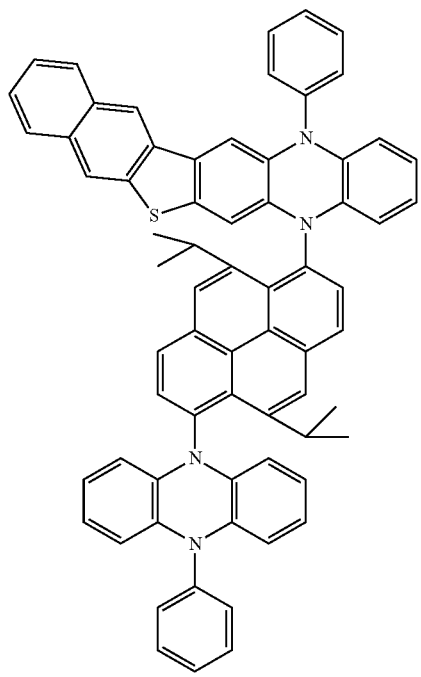
Compound 149
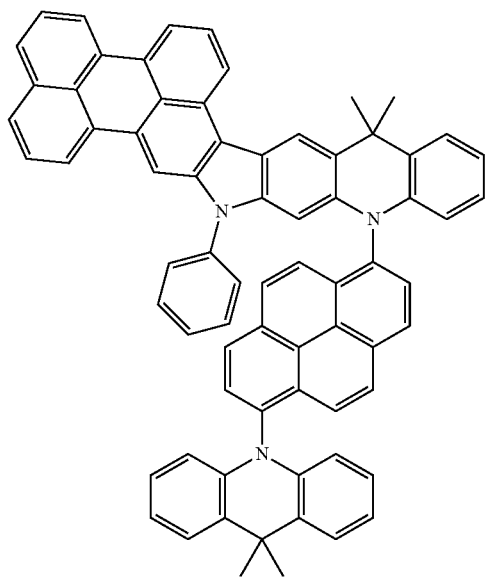
Compound 150
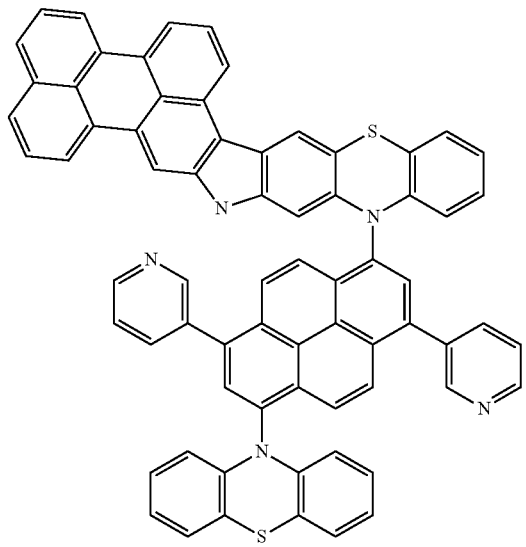
Compound 151
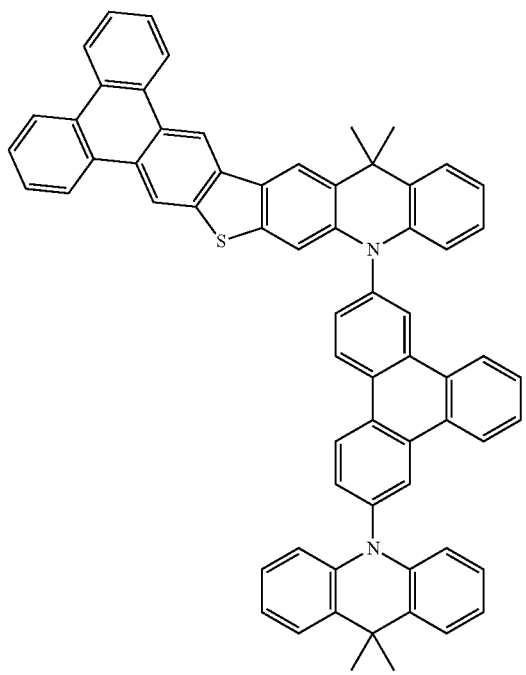

Compound 152
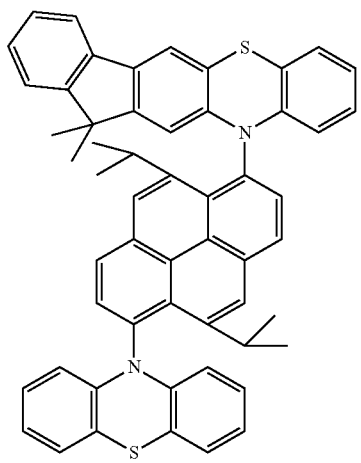
Compound 153
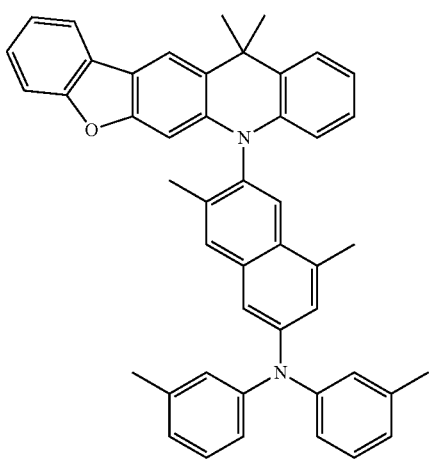
Compound 154
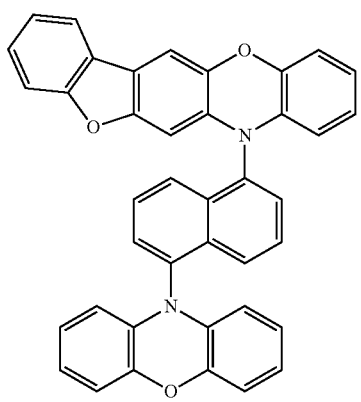
Compound 155
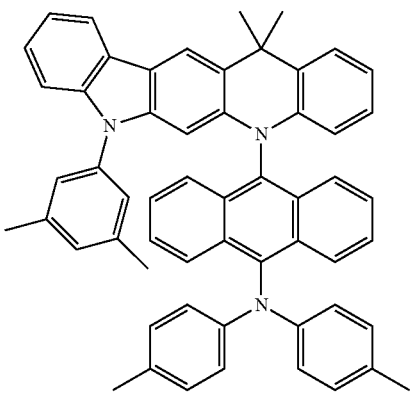
Compound 156
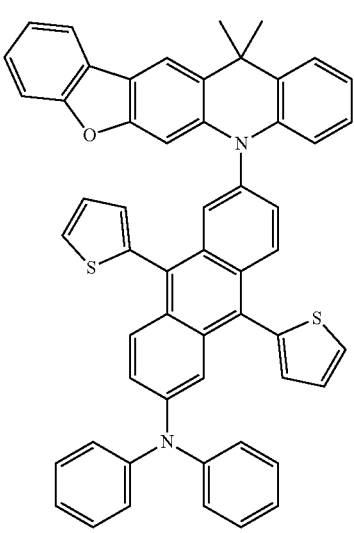
Compound 157
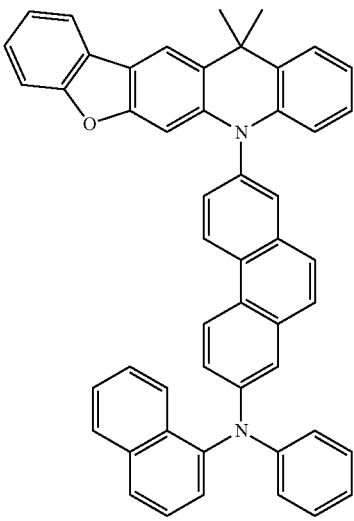

Compound 158
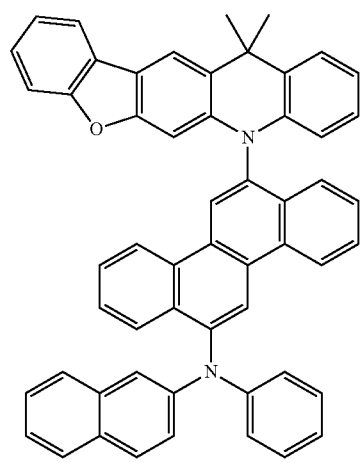
Compound 159
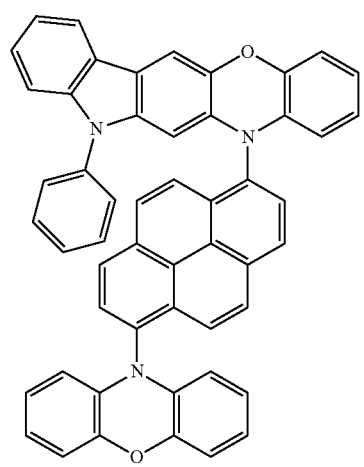
Compound 160
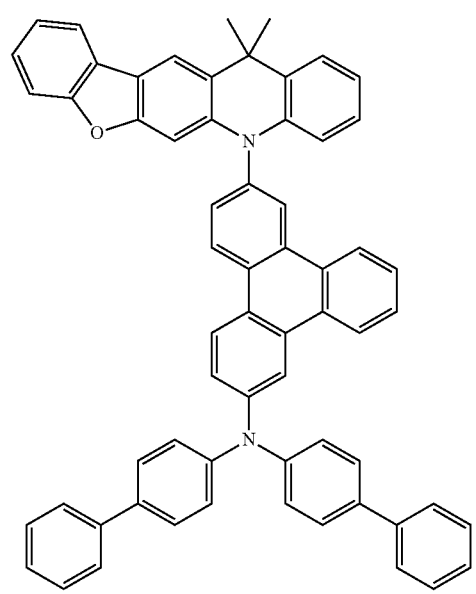
Compound 161
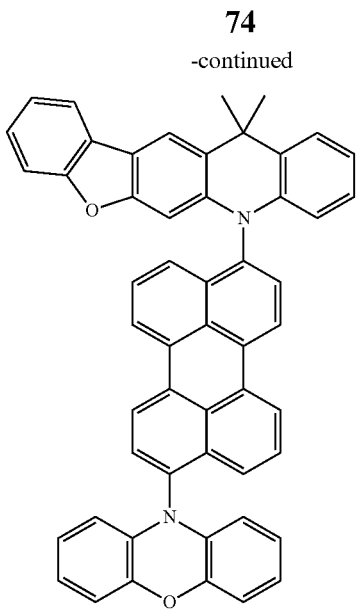
Compound 162
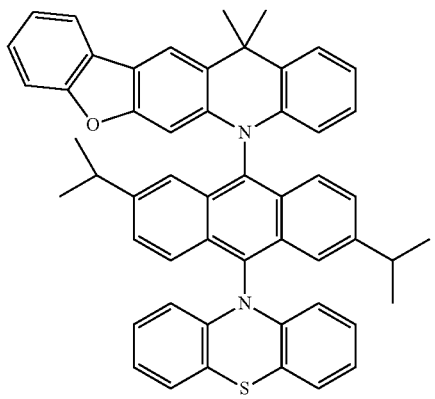
Compound 163
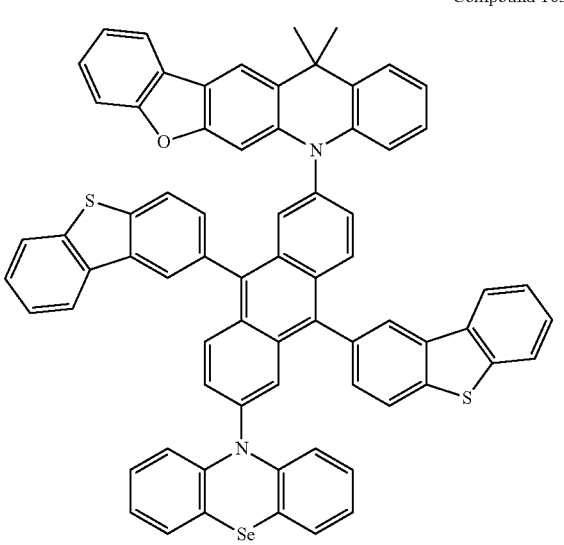

Compound 164
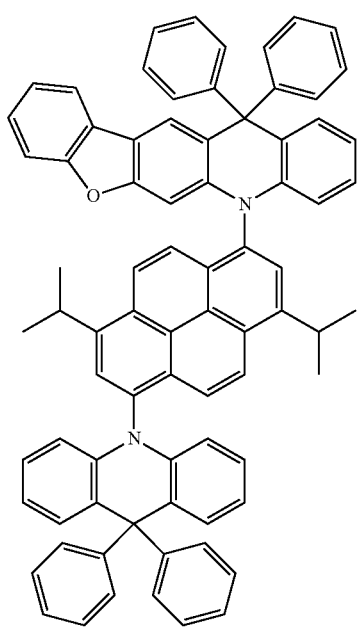
Compound 165
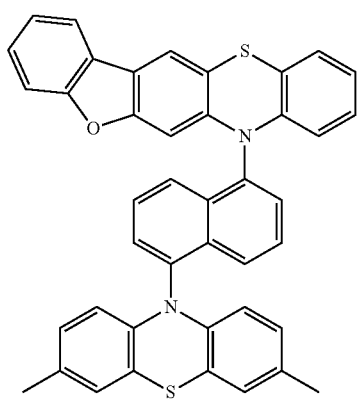
Compound 166
Compound 167
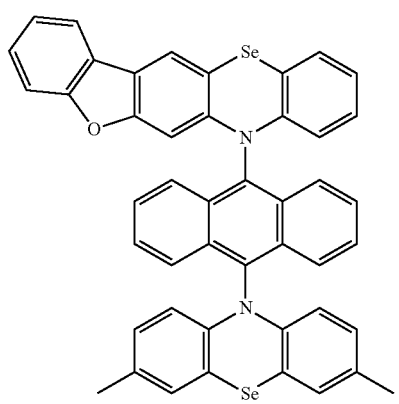
Compound 168
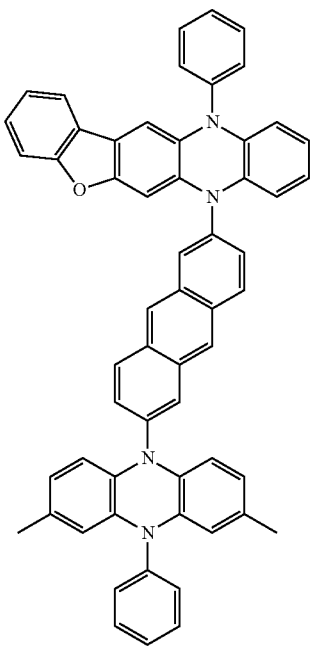

Compound 169
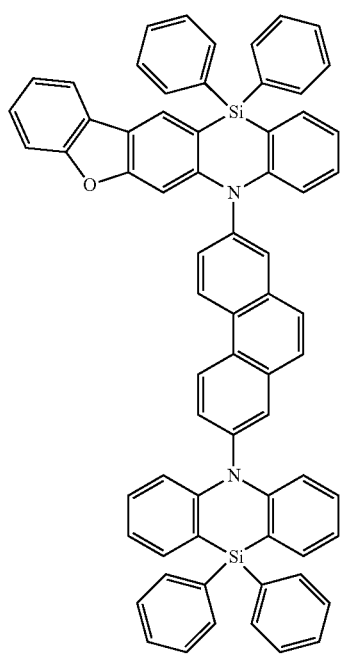
Compound 170
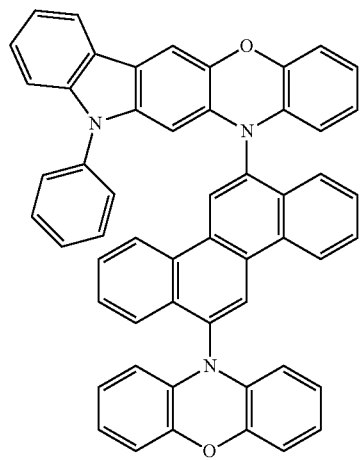
Compound 171
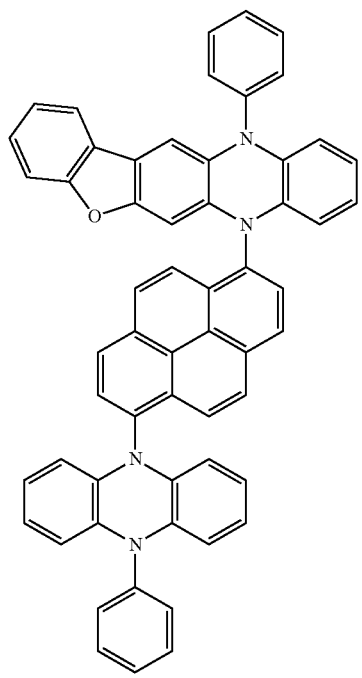
Compound 172
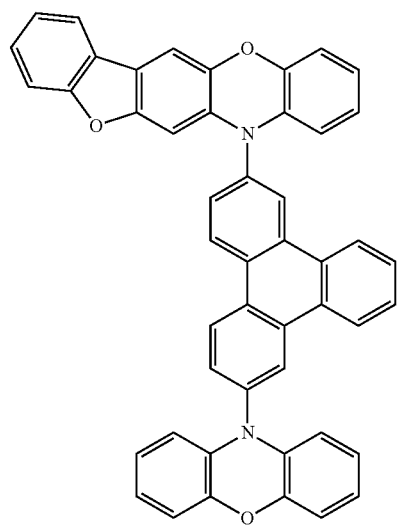

Compound 173
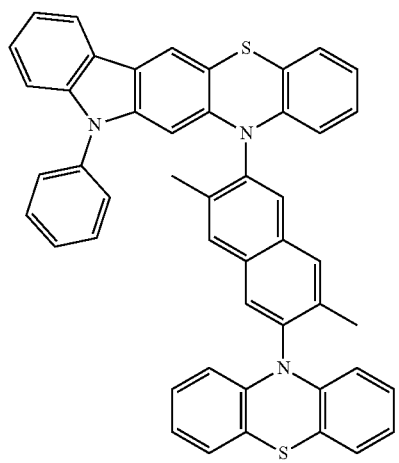
Compound 174
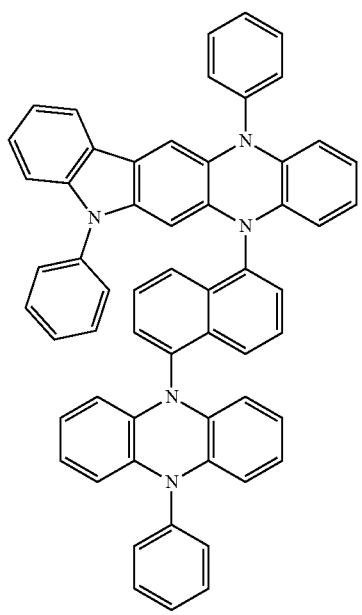
Compound 175
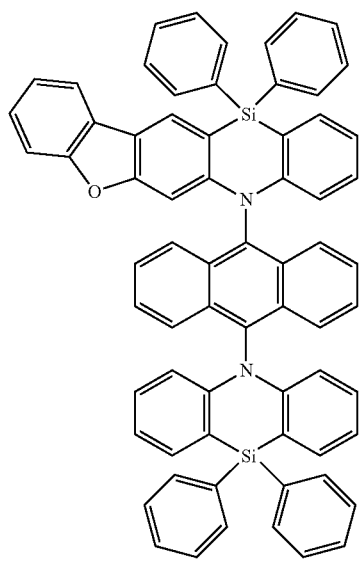
Compound 176
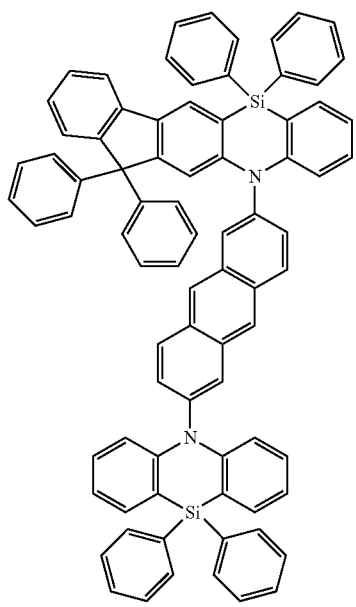

-continued
Compound 177
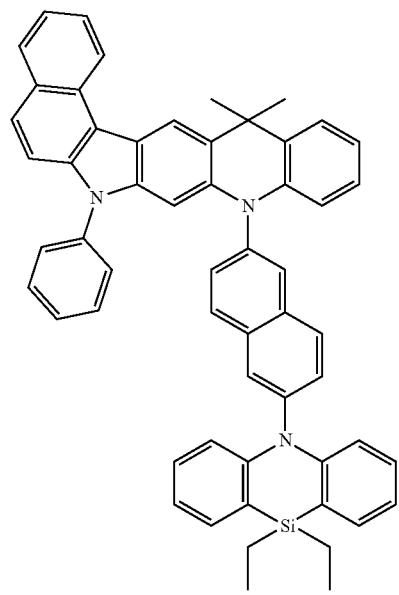
Compound 178
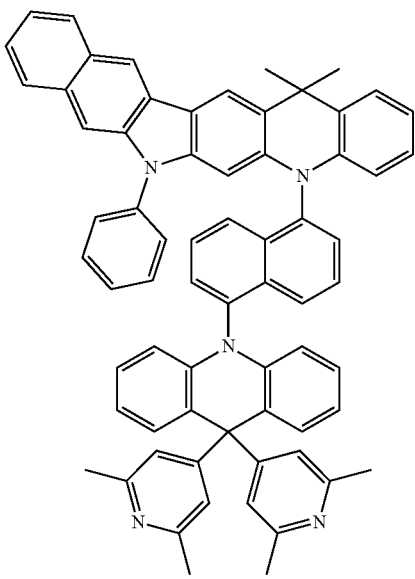
Compound 179
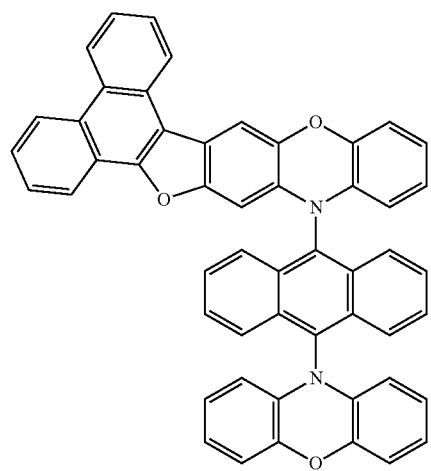
Compound 180
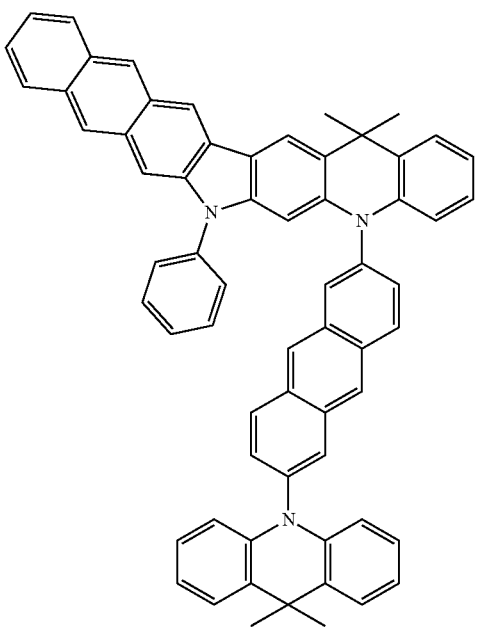

-continued
Compound 181
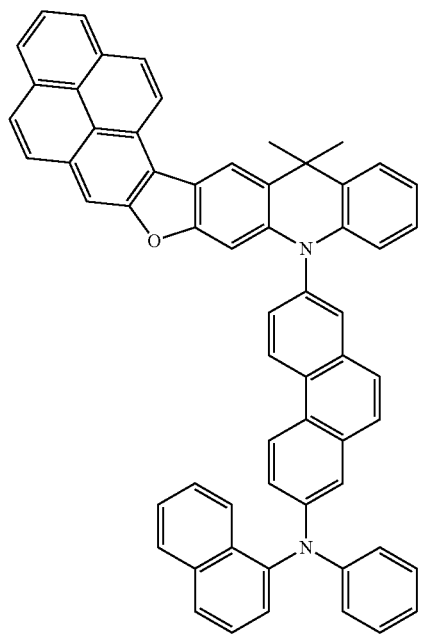
Compound 182
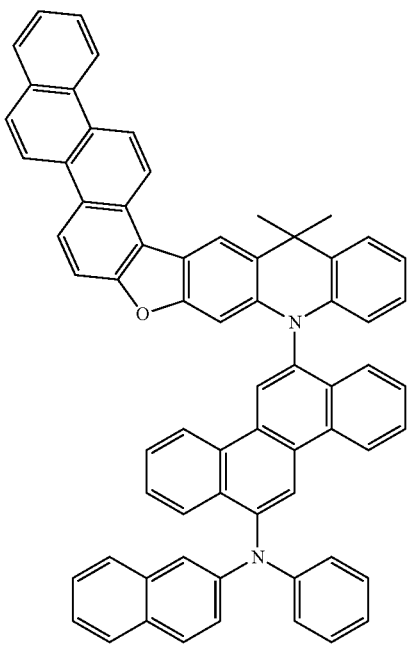
Compound 183
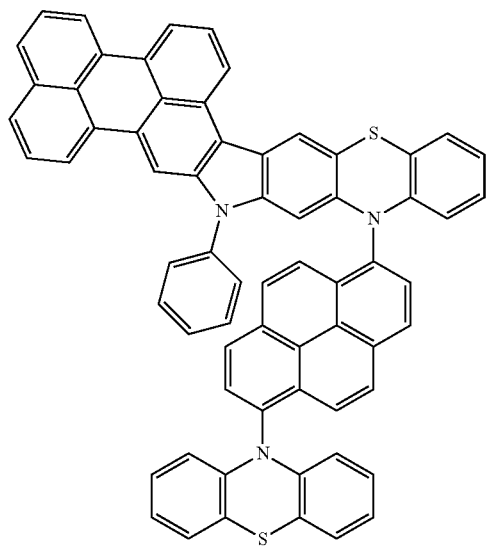
Compound 184
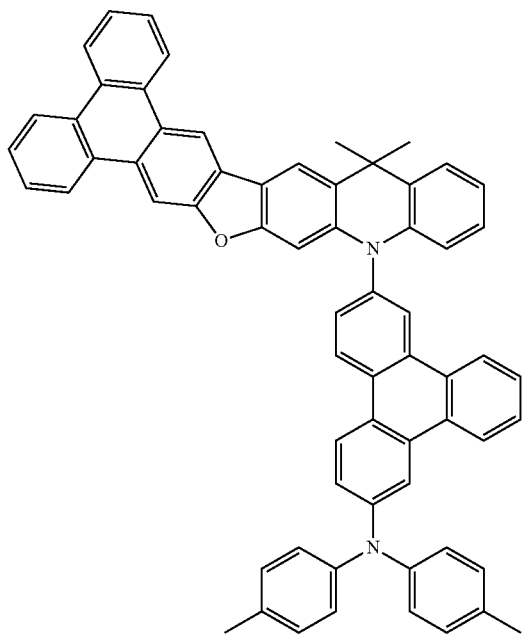

-continued
Compound 185
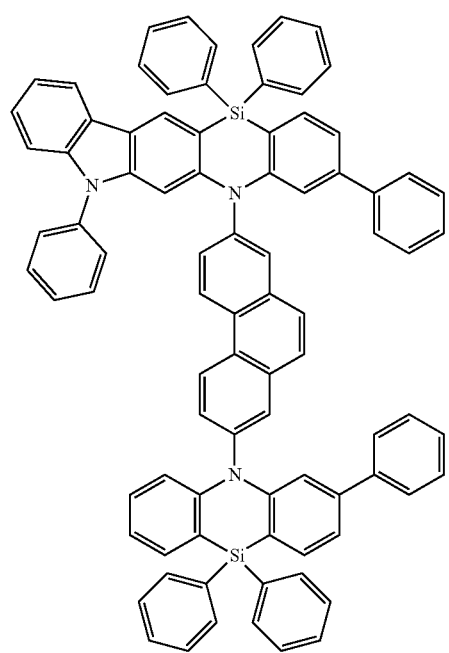
Compound 186
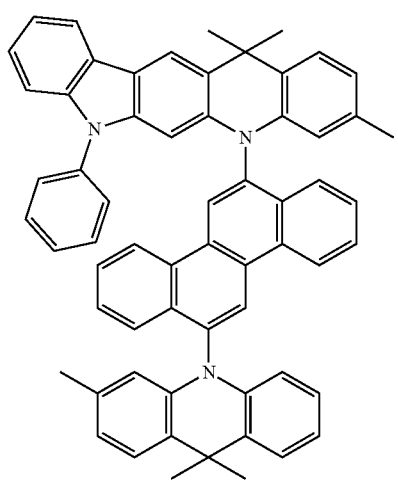
Compound 187
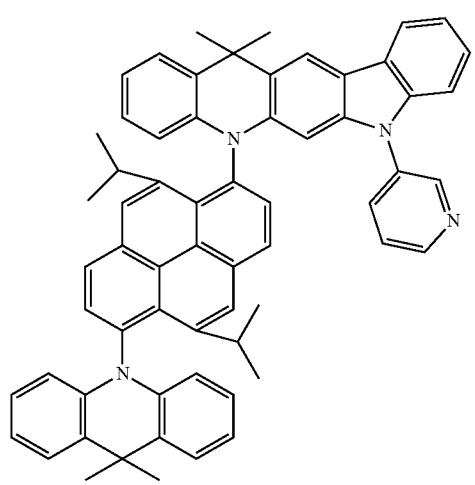
Compound 188
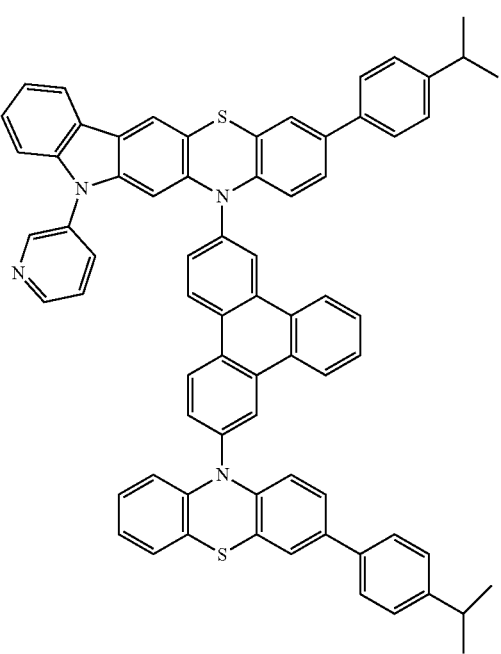

-continued
Compound 189
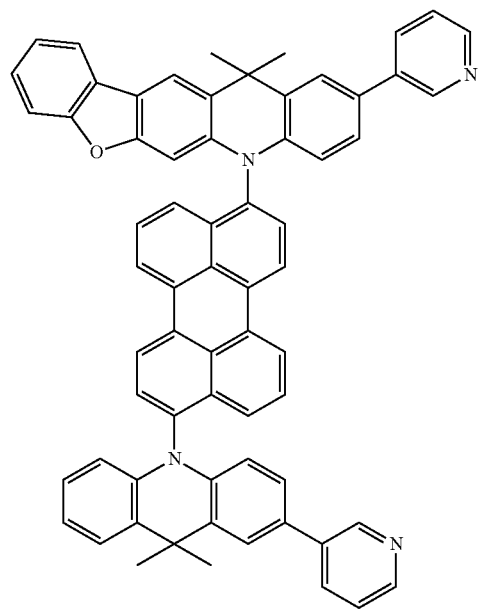
Compound 190
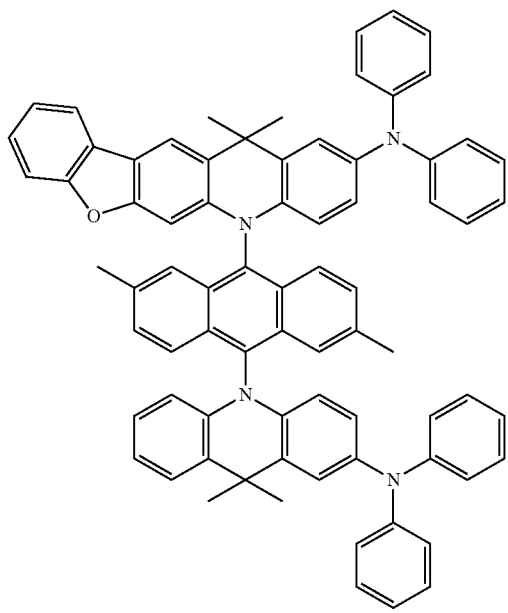
Compound 191
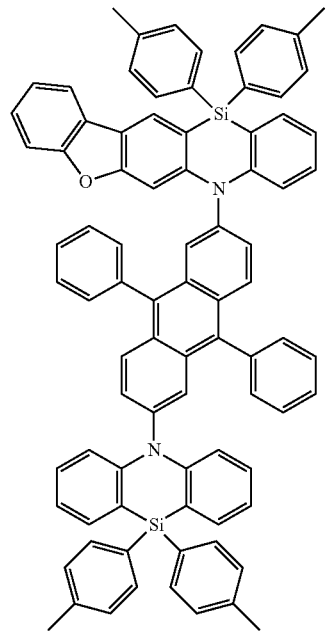
Compound 192
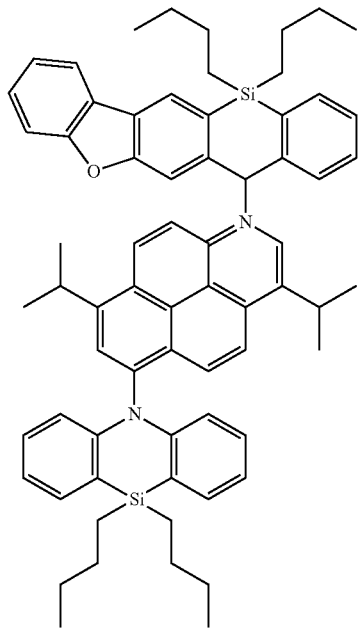

-continued
Compound 193
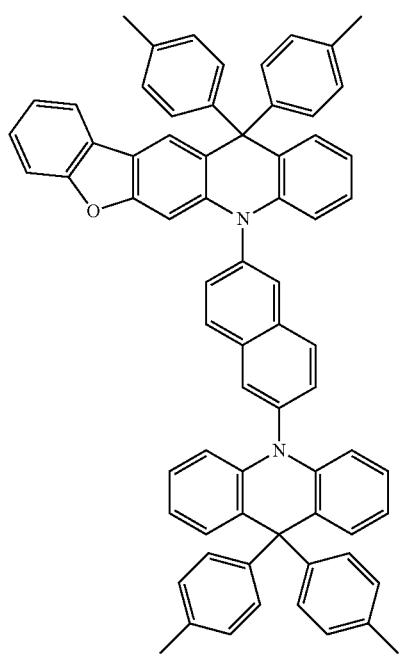
Compound 194
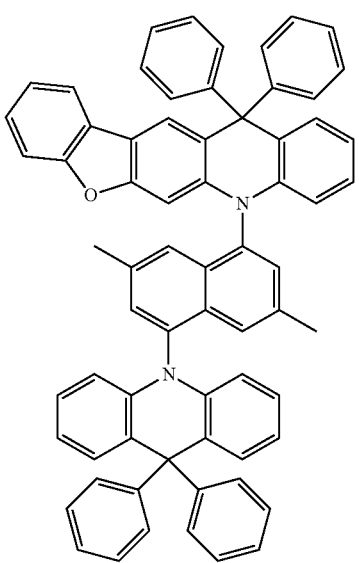
Compound 195
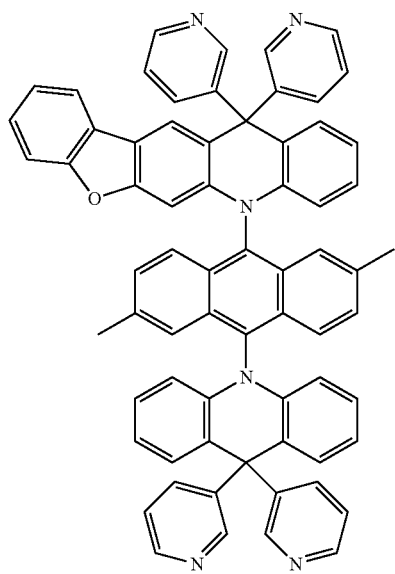
Compound 196
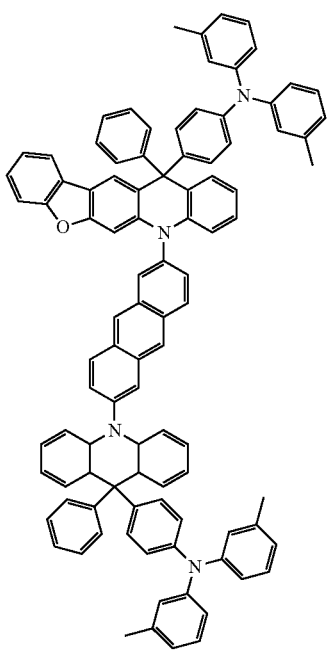

Compound 197
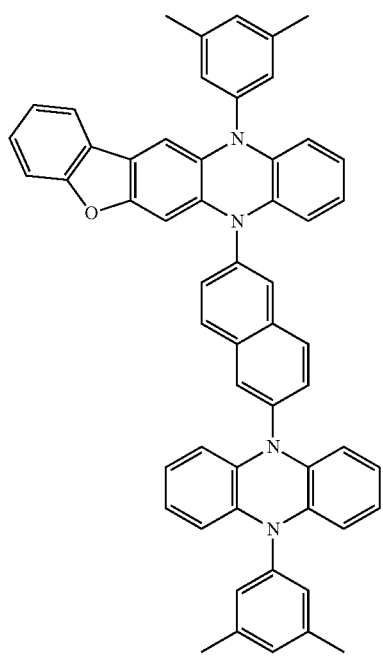
Compound 198
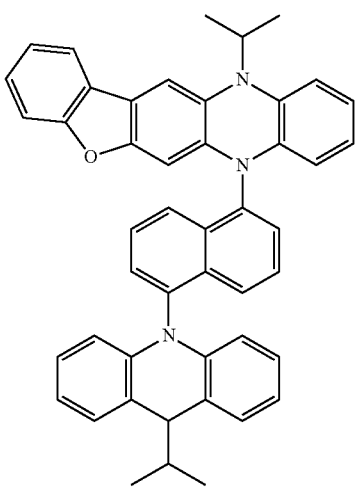
Compound 199
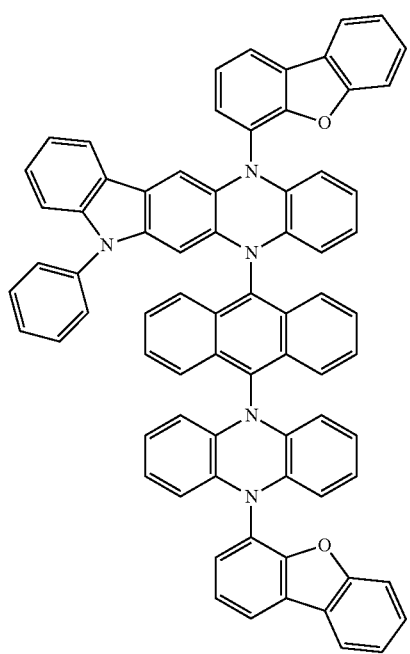
Compound 200
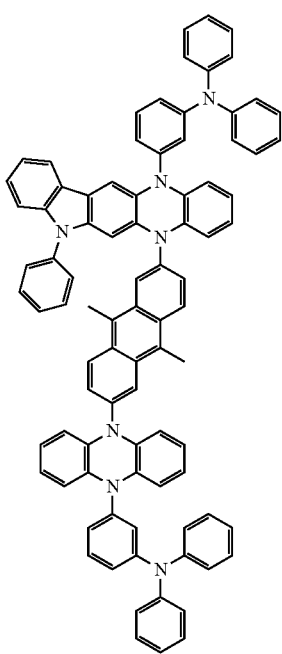

Compound 201
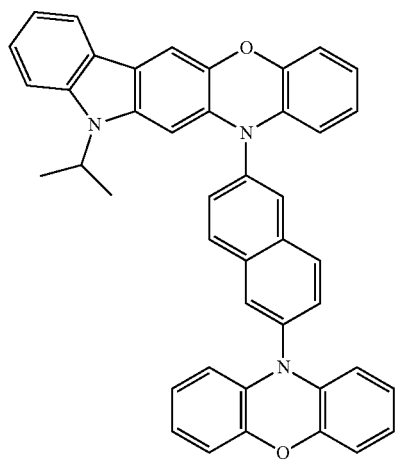
Compound 202
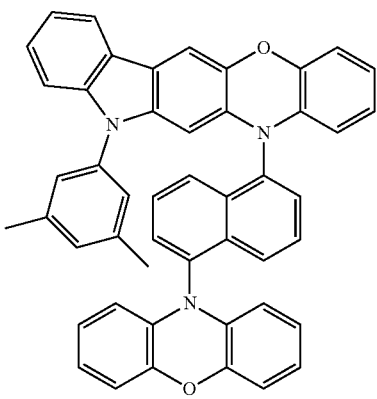
Compound 203
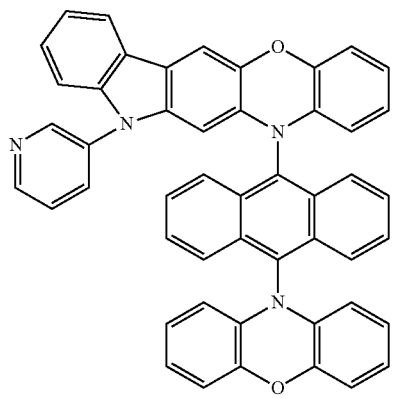
Compound 204
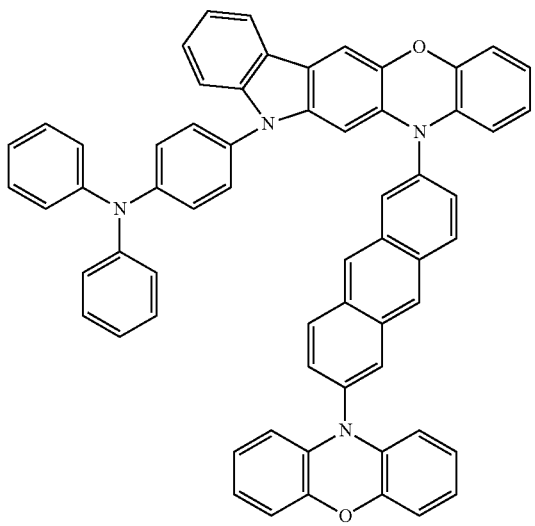
Compound 205
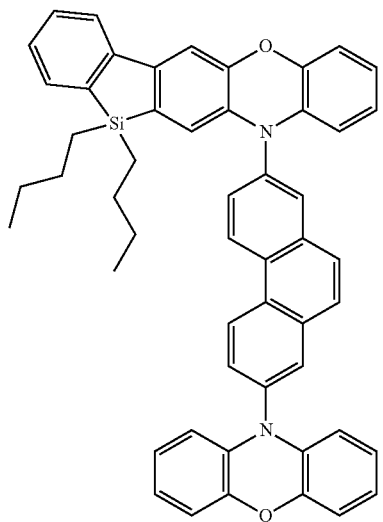
Compound 206
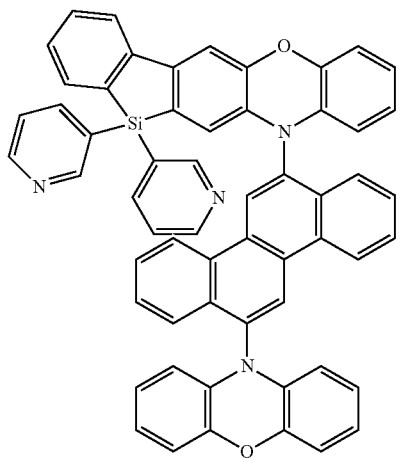

-continued
Compound 207
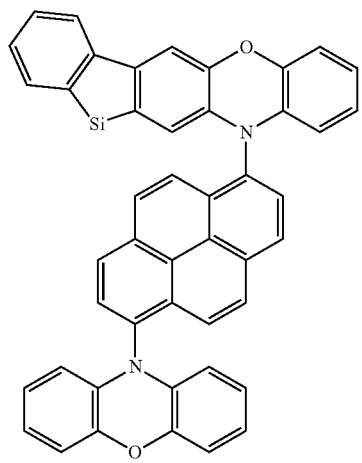
Compound 208
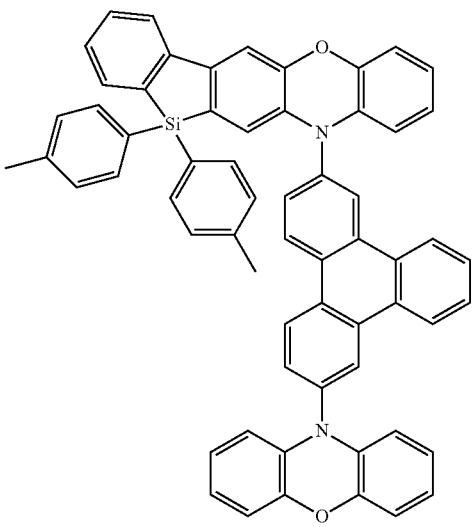
Compound 209
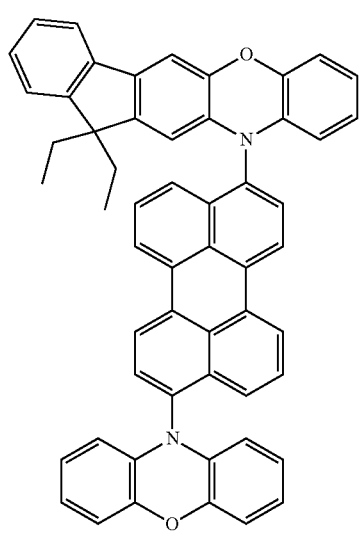
Compound 210
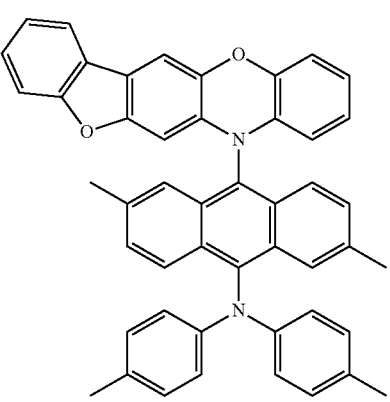
Compound 211
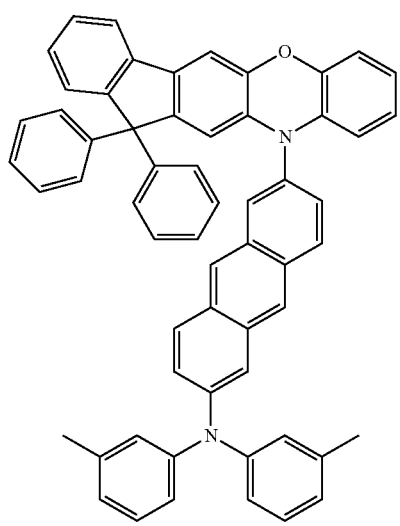
Compound 212
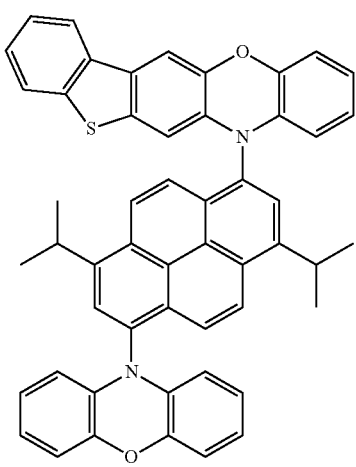

-continued
Compound 213
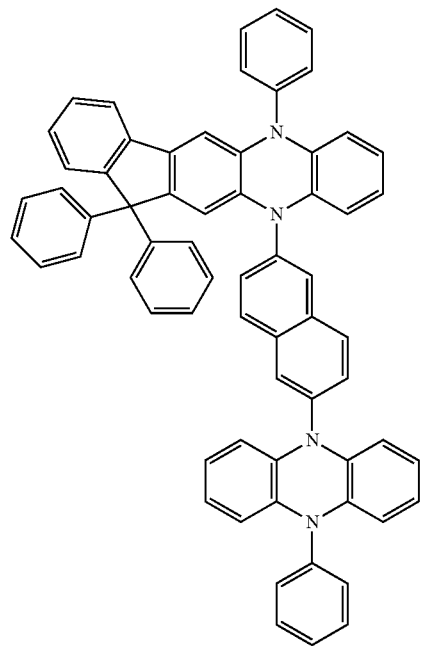
Compound 214
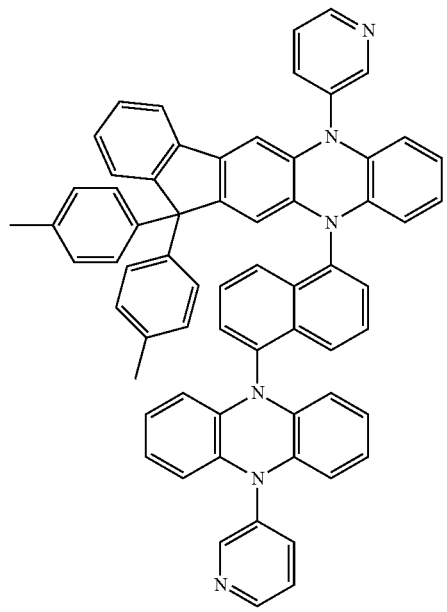
Compound 215
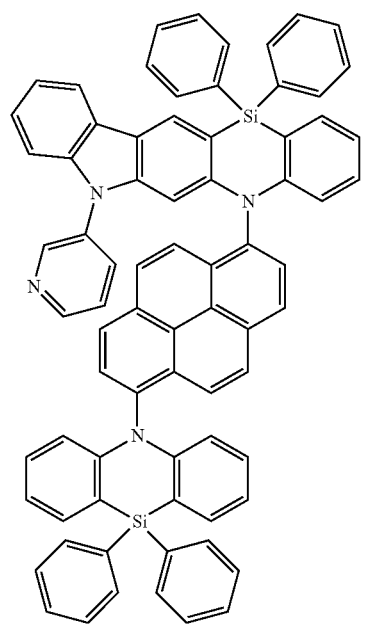
Compound 216
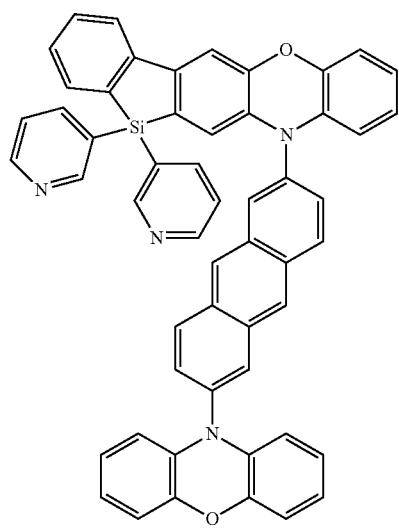

-continued
Compound 217
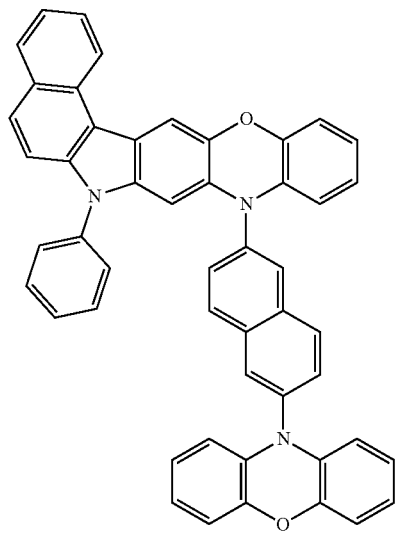
Compound 218
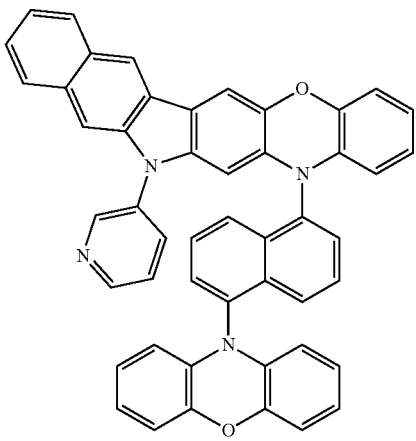
Compound 219
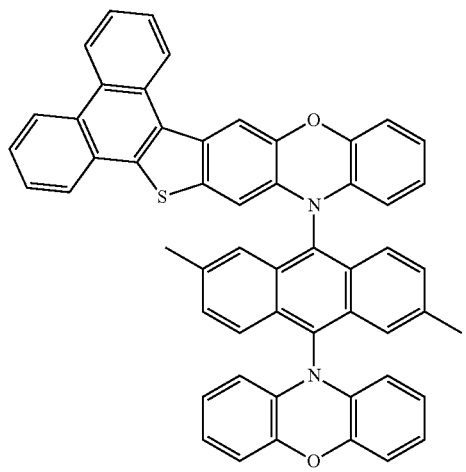
Compound 220
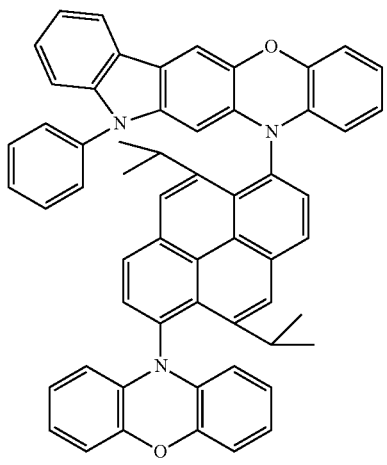
Compound 221
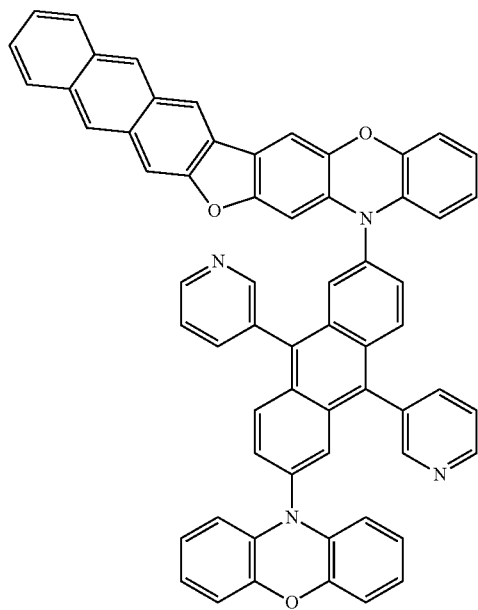
Compound 222
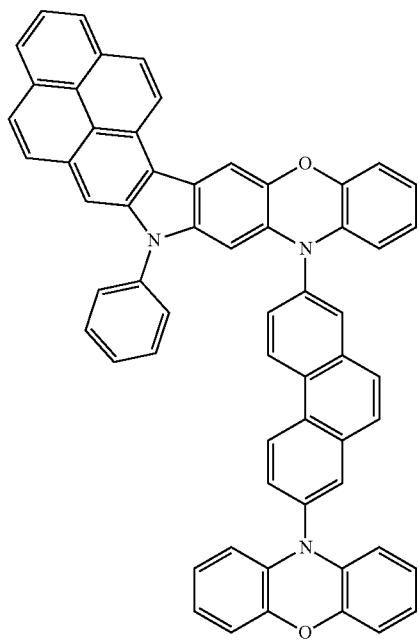

-continued
Compound 223
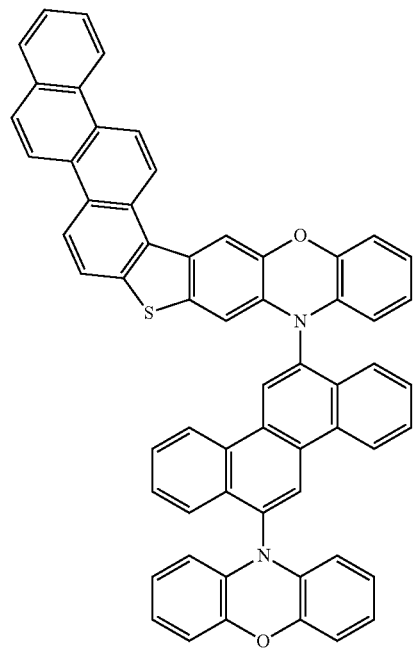
Compound 224
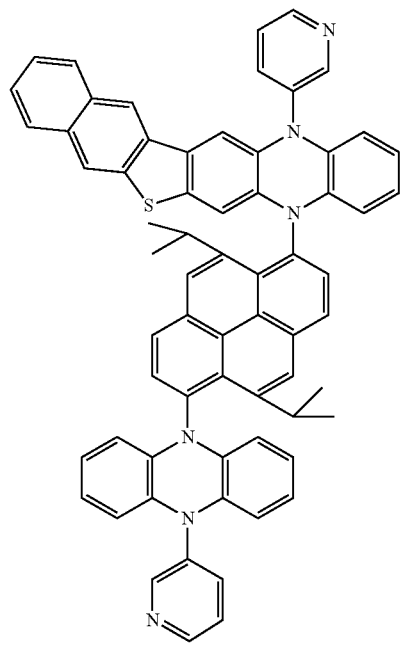
Compound 225
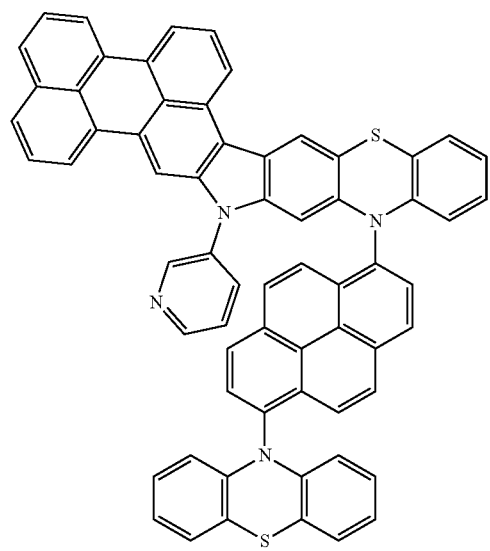
Compound 226
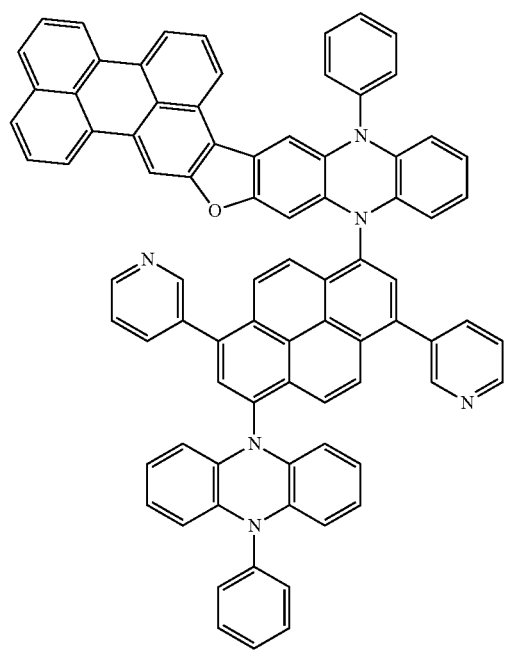

Compound 227
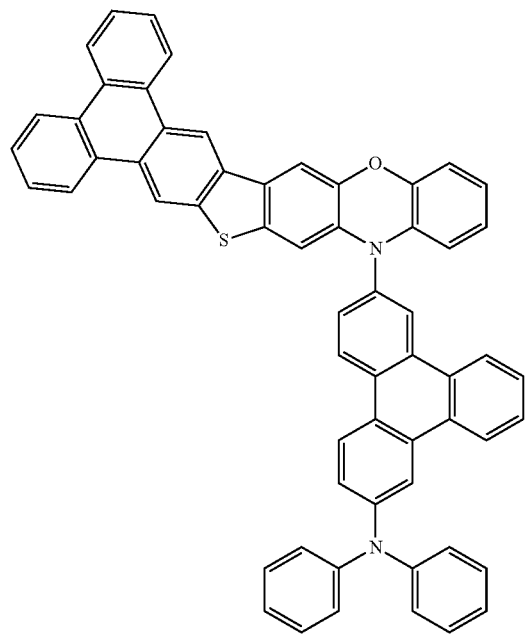
Compound 228
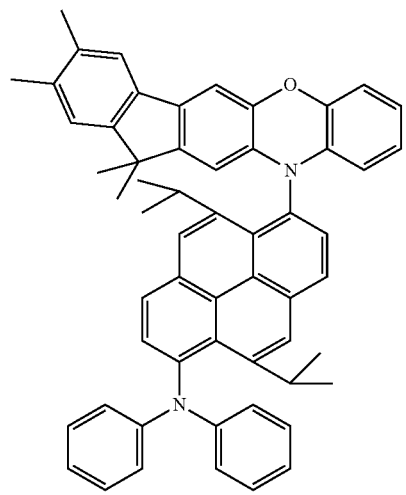
Compound 229
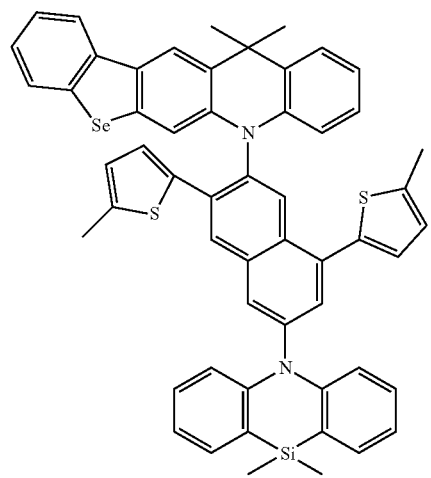
Compound 230
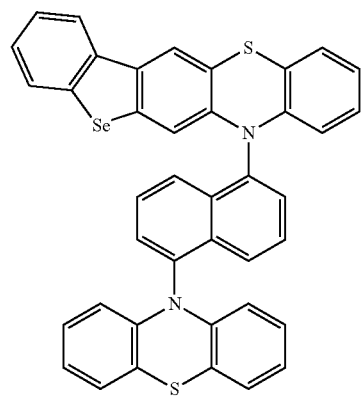

-continued
Compound 231
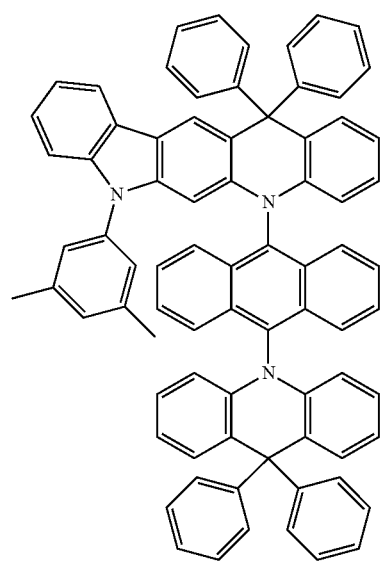
Compound 232
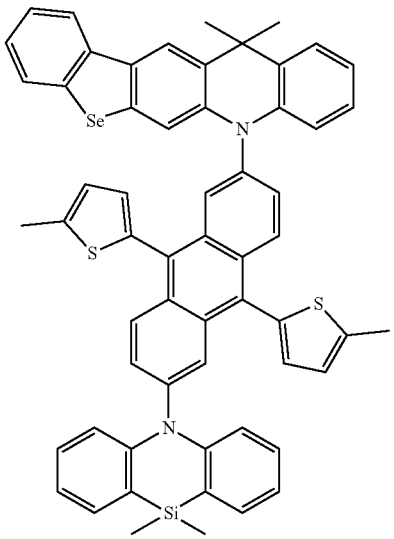
Compound 233
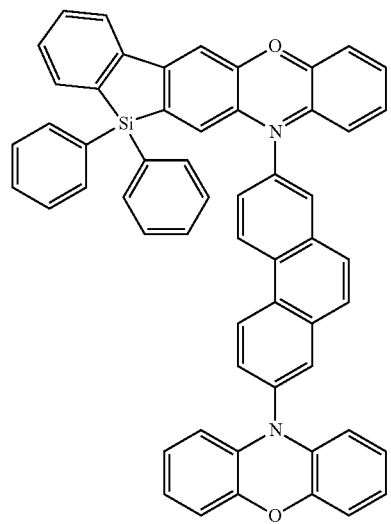
Compound 234
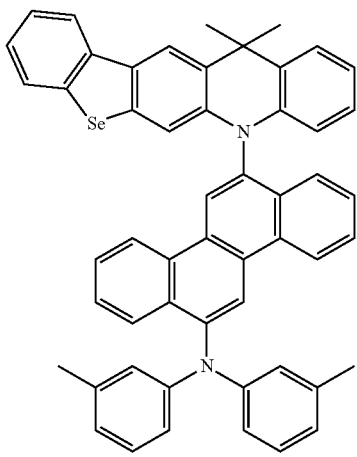

-continued
Compound 235
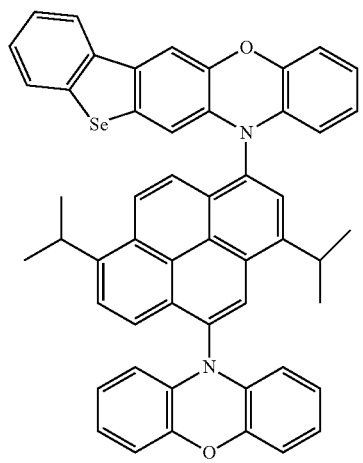
Compound 236
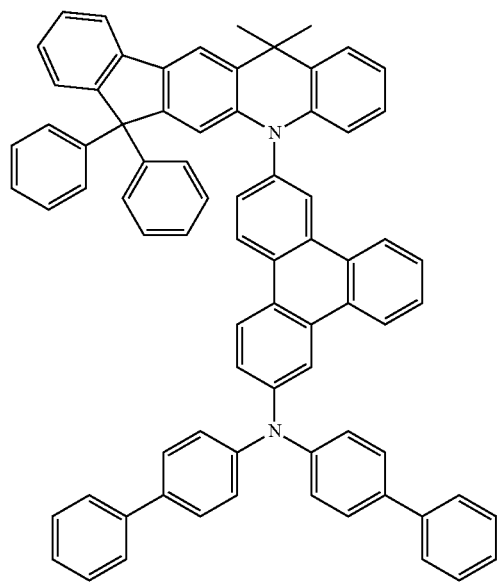
Compound 237
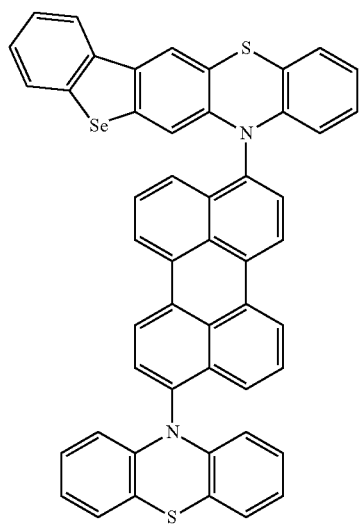
Compound 238
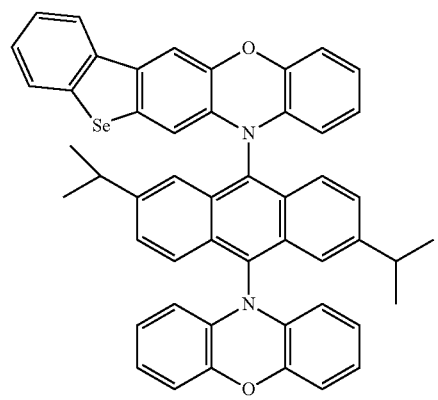

-continued
Compound 239
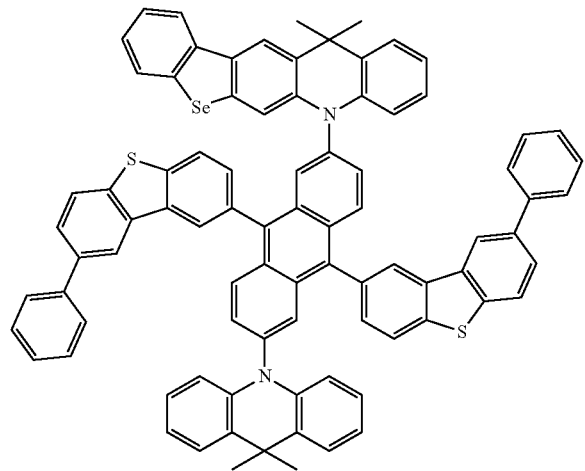
Compound 240
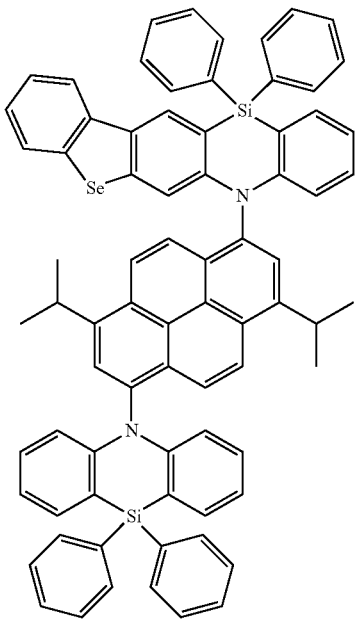
Compound 241
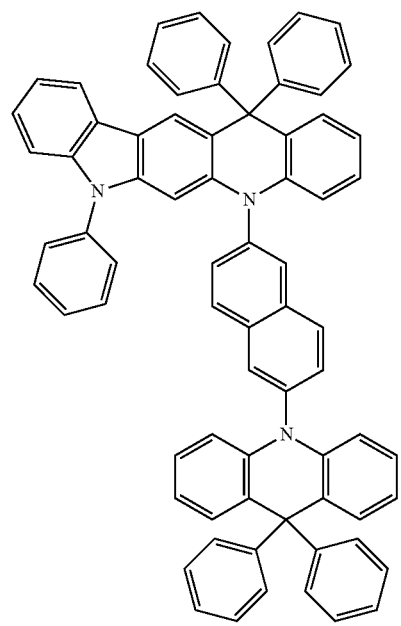
Compound 242

-continued
Compound 243
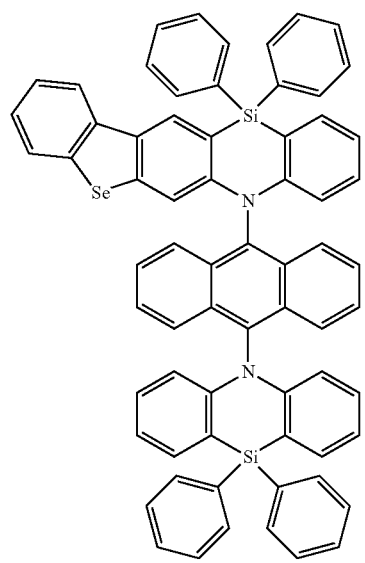
Compound 244
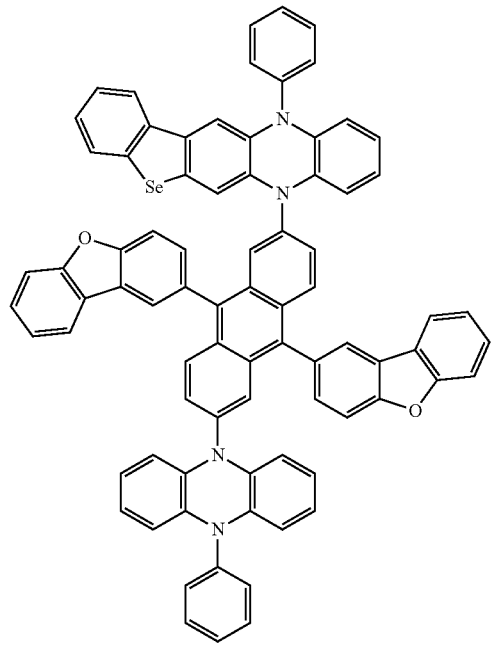
Compound 245
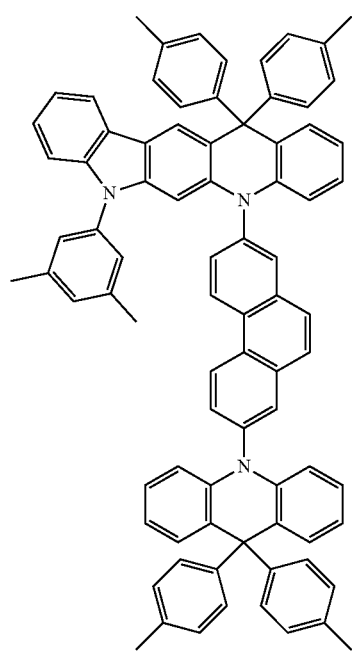
Compound 246
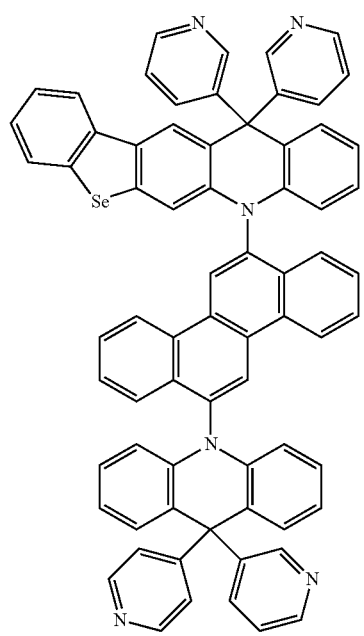

113 114
-continued
Compound 247
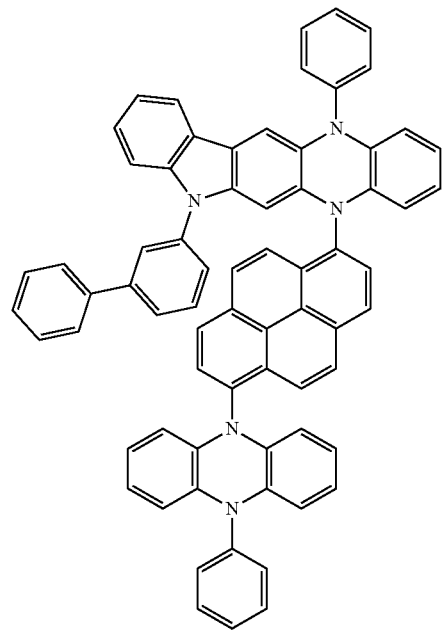
Compound 248
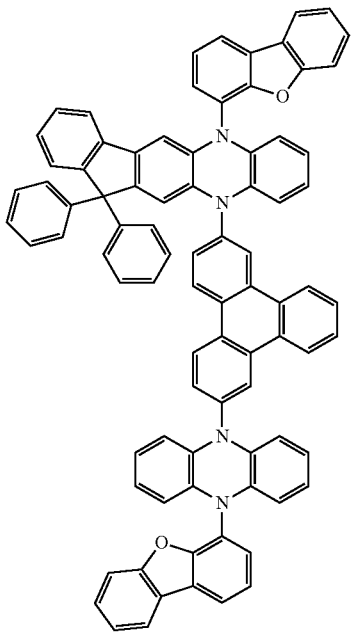
Compound 249
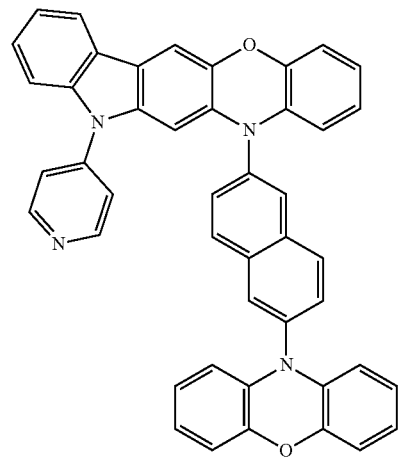
Compound 250
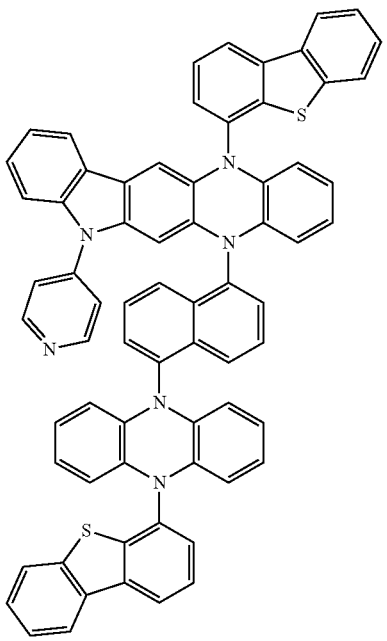

-continued
Compound 251
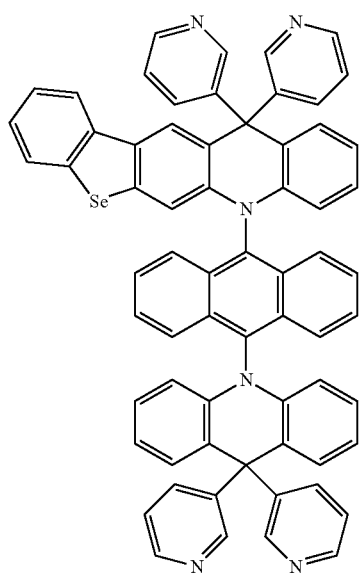
Compound 252
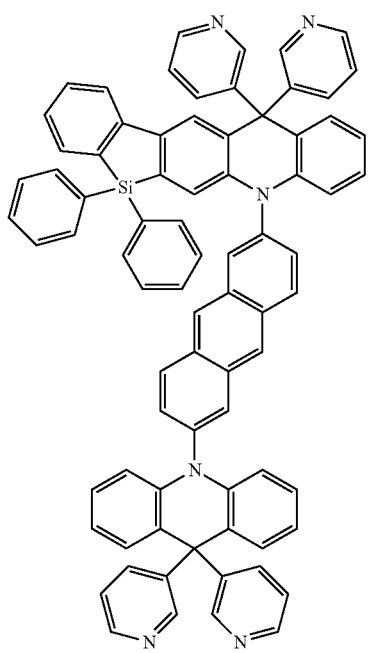
Compound 253
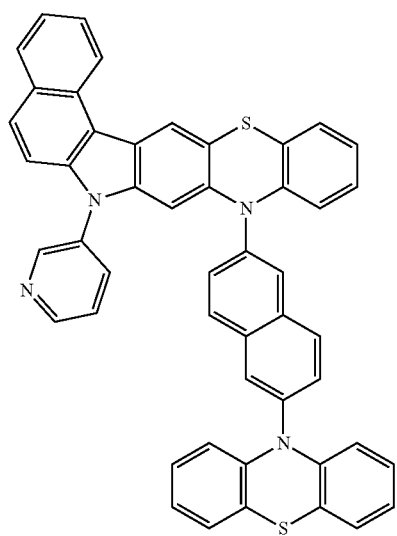
Compound 254
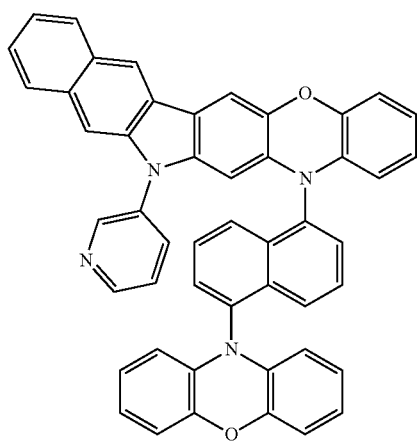

-continued
Compound 255
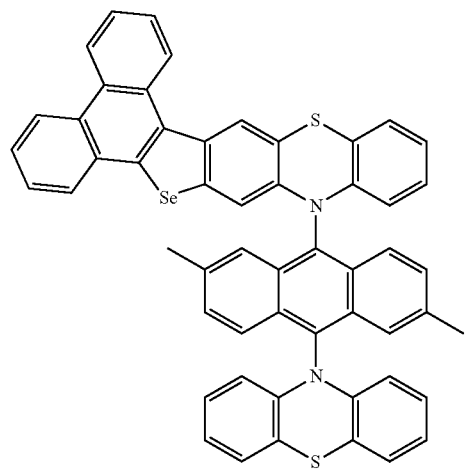
Compound 256
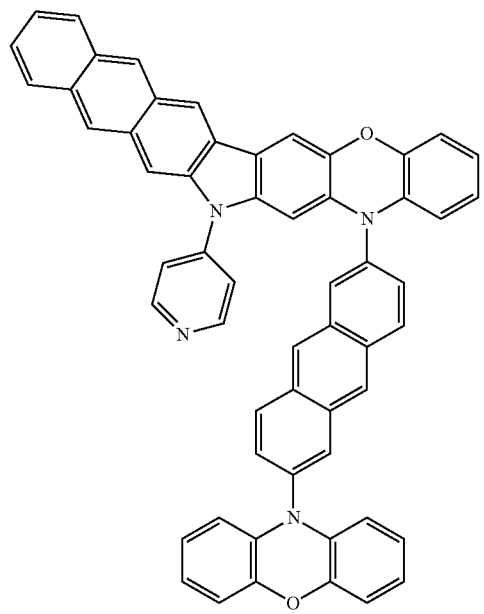
Compound 257
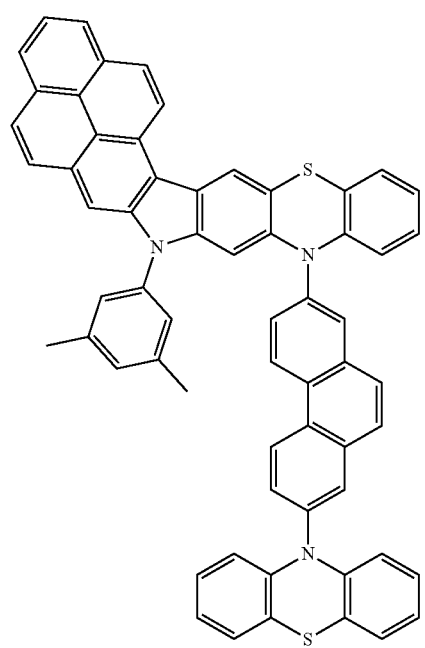
Compound 258
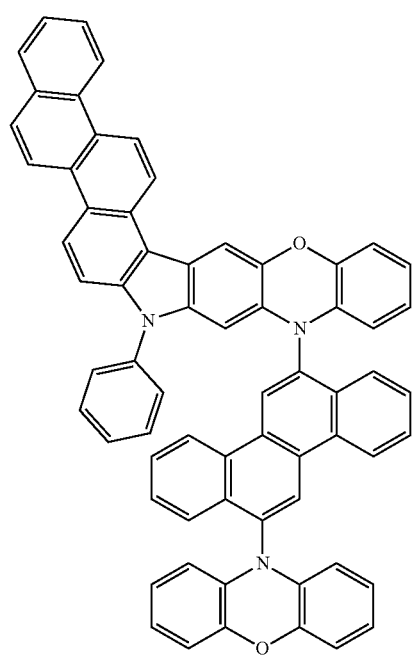

-continued
Compound 259
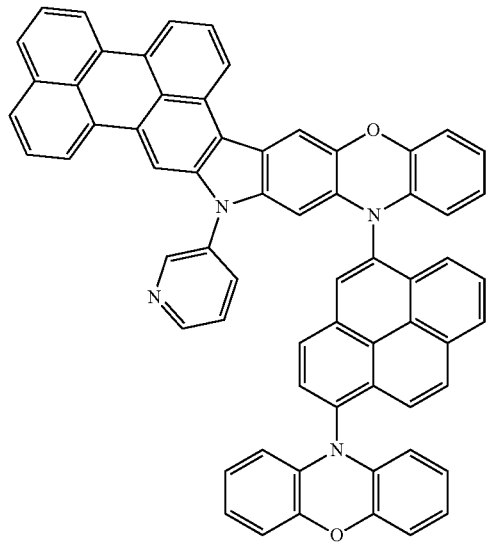
Compound 260
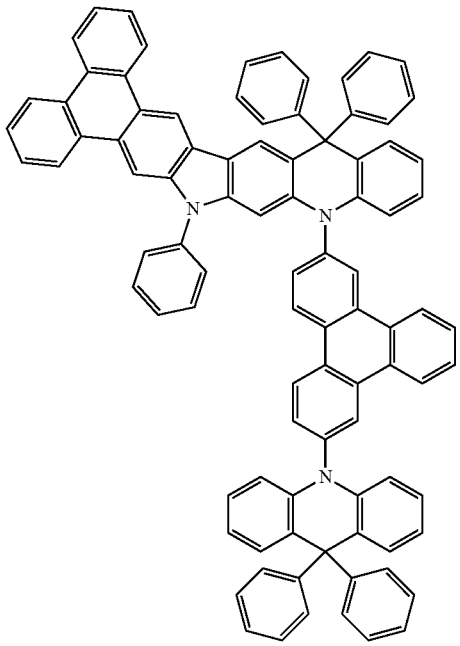
Compound 261
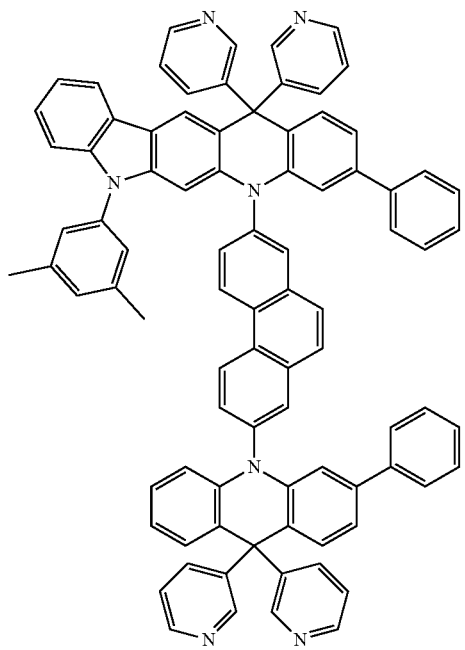
Compound 262
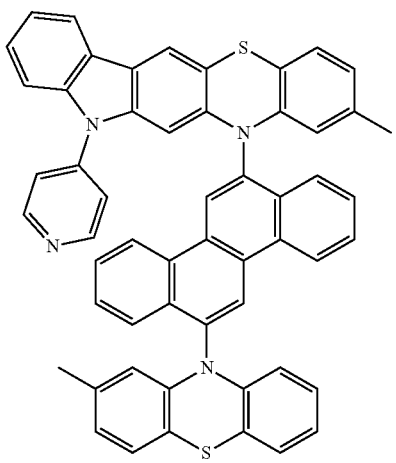

-continued
Compound 263
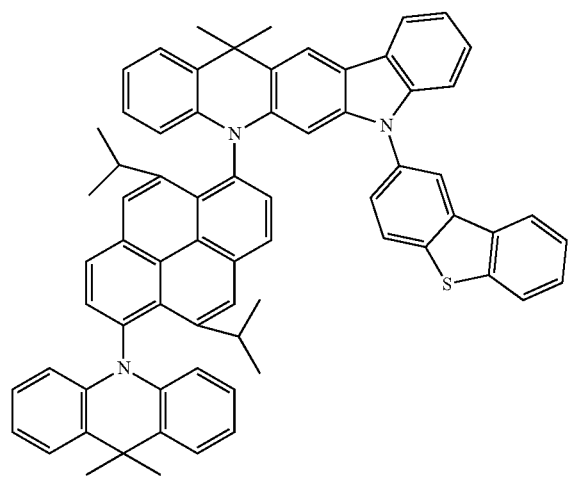
Compound 264
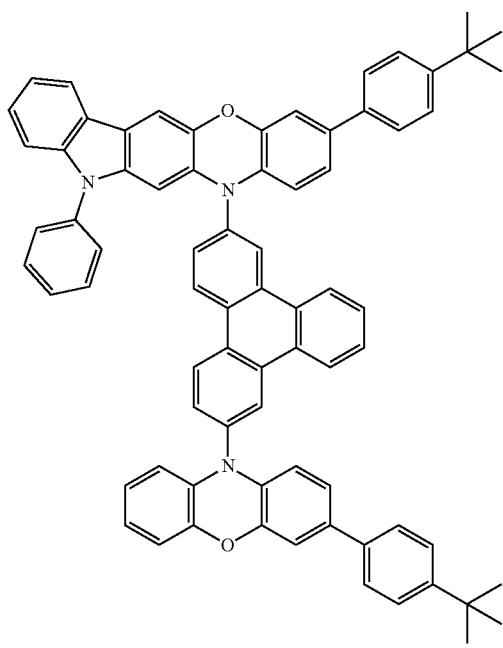
Compound 265
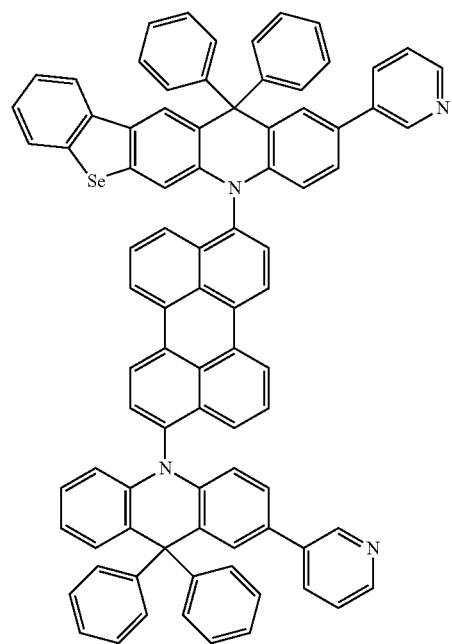
Compound 266
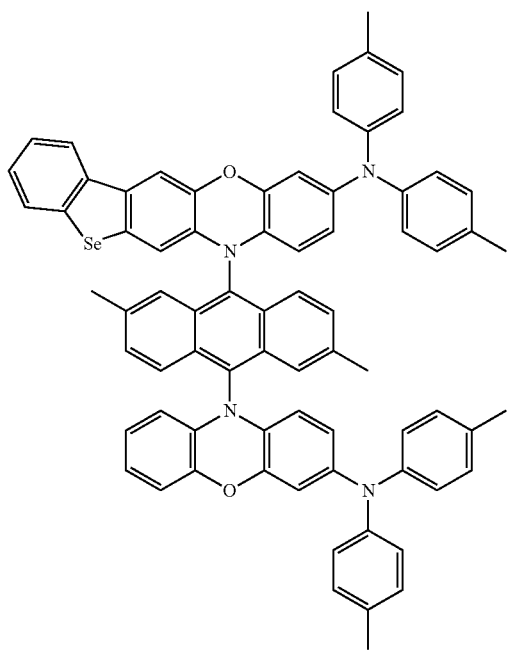

-continued
Compound 267
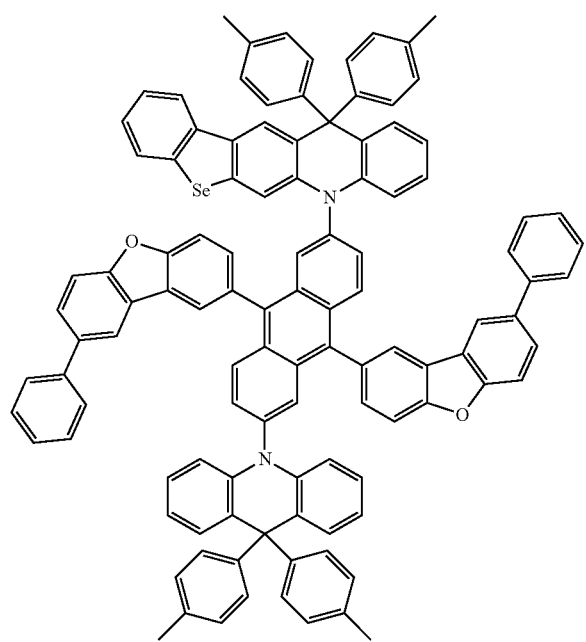
Compound 268
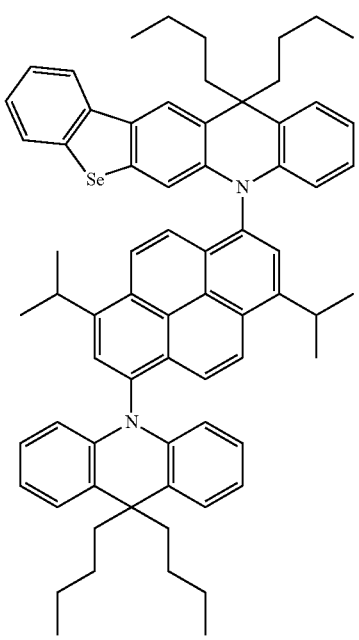
Compound 269
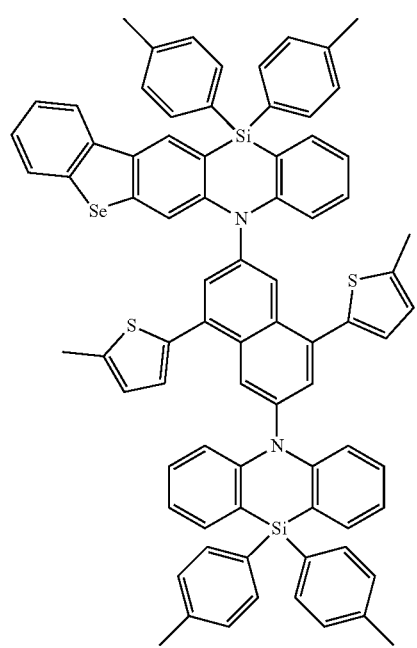
Compound 270
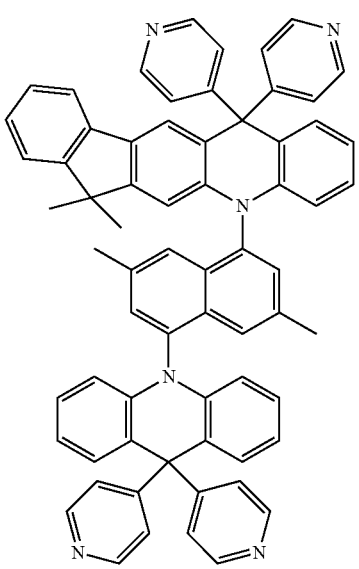

-continued
Compound 271
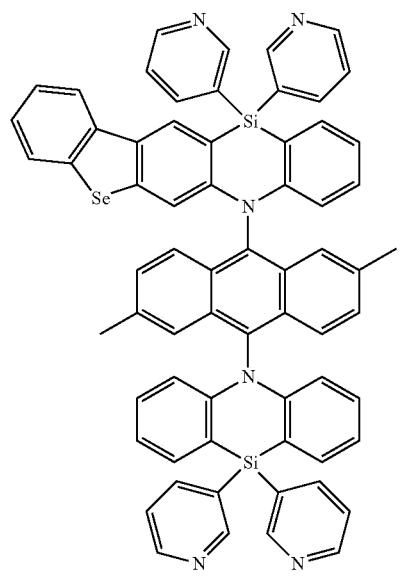
Compound 272
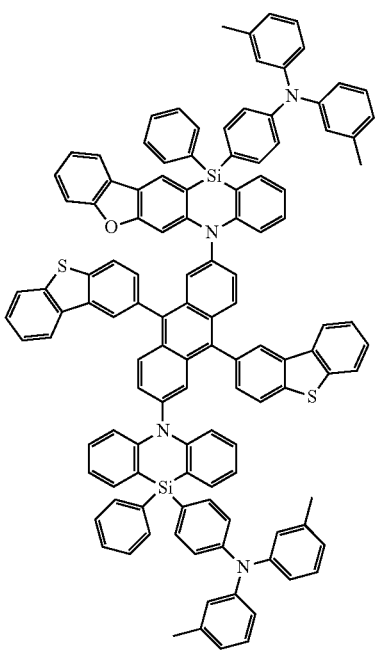
Compound 273
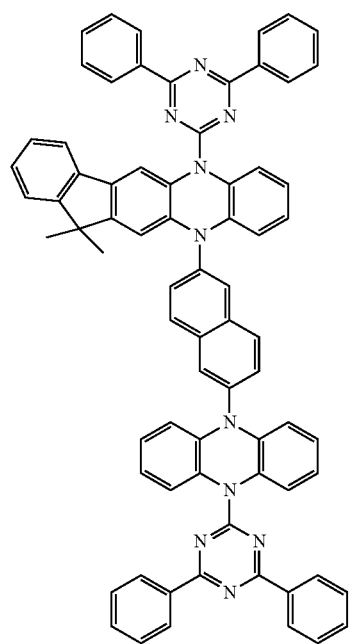
Compound 274
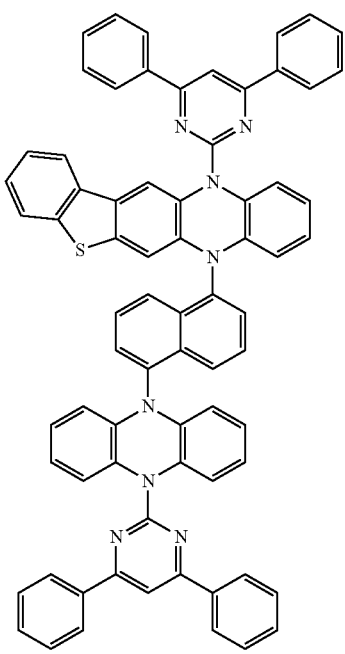

-continued
Compound 275
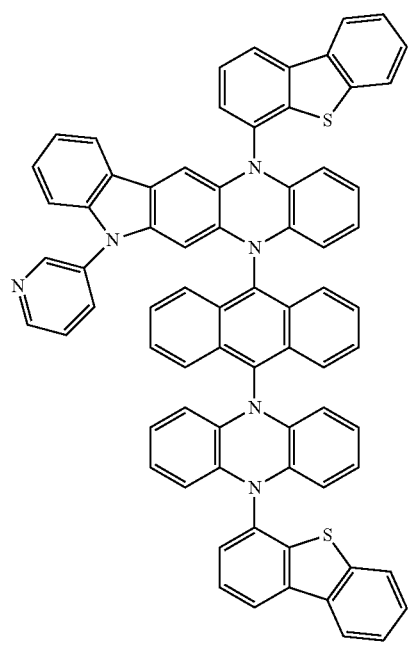
Compound 276
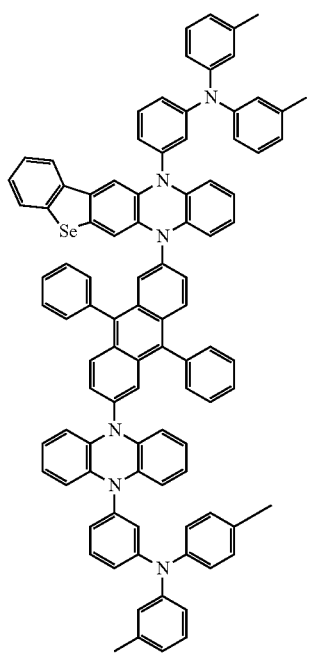
Compound 277
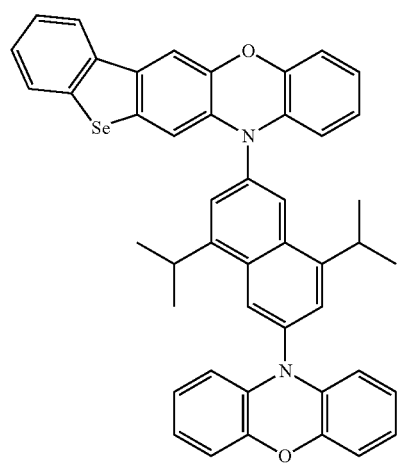
Compound 278
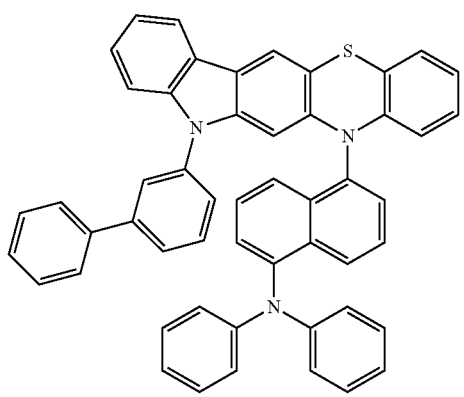

-continued
Compound 279
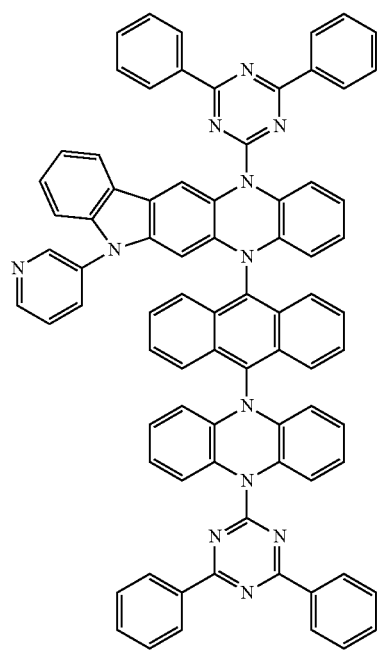
Compound 280
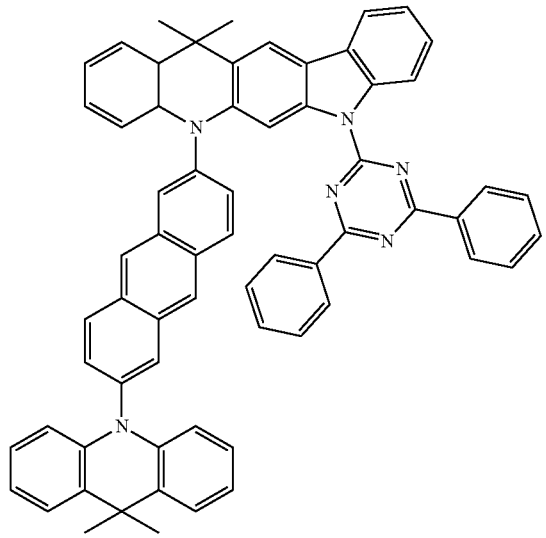
Compound 281
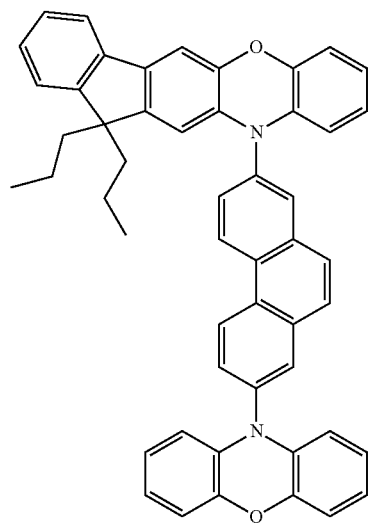
Compound 282
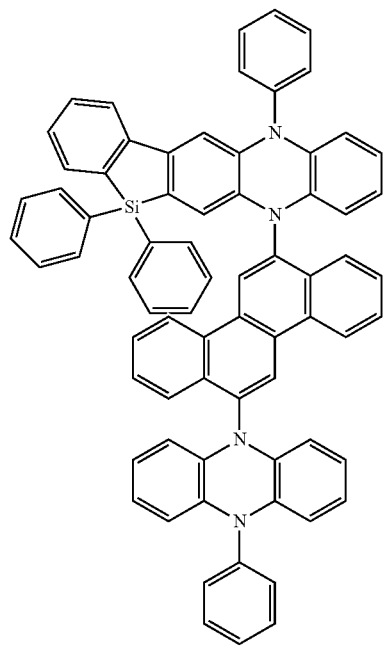

-continued
Compound 283
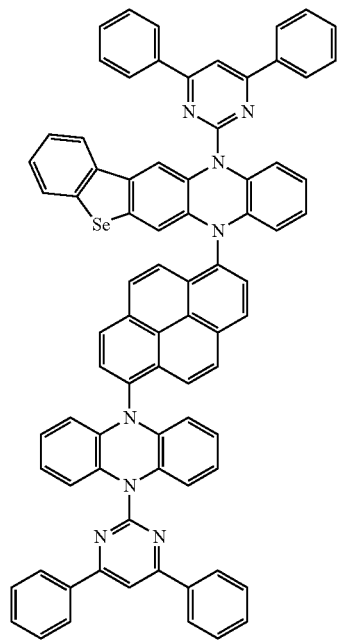
Compound 284
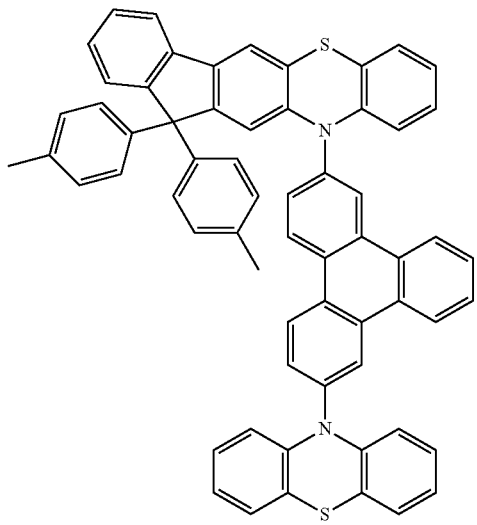
Compound 285
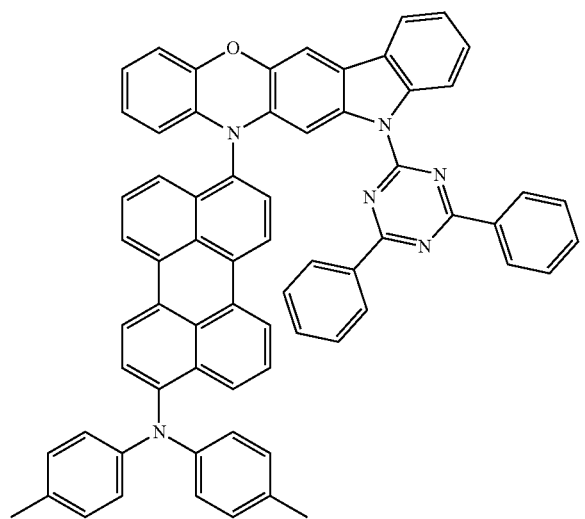
Compound 286
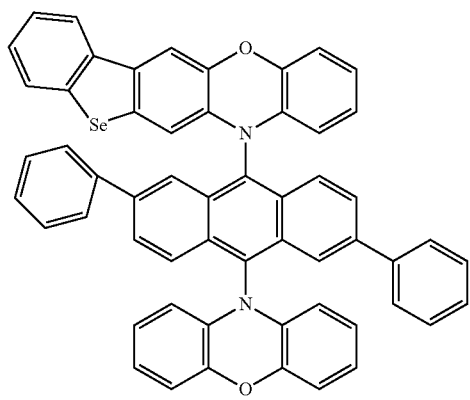

-continued
Compound 287
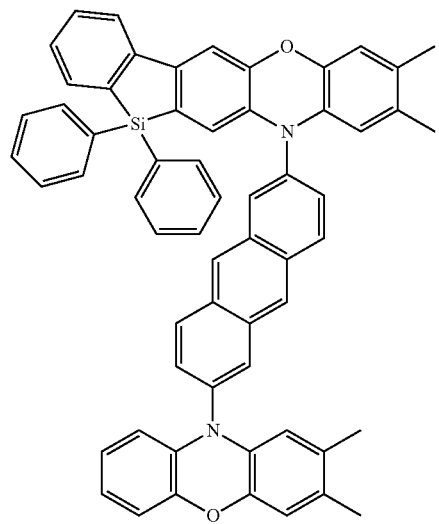
Compound 288
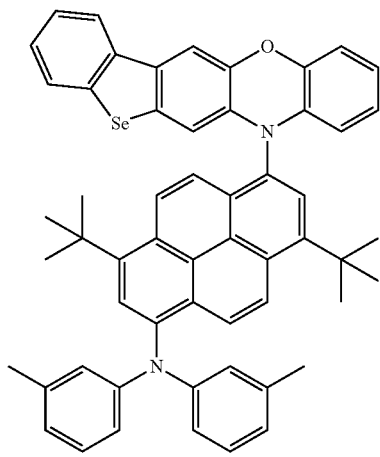
Compound 289
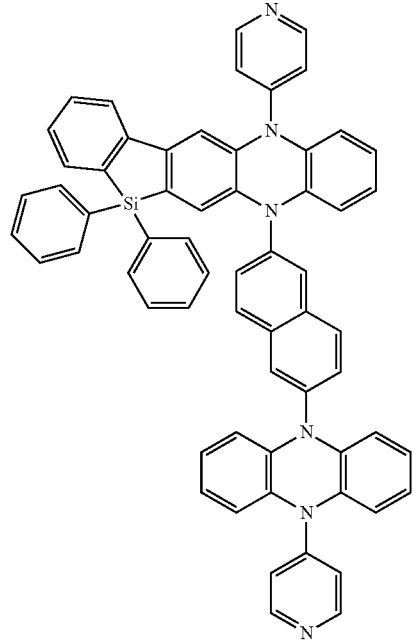
Compound 290
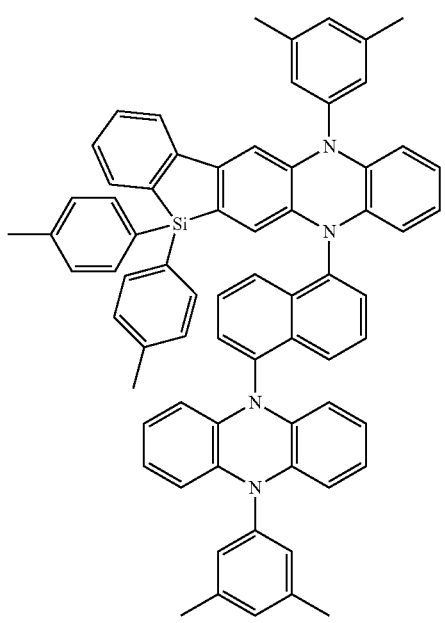

-continued
Compound 291
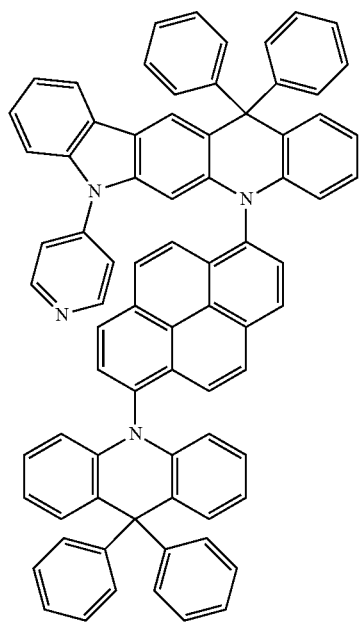
Compound 292
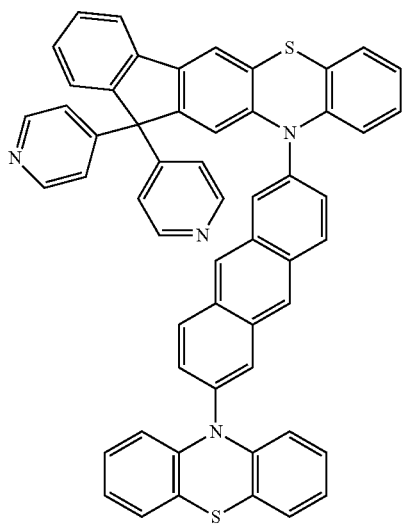
Compound 293
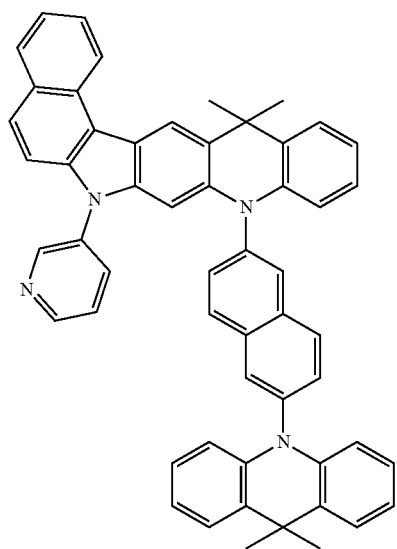
Compound 294
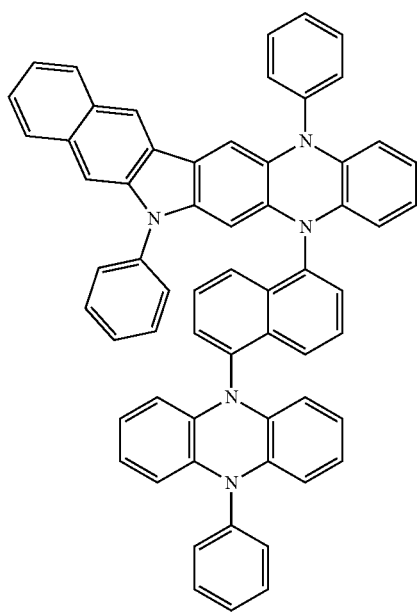

-continued
Compound 295
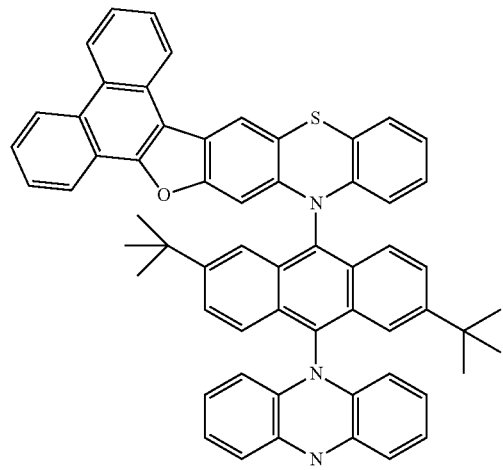
Compound 296
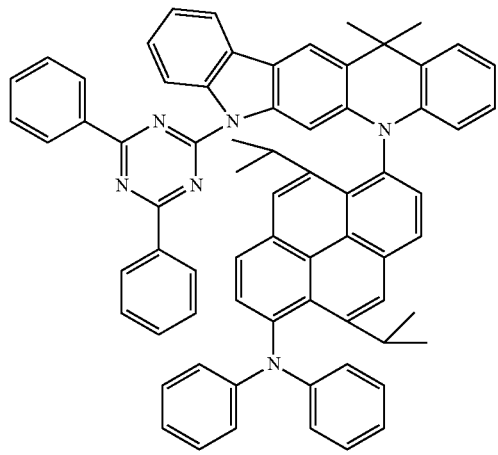
Compound 297
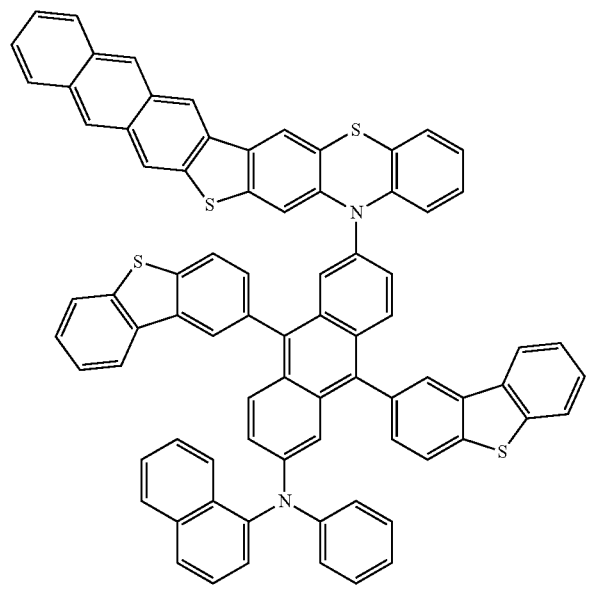
Compound 298
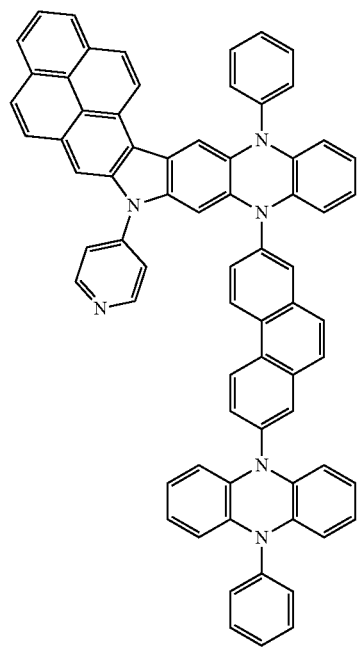

Compound 299
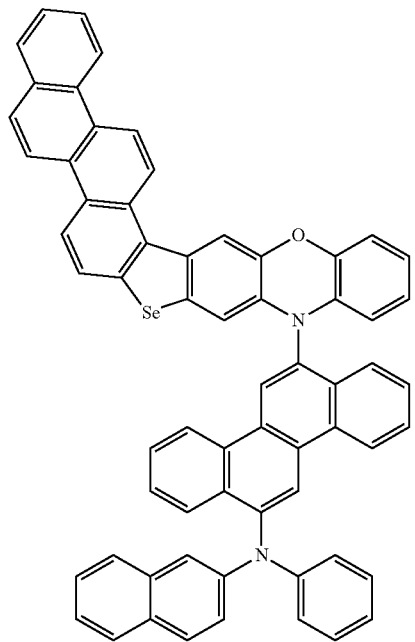
Compound 300
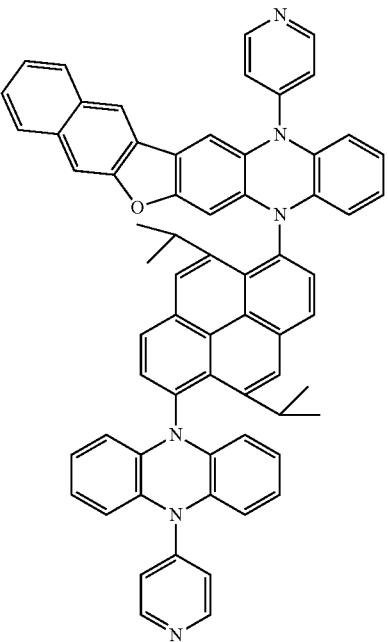
Compound 301
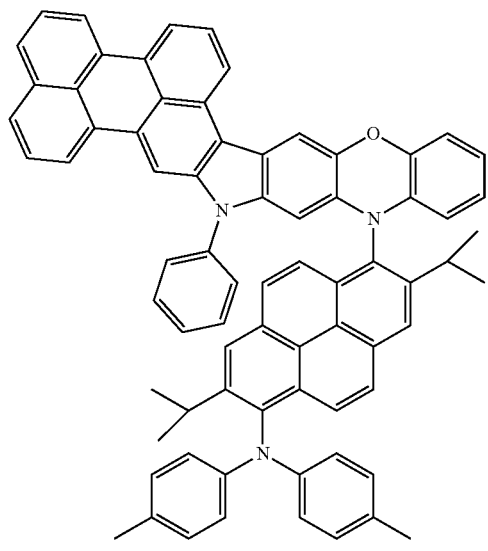
Compound 302
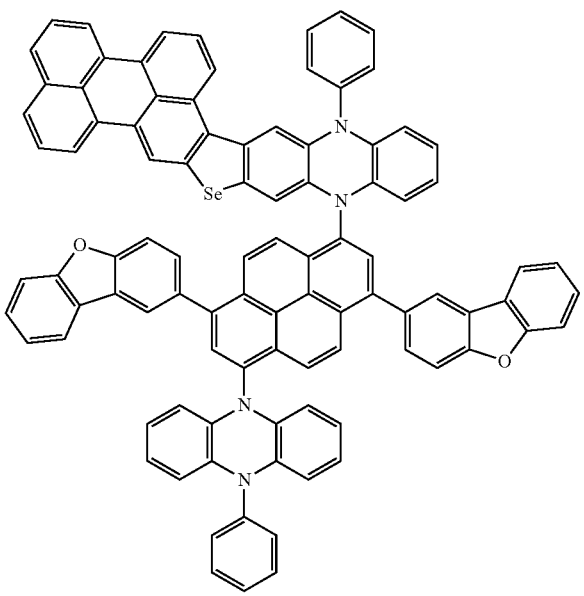

Compound 303
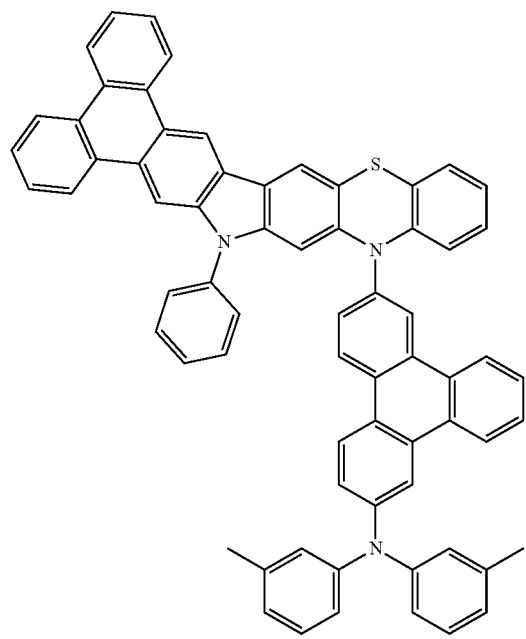
Compound 304
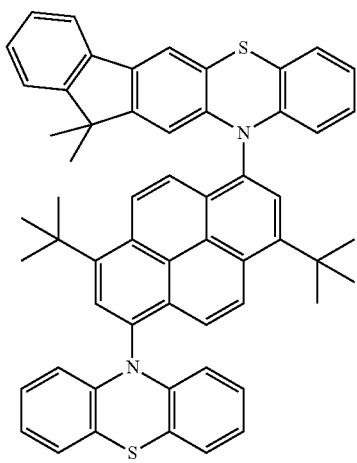
Compound 305
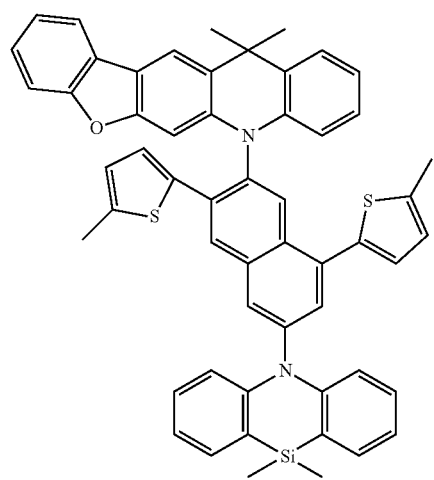
Compound 306
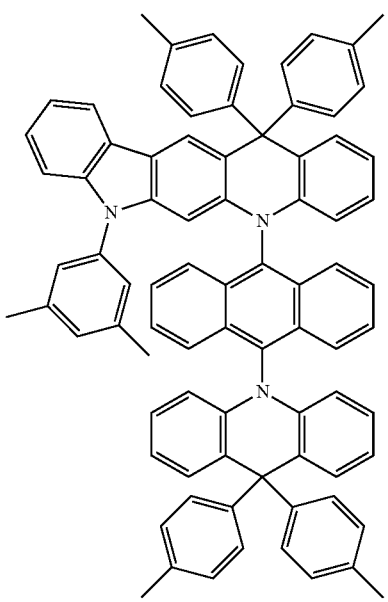

Compound 307
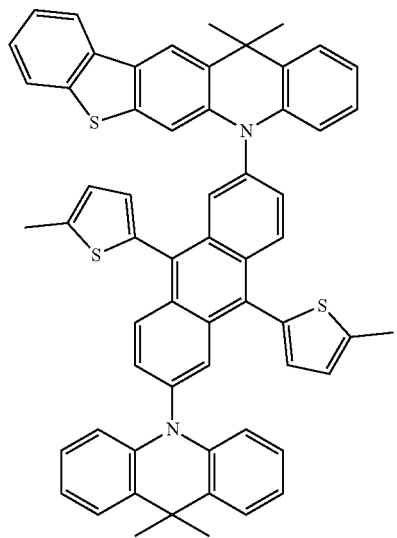
Compound 308
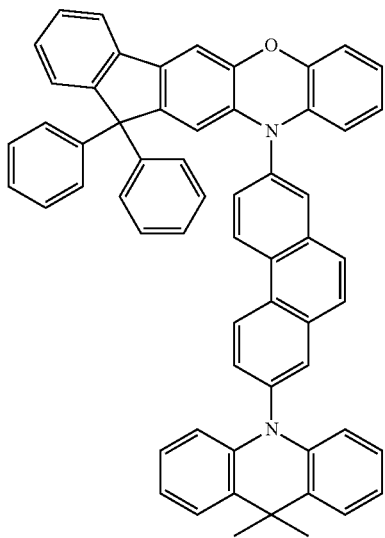
Compound 309
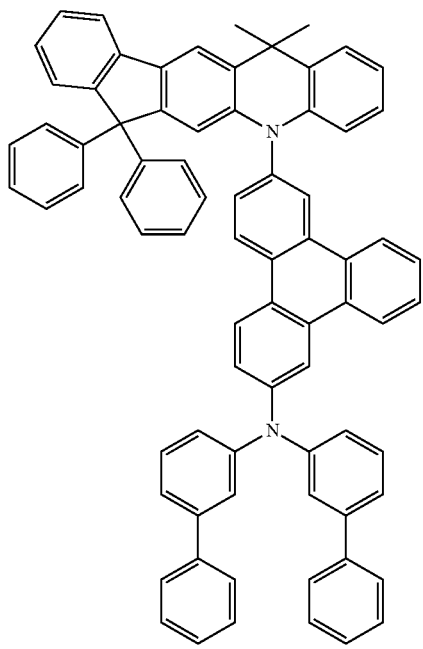
Compound 310
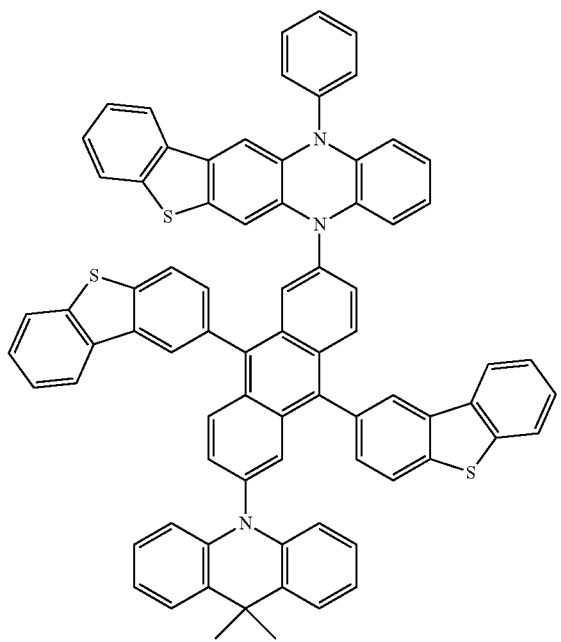

-continued
Compound 311
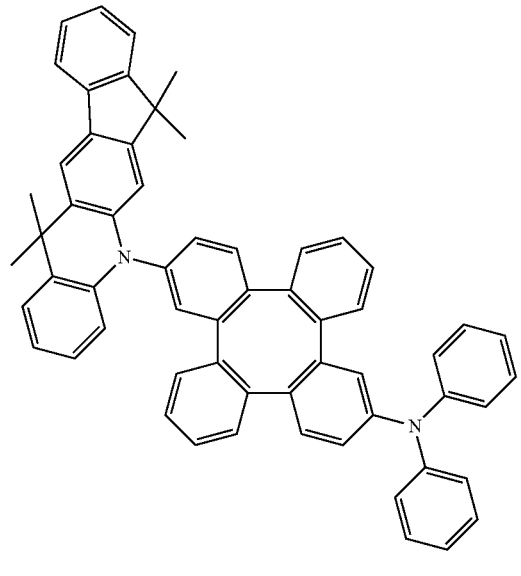
Compound 312
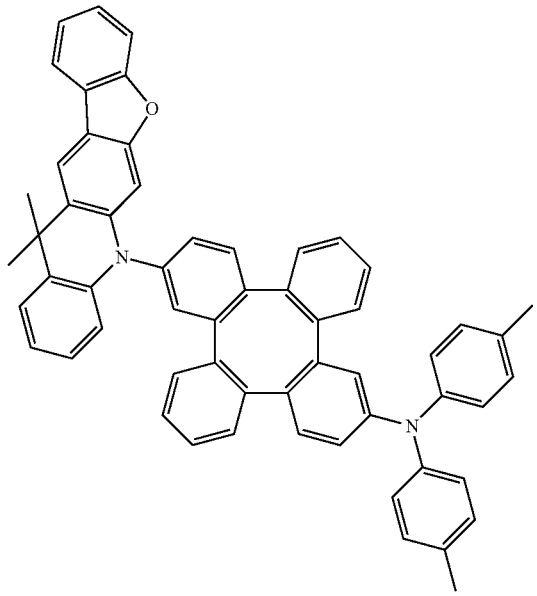
Compound 313
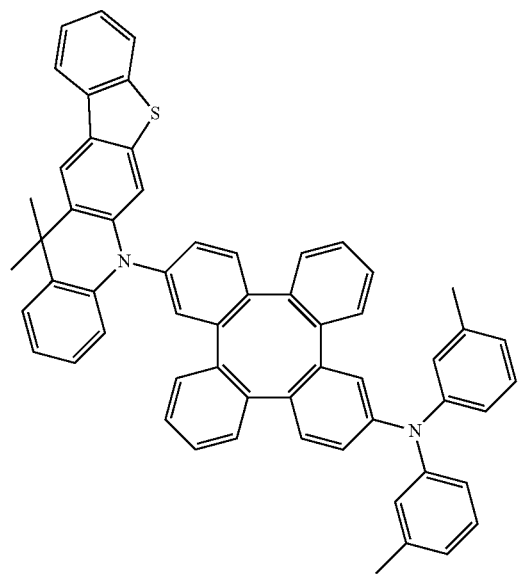
Compound 314
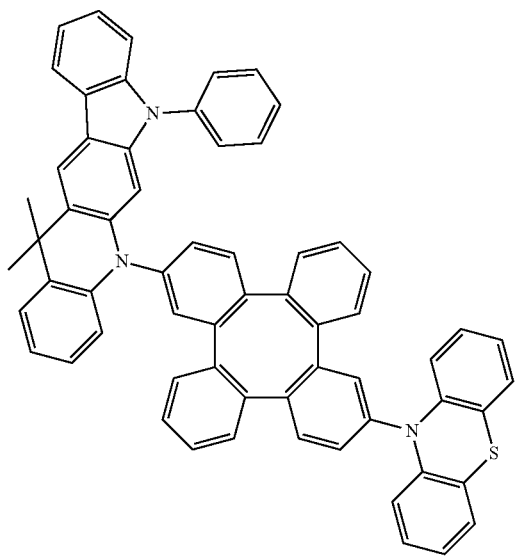

-continued
Compound 315
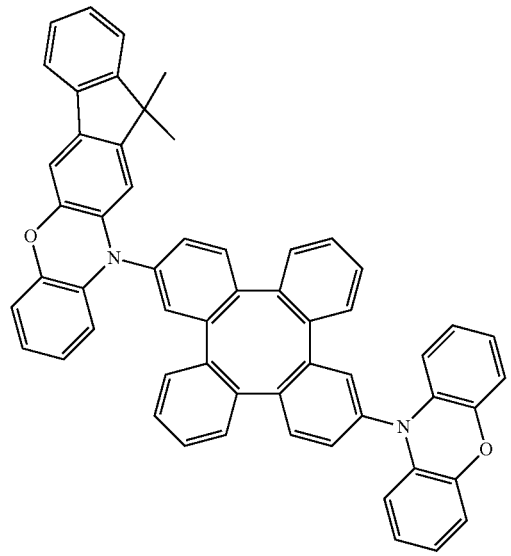
Compound 316
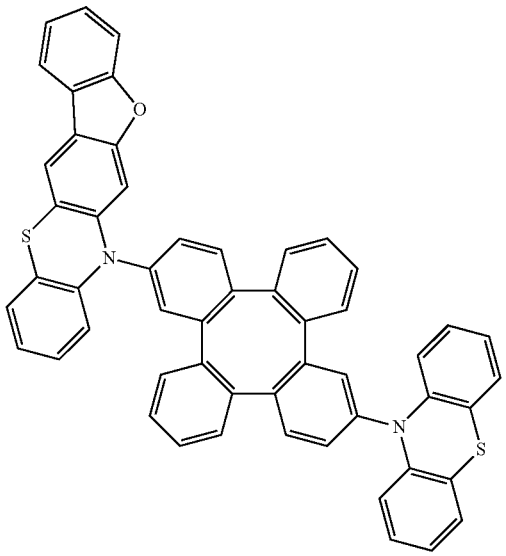
Compound 317
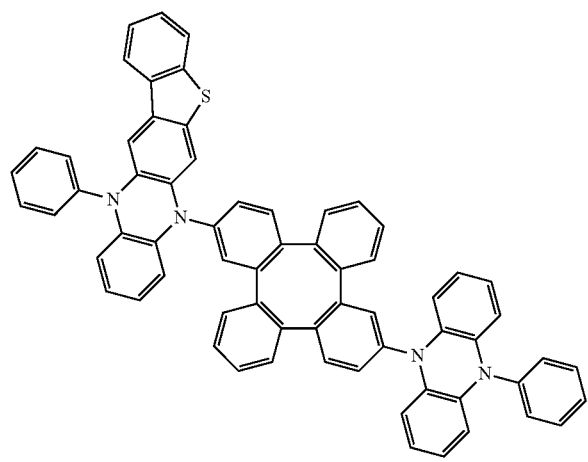
Compound 318
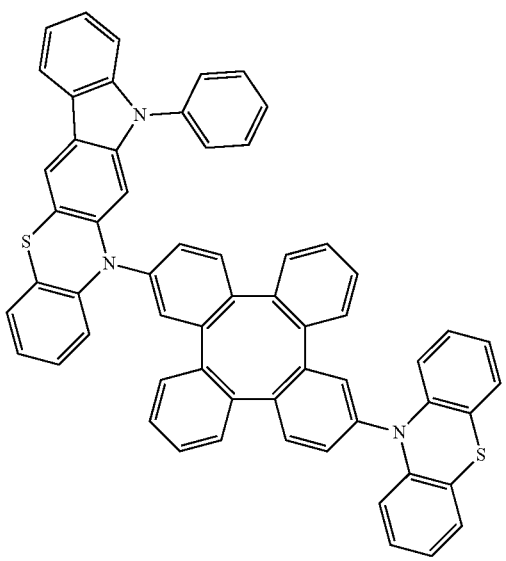

-continued
Compound 319
Compound 320
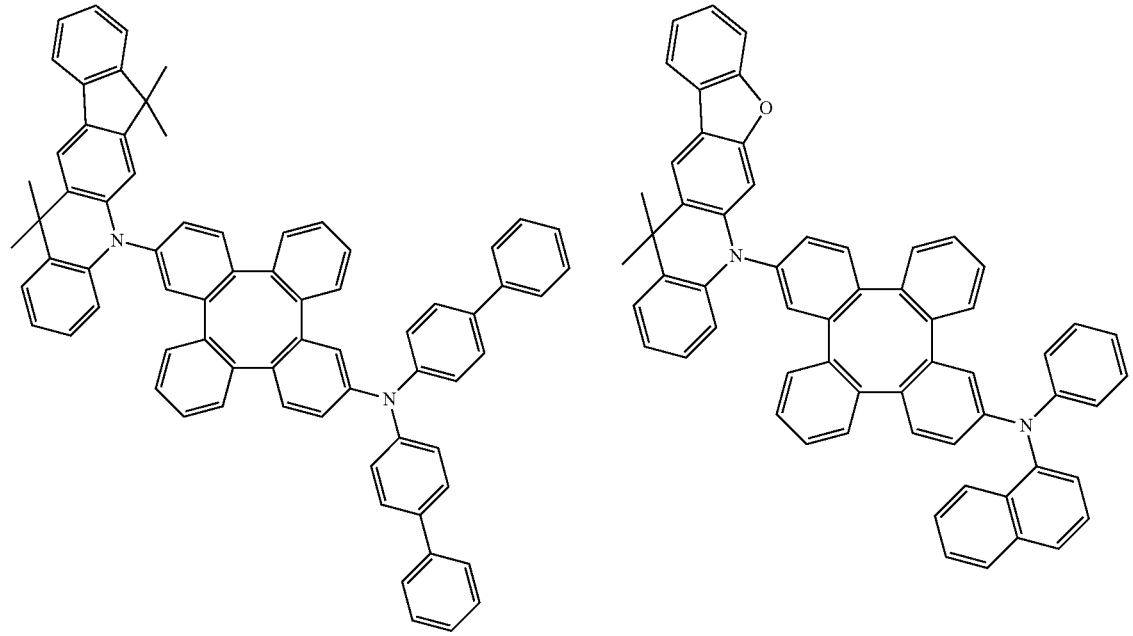
Compound 321
Compound 322
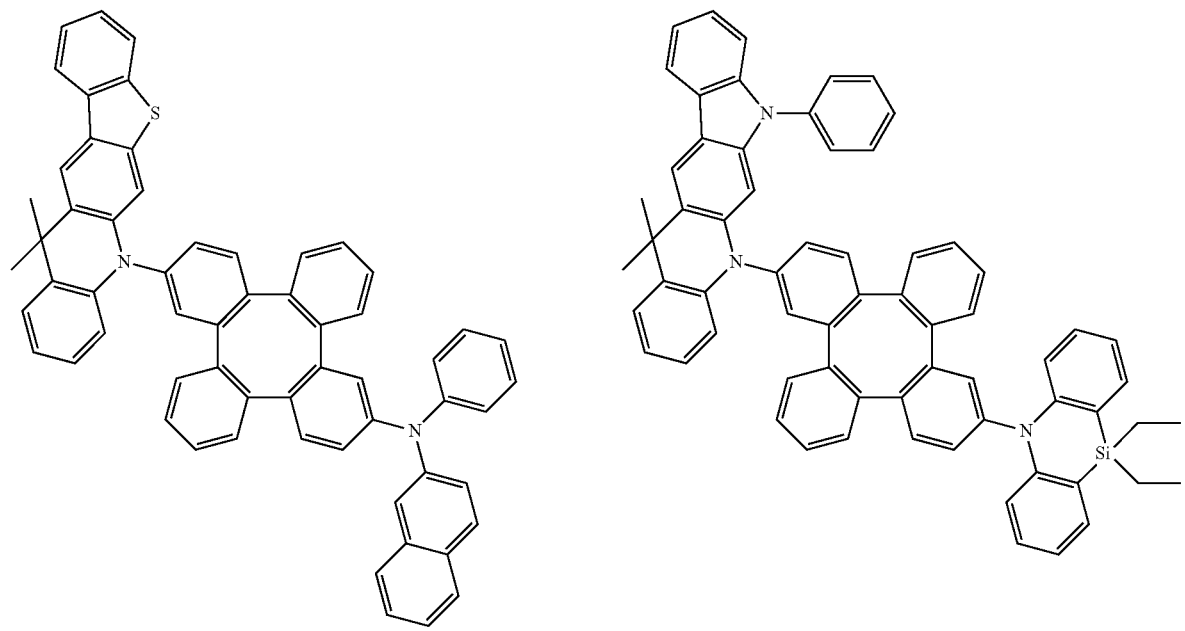

Compound 323
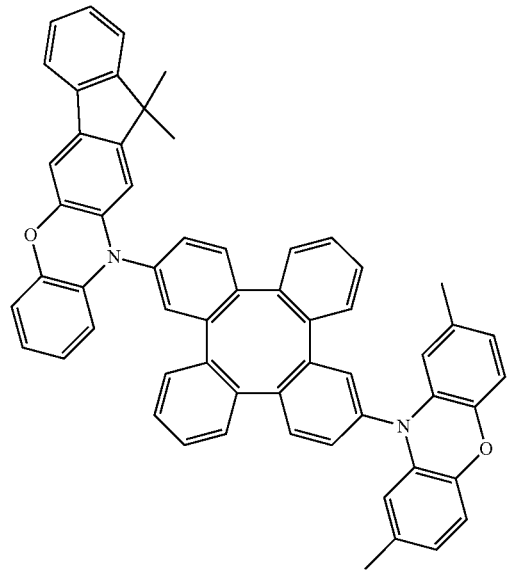
Compound 324
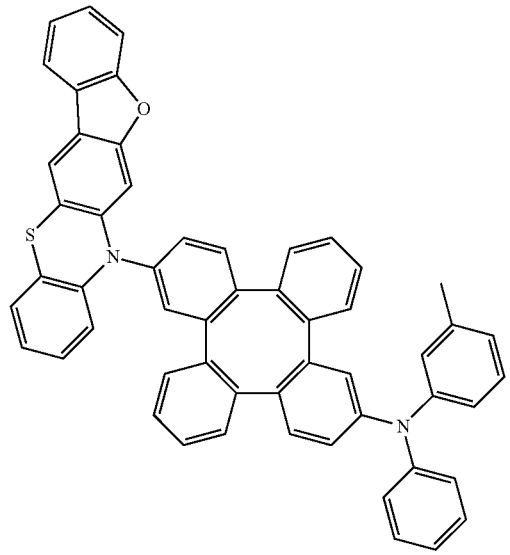
Compound 325
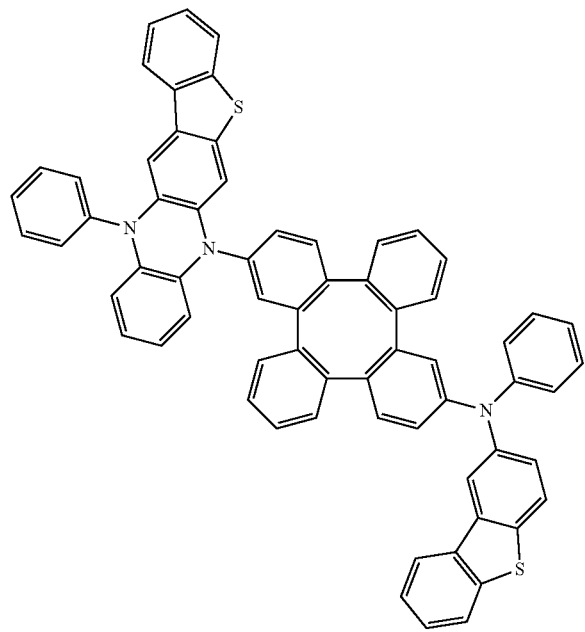
Compound 326
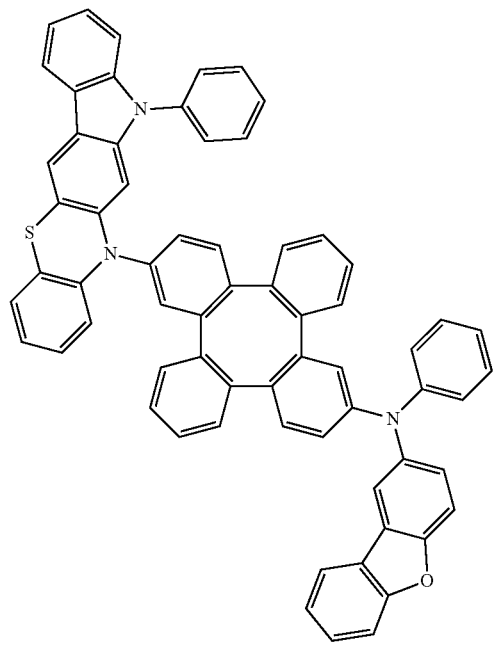

-continued
Compound 327
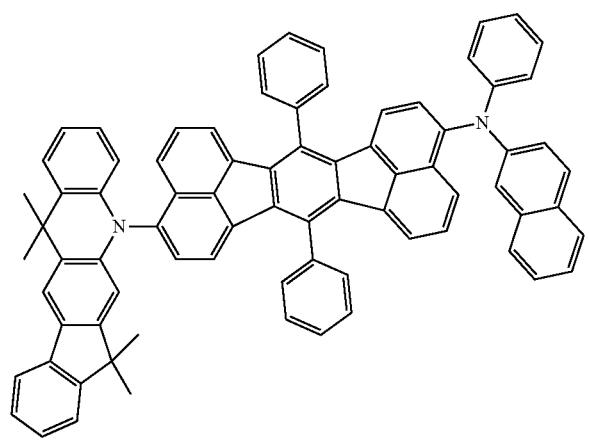
Compound 328
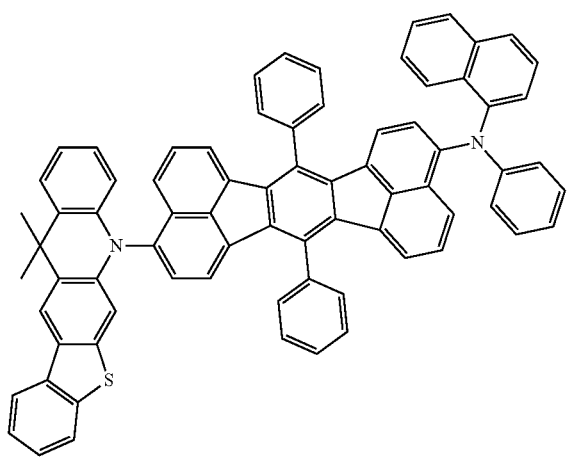
Compound 329
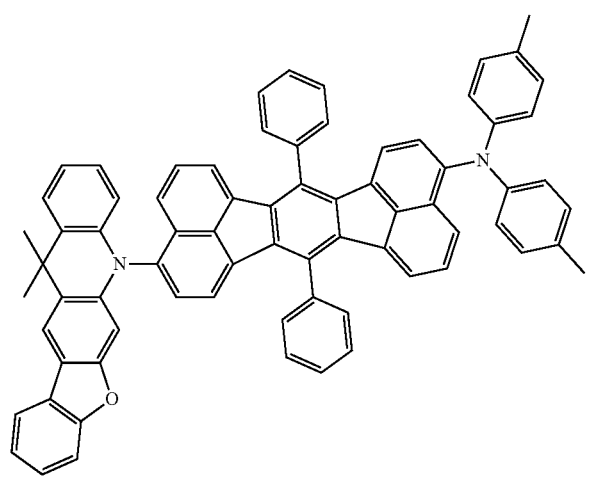
Compound 330
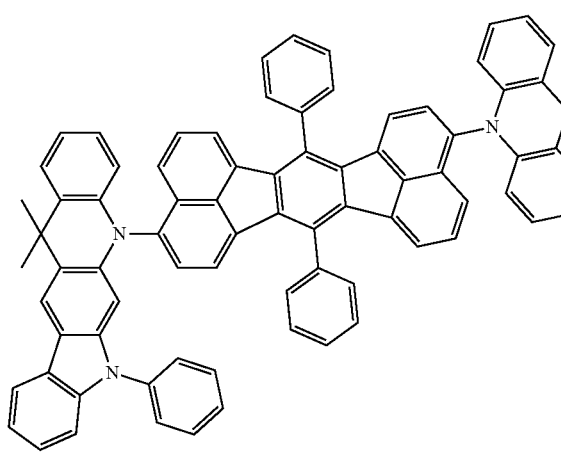
Compound 331
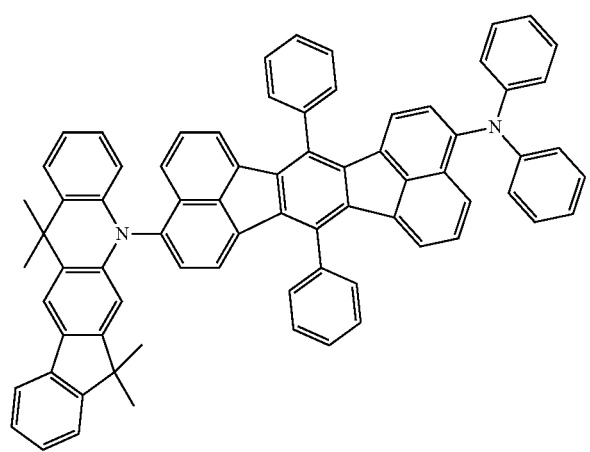
Compound 332
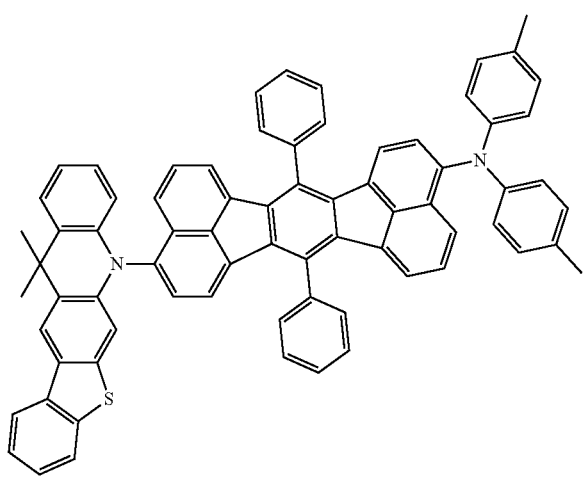

Compound 333
Compound 334
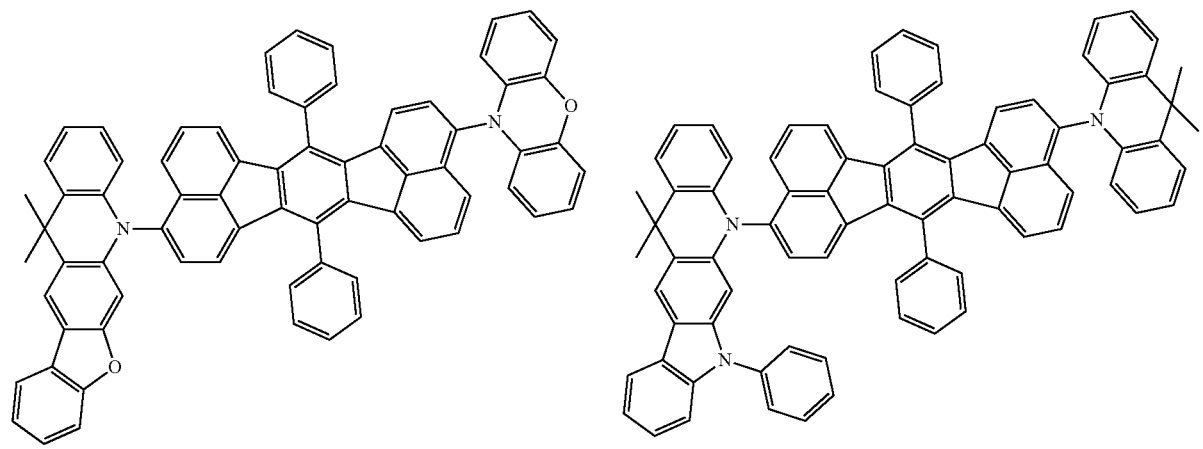
Compound 335
Compound 336
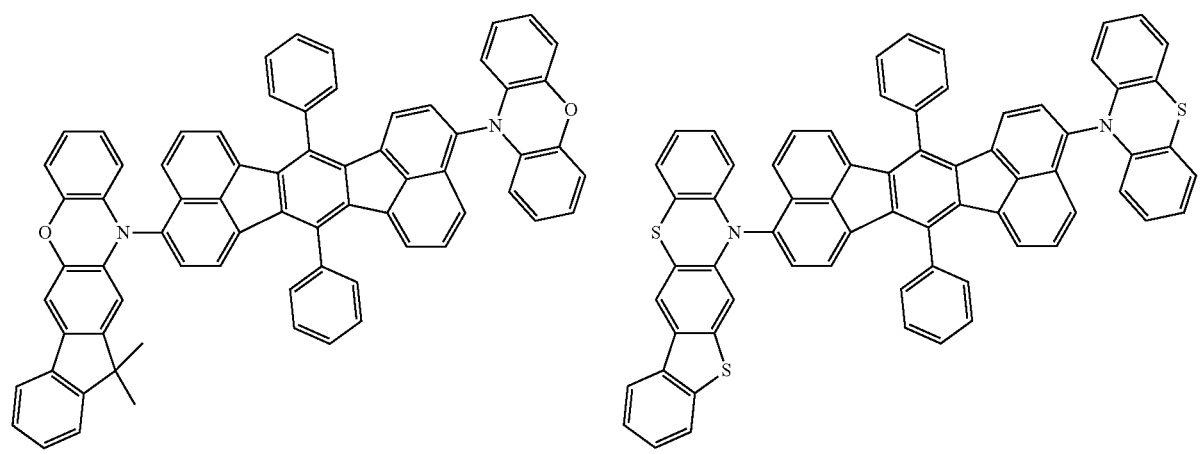
Compound 337
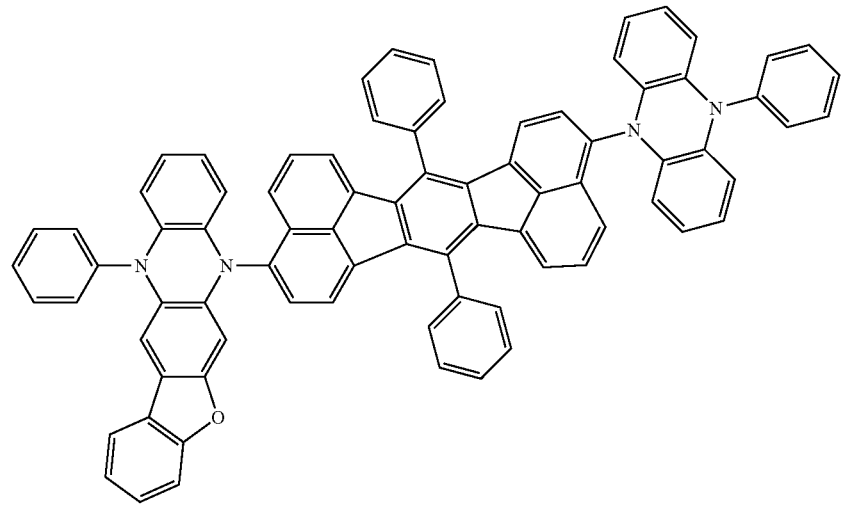

Compound 338
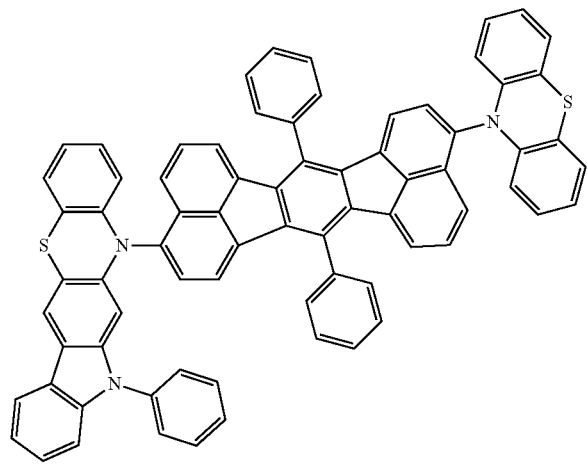
Compound 339
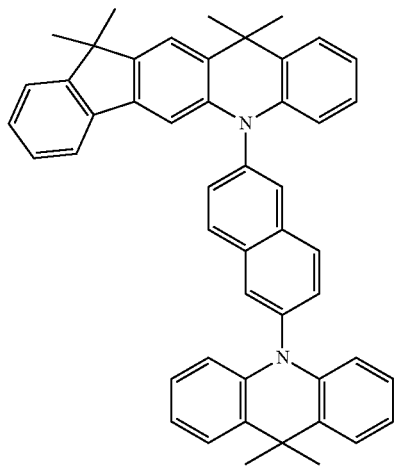
Compound 340
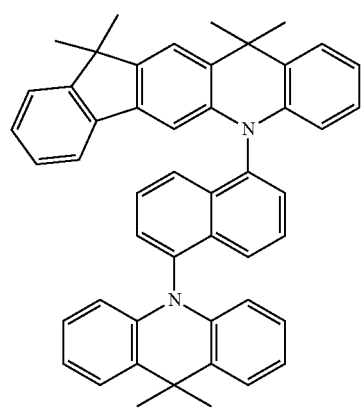
Compound 341
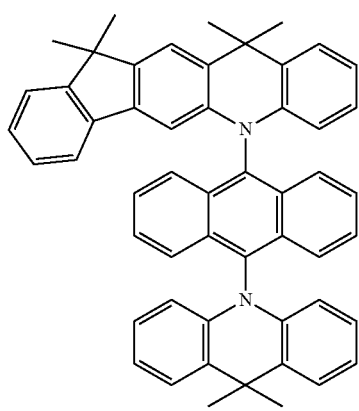
Compound 342
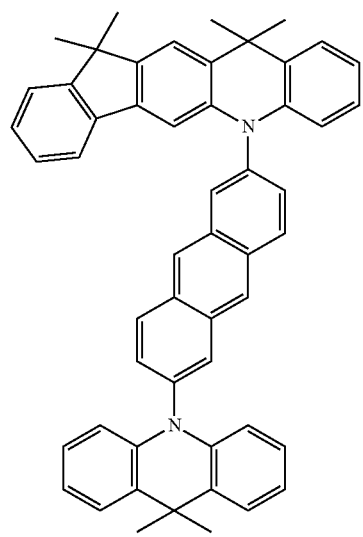
Compound 343
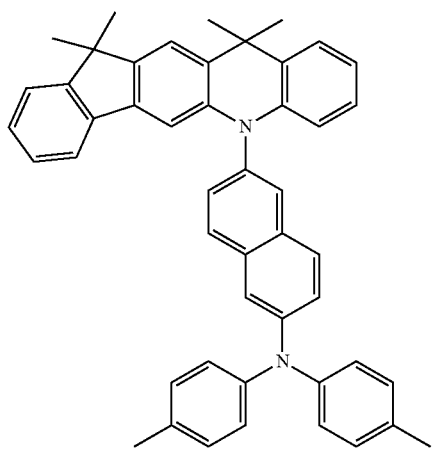

-continued
Compound 344
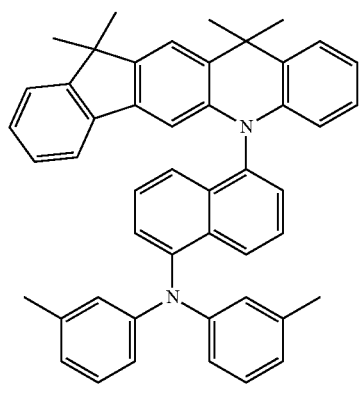
Compound 345
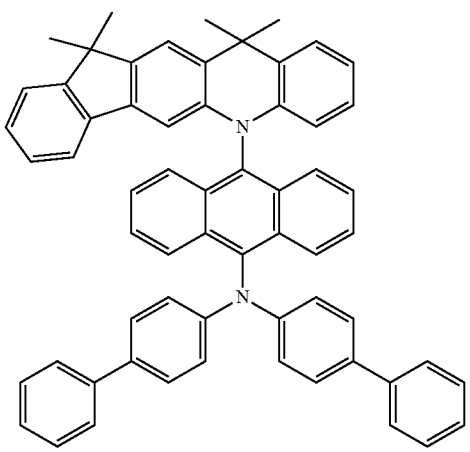
Compound 346
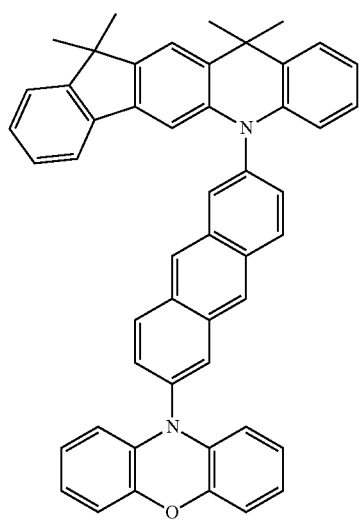
Compound 347
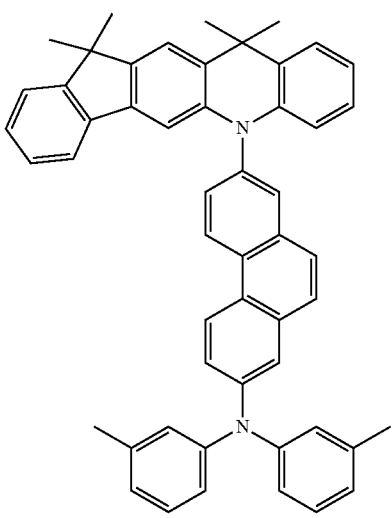
Compound 348
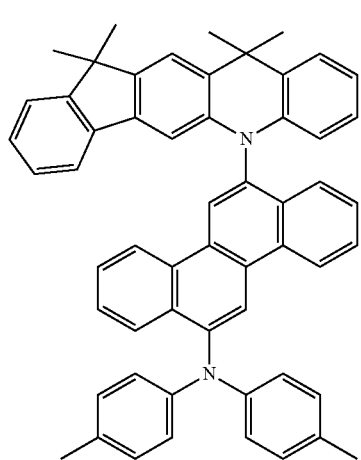
Compound 349
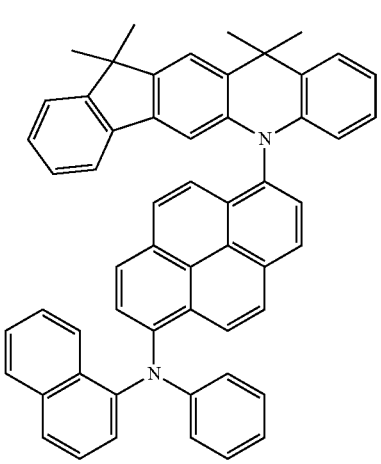

-continued
Compound 350
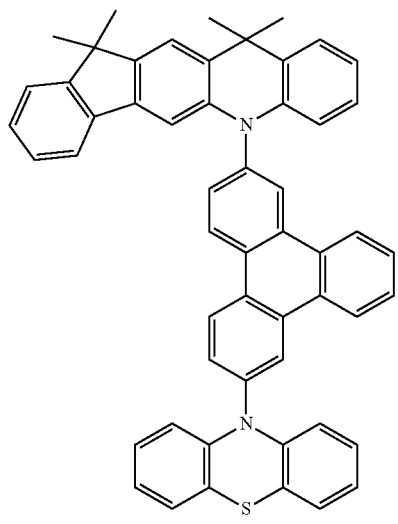
Compound 351
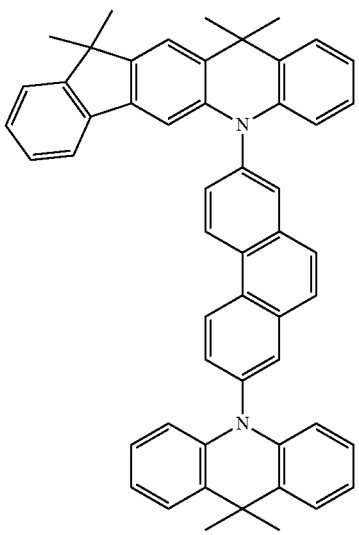
Compound 352
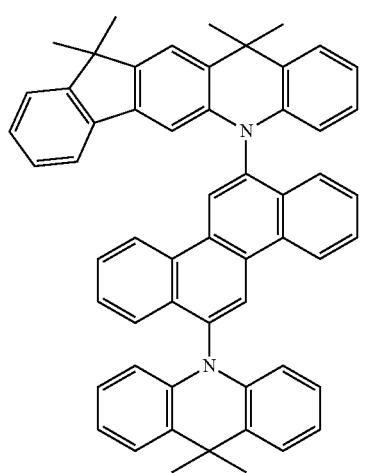
Compound 353
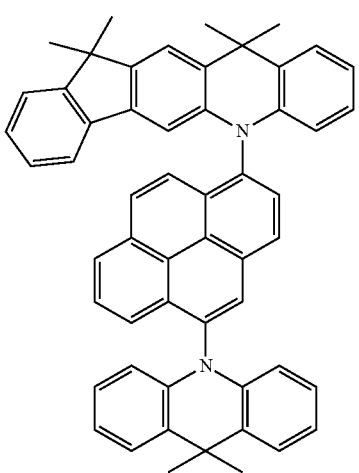
Compound 354
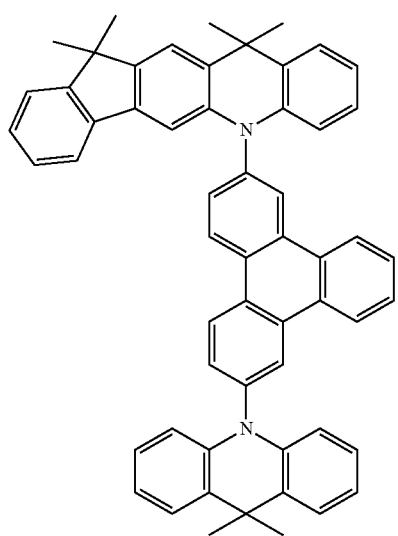
Compound 355
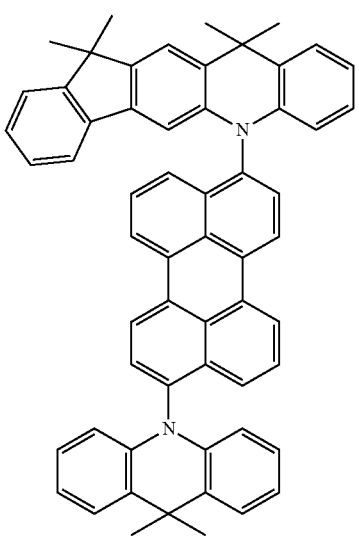

Compound 356

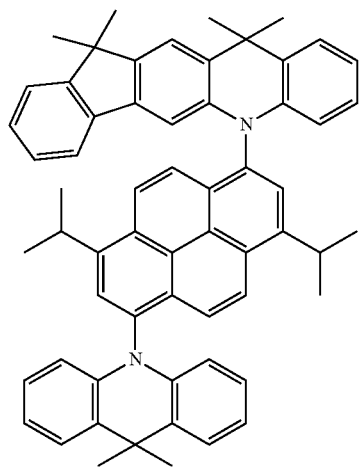

Compound 357

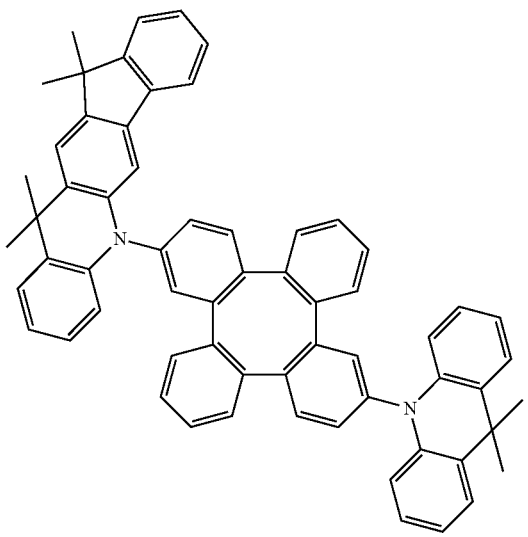

Compound 358

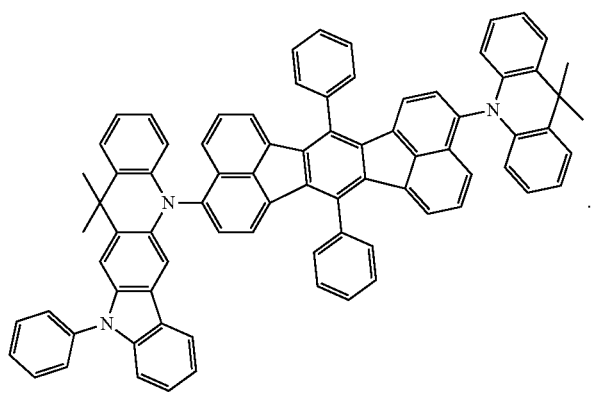

In another embodiment of the present invention, an organic electroluminescence device is disclosed. The organic electroluminescence device comprises a pair of electrodes composed of a cathode and an anode, and a light emitting layer between the pair of electrodes. The light emitting layer comprises the heteroaromatic compound of formula (1).

In some embodiments, the light emitting layer comprising the heteroaromatic compound of formula (1) is a fluorescent guest material. In particular, the light emitting layer emits blue fluorescence.

In a further embodiment of the present invention, the organic electroluminescence device is a lighting panel. In other embodiment of the present invention, the organic electroluminescence device is a backlight panel.

Detailed preparation of the heteroaromatic compounds of the present invention will be clarified by exemplary embodiments below, but the present invention is not limited thereto. EXAMPLES 1 to 18 show the preparation of the heteroaromatic compounds of the present invention, and EXAMPLE 19 shows the fabrication and test reports of the organic EL devices.

Example 1

Synthesis of methyl 2-((9,9-dimethyl-9H-fluoren-2-yl)amino)-benzoate

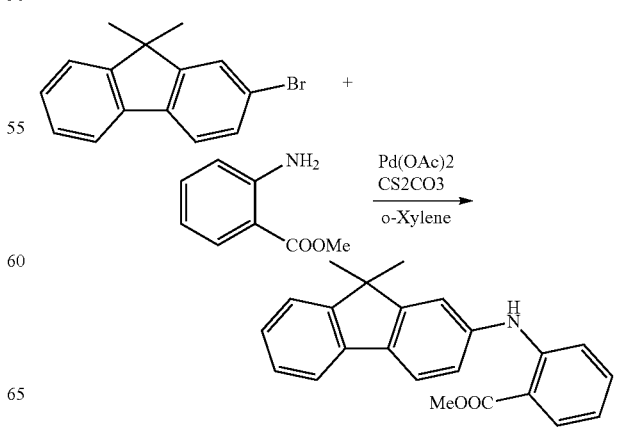

A mixture of 10 g (36.6 mmol) of 2-bromo-9,9-dimethyl-9H-fluorene, 6.64 g (43.9 mmol) of methyl 2-aminobenzoate, 0.3 g (1.46 mmol) of Pd(OAc)$_2$, 17.9 g (54.9 mmol) of cesium carbonate, and 120 ml of o-xylene was degassed and placed under nitrogen, and then heated to reflux for 12 hrs. After the reaction was finished, the mixture was allowed to cool to room temperature. Subsequently, the solvent was removed under reduced pressure, and the crude product was purified by column chromatography, yielding 10 g of methyl 2-((9,9-dimethyl-9H-fluoren-2-yl)amino)benzoate as yellow oil (79.6%), $^1$H NMR (CDCl$_3$, 400 MHz): chemical shift (ppm) 8.97 (s, 1H), 8.11 (d, 1H), 7.87 (d, 1H), 7.75-7.64 (m, 3H), 7.41-7.29 (m, 3H), 7.08 (m, 1H), 6.92 (d, 1H), 6.77 (d, 1H), 3.79 (s, 3H), 1.57 (s, 3H), 1.54 (s, 3H).

Synthesis of 2-(2-((9,9-dimethyl-9H-fluoren-2-yl)amino)phenyl)-propan-2-ol

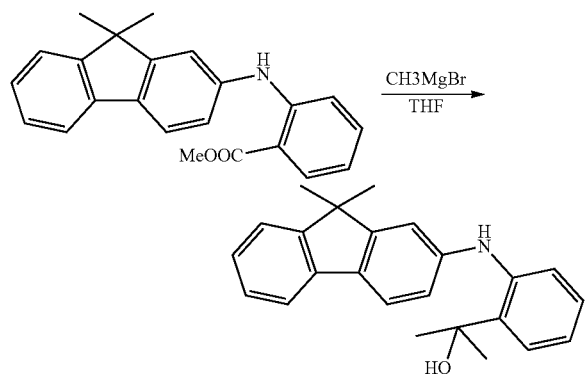

The compound methyl 2-((9,9-dimethyl-9H-fluoren-2-yl)amino)benzoate (10 g, 29.1 mmol) was mixed with 100 ml of THF. To the mixture, 58 ml of 3M methylmagnesium bromide was added slowly at room temperature and then stirred at room temperature for 3 hrs. After the reaction was finished, ammonium chloride solution was added to the reaction mixture and the reaction mixture was extracted with ethyl acetate/water and received the organic layer. The solvent was removed under reduced pressure, and the crude product was purified by column chromatography, yielding 9 g of 2-(2-((9,9-dimethyl-9H-fluoren-2-yl)amino)-phenyl)-propan-2-ol as yellow oil (90%). $^1$H NMR (CDCl$_3$, 400 MHz): chemical shift (ppm) 8.91 (s, 1H), 7.81 (d, 1H), 7.59 (d, 1H), 7.54 (d, 1H), 7.35-7.39 (m, 3H), 7.29 (m, 1H), 6.92 (m, 1H), 6.76-6.74 (d, 2H), 6.58 (d, 1H), 3.88 (s, 1H), 1.53 (s, 3H), 1.51 (s, 3H), 1.35 (s, 6H).

Synthesis of 7,7,13,13-tetramethyl-7,13-dihydro-5H-indeno-[1,2-b]acridine

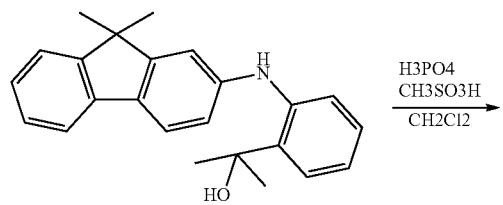

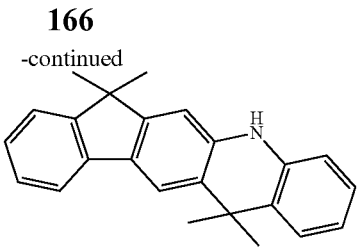

The compound 2-(2-((9,9-dimethyl-9H-fluoren-2-yl)amino)phenyl)-propan-2-ol (27 g, 78.6 mmol) was mixed with 400 ml of CH2Cl2. To the mixture, 51 ml of methane sulfonic acid and 37 ml of phosphoric acid was added slowly at room temperature and then stirred at room temperature for 12 hrs. After the reaction was finished, ice-cold water was added to the reaction mixture and 20% sodium hydroxide solution was added to the reaction mixture and the reaction mixture was extracted with ethyl acetate/water and received the organic layer. The solvent was removed under reduced pressure, and the crude product was purified by column chromatography, yielding 15 g of 7,7,13,13-tetramethyl-7,13-dihydro-5H-indeno-[1,2-b]acridine as yellow solid (58.8%). 1H NMR (CDCl$_3$, 400 MHz): chemical shift (ppm) 8.95 (s, 1H), 7.79 (s, 1H), 7.72 (d, 1H), 7.43 (d, 1H), 7.36 (d, 1H), 7.25 (m, 1H), 7.16 (dd, 1H), 7.04 (m, 1H), 6.87 (s, 1H), 6.81-6.78 (m, 2H) 1.55 (s, 6H), 1.38 (s, 6H).

Synthesis of 5-(10-bromoanthracen-9-yl)-7,7,13,13-tetramethyl-7,13-dihydro-5H-indeno[1,2-b]acridine

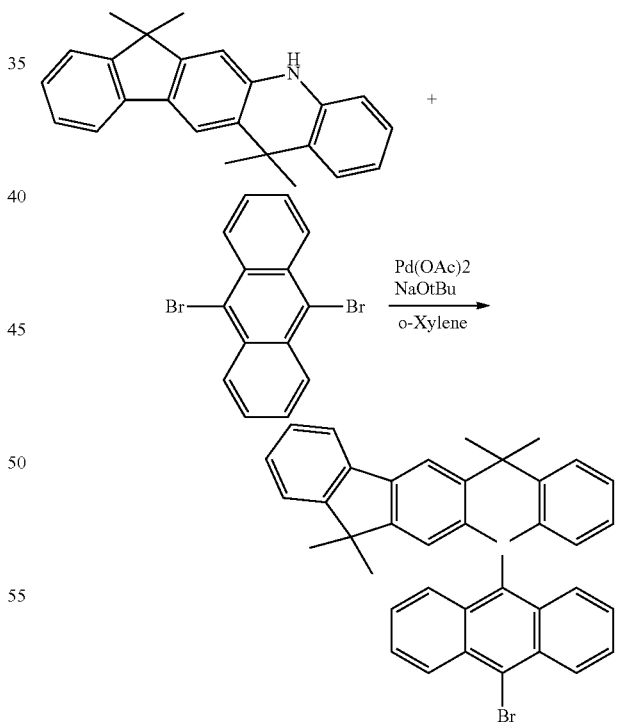

A mixture of 2.9 g (8.9 mmol) of 7,7,13,13-tetramethyl-7,13-dihydro-5H-indeno-[1,2-b]acridine, 3 g (8.9 mmol) of 9,10-dibromoanthracene, 0.04 g (0.18 mmol) of Pd(OAc)$_2$, 1.28 g (13.4 mmol) of sodium tert-butoxide, and 50 ml of o-xylene was degassed and placed under nitrogen, and then heated at 140° C. for 12 hrs. After the reaction was finished, the mixture was allowed to cool to room temperature. Subsequently, 150 ml of methanol was added, and then filtered and washed by methanol. The crude product was purified by column chromatography to get a yellow solid. Yield: 1.23 g, 23%. ¹H NMR (CDCl₃, 400 MHz): chemical shift (ppm) 8.11 (d, 2H), 7.91 (d, 2H), 7.83 (d, H), 7.54 (d, H), 7.45-7.41 (m, 5H), 7.35 (m, H), 7.25 (m, H), 7.05-7.02 (m, 2H), 6.79 (m, H), 6.69 (d, H), 6.58 (d, H), 1.56 (s, 6H), 1.39 (s, 6H).

Synthesis of 10-(7,7,13,13-tetramethyl-7,13-dihydro-5H-indeno-[1,2-b]acridin-5-yl)-N,N-di-m-tolylanthracen-9-amine (Compound 3)

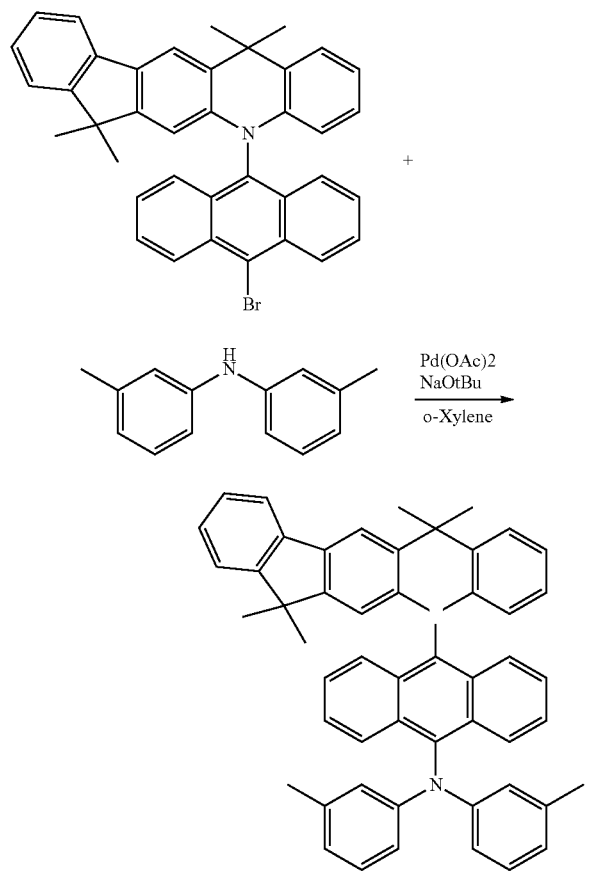

A mixture of 1.2 g (2.07 mmol) of 5-(10-bromoanthracen-9-yl)-7,7,13,13-tetramethyl-7,13-dihydro-5H-indeno[1,2-b]acridine, 0.45 g (2.27 mmol) of di-m-tolylamine, 0.004 g (0.02 mmol) of Pd(OAc)₂, 0.3 g (3.1 mmol) of sodium tert-butoxide, and 20 ml of o-xylene was degassed and placed under nitrogen, and then heated at 140° C. for 12 hrs. After the reaction was finished, the mixture was allowed to cool to room temperature. Subsequently, 60 ml of methanol was added, and then filtered and washed by methanol to get a yellow solid. Yield: 0.68 g, 47%. ¹H NMR (CDCl₃, 400 MHz): chemical shift (ppm) 8.13 (d, 2H), 7.92 (d, 2H), 7.85 (d, H), 7.52 (d, H), 7.47-7.42 (m, 5H), 7.36 (m, H), 7.27 (m, H), 7.07-7.03 (m, 4H), 6.79 (m, H), 6.71 (m, 3H), 6.59-6.54 (m, 5H), 2.35 (s, 6H), 1.57 (s, 6H), 1.38 (s, 6H). MS (m/z, EI⁺): 696.7.

Example 2

Synthesis of 5-(5-bromonaphthalen-1-yl)-7,7,13,13-tetramethyl-7,13-dihydro-5H-indeno[1,2-b]acridine

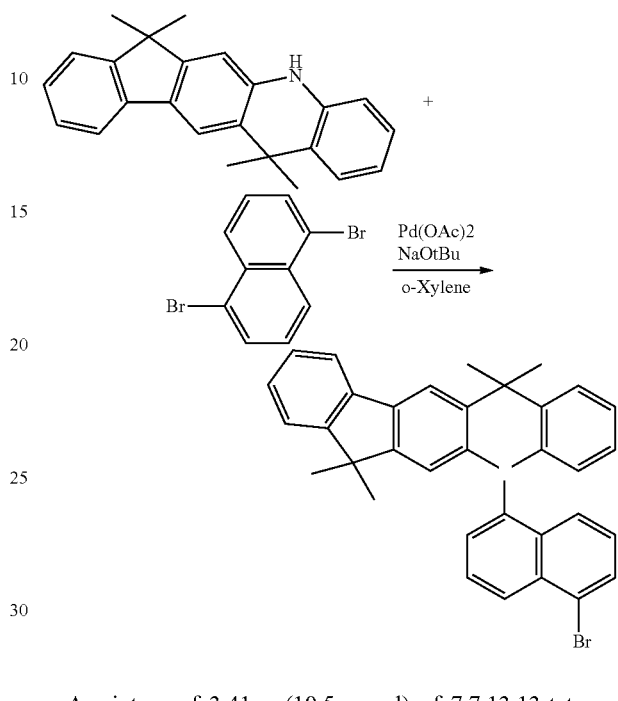

A mixture of 3.41 g (10.5 mmol) of 7,7,13,13-tetramethyl-7,13-dihydro-5H-indeno-[1,2-b]acridine, 3 g (10.5 mmol) of 1,5-dibromonaphthalene, 0.02 g (0.1 mmol) of Pd(OAc)₂, 1.51 g (15.8 mmol) of sodium tert-butoxide, and 50 ml of o-xylene was degassed and placed under nitrogen, and then heated at 140° C. for 12 hrs. After the reaction was finished, the mixture was allowed to cool to room temperature. Subsequently, 150 ml of methanol was added, and then filtered and washed by methanol. The crude product was purified by column chromatography to get a yellow solid. Yield: 1.5 g, 27%. 1H NMR (CDCl₃, 400 MHz): chemical shift (ppm) 8.09 (d, 2H), 7.93 (d, H), 7.84 (d, H), 7.55 (d, 2H), 7.45-7.41 (m, 2H), 7.37 (m, H), 7.26 (m, H), 7.07-7.03 (m, 3H), 6.76 (m, H), 6.69 (s, H), 6.56 (d, H), 1.56 (s, 6H), 1.39 (s, 6H).

Synthesis of 5-(7,7,13,13-tetramethyl-7,13-dihydro-5H-indeno-[1,2-b]acridin-5-yl)-N,N-di-p-tolylnaphthalen-1-amine (Compound 2)

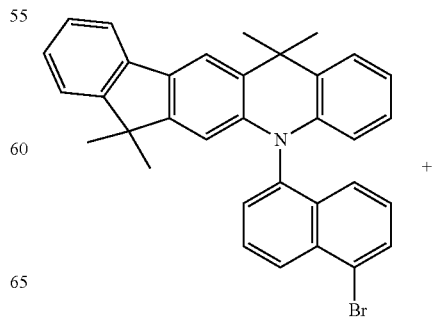

-continued

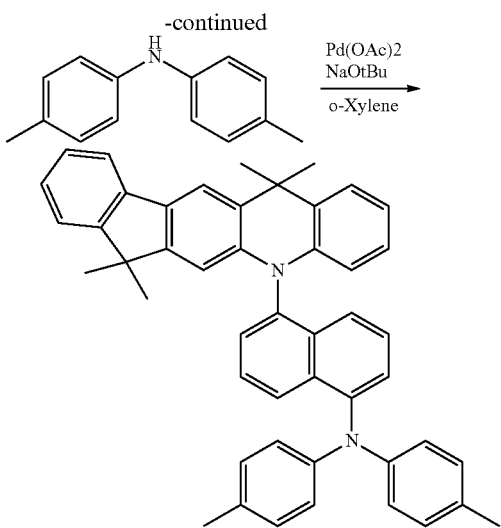

A mixture of 1.5 g (2.83 mmol) of 5-(5-bromonaphthalen-1-yl)-7,7,13,13-tetramethyl-7,13-dihydro-5H-indeno[1,2-b]acridine, 0.61 g (3.11 mmol) of di-p-tolylamine, 0.006 g (0.02 mmol) of Pd(OAc)$_2$, 0.41 g (4.2 mmol) of sodium tert-butoxide, and 30 ml of o-xylene was degassed and placed under nitrogen, and then heated at 140° C. for 12 hrs. After the reaction was finished, the mixture was allowed to cool to room temperature. Subsequently, 60 ml of methanol was added, and then filtered and washed by methanol to get a yellow solid. Yield: 0.95 g, 52%. $^1$H NMR (CDCl$_3$, 400 MHz): chemical shift (ppm) 8.01 (d, H), 7.75-7.71 (m, 3H), 7.64 (s, H), 7.45 (m, 2H), 7.37 (m, H), 7.17-7.11 (m, 2H), 7.04-6.97 (m, 6H), 6.83 (m, 2H), 6.75 (s, H), 6.68 (d, H), 6.59-6.54 (m, 4H), 2.37 (s, 6H), 1.55 (s, 6H), 1.37 (s, 6H). MS (m/z, EI$^+$): 646.6.

Example 3-9

We have used the same synthesis methods to get a series of intermediates and the following compounds are synthesized analogously.

| Ex. | Intermediate I | Intermediate II | Product | Yield |
|---|---|---|---|---|
| 3 | [structure] | [structure] | [structure] Compound 1 | 56% |
| 4 | [structure] | [structure] | [structure] Compound 4 | 43% |

-continued

| Ex. | Intermediate I | Intermediate II | Product | Yield |
|---|---|---|---|---|
| 5 | | | Compound 5 | 41% |
| 6 | | | Compound 7 | 47% |
| 7 | | | Compound 8 | 54% |

| Ex. | Intermediate I | Intermediate II | Product | Yield |
|---|---|---|---|---|
| 8 | | | Compound 9 | 45% |
| 9 | | | Compound 35 | 39% |

Example 10

Synthesis of methyl 2-(dibenzo[b,d]thiophen-3-ylamino)benzoate

A mixture of 5 g (19 mmol) of 3-bromodibenzo[b,d]thiophene, 3.45 g (22.8 mmol) of methyl 2-aminobenzoate, 0.17 g (0.76 mmol) of Pd(OAc)$_2$, 9.28 g (28.5 mmol) of cesium carbonate, and 60 ml of o-xylene was degassed and placed under nitrogen, and then heated to reflux for 12 hrs. After the reaction was finished, the mixture was allowed to cool to room temperature. Subsequently, the solvent was removed under reduced pressure, and the crude product was purified by column chromatography, yielding 4.8 g of methyl 2-(dibenzo[b,d]thiophen-3-ylamino)benzoate as yellow oil (75.8%), $^1$H NMR (CDCl$_3$, 400 MHz): chemical shift (ppm) 8.99 (s, 1H), 8.14 (d, 1H), 7.89 (d, 1H), 7.79-7.68 (m, 3H), 7.45-7.33 (m, 3H), 7.12 (m, 1H), 6.97 (d, 1H), 6.81 (d, 1H), 3.79 (s, 3H).

Synthesis of 2-(2-(dibenzo[b,d]thiophen-3-ylamino)phenyl)propan-2-ol

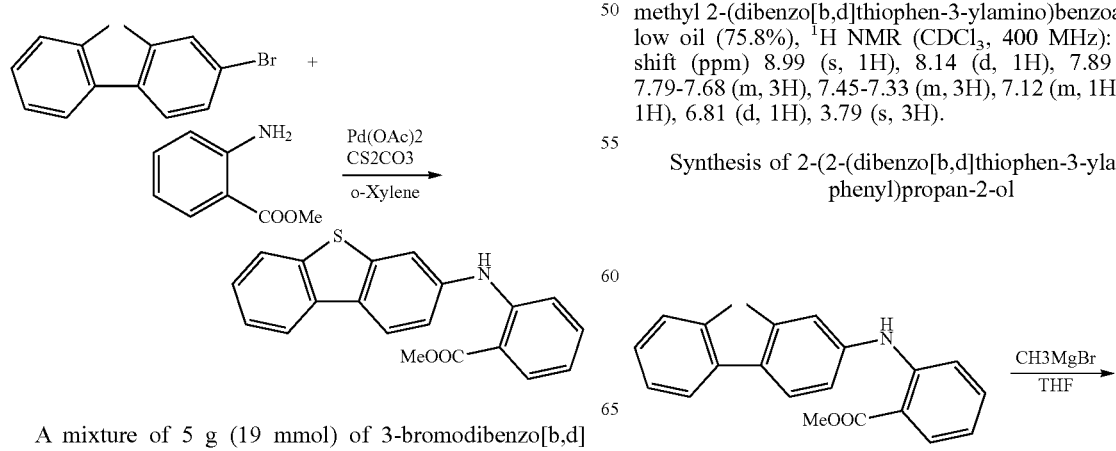

-continued

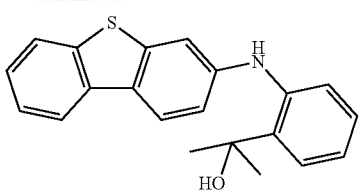

The compound methyl 2-(dibenzo[b,d]thiophen-3-ylamino)benzoate (4.8 g, 14.4 mmol) was mixed with 50 ml of THF. To the mixture, 28 ml of 3M methylmagnesium bromide was added slowly at room temperature and then stirred at room temperature for 3 hrs. After the reaction was finished, ammonium chloride solution was added to the reaction mixture and the reaction mixture was extracted with ethyl acetate/water and received the organic layer. The solvent was removed under reduced pressure, and the crude product was purified by column chromatography, yielding 4.5 g of 2-(2-(dibenzo[b,d]thiophen-3-ylamino)phenyl)propan-2-ol as yellow oil (93.7%). 1H NMR (CDCl$_3$, 400 MHz): chemical shift (ppm) 8.94 (s, 1H), 7.83 (d, 1H), 7.62 (d, 1H), 7.55 (d, 1H), 7.41-7.36 (m, 3H), 7.29 (m, 1H), 6.94 (m, 1H), 6.78-6.75 (d, 2H), 6.59 (d, 1H), 3.91 (s, 1H), 1.35 (s, 6H).

Synthesis of 12,12-dimethyl-7,12-dihydrobenzo[4,5]thieno[3,2-b]-acridine

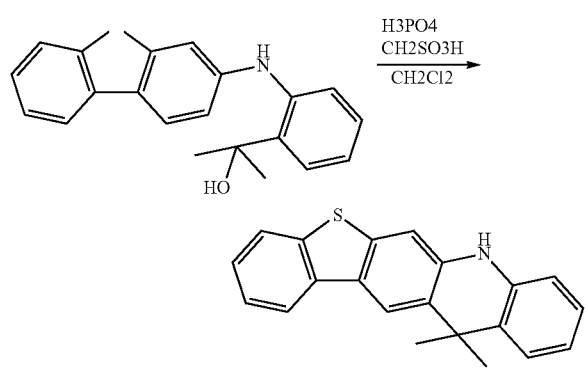

The compound 2-(2-(dibenzo[b,d]thiophen-3-ylamino)phenyl)-propan-2-ol (10 g, 30 mmol) was mixed with 150 ml of CH2Cl2. To the mixture, 19 ml of methane sulfonic acid and 14 ml of phosphoric acid was added slowly at room temperature and then stirred at room temperature for 12 hrs. After the reaction was finished, ice-cold water was added to the reaction mixture and 20% sodium hydroxide solution was added to the reaction mixture and the reaction mixture was extracted with ethyl acetate/water and received the organic layer. The solvent was removed under reduced pressure, and the crude product was purified by column chromatography, yielding 5.3 g of 12,12-dimethyl-7,12-dihydrobenzo[4,5]-thieno[3,2-b]-acridine as yellow solid (56%). $^1$H NMR (CDCl$_3$, 400 MHz): chemical shift (ppm) 8.97 (s, 1H), 7.81 (s, 1H), 7.73 (d, 1H), 7.45 (d, 1H), 7.38 (d, 1H), 7.28 (m, 1H), 7.18 (dd, 1H), 7.07 (m, 1H), 6.89 (s, 1H), 6.83-6.79 (m, 2H), 1.38 (s, 6H).

Synthesis of 7-(6-bromopyren-1-yl)-12,12-dimethyl-7,12-dihydrobenzo[4,5]thieno[3,2-b]acridine

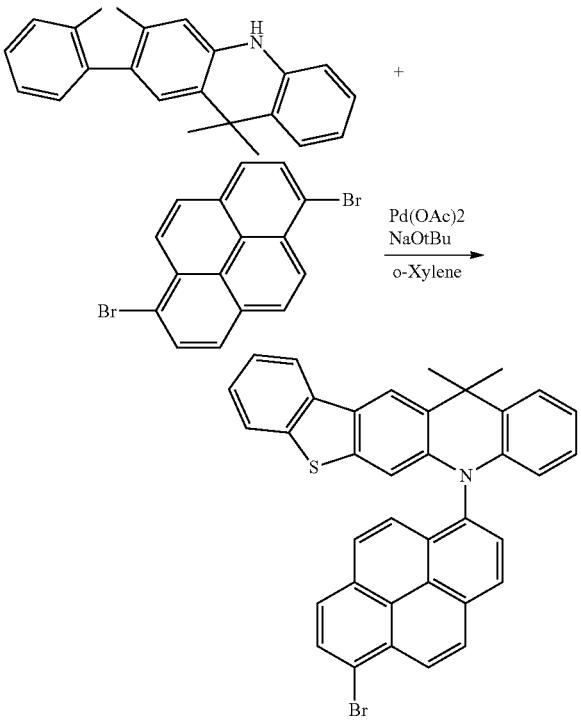

A mixture of 2.63 g (8.33 mmol) of 12,12-dimethyl-7,12-dihydrobenzo-[4,5]-thieno[3,2-b]-acridine, 3 g (8.33 mmol) of 1,6-dibromopyrene, 0.02 g (0.08 mmol) of Pd(OAc)$_2$, 1.2 g (12.5 mmol) of sodium tert-butoxide, and 50 ml of o-xylene was degassed and placed under nitrogen, and then heated at 140° C. for 12 hrs. After the reaction was finished, the mixture was allowed to cool to room temperature. Subsequently, 150 ml of methanol was added, and then filtered and washed by methanol. The crude product was purified by column chromatography to get a yellow solid. Yield: 1.54 g, 32%. $^1$H NMR (CDCl$_3$, 400 MHz): chemical shift (ppm) 8.33 (d, H), 7.89-7.81 (m, 3H), 7.54 (d, 4H), 7.42 (d, H), 7.36-7.32 (m, 2H), 7.27 (s, H), 7.08-7.03 (m, 3H), 6.94 (s, H), 6.74 (m, H), 6.57 (d, H), 1.41 (s, 6H).

Synthesis of 6-(12,12-dimethylbenzo[4,5]thieno[3,2-b]acridin-7(12H)-yl)-N,N-di-p-tolylpyren-1-amine (Compound 19)

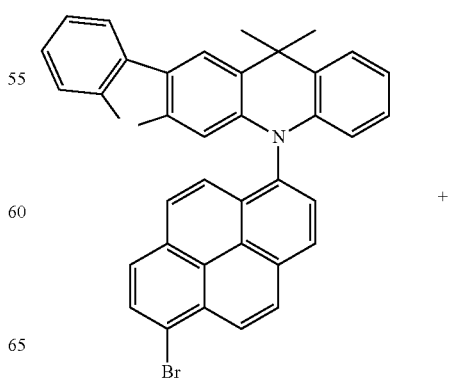

-continued

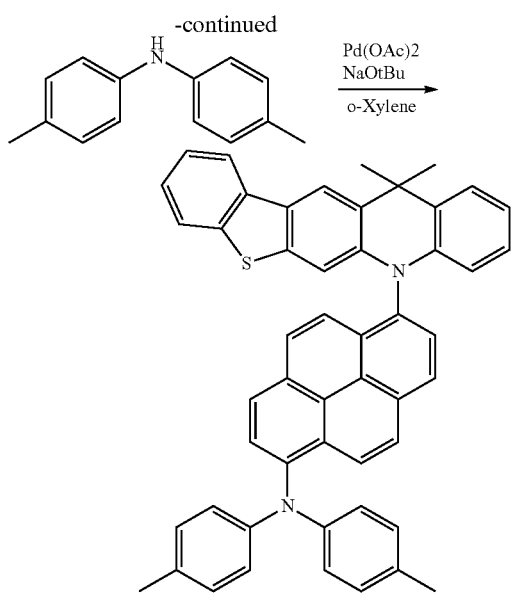

A mixture of 1.5 g (2.52 mmol) of 7-(6-bromopyren-1-yl)-12,12-dimethyl-7,12-dihydrobenzo[4,5]thieno[3,2-b]acridine, 0.55 g (2.77 mmol) of di-p-tolylamine, 0.006 g (0.02 mmol) of Pd(OAc)$_2$, 0.36 g (3.78 mmol) of sodium tert-butoxide, and 30 ml of o-xylene was degassed and placed under nitrogen, and then heated at 140° C. for 12 hrs. After the reaction was finished, the mixture was allowed to cool to room temperature. Subsequently, 60 ml of methanol was added, and then filtered and washed by methanol to get a yellow solid. Yield: 0.86 g, 48%. $^1$H NMR (CDCl$_3$, 400 MHz): chemical shift (ppm) 8.35 (d, H), 8.03 (d, H), 7.92 (d, H), 7.75 (d, 4H), 7.55-7.59 (m, 3H), 7.33 (s, H), 7.15-7.01 (m, 9H), 6.84 (m, H), 6.55-6.59 (m, 5H), 2.36 (s, 6H), 1.42 (s, 6H). MS (m/z, EI$^+$): 710.6.

Example 11-18

We have used the same synthesis methods to get a series of intermediates and the following compounds are synthesized analogously.

| Ex. | Intermediate I | Intermediate II | Product | Yield |
|---|---|---|---|---|
| 11 | | | Compound 23 | 36% |
| 12 | | | Compound 55 | 44% |

-continued

| Ex. | Intermediate I | Intermediate II | Product | Yield |
|---|---|---|---|---|
| 13 | | | Compound 59 | 41% |
| 14 | | | Compound 72 | 42% |
| 15 | | | Compound 77 | 52% |

-continued

| Ex. | Intermediate I | Intermediate II | Product | Yield |
|---|---|---|---|---|
| 16 | | | Compound 80 | 42% |
| 17 | | | Compound 81 | 43% |
| 18 | | | Compound 82 | 35% |

General Method of Producing Organic EL Device

ITO-coated glasses with 9-12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, i.e. in general a host material doped with a dopant material and/or co-deposited with a co-host. This is successfully achieved by co-vaporization from two or more sources, which means the 5,12-dihydrotetracene derivatives of the present invention are thermally stable.

Dipyrazino[2,3-f:2,3-]quinoxaline-2,3,6,7,10,11-hexacarbonitrile (HA T-CN) is used as hole injection layer in this organic EL device. N,N-Bis(naphthalene-1-yl)-N,N-bis(phenyl)-benzidine (NPB) is most widely used as the hole transporting layer. 10,10-dimethyl-13-(3-(pyren-1-yl)phenyl)-10H-indeno[2,1-b]triphenylene (H1) and 10,10-dimethyl-13-(10-(3-(naphthalen-2-yl)phenyl)anthracen-9-yl)-10H-indeno-[2,1-b]triphenylene (H2) are used as emitting hosts in organic EL devices, and N1,N1,N6,N6-tetram-tolylpyrene-1,6-diamine (D1) is used as blue guest for comparison. HB3 (see the following chemical structure) is used as hole blocking material (HBM), and 2-(naphthalen-1-yl)-9-(4-(1-(4-(10-(naphthalene-2-yl)anthracen-9-yl)phenyl)-1H-benzo[d]imidazol-2-yl)phenyl)-1,10-phenanthroline (ET2) is used as electron transporting material to co-deposit with 8-hydroxyquinolato-lithium (LiQ) in organic EL devices. The chemical structures of conventional OLED materials and the exemplary heteroaromatic compounds of the present invention for producing control and exemplary organic EL devices in this invention are shown as follows:

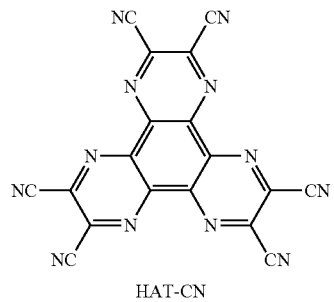

HAT-CN

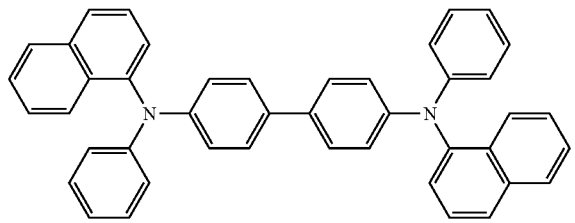

NPB

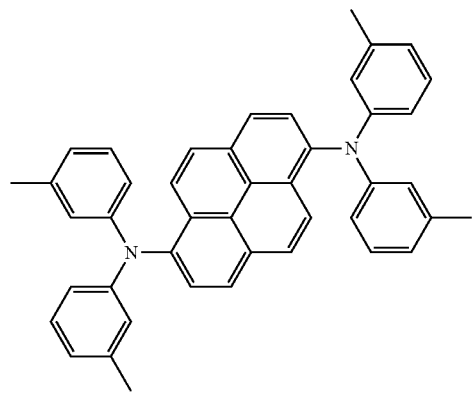

D1

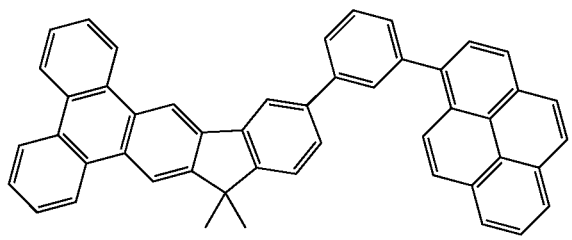

H1

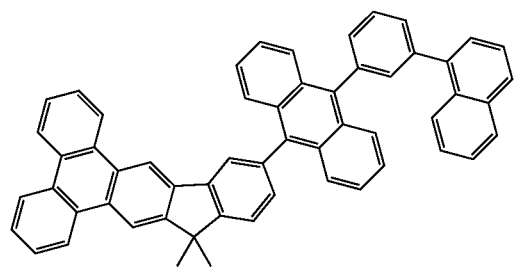

H2

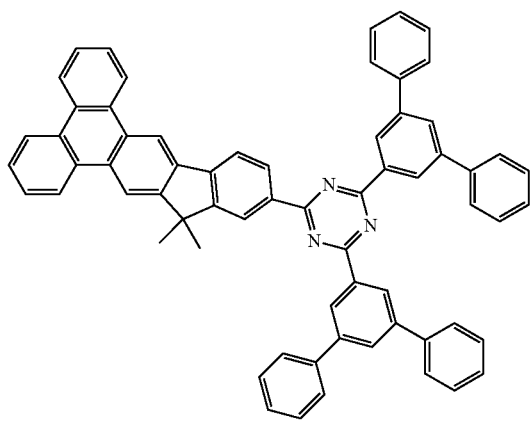

HB3

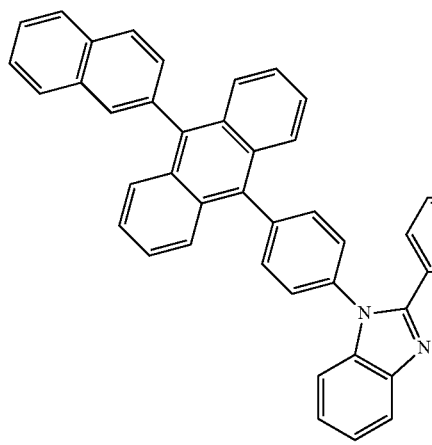
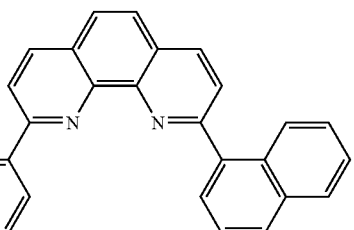
ET2
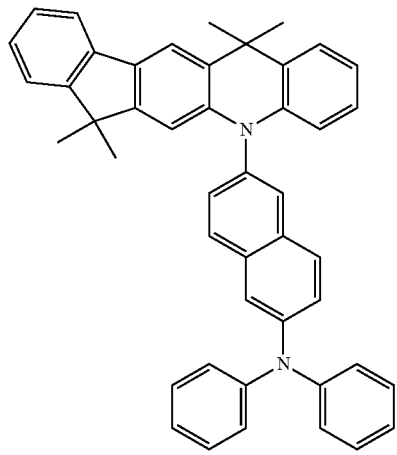
Compound 1
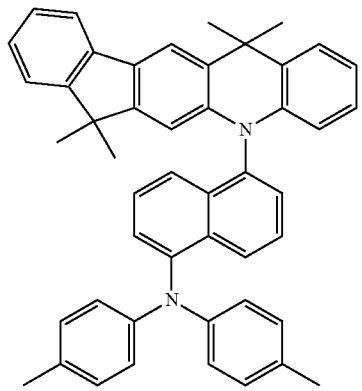
Compound 2
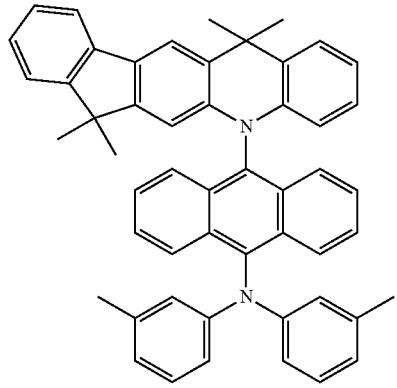
Compound 3
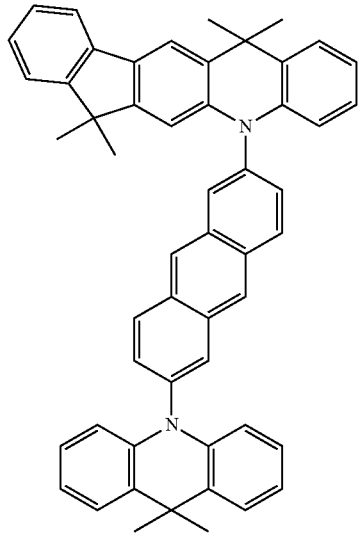
Compound 4

-continued

Compound 5

Compound 7

Compound 8

Compound 9

Compound 19

Compound 23

-continued
Compound 35
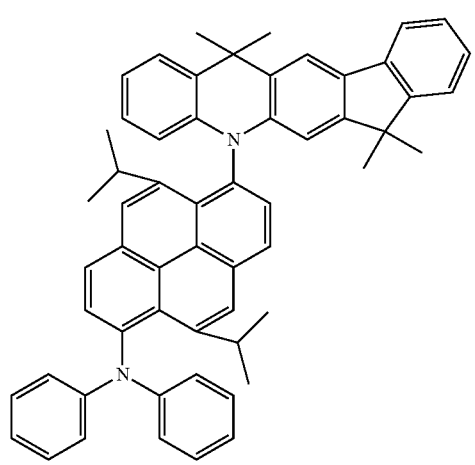
Compound 55
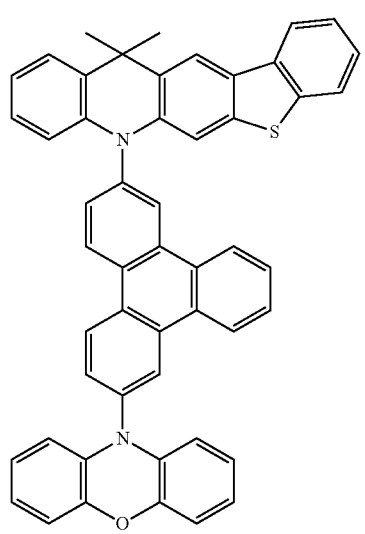
Compound 59
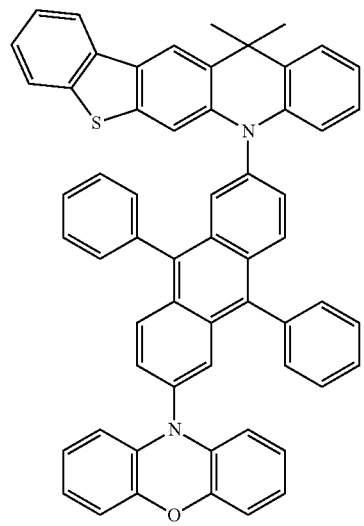
Compound 72
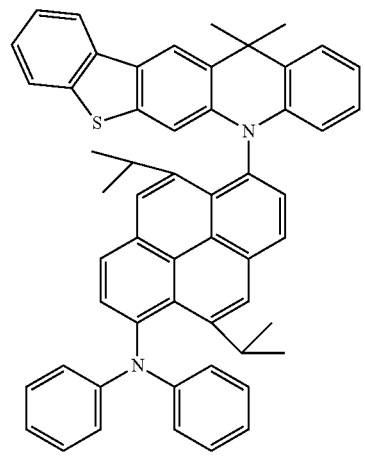
Compound 77
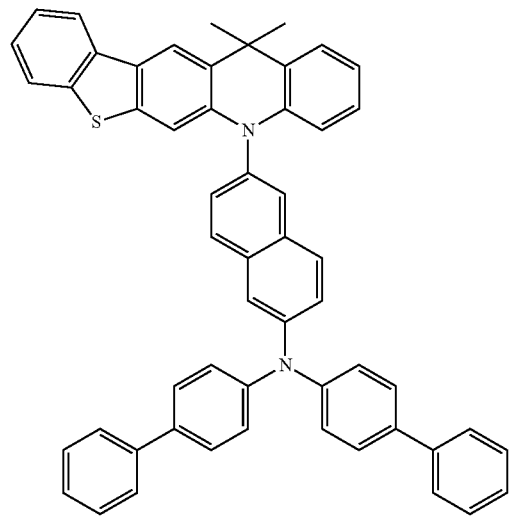
Compound 80
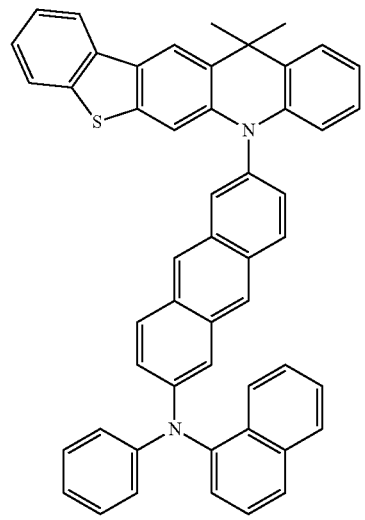

Compound 81

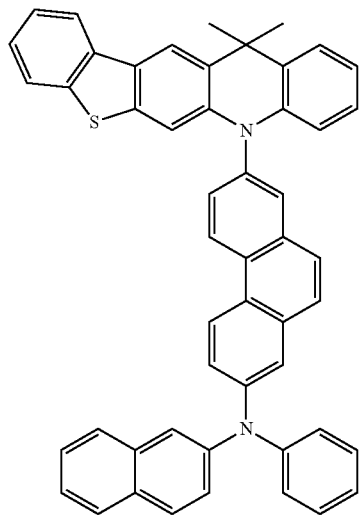

Compound 82

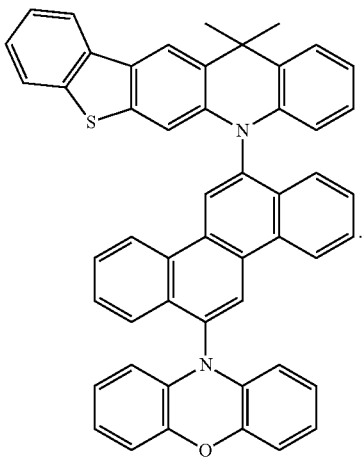

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

Example 19

Using a procedure analogous to the above mentioned general method, organic EL devices emitting blue light and having the following device structure as shown in the FIGURE were produced: ITO/HAT-CN (20 nm)/NPB (110 nm)/Emitting host doped with 5% Emitting guest (30 nm)/HB3/ET2 doped 50% LiQ (35 nm)/LiQ (1 nm)/Al (160 nm). In the device illustrated in the FIGURE, the hole injection layer 20 is deposited onto the transparent electrode 10, the hole transport layer 30 is deposited onto the hole injection layer 20, the emitting layer 40 is deposited onto the hole transport layer 30, the hole blocking layer 50 is deposited onto the emitting layer 40, the electron transport layer 60 is deposited onto the hole blocking layer 50, the electron injection layer 70 is deposited onto the electron transport layer 60, and the metal electrode 80 is deposited onto the electron injection layer 70. The I-V-B (at 1000 nits) test reports of these organic EL devices are summarized in Table 1 below. The half-life time is defined as the time the initial luminance of 1000 cd/m² has dropped to half.

TABLE 1

| Emitting Host | Emitting Guest | Voltage (V) | Efficiency (cd/A) | Device Colour | Half-life time (hr) |
|---|---|---|---|---|---|
| H1 | Compound 1 | 3.4 | 5.5 | blue | 180 |
| H1 | Compound 2 | 3.4 | 5.6 | blue | 190 |
| H1 | Compound 3 | 3.3 | 5.8 | blue | 220 |
| H1 | Compound 4 | 3.3 | 5.7 | blue | 210 |
| H1 | Compound 5 | 3.4 | 5.8 | blue | 230 |
| H1 | Compound 7 | 3.2 | 6.3 | blue | 260 |
| H1 | Compound 8 | 3.2 | 6.1 | blue | 240 |
| H1 | Compound 9 | 3.3 | 6.0 | blue | 235 |
| H1 | Compound 35 | 3.1 | 6.6 | blue | 280 |
| H1 | Compound 19 | 3.3 | 6.1 | blue | 245 |
| H1 | Compound 23 | 3.3 | 5.6 | blue | 200 |
| H1 | Compound 55 | 3.4 | 5.9 | blue | 230 |
| H1 | Compound 59 | 3.3 | 5.7 | blue | 205 |
| H1 | Compound 72 | 3.2 | 6.3 | blue | 265 |
| H1 | Compound 77 | 3.4 | 5.4 | blue | 185 |
| H1 | Compound 80 | 3.3 | 5.6 | blue | 220 |
| H1 | Compound 81 | 3.5 | 5.6 | blue | 210 |
| H1 | Compound 82 | 3.5 | 5.4 | blue | 195 |
| H1 | D1 | 3.5 | 5.3 | blue | 180 |
| H2 | Compound 7 | 3.1 | 6.6 | blue | 410 |
| H2 | Compound 8 | 3.3 | 6.3 | blue | 400 |
| H2 | Compound 9 | 3.3 | 6.0 | blue | 350 |
| H2 | Compound 35 | 3.0 | 6.9 | blue | 450 |
| H2 | Compound 19 | 3.2 | 6.4 | blue | 400 |
| H2 | Compound 55 | 3.4 | 6.1 | blue | 380 |
| H2 | Compound 72 | 3.1 | 6.7 | blue | 420 |
| H2 | D1 | 3.5 | 5.5 | blue | 170 |

In the above test report of organic EL devices (see Table 1), we show that the organic material with formula (1) used as emitting guest material for organic EL devices in the present invention displays better performance than the prior art organic EL materials. More specifically, the organic EL devices of the present invention use the organic material with formula (1) as emitting guest material to collocate with emitting host material, such as H1 and H2, show lower power consumption, higher efficiency, and longer half-life time.

To sum up, the present invention discloses a heteroaromatic compound, which can be used as the fluorescent guest material of the light emitting layer in organic EL devices. The mentioned heteroaromatic compound is represented by the following formula (1):

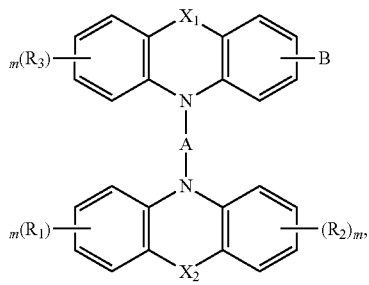

formula (1)

wherein $X_1$ is a divalent bridge selected from the group consisting of O, S, Se, $CR_4R_5$, $NR_6$, and $SiR_7R_8$; $X_2$ is absent or a divalent bridge selected from the group consisting of O, S, Se, $CR_9R_{10}$, $NR_{11}$, and $SiR_{12}R_{13}$; A represents a substituted or unsubstituted fused ring hydrocarbon unit with two to nine rings; m is an integer of 0 to 4; B represents formula (2) below:

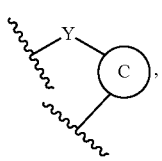

formula (2)

wherein ring C represents a phenyl ring or a fused ring hydrocarbon unit with two to five rings; Y represents a divalent bridge selected from the group consisting of O, S, Se, $CR_{14}R_{15}$, $NR_{16}$, and $SiR_{17}R_{18}$; when $X_2$ is absent, $R_1$ and $R_2$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, a substituted or unsubstituted arylamine group having 6 to 60 carbon atoms, or fused with the connected phenyl group to form a naphthyl group, a dibenzofuranyl group, or a dibenzothiophenyl group; when $X_2$ is a divalent bridge selected from the group consisting of O, S, Se, $CR_9R_{10}$, $NR_{11}$, and $SiR_{12}R_{13}$, $R_1$ and $R_2$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, or a substituted or unsubstituted arylamine group having 6 to 60 carbon atoms; and $R_3$ to $R_{18}$ are independently a hydrogen atom, a substituted or unsubstituted alkyl group having 1 to 60 carbon atoms, a substituted or unsubstituted aryl group having 6 to 60 carbon atoms, a substituted or unsubstituted aralkyl group having 6 to 60 carbon atoms, a substituted or unsubstituted heteroaryl group having 3 to 60 carbon atoms, or a substituted or unsubstituted arylamine group having 6 to 60 carbon atoms.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A heteroaromatic compound of formula (1) below:

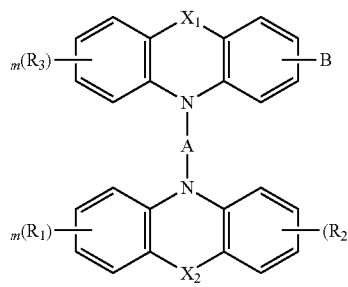

formula (1)

wherein $X_1$ is a divalent bridge selected from the group consisting of O, S, Se, $CR_4R_5$, $NR_6$, and $SiR_7R_8$; $X_2$ is absent or a divalent bridge selected from the group consisting of O, S, Se, $CR_9R_{10}$, $NR_{11}$, and $SiR_{12}R_{13}$; A represents an unsubstituted fused ring hydrocarbon unit with two to nine rings; m is an integer of 0 to 4; B represents formula (2) below:

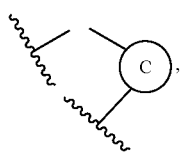

formula (2)

wherein ring C represents a phenyl ring or a fused ring hydrocarbon unit with two to five rings; Y represents a divalent bridge selected from the group consisting of O, S, Se, $CR_{14}R_{15}$, $NR_{16}$, and $SiR_{17}R_{18}$; when $X_2$ is absent, $R_1$ and $R_2$ are independently a hydrogen atom, an unsubstituted alkyl group having 1 to 60 carbon atoms, an unsubstituted aryl group having 6 to 60 carbon atoms, an unsubstituted aralkyl group having 6 to 60 carbon atoms, an unsubstituted heteroaryl group having 3 to 60 carbon atoms, an unsubstituted arylamine group having 6 to 60 carbon atoms, or fused with the connected phenyl group to form a naphthyl group, a dibenzofuranyl group, or a dibenzothiophenyl group; when $X_2$ is a divalent bridge selected from the group consisting of O, S, Se, $CR_9R_{10}$, $NR_{11}$, and $SiR_{12}R_{13}$, $R_1$ and $R_2$ are independently a hydrogen atom, an unsubstituted alkyl group having 1 to 60 carbon atoms, an unsubstituted aryl group having 6 to 60 carbon atoms, an unsubstituted aralkyl group having 6 to 60 carbon atoms, an unsubstituted heteroaryl group having 3 to 60 carbon atoms, or an unsubstituted arylamine group having 6 to 60 carbon atoms; and $R_3$ to $R_{18}$ are independently a hydrogen atom, an unsubstituted alkyl group having 1 to 60 carbon atoms, an unsubstituted aryl group having 6 to 60 carbon atoms, an unsubstituted aralkyl group having 6 to 60 carbon atoms, an unsubstituted heteroaryl group having 3 to 60 carbon atoms, or an unsubstituted arylamine group having 6 to 60 carbon atoms.

2. The heteroaromatic compound according to claim 1, wherein A represents an unsubstituted naphthyl group, an unsubstituted phenanthrenyl group, an unsubstituted anthracenyl group, an unsubstituted pyrenyl group, an unsubstituted chrysenyl group, an unsubstituted triphenylenyl group, an unsubstituted perylenyl group, an unsubstituted tetraphenylenyl group, or an unsubstituted 7,14-diphenylacenaphtho[1,2-k]fluoranthene group.

3. The heteroaromatic compound according to claim 1, wherein A represents one of the following formulas:

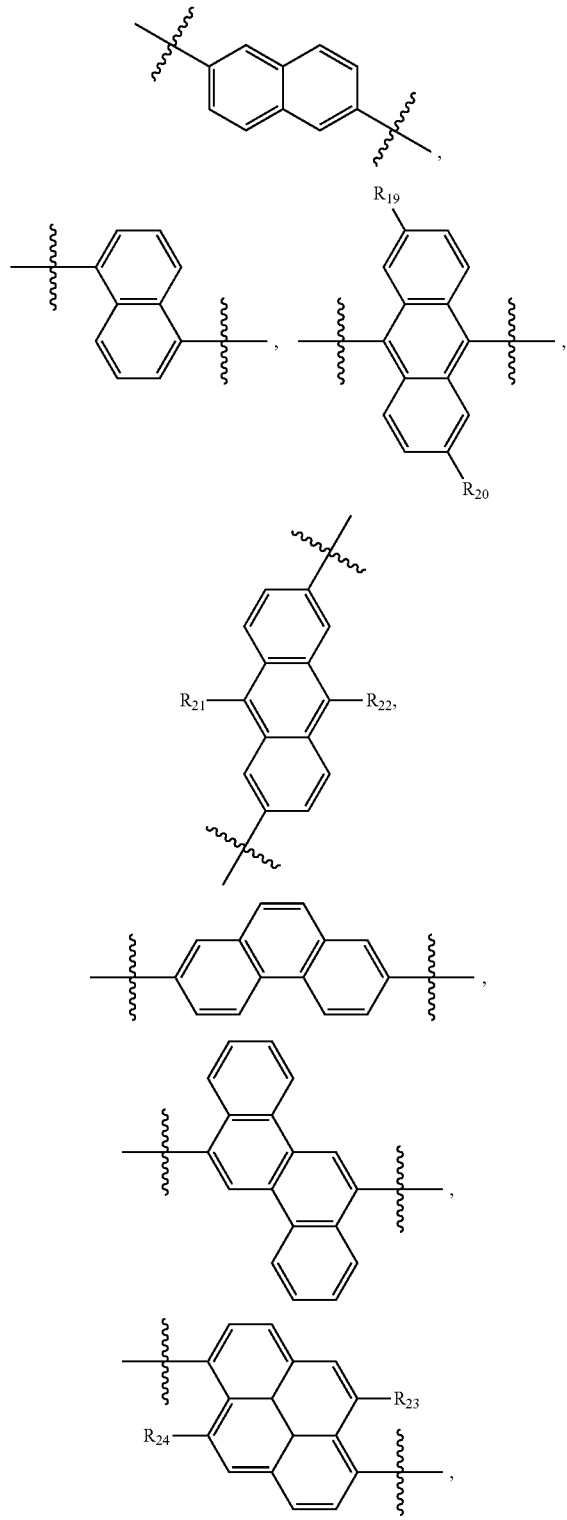

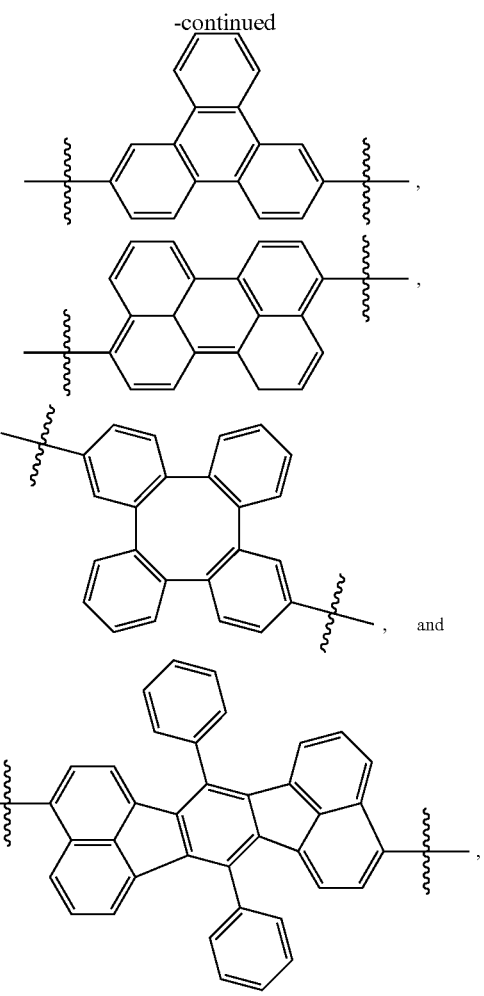

wherein $R_{19}$ to $R_{24}$ are independently a hydrogen atom, an unsubstituted alkyl group having 1 to 30 carbon atoms, an unsubstituted aryl group having 6 to 30 carbon atoms, an unsubstituted aralkyl group having 6 to 30 carbon atoms, an unsubstituted heteroaryl group having 3 to 30 carbon atoms, or an unsubstituted arylamine group having 6 to 30 carbon atoms.

4. The heteroaromatic compound according to claim 1, wherein the heteroaromatic compound is represented by one of the following formula (3) to formula (13):

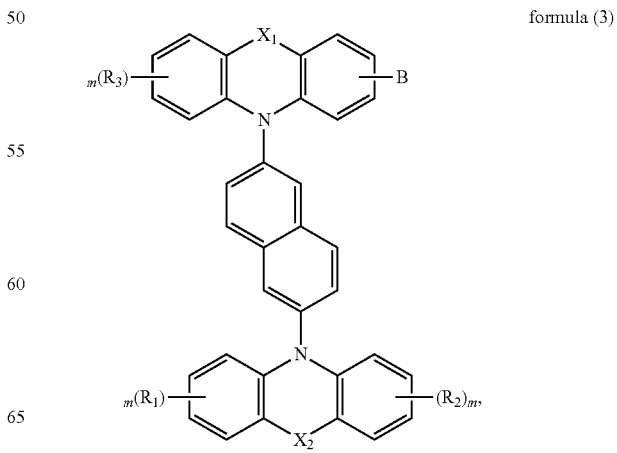

formula (3)

formula (4)
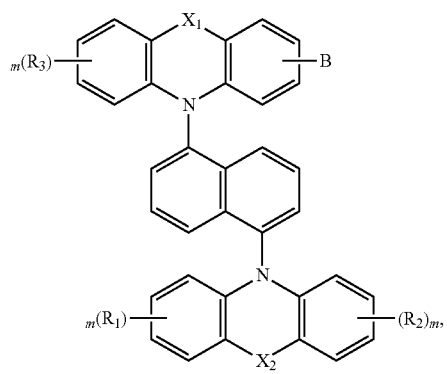
formula (5)
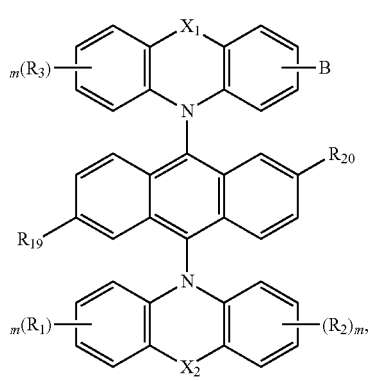
formula (6)
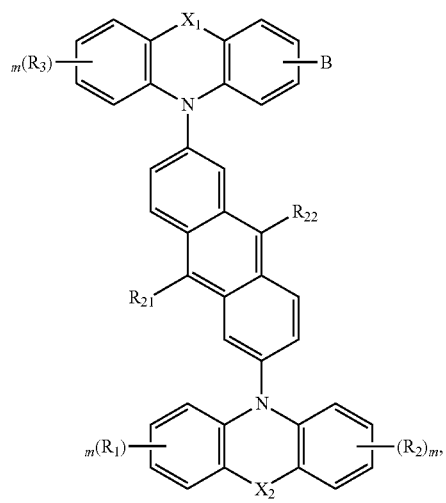
formula (7)
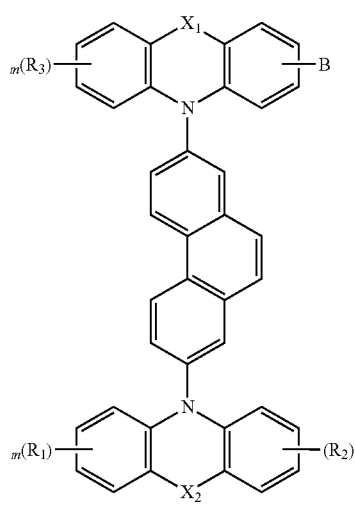
formula (8)
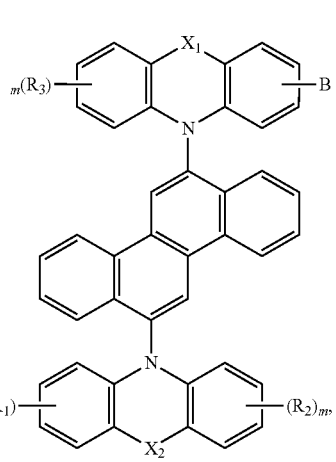
formula (9)
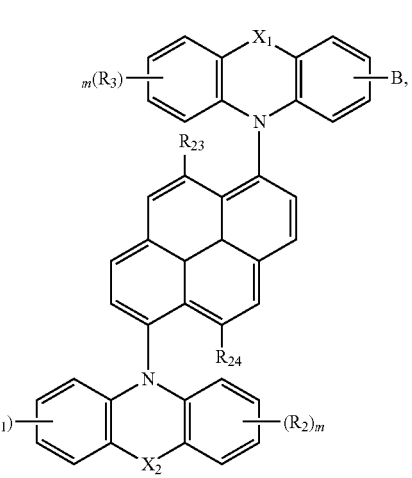

-continued
formula (10)
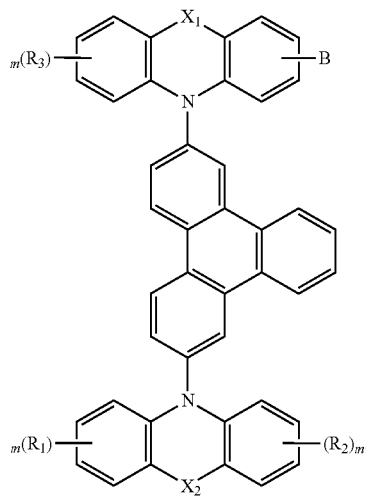
formula (11)
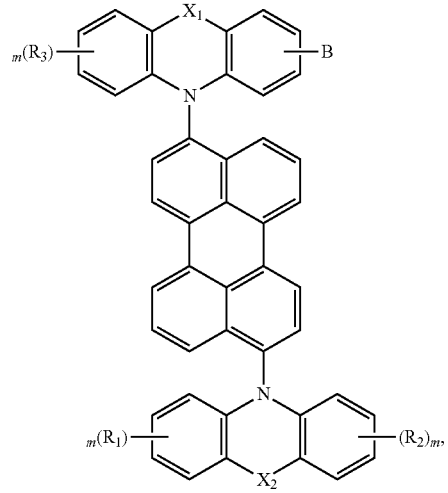
formula (12)
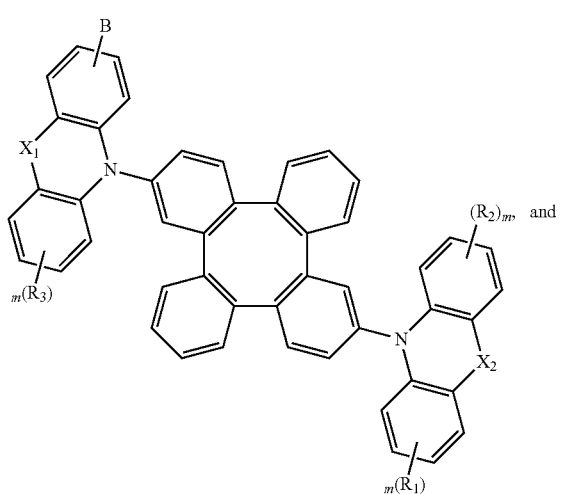
-continued
formula (13)
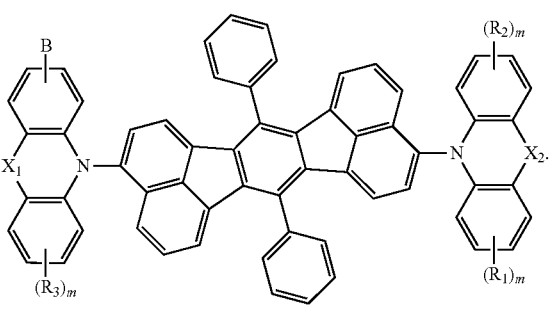
5. A heteroaromatic compound selected from the group consisting of compound 1 to compound 358:
Compound 1
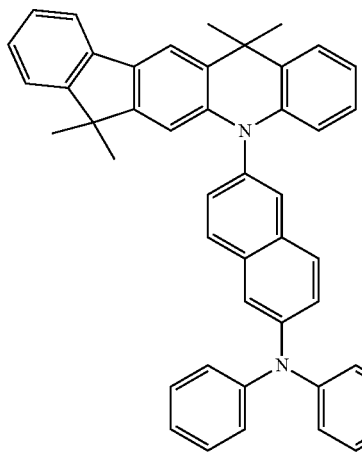
Compound 2
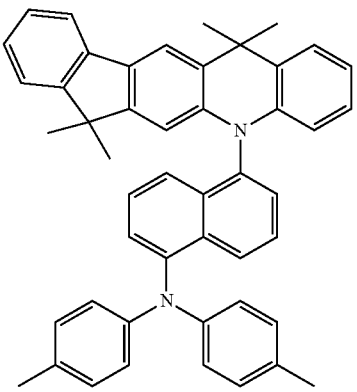
Compound 3
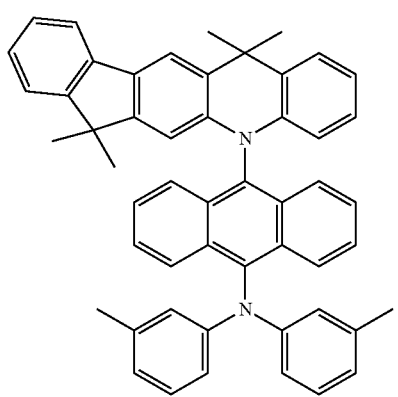

-continued
Compound 4
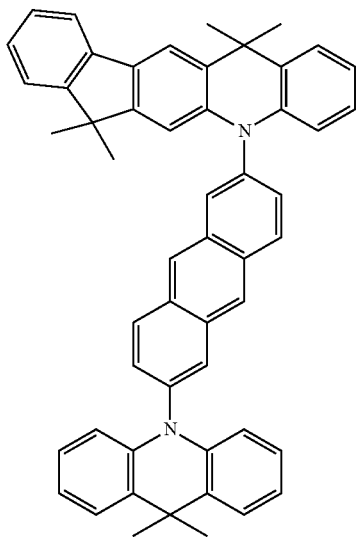
Compound 5
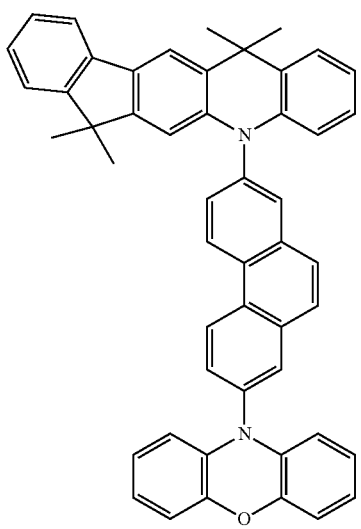
Compound 6
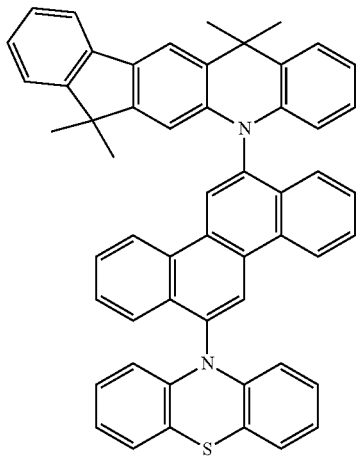
Compound 7
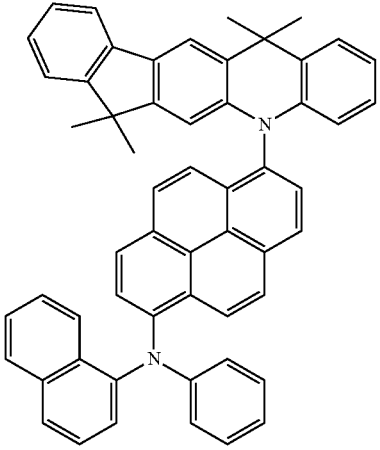
Compound 8
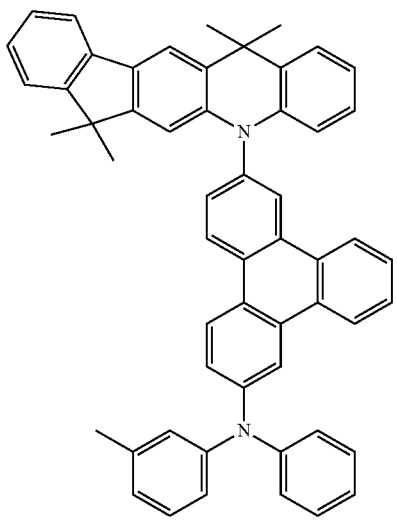
Compound 9
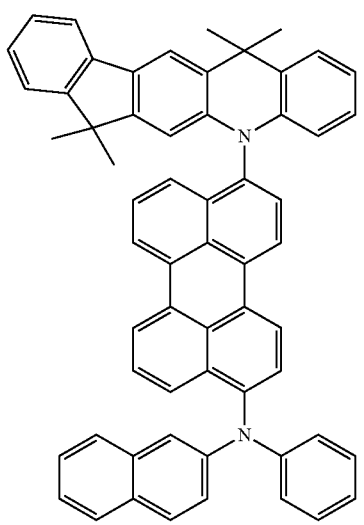

-continued
Compound 10
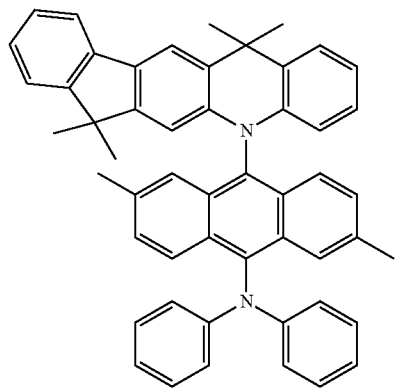
Compound 11
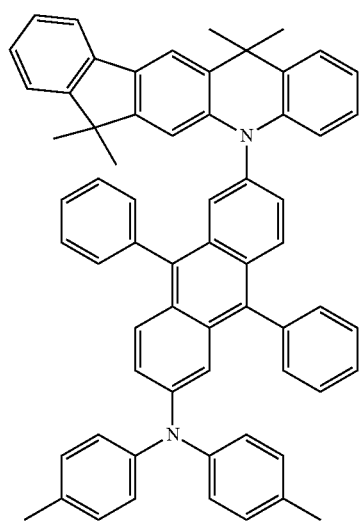
Compound 12
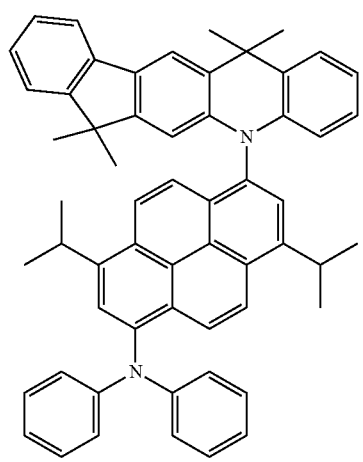
-continued
Compound 13
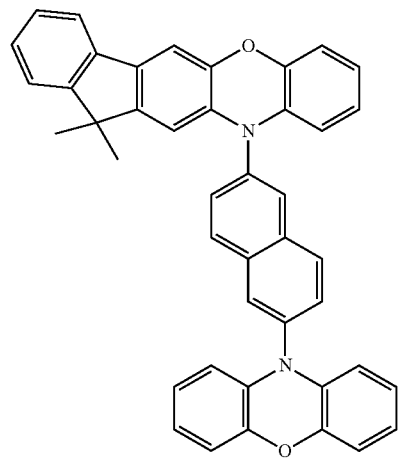
Compound 14
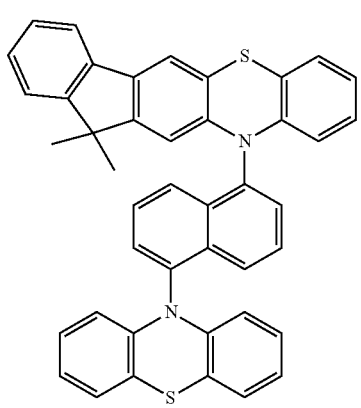
Compound 15
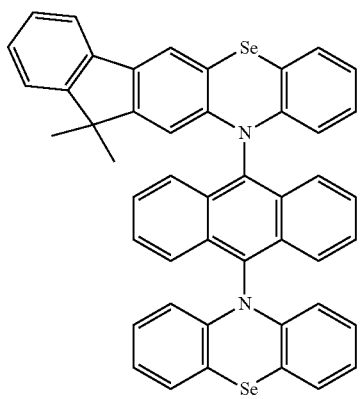

Compound 16
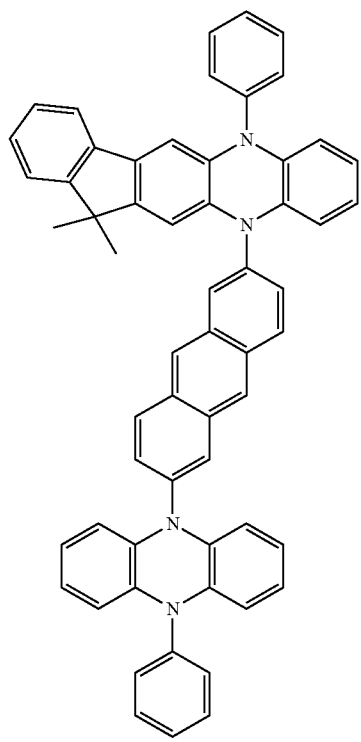
Compound 17
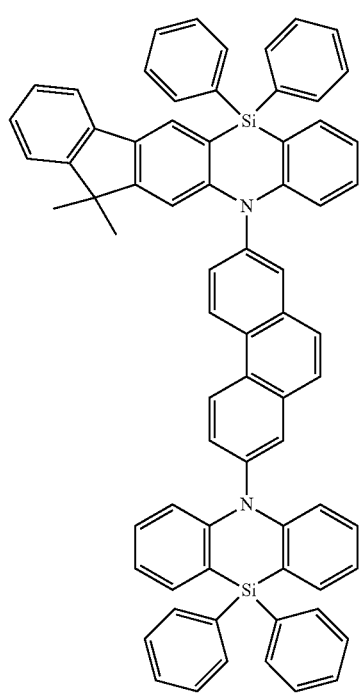
Compound 18
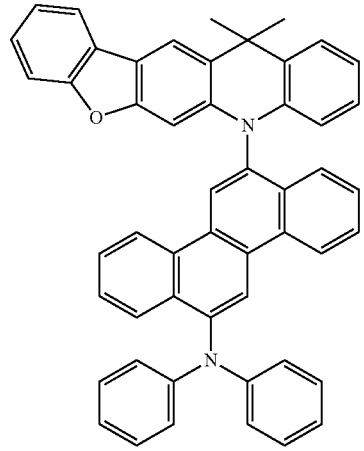
Compound 19
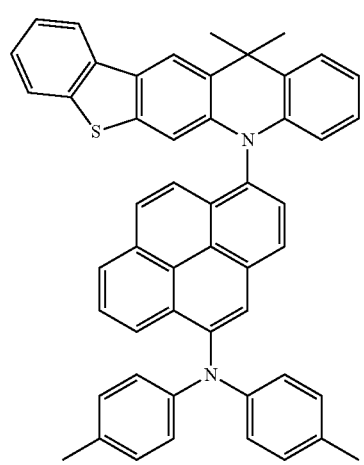
Compound 20
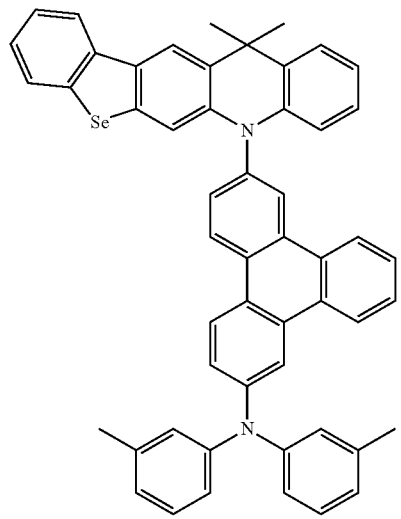

-continued
Compound 21
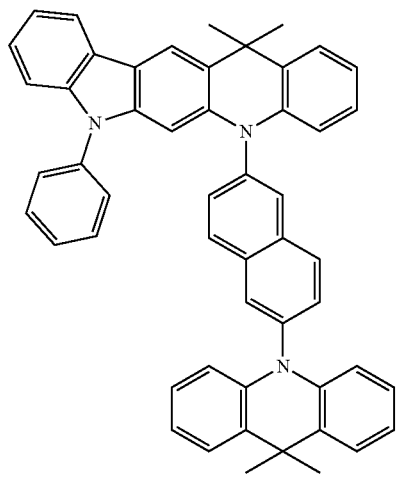
Compound 22
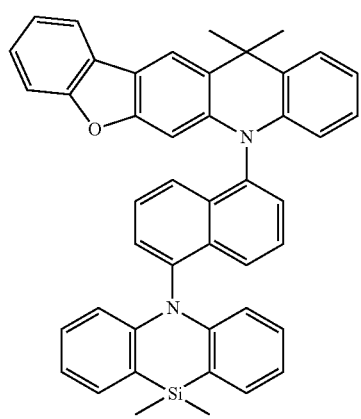
Compound 23
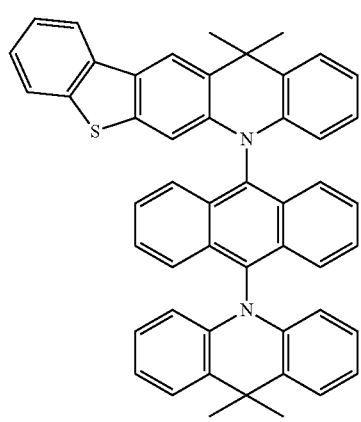
-continued
Compound 24
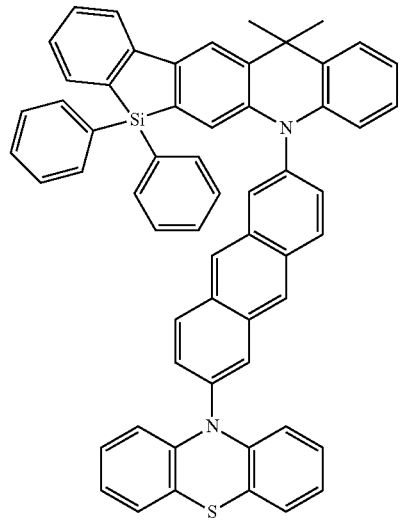
Compound 25
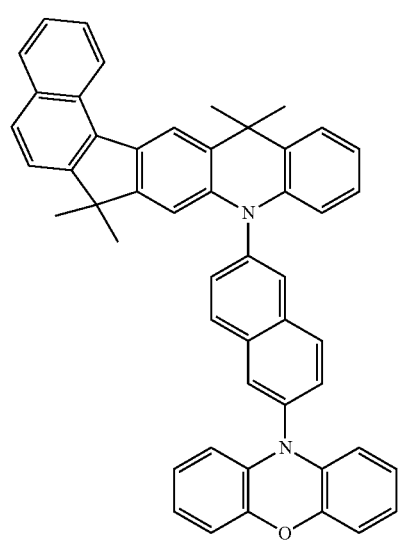
Compound 26
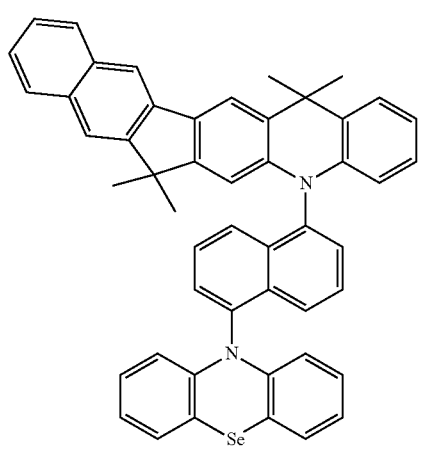

Compound 27
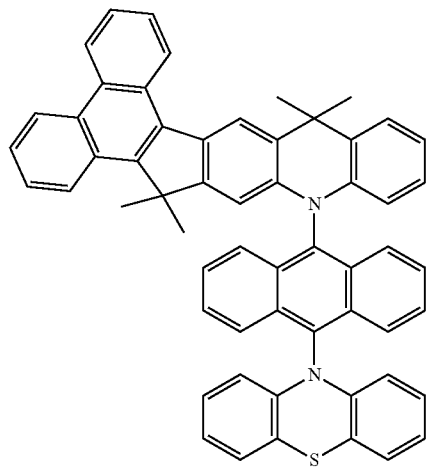
Compound 29
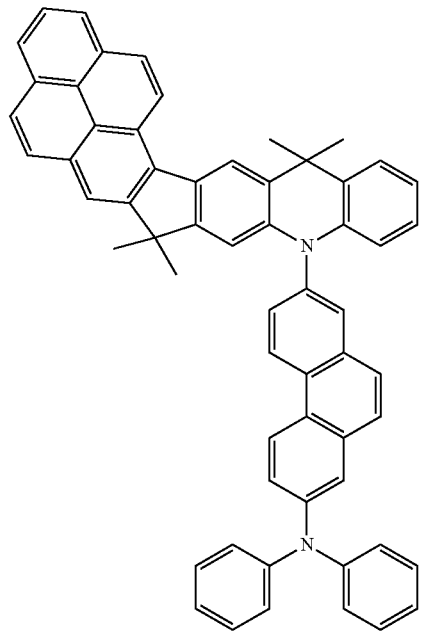
Compound 28
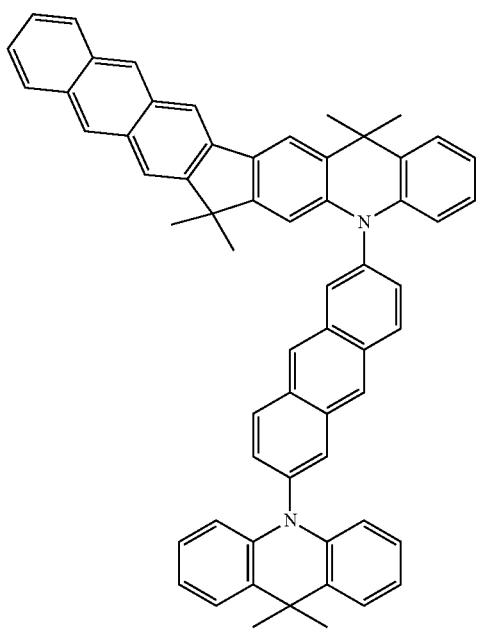
Compound 30
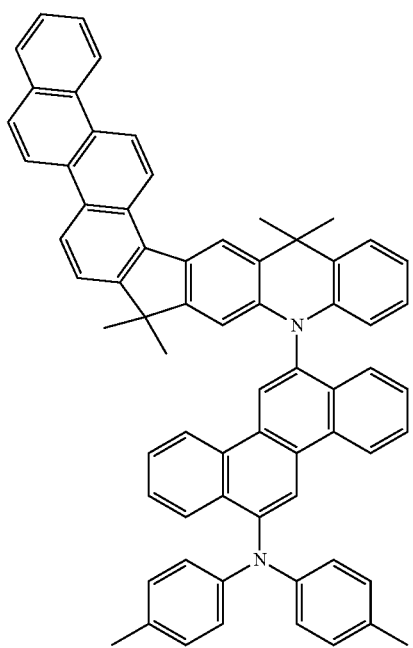

Compound 31
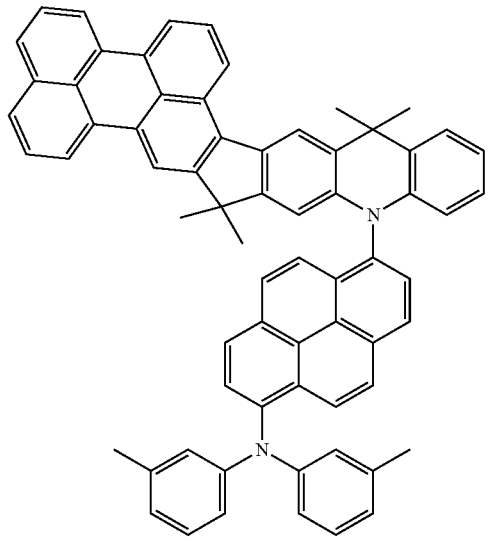
Compound 32
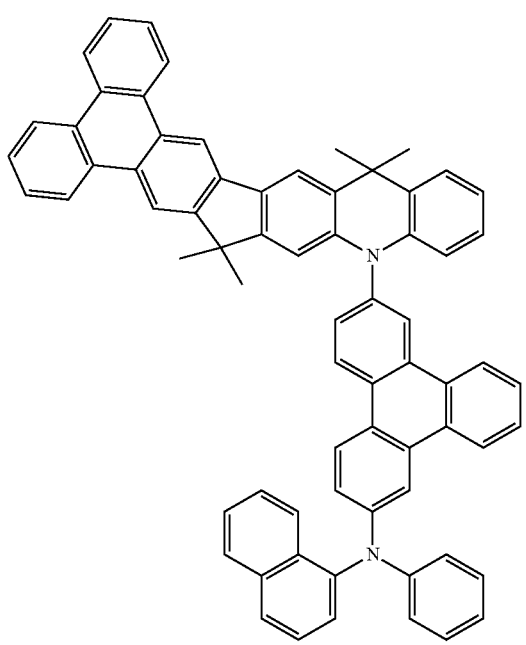
Compound 33
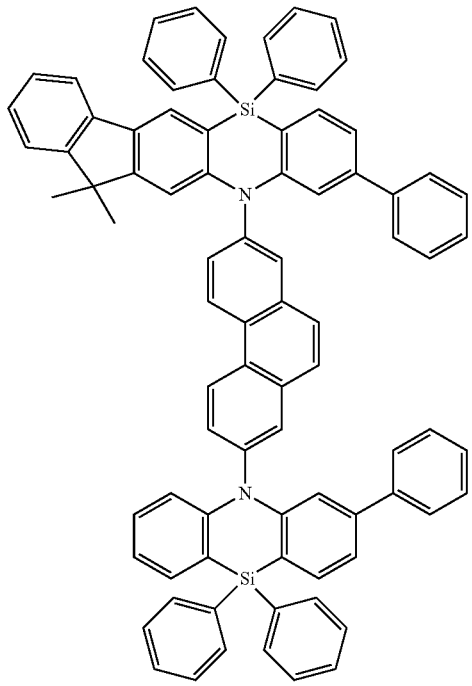
Compound 34
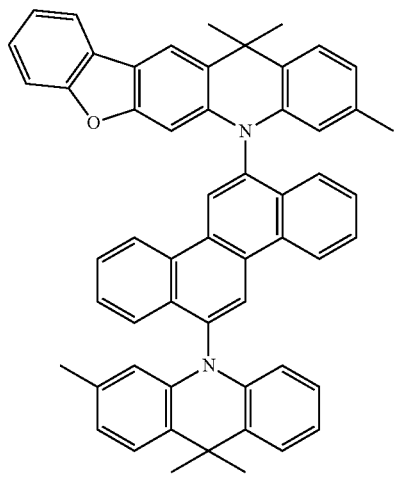
Compound 35
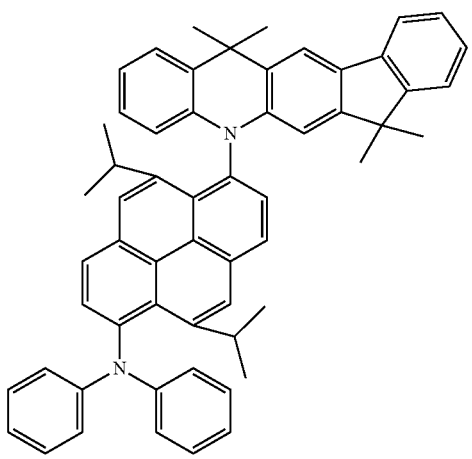

Compound 36
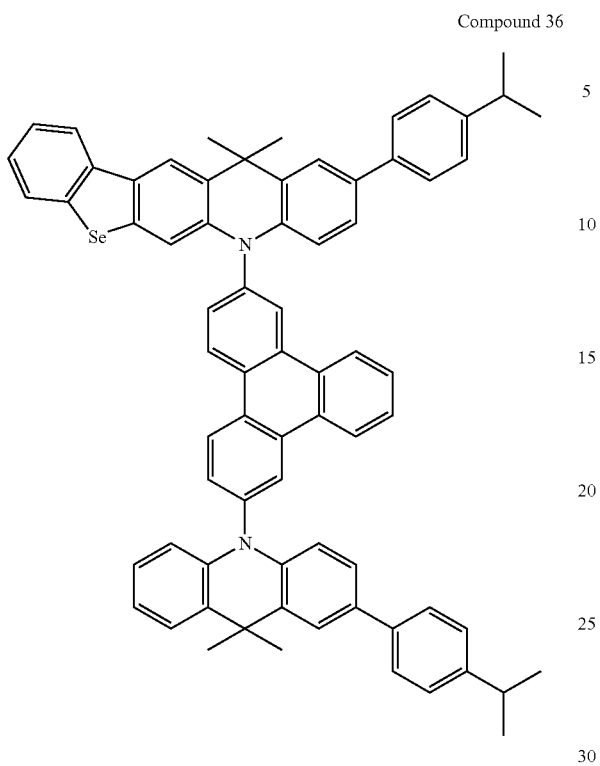
Compound 37
Compound 38
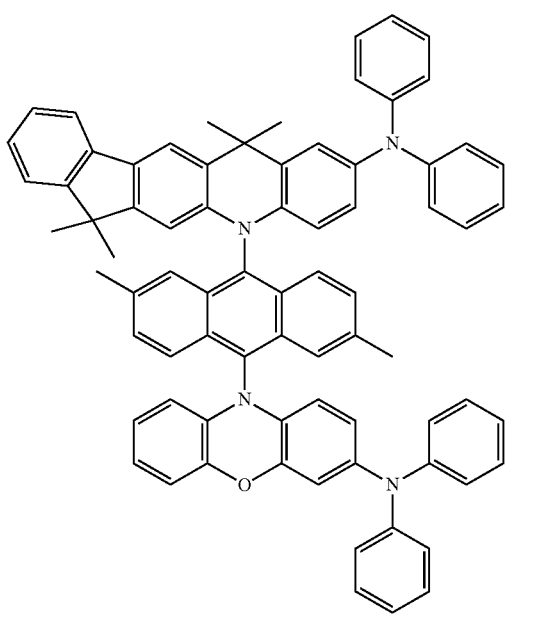
Compound 39
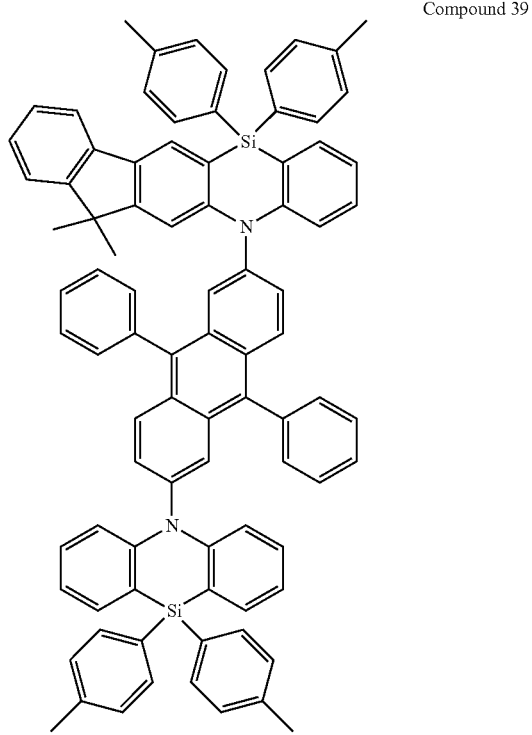

Compound 40
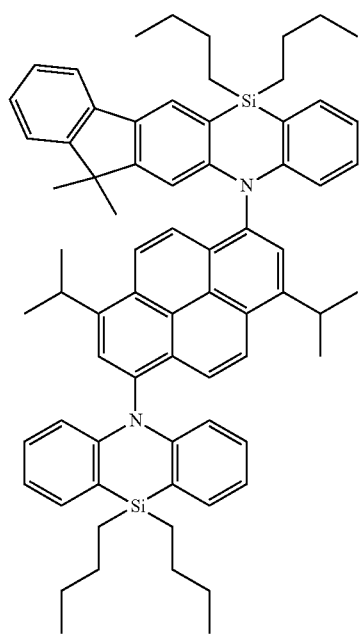
Compound 41
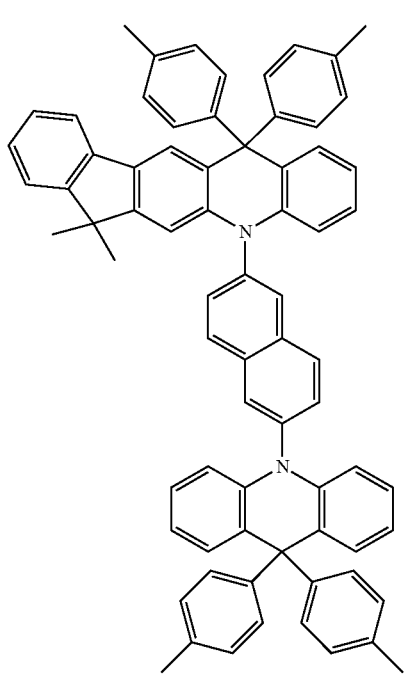
Compound 42
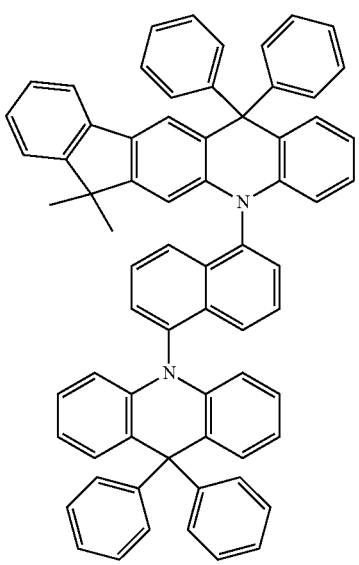
Compound 43
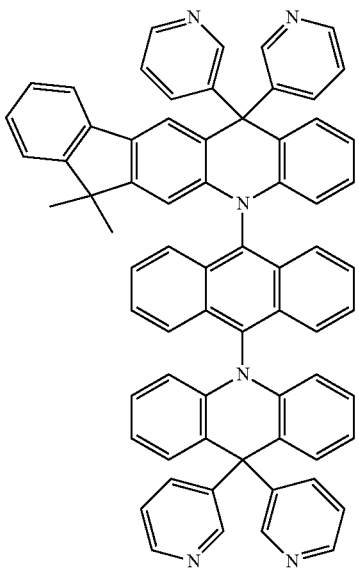

Compound 44
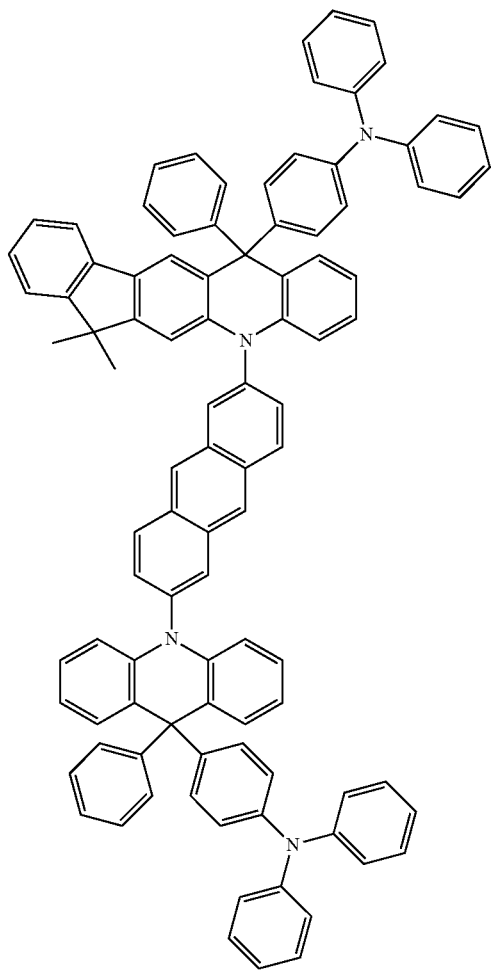
Compound 45
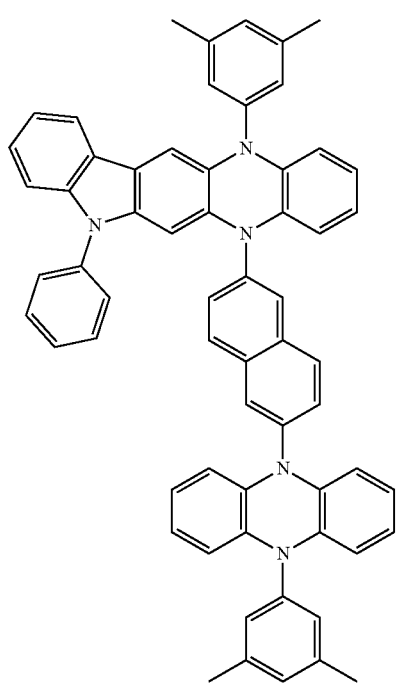
Compound 46
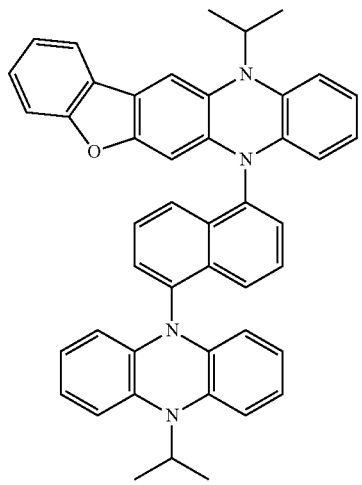
Compound 47
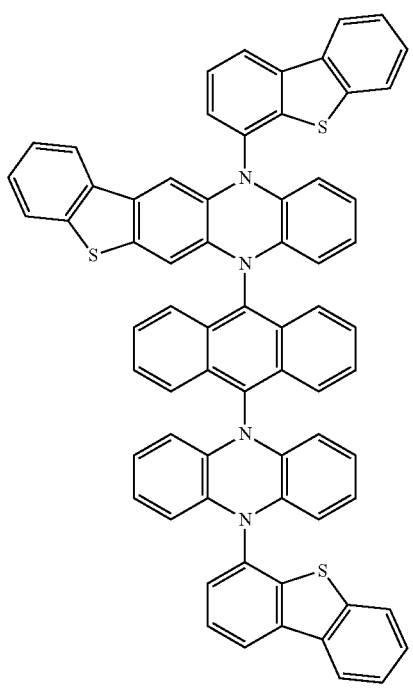

Compound 48
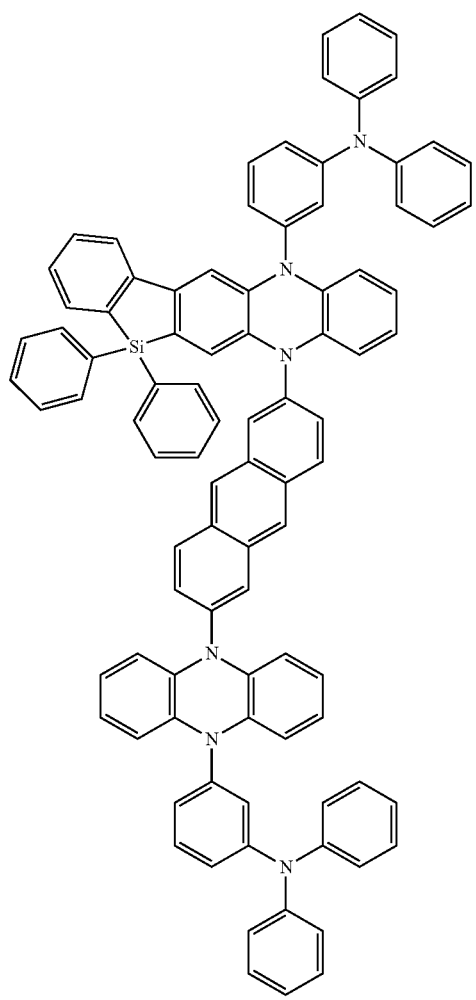
Compound 50
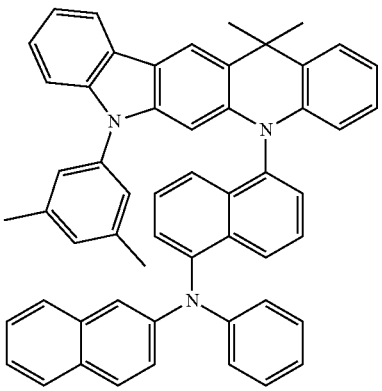
Compound 51
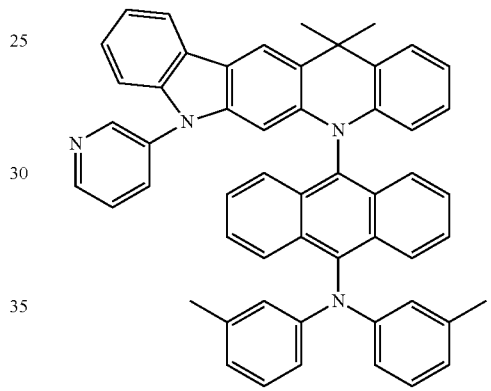
Compound 49
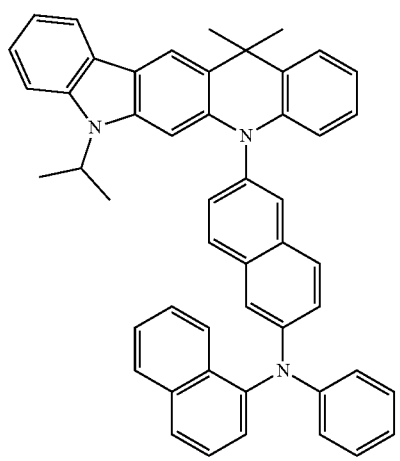
Compound 52
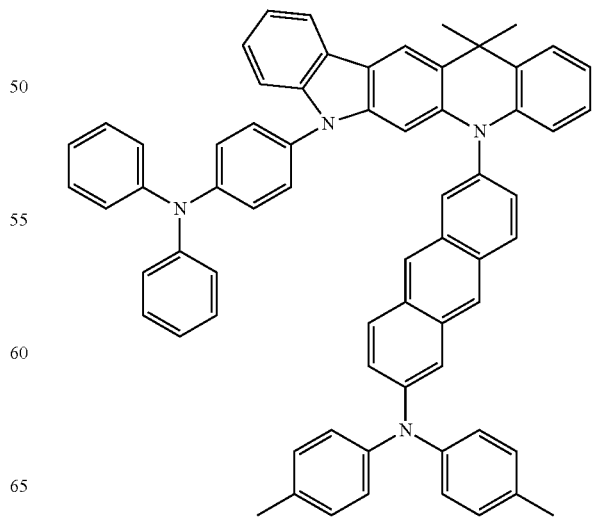

Compound 53
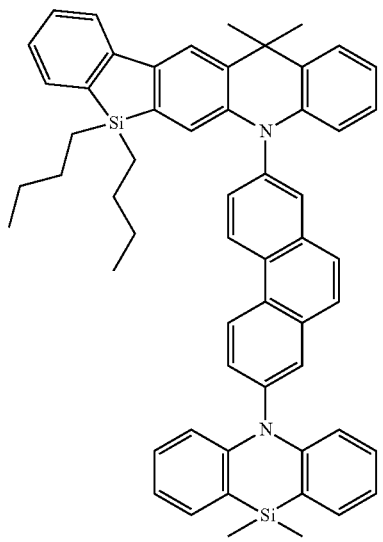
Compound 54
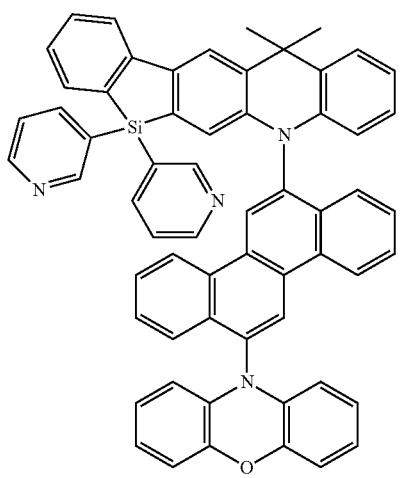
Compound 55
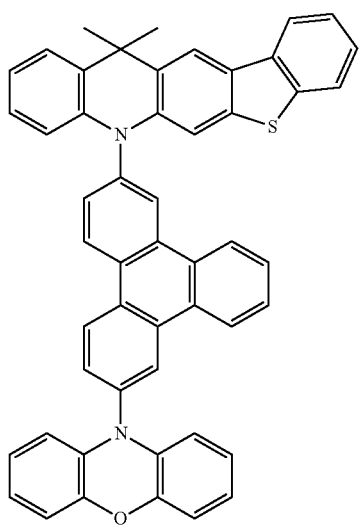
Compound 56
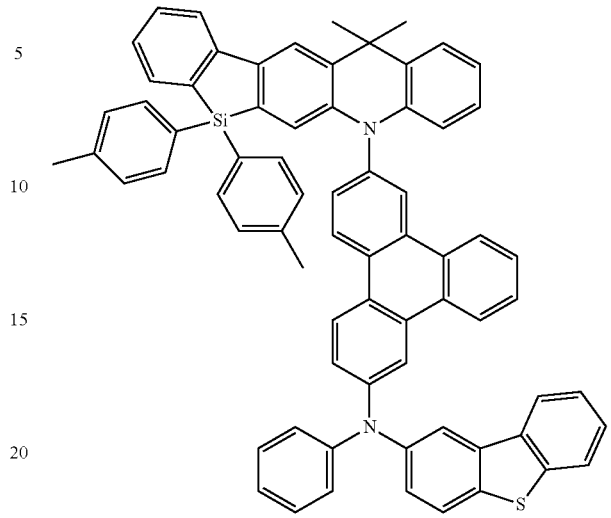
Compound 57
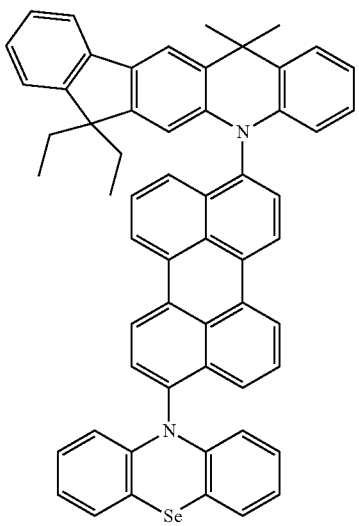
Compound 58
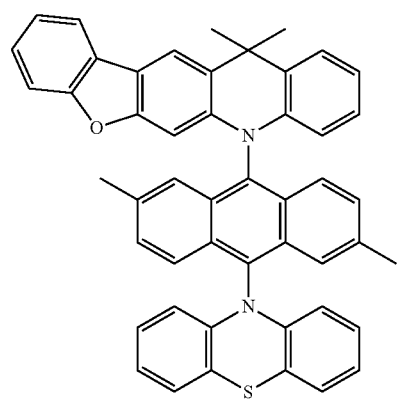

Compound 59
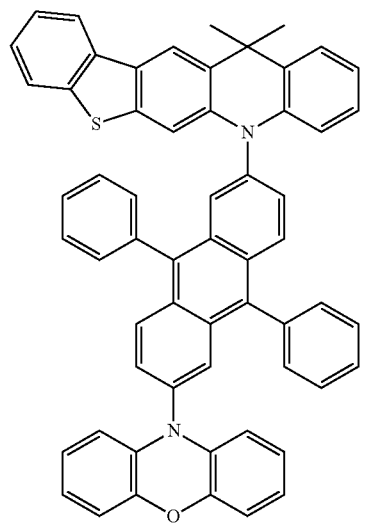
Compound 60
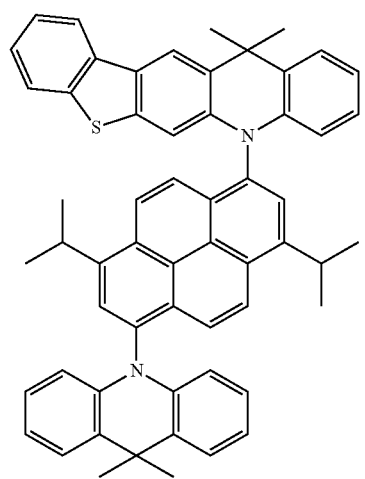
Compound 61
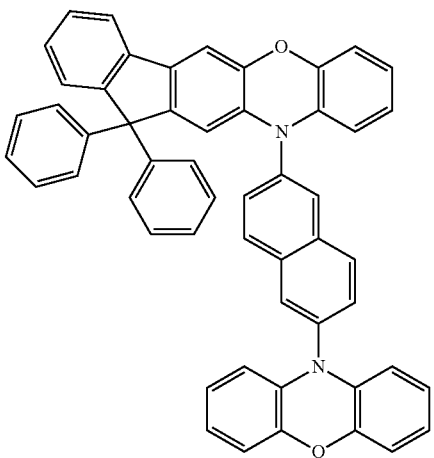
Compound 62
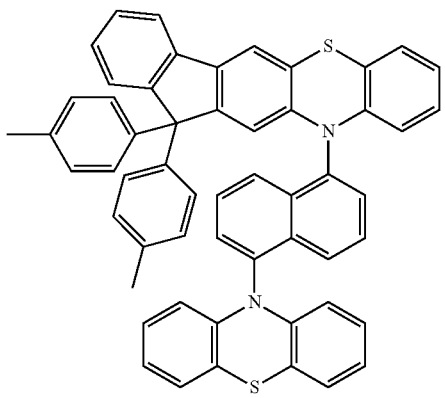
Compound 63
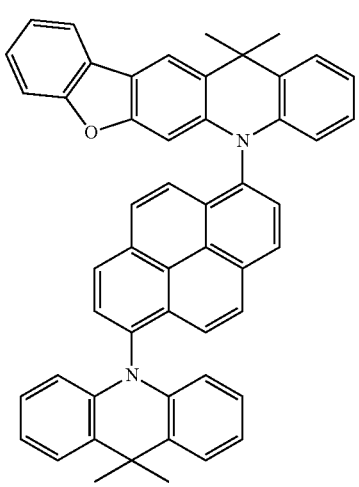
Compound 64
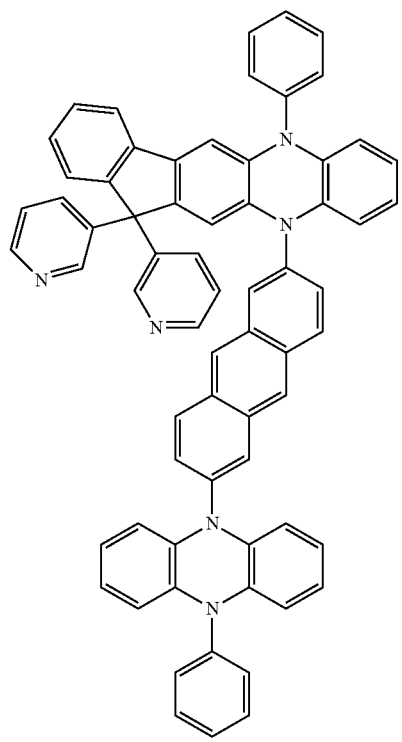

Compound 65
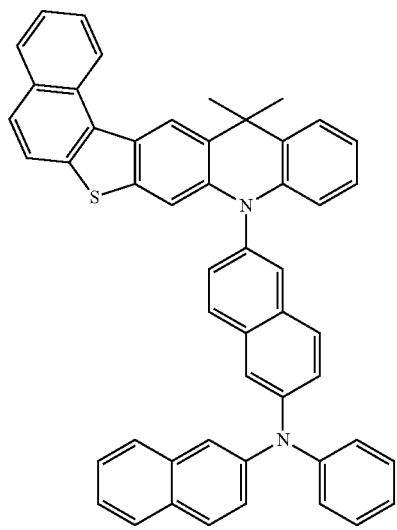
Compound 66
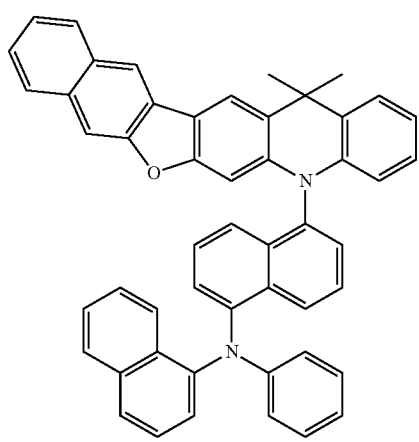
Compound 67
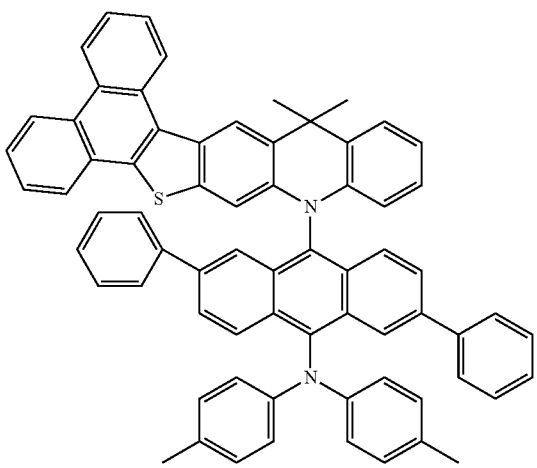
Compound 68
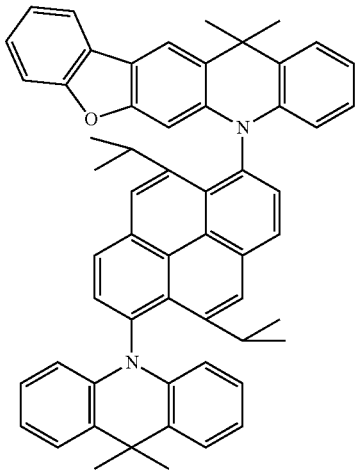
Compound 69
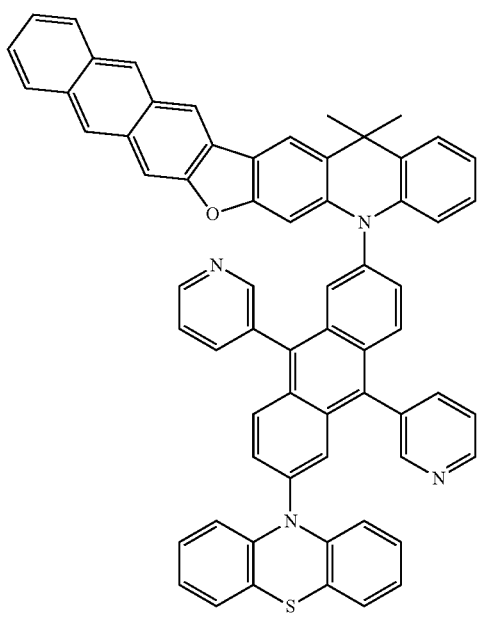

Compound 70
Compound 71
Compound 72
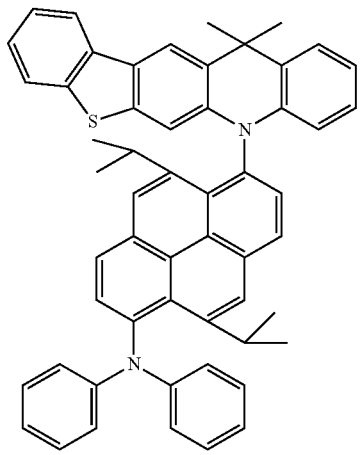
Compound 73
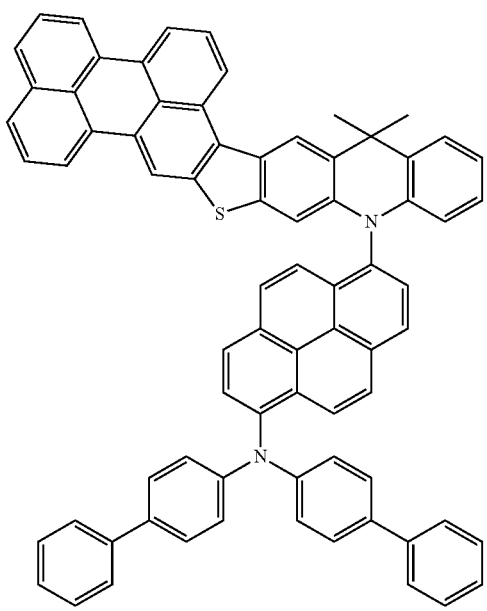
Compound 74
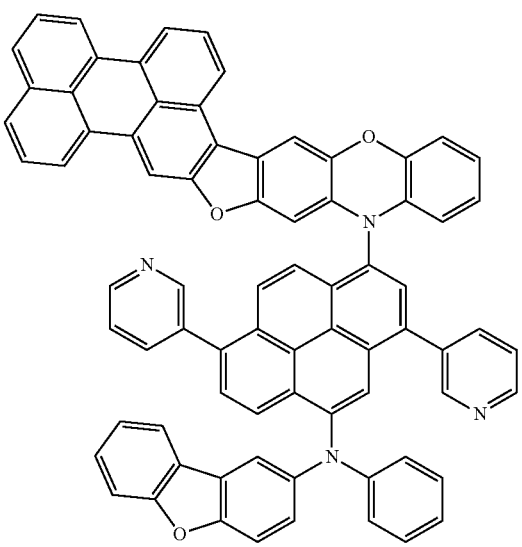

Compound 75
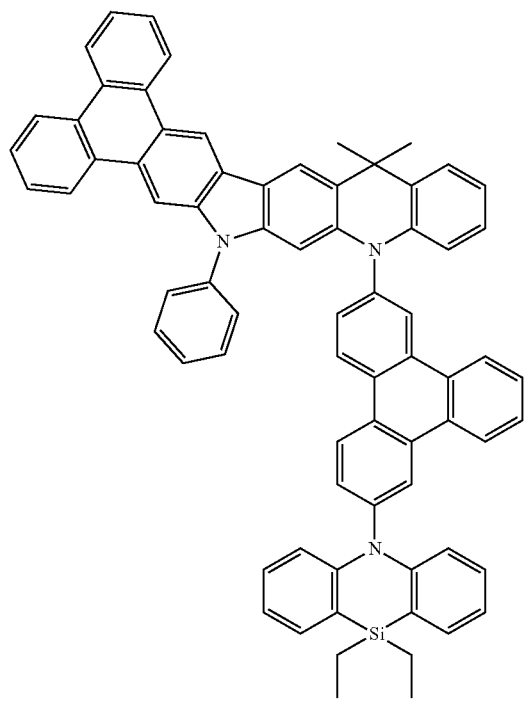
Compound 76
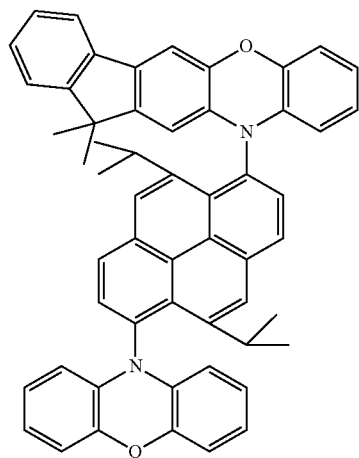
Compound 77
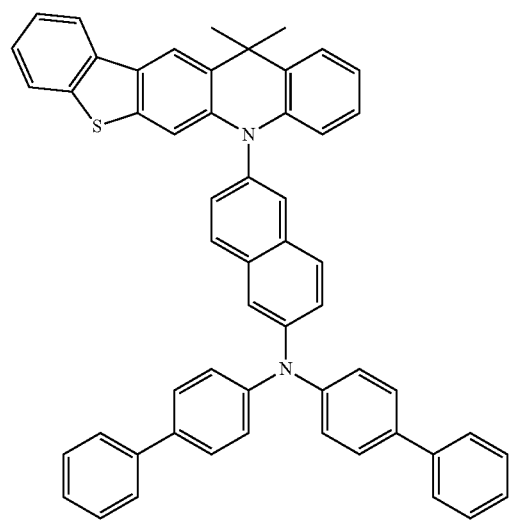
Compound 78
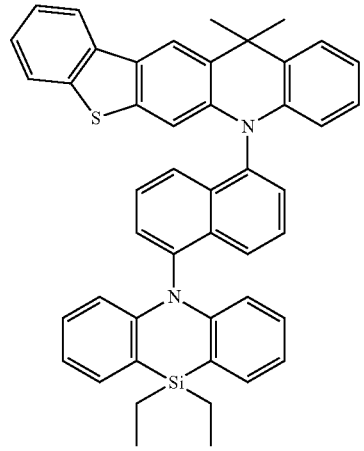
Compound 79
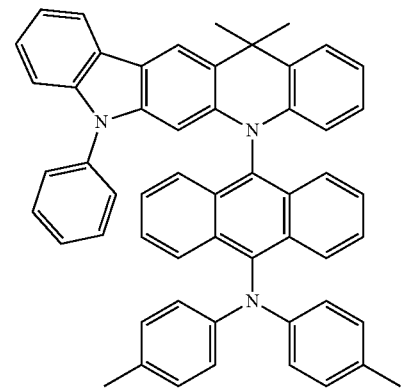

Compound 80
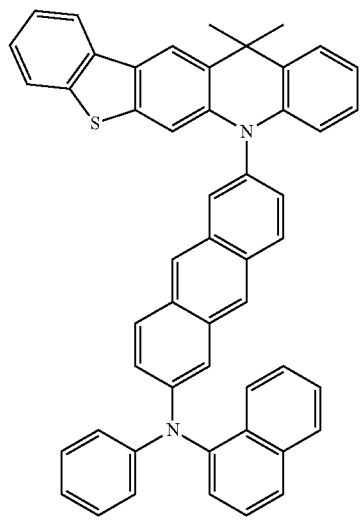
Compound 83
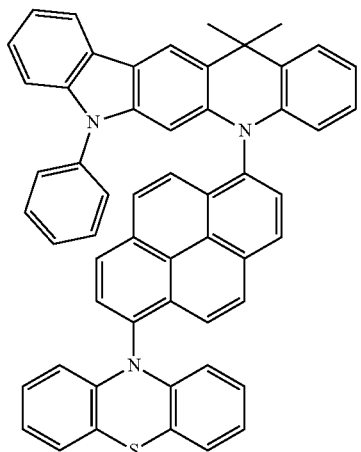
Compound 81
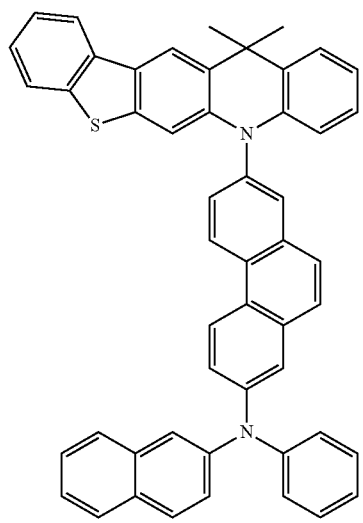
Compound 84
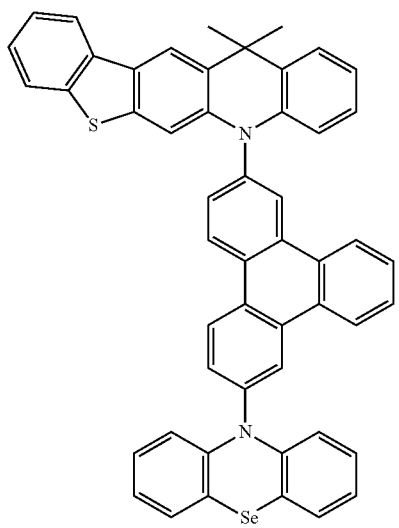
Compound 82
Compound 85
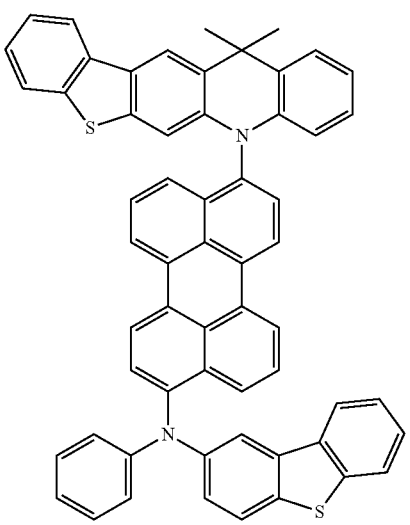

Compound 86
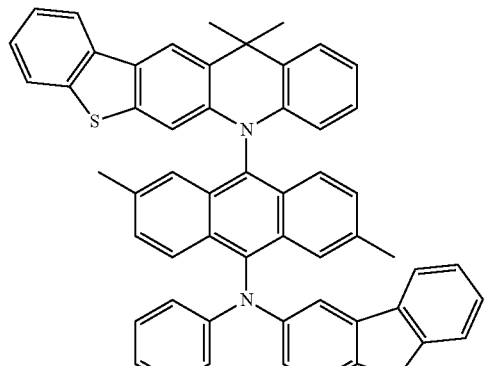
Compound 87
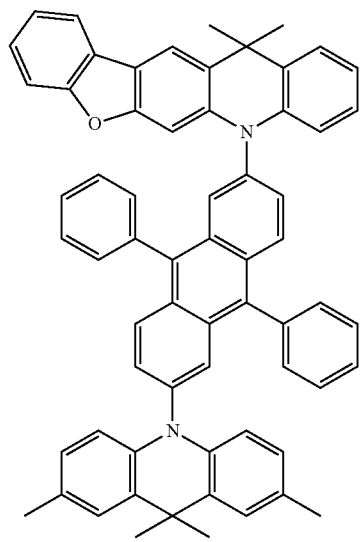
Compound 88
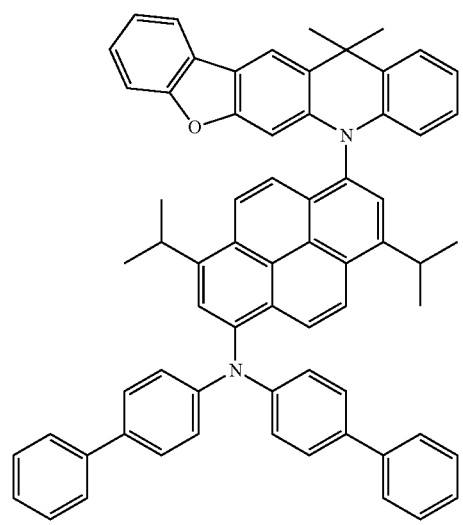
Compound 89
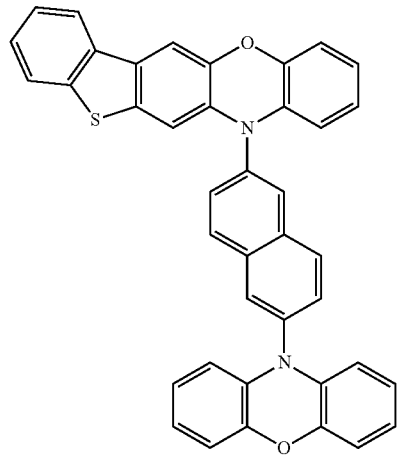
Compound 90
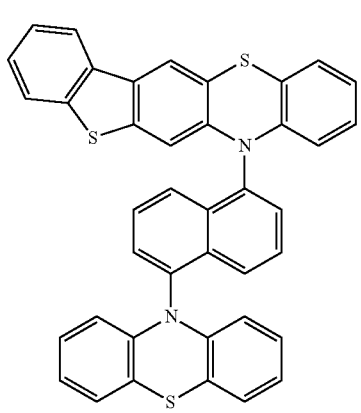
Compound 91
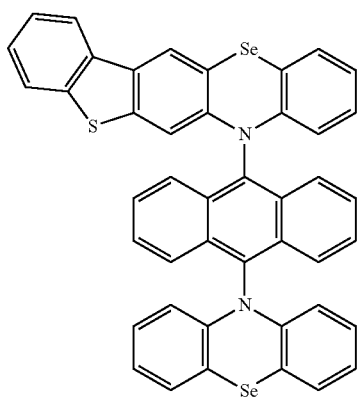

Compound 92
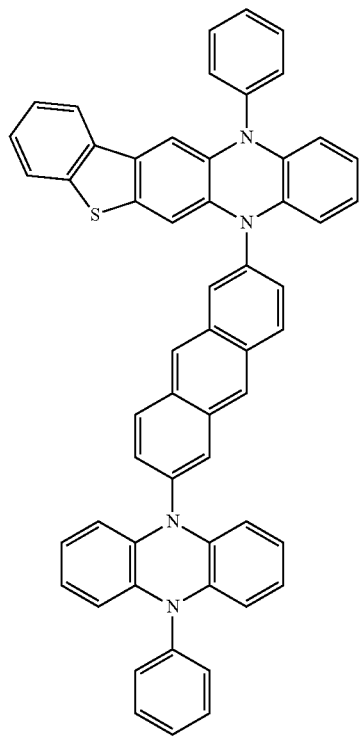
Compound 93
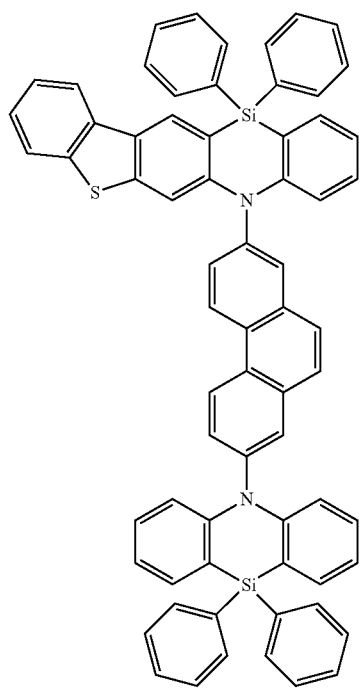
Compound 94
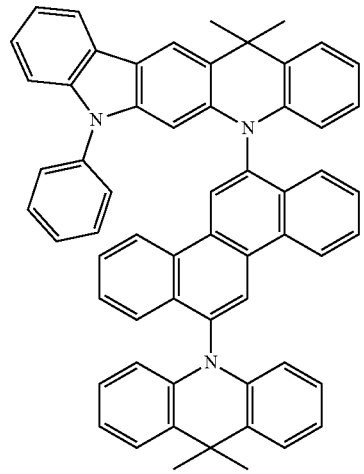
Compound 95
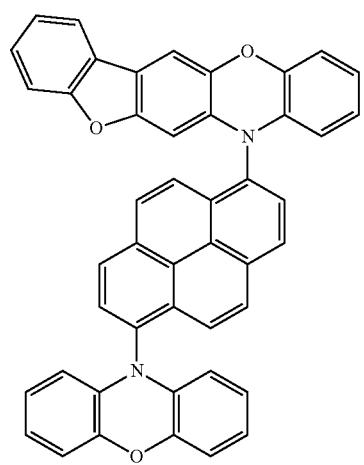
Compound 96
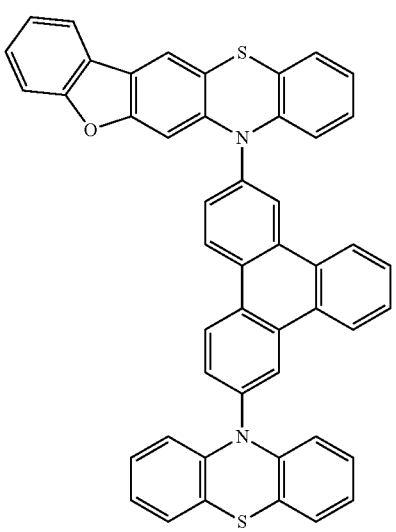

Compound 97
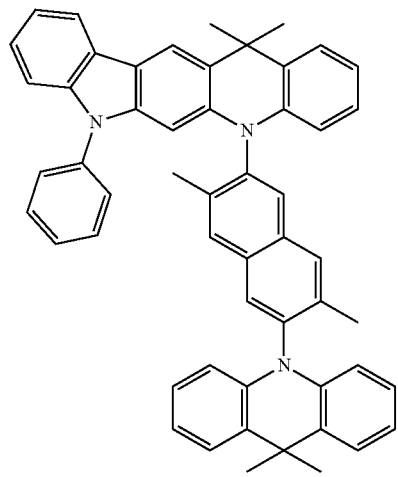
Compound 98
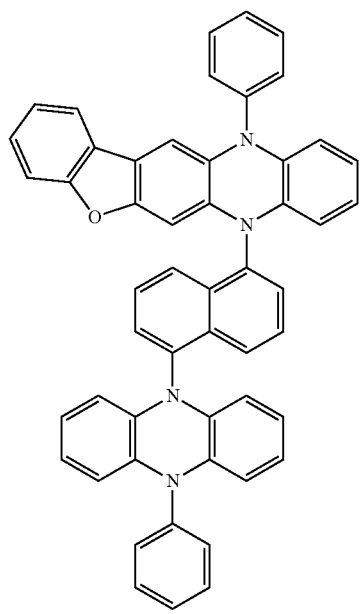
Compound 99
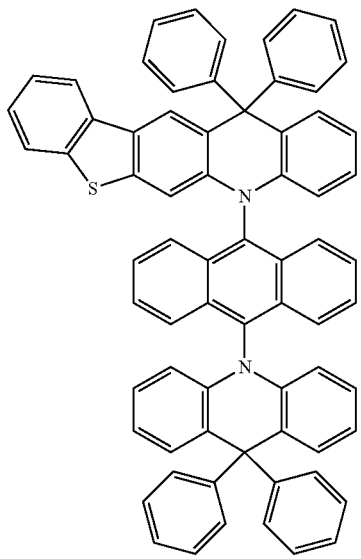
Compound 100
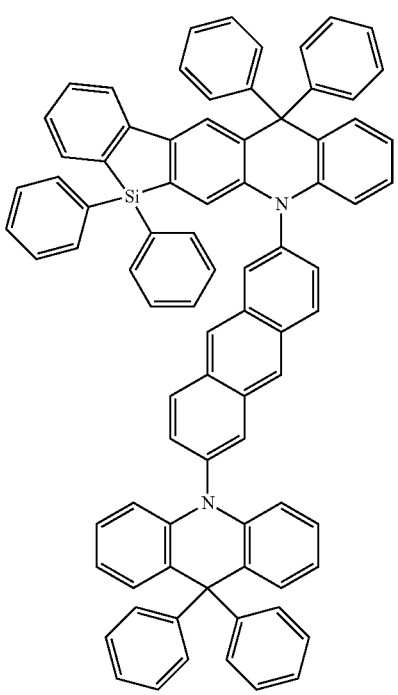

Compound 101
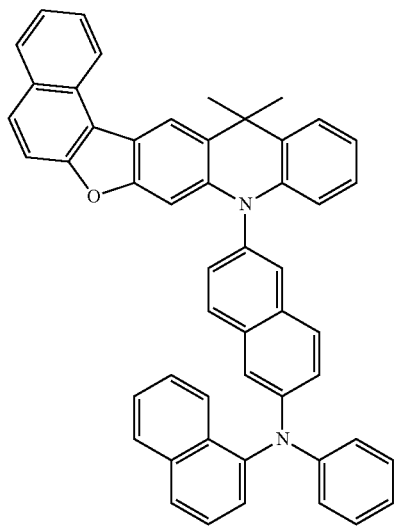
Compound 102
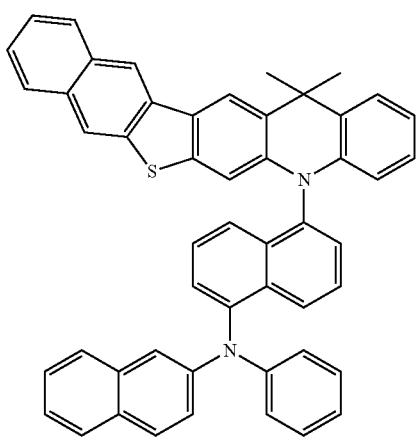
Compound 103
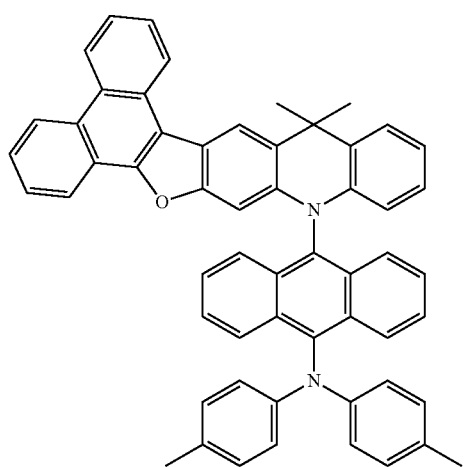
Compound 104
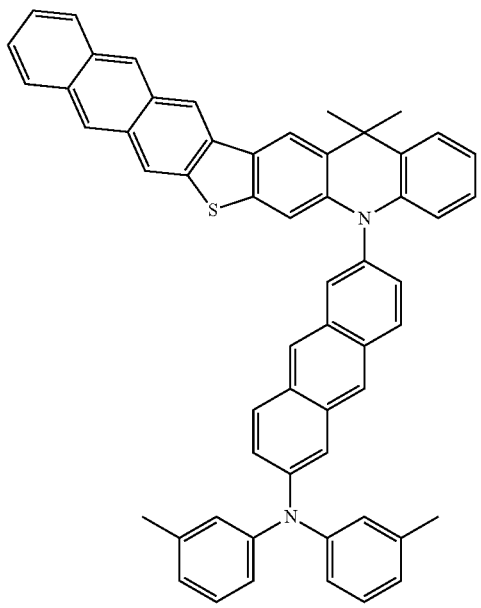
Compound 105
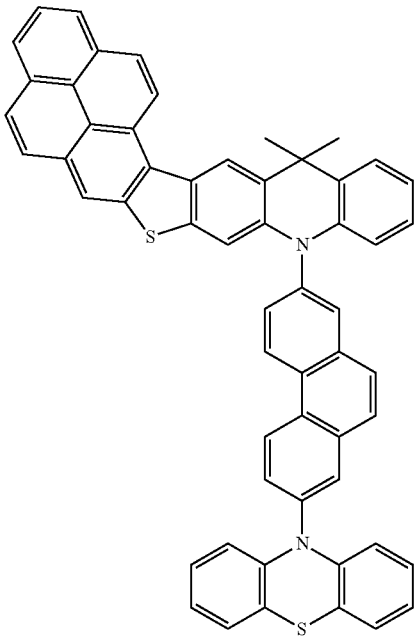

Compound 106
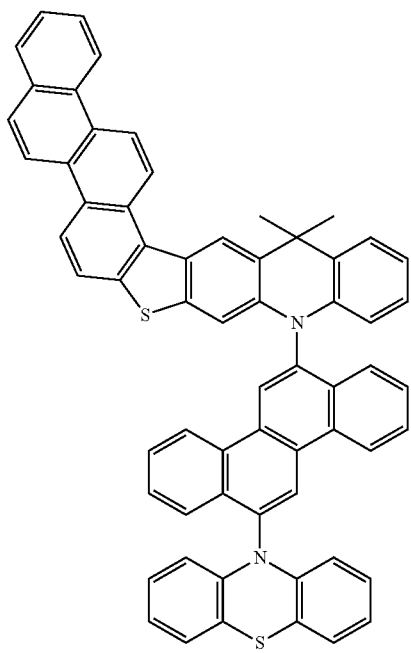
Compound 108
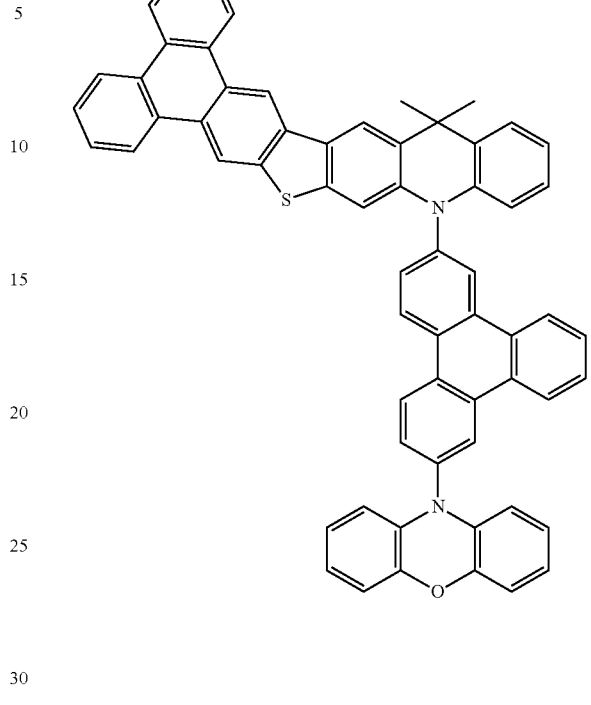
Compound 107
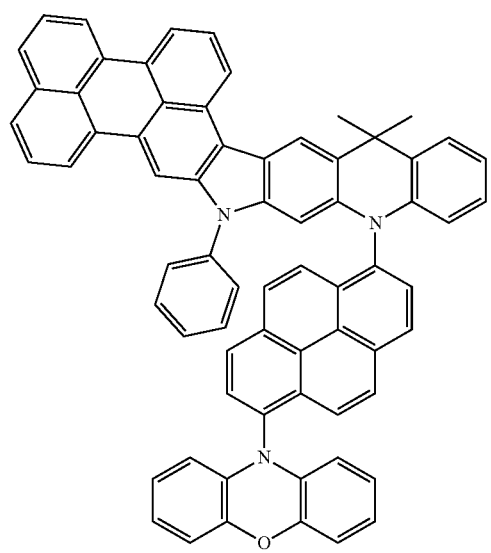
Compound 109
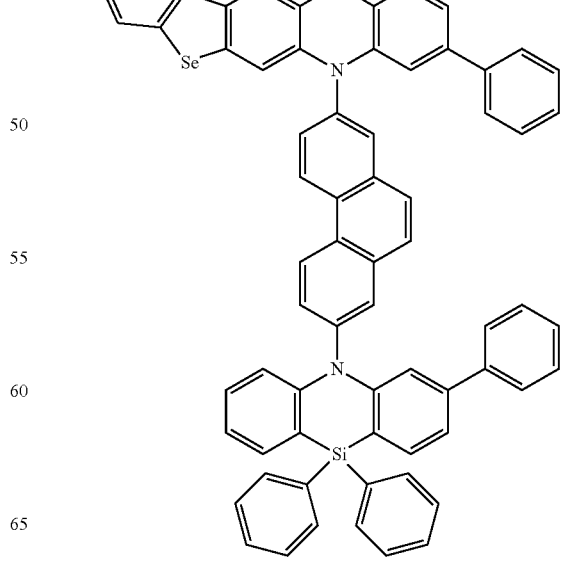

Compound 110
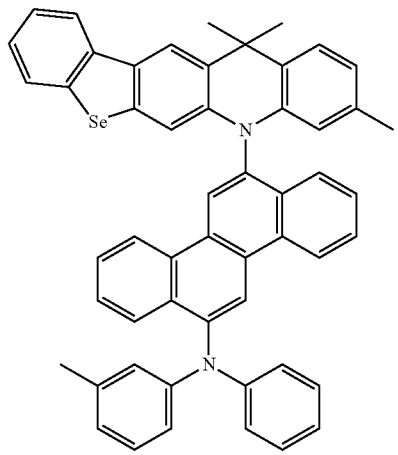
Compound 111
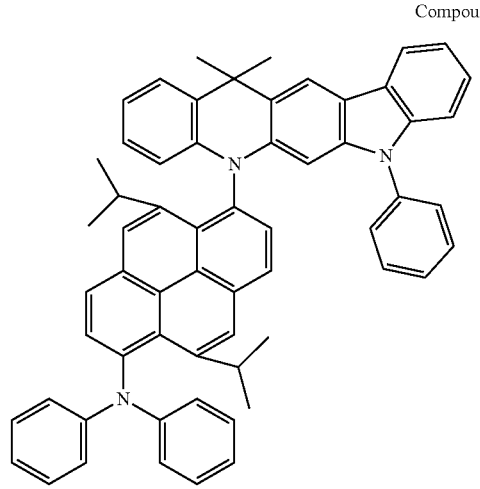
Compound 112
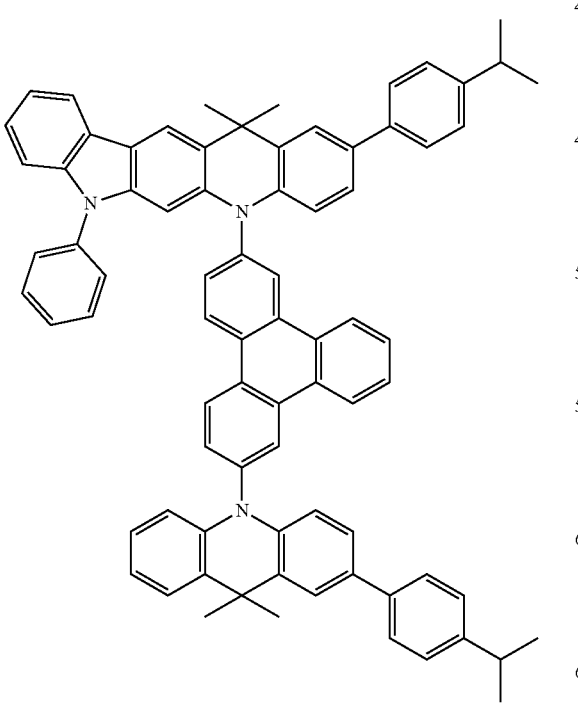
Compound 113
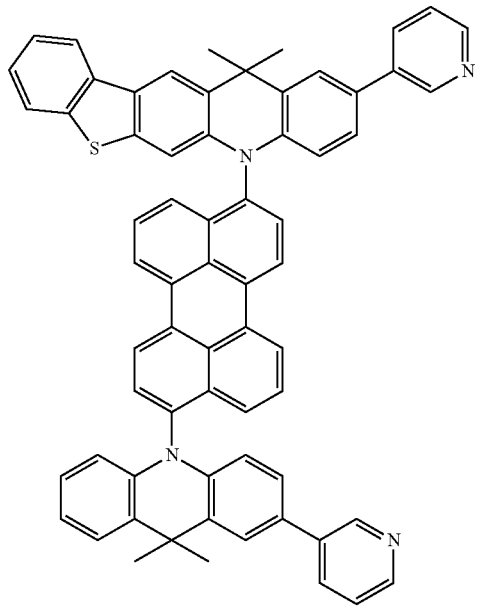
Compound 114
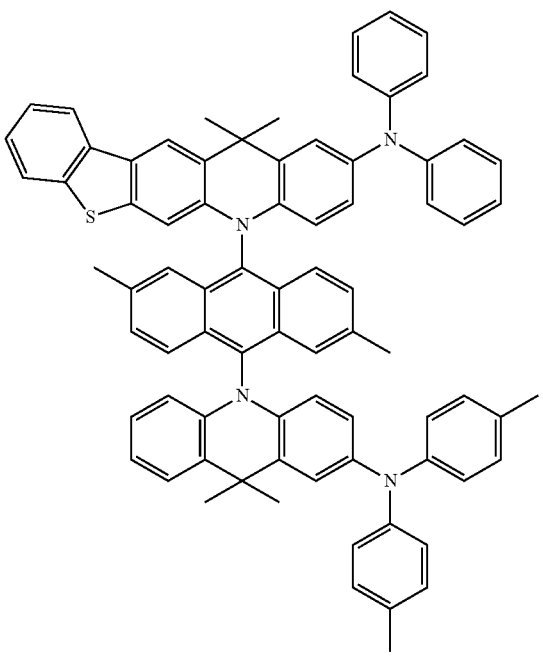

Compound 115
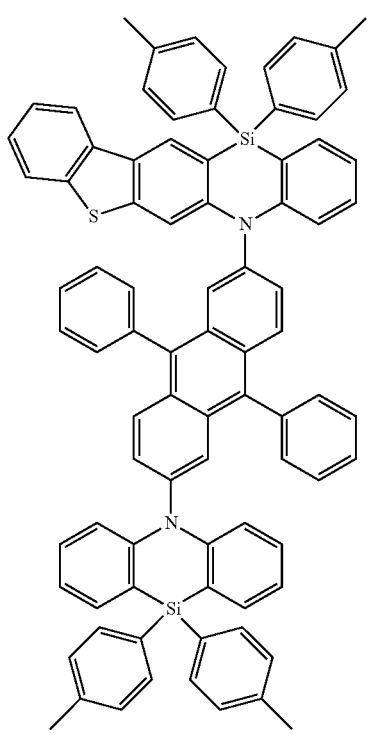
Compound 116
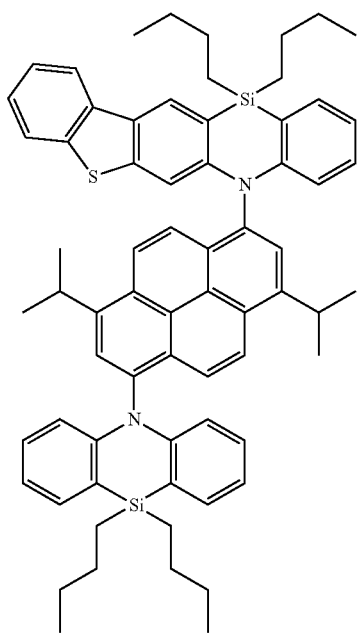
Compound 117
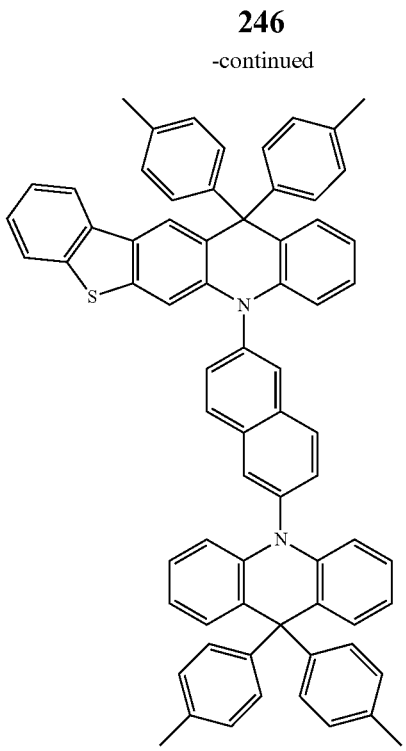
Compound 118
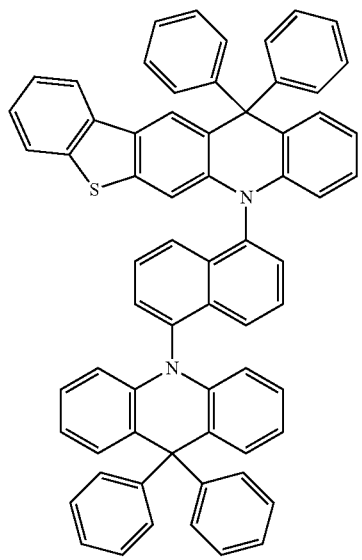

Compound 119
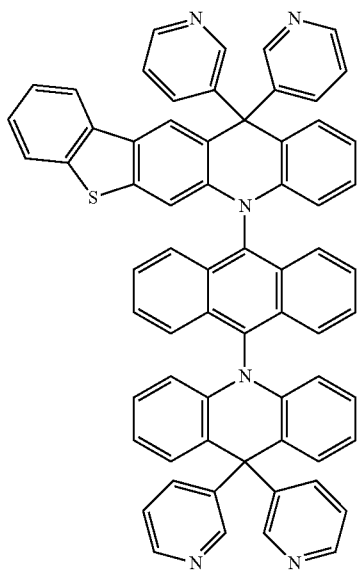
Compound 121
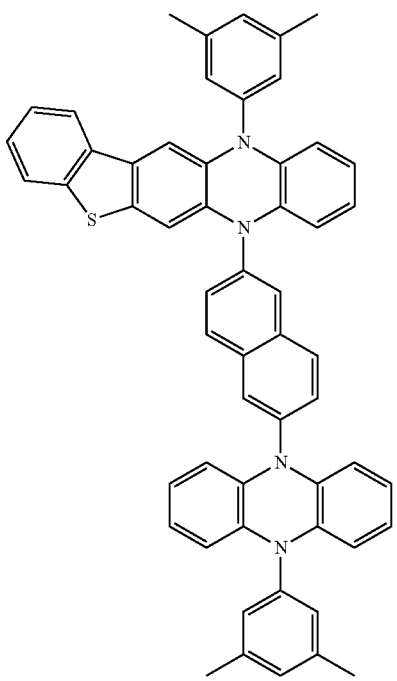
Compound 120
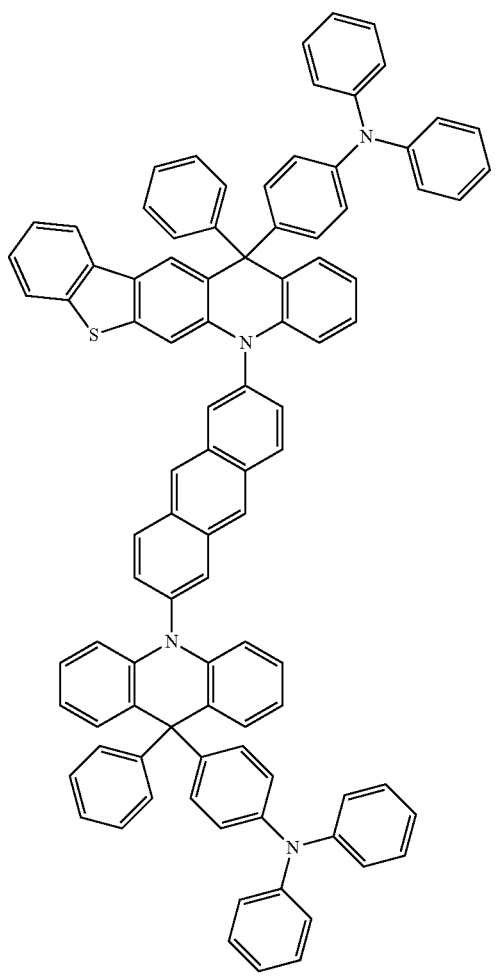
Compound 122
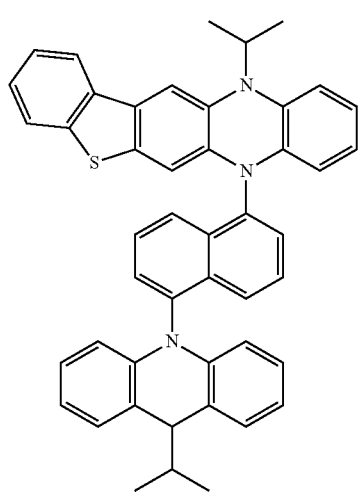

Compound 123
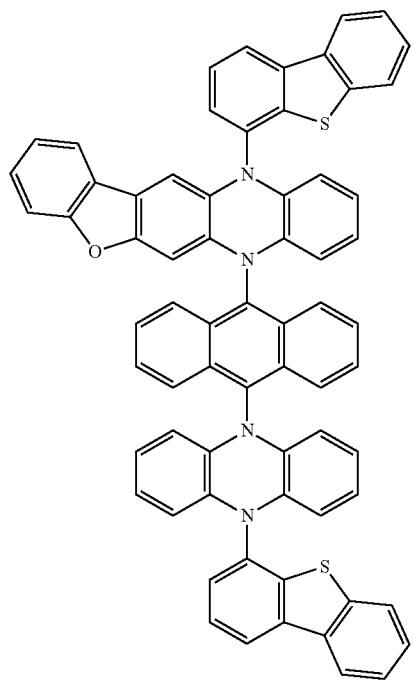
Compound 125
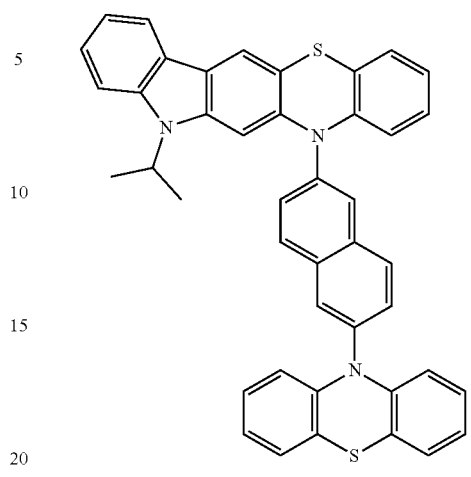
Compound 124
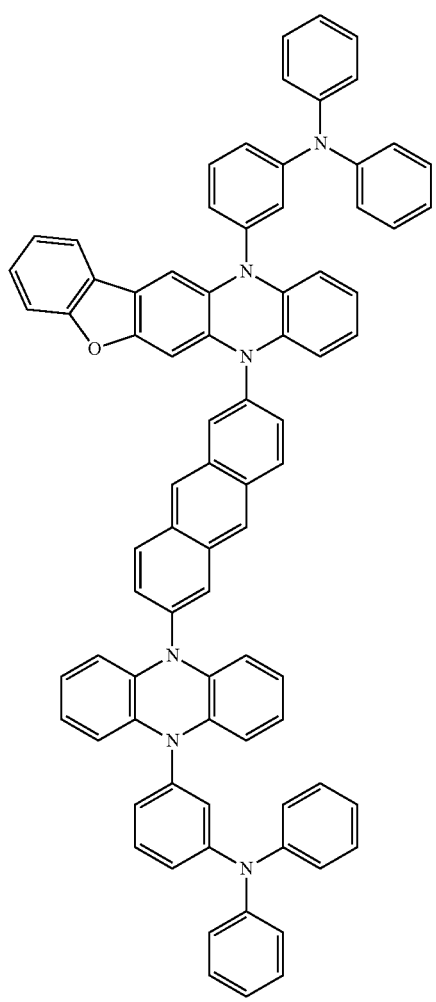
Compound 126
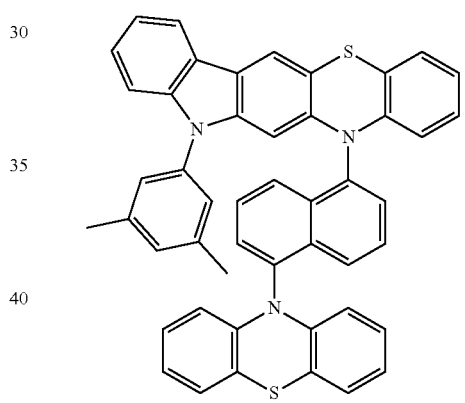
Compound 127
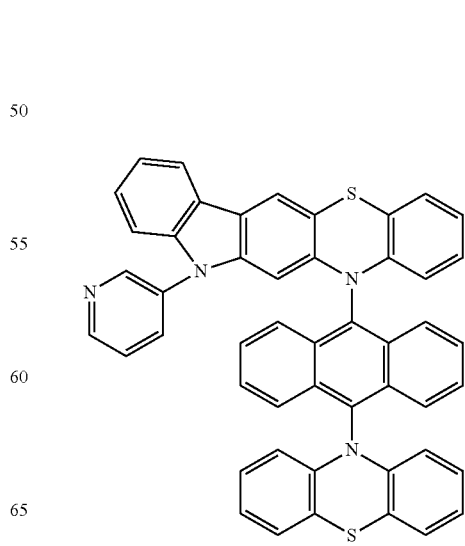

-continued
Compound 128
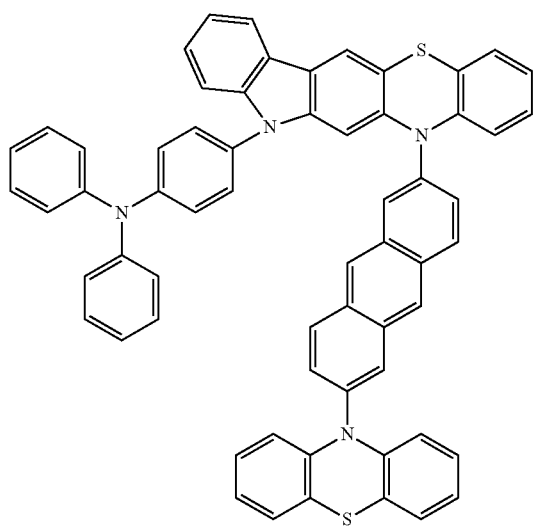
Compound 129
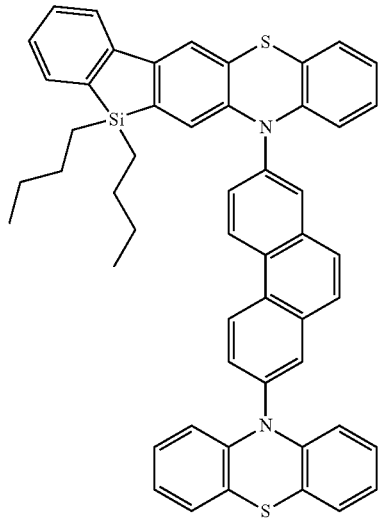
Compound 130
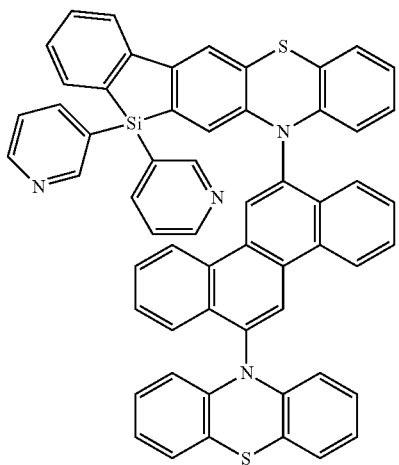
-continued
Compound 131
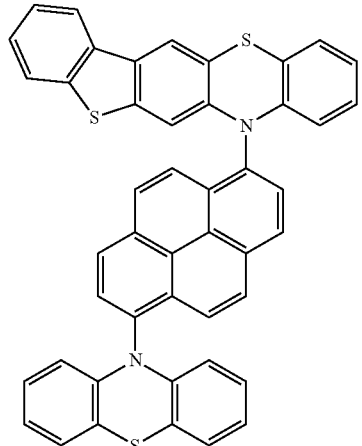
Compound 132
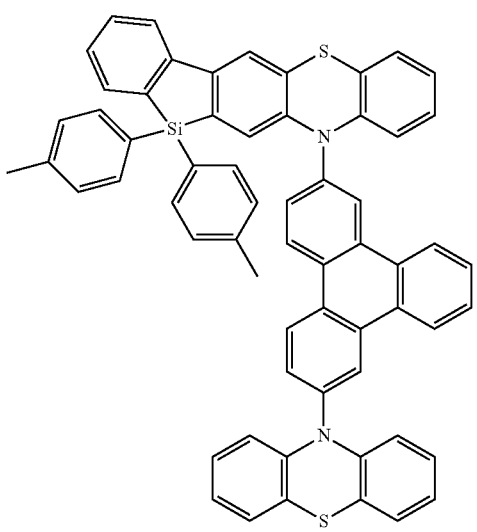
Compound 133
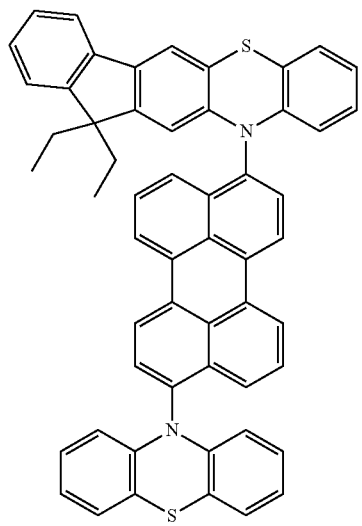

Compound 134
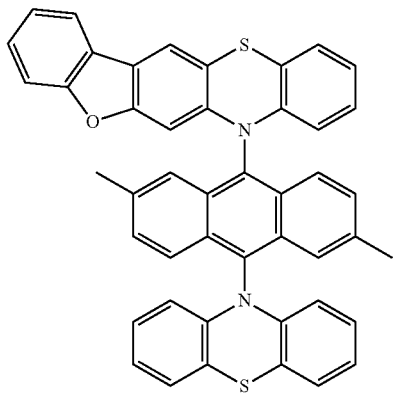
Compound 135
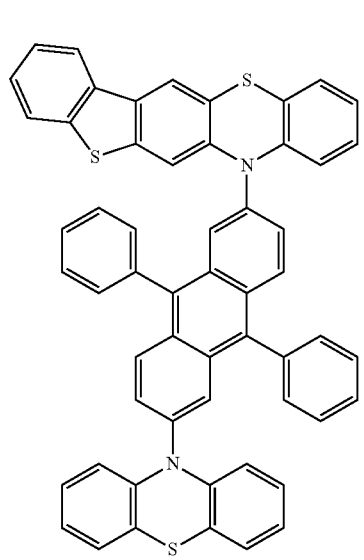
Compound 136
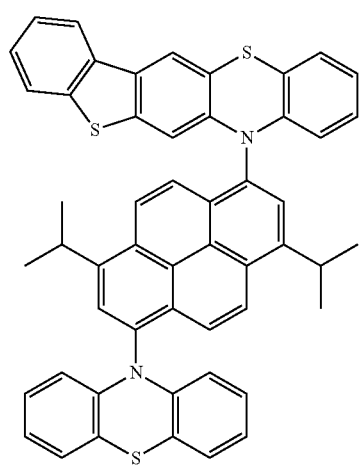
Compound 137
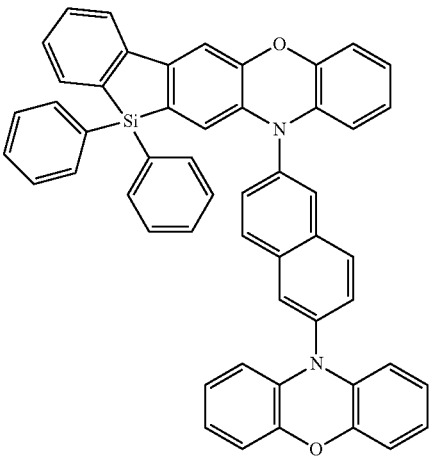
Compound 138
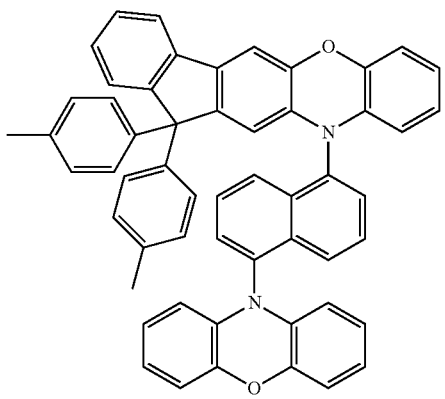
Compound 139
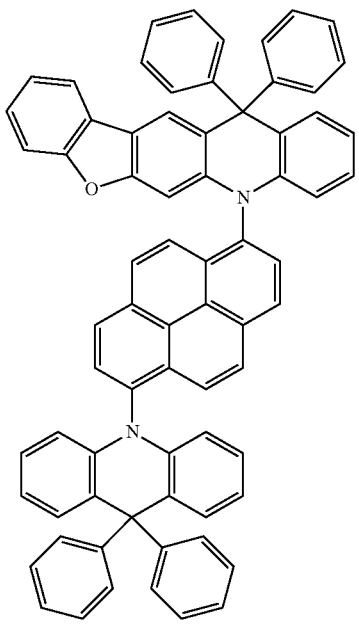

-continued
Compound 140
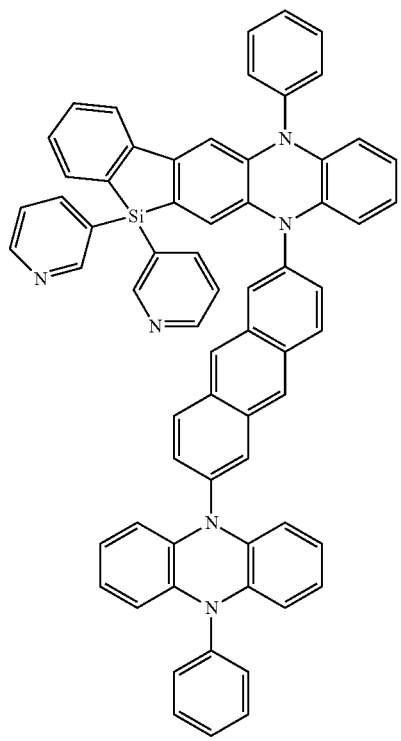
Compound 141
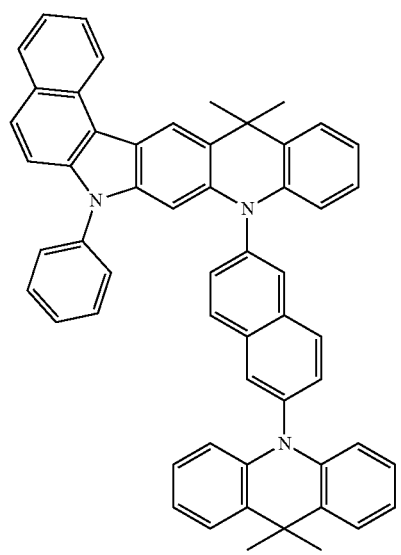
-continued
Compound 142
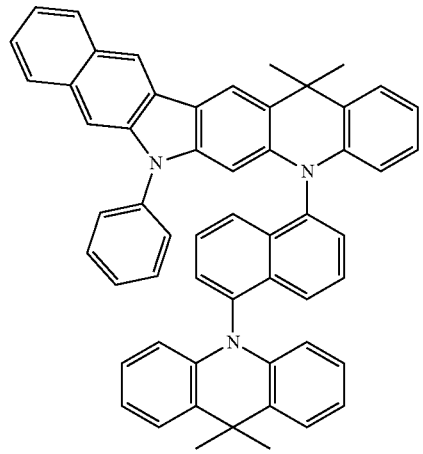
Compound 143
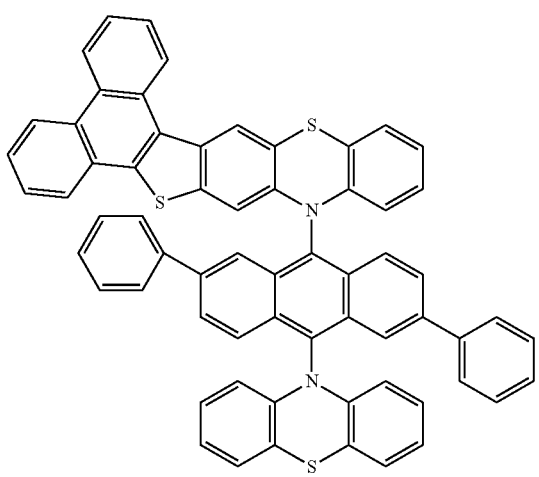
Compound 144
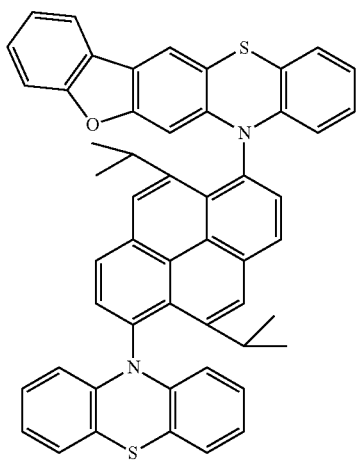

Compound 145
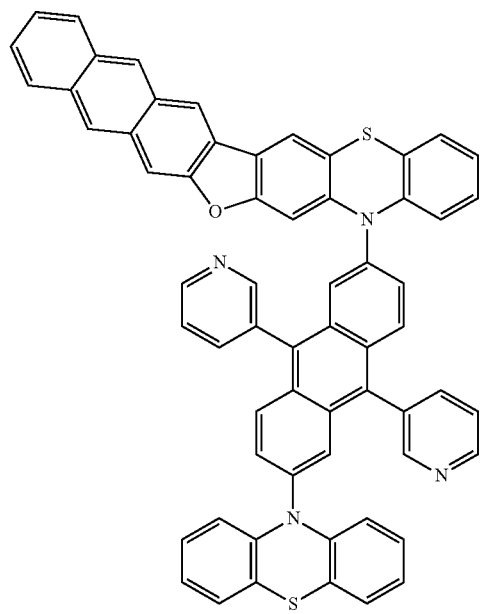
Compound 146
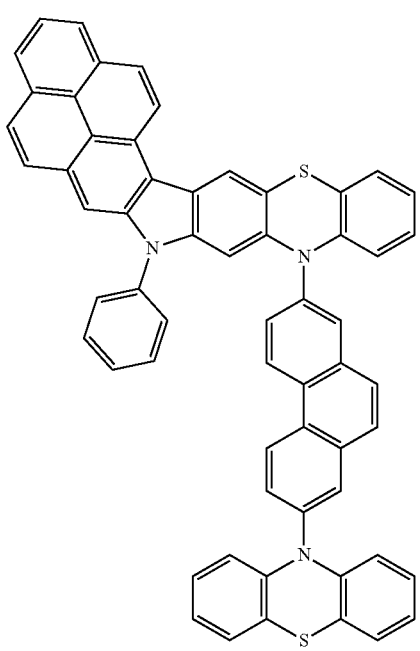
Compound 147
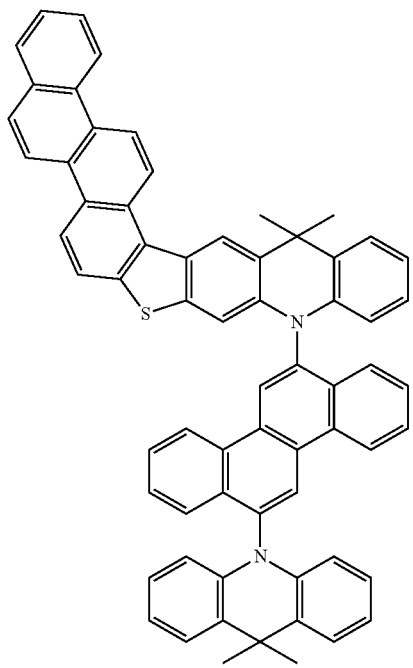
Compound 148
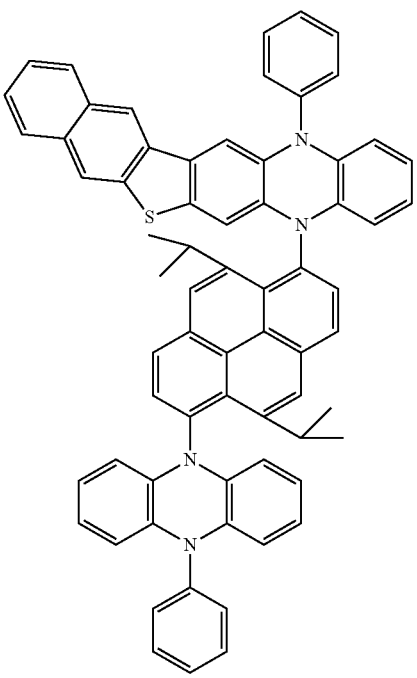

Compound 149
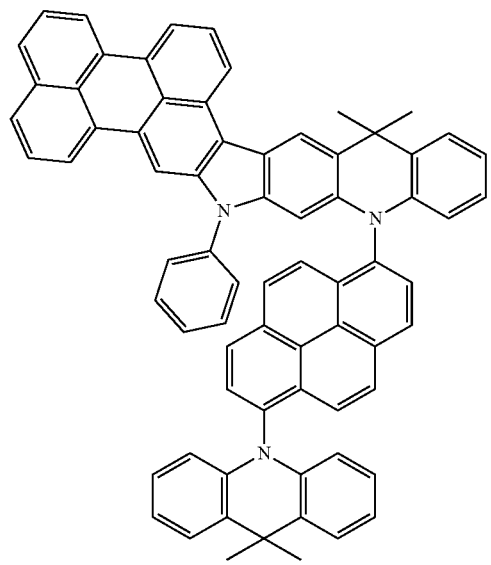
Compound 150
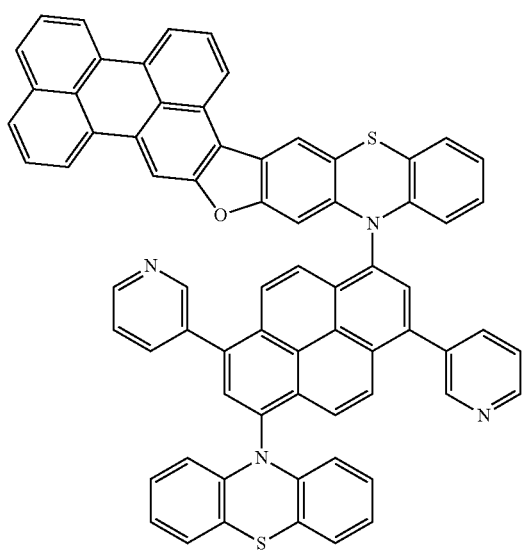
Compound 151
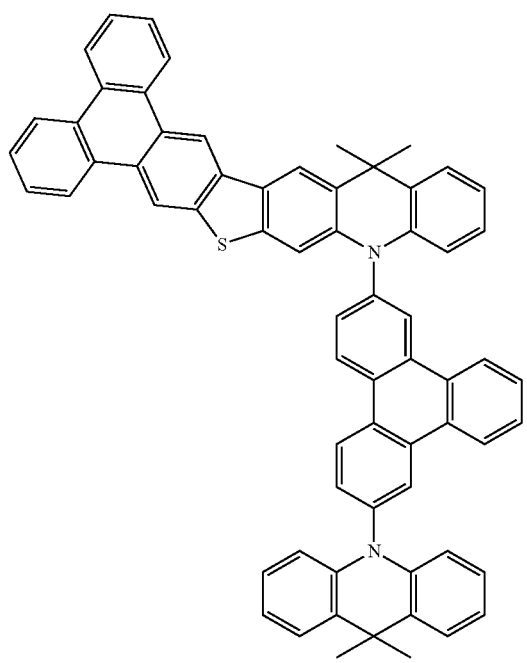
Compound 152
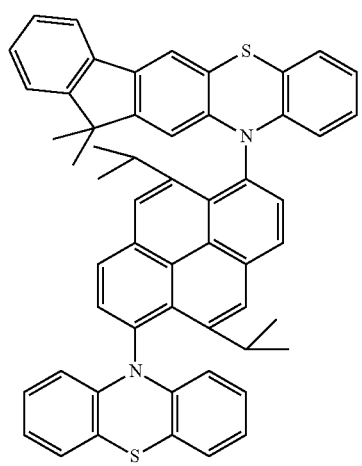
Compound 153
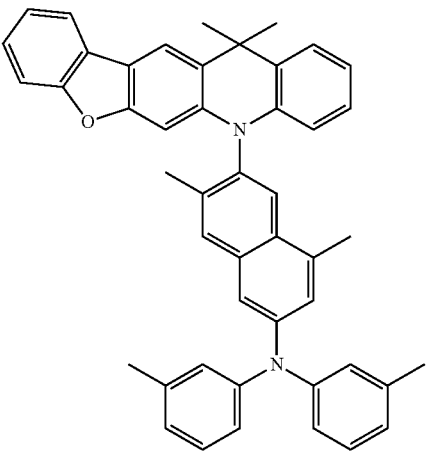

Compound 154
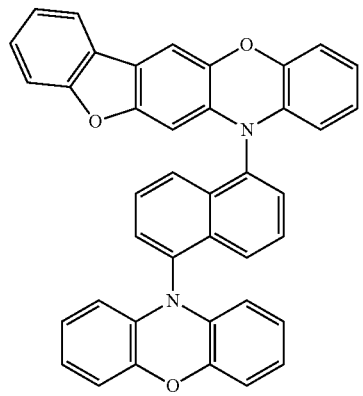
Compound 155
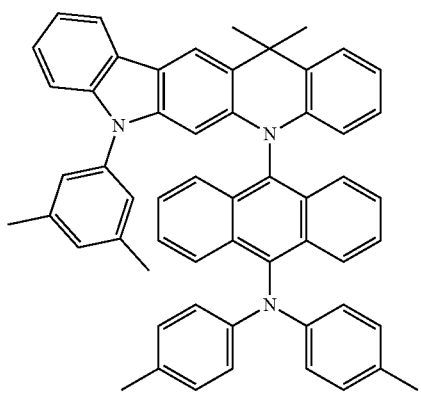
Compound 156
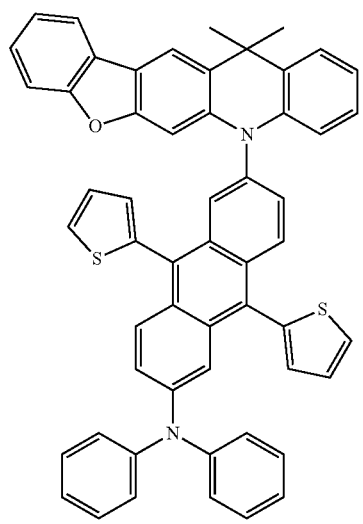
Compound 157
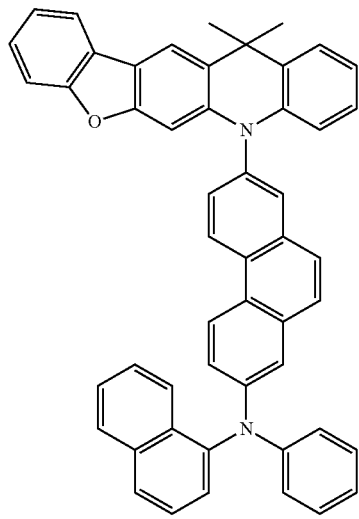
Compound 158
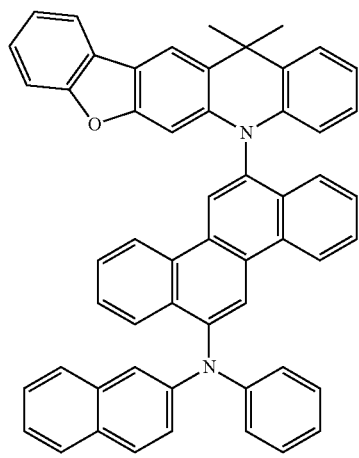
Compound 159
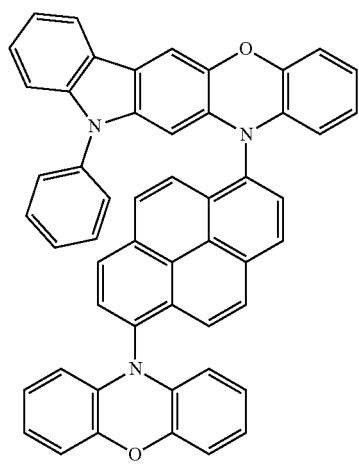

Compound 160
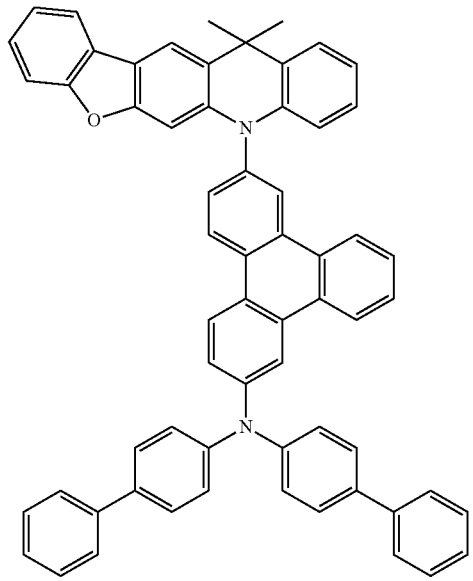
Compound 163
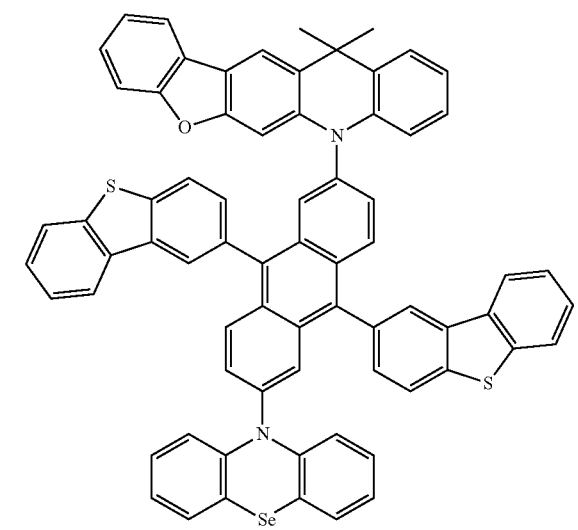
Compound 161
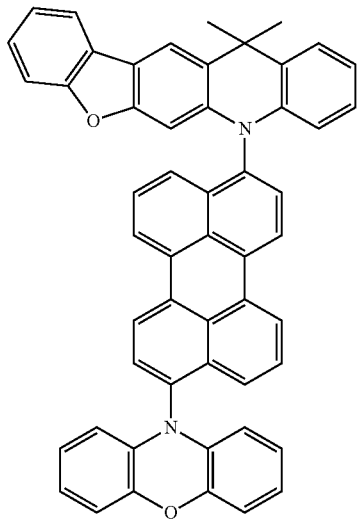
Compound 164
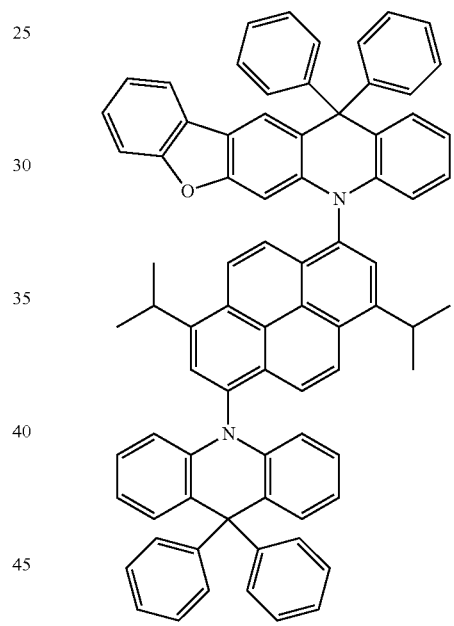
Compound 162
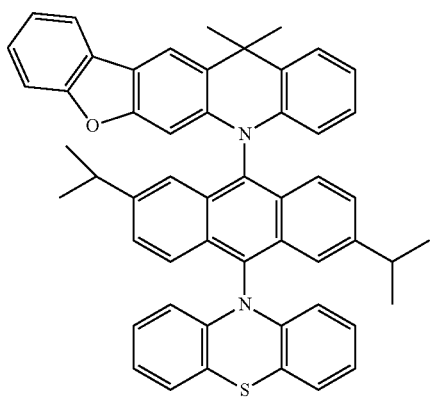
Compound 165
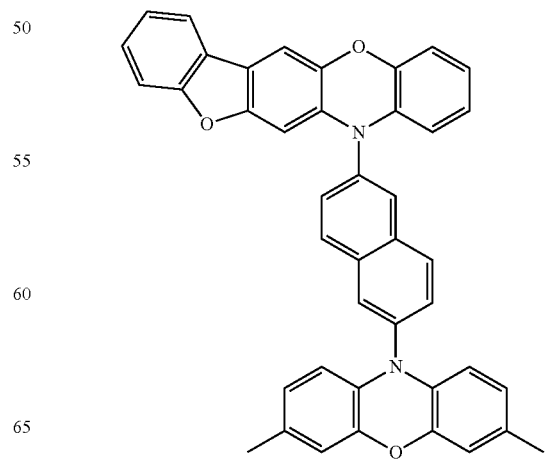

Compound 166
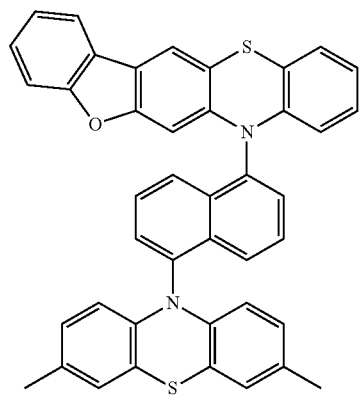
Compound 167
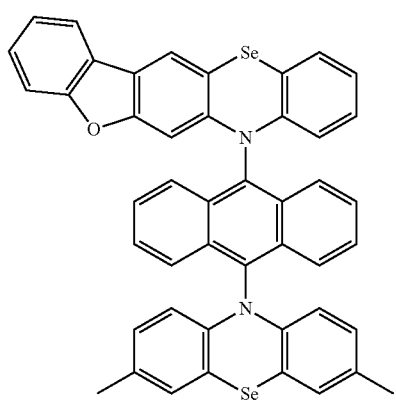
Compound 168
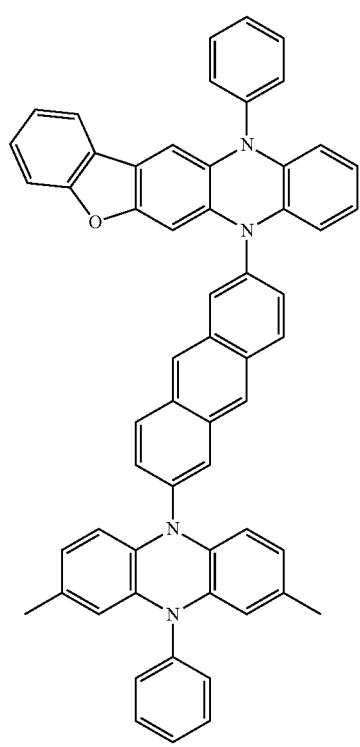
Compound 169
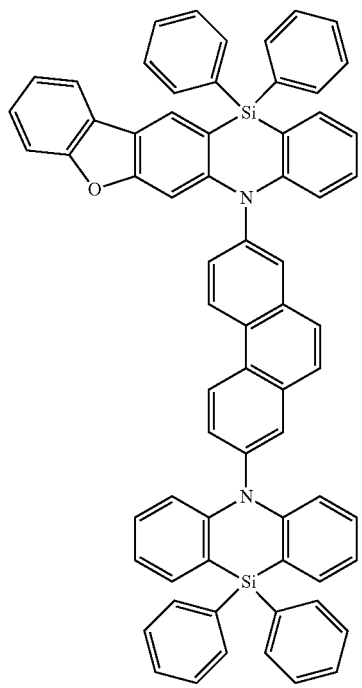
Compound 170
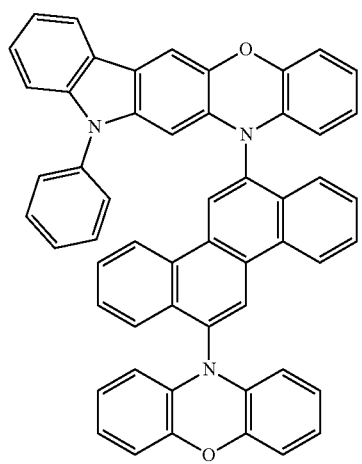

Compound 171
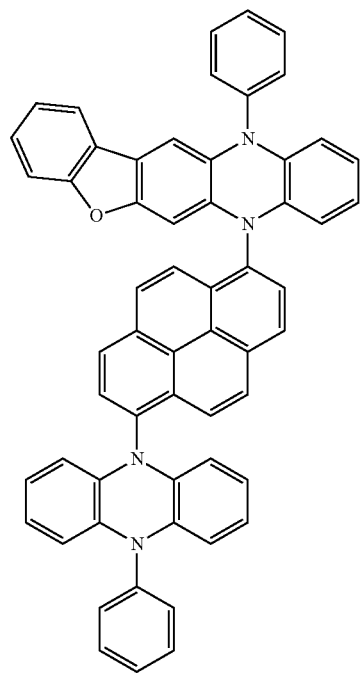
Compound 172
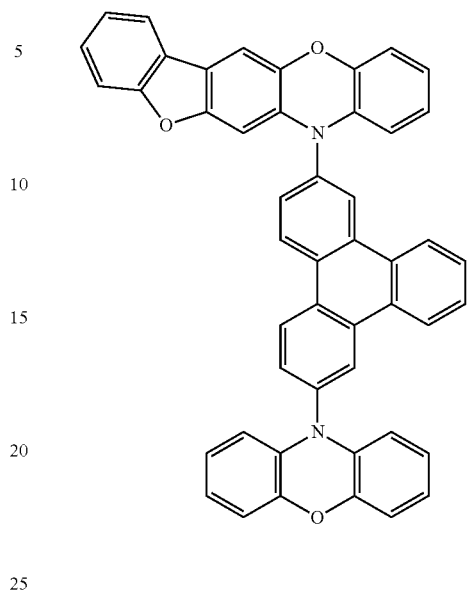
Compound 173
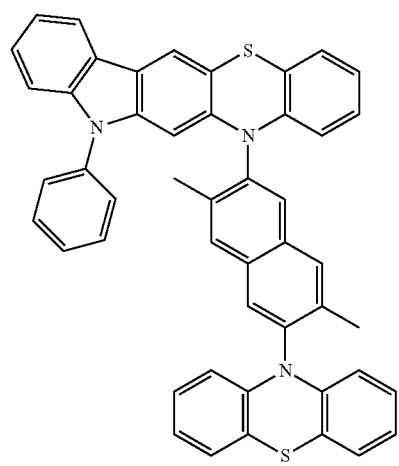
Compound 174
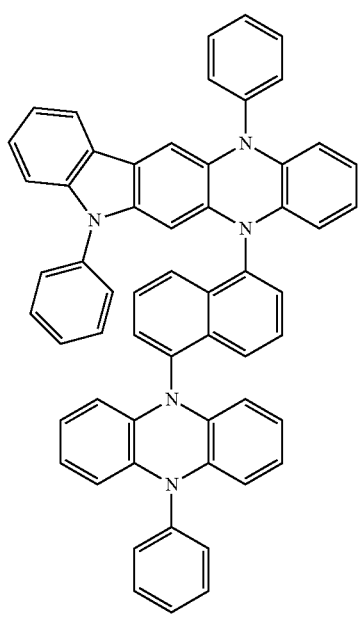

Compound 175
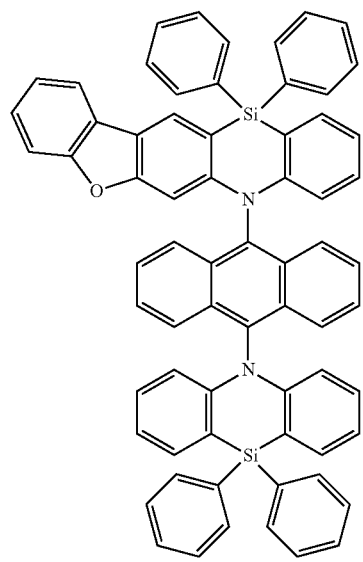
Compound 176
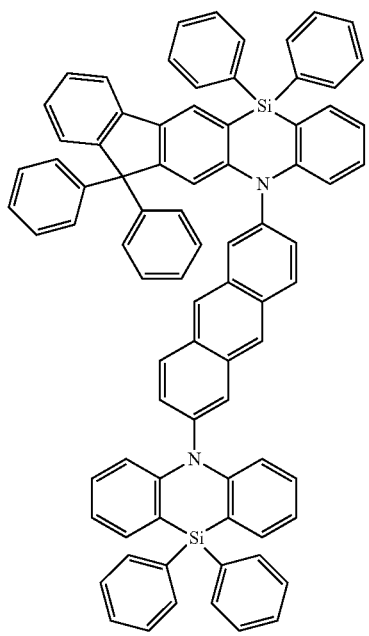
Compound 177
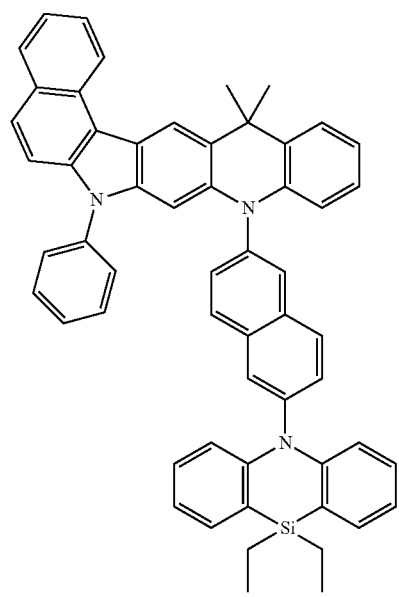
Compound 178
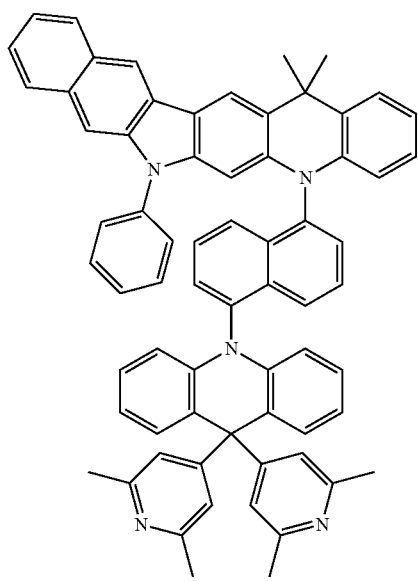

Compound 179
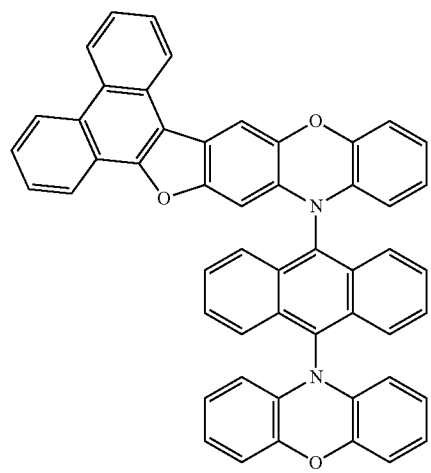
Compound 180
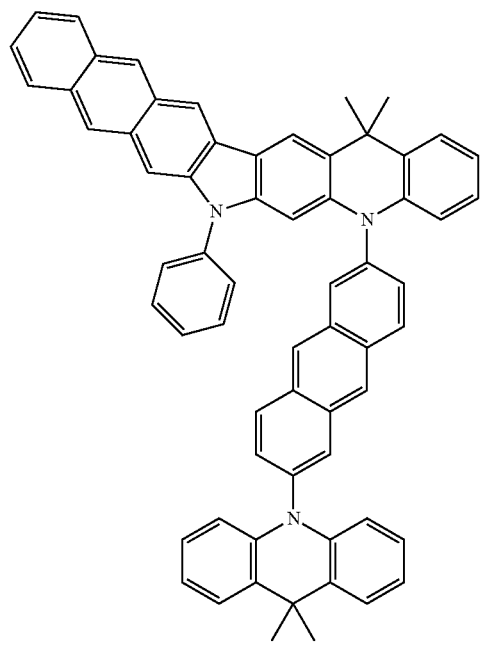
Compound 181
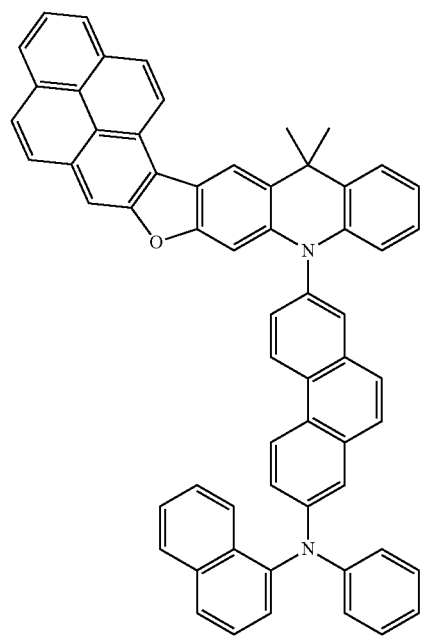
Compound 182
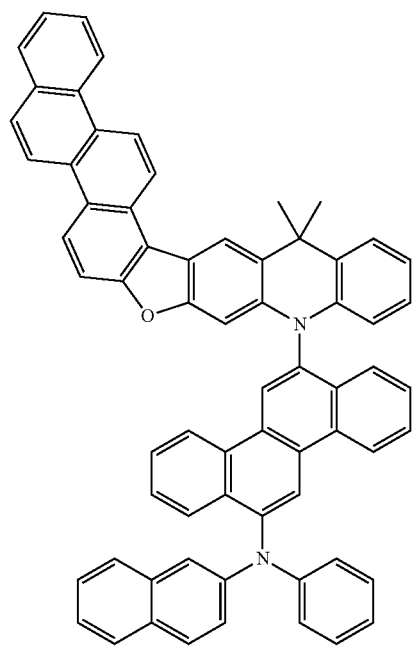

Compound 183
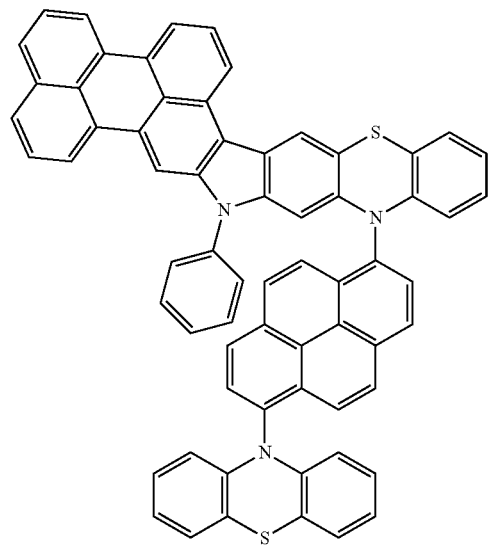
Compound 184
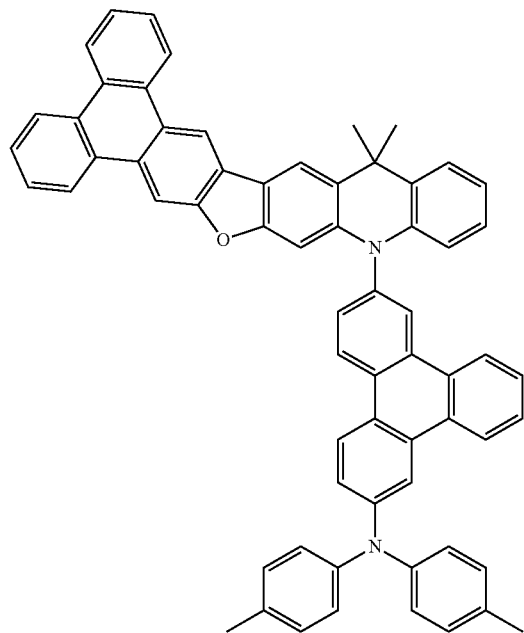
Compound 185
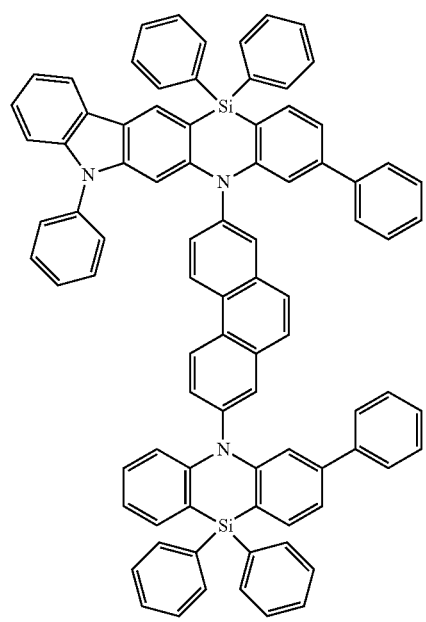
Compound 186
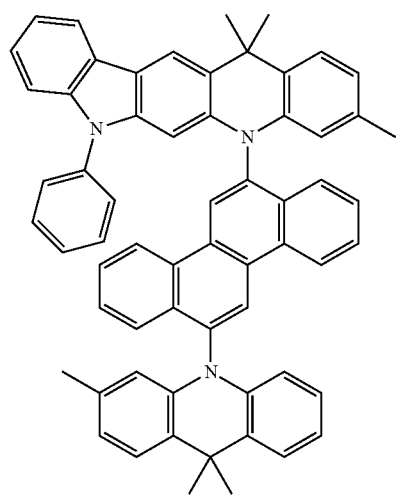

-continued
Compound 187
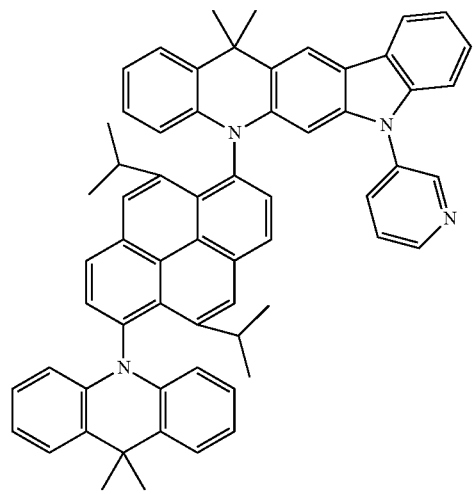
Compound 188
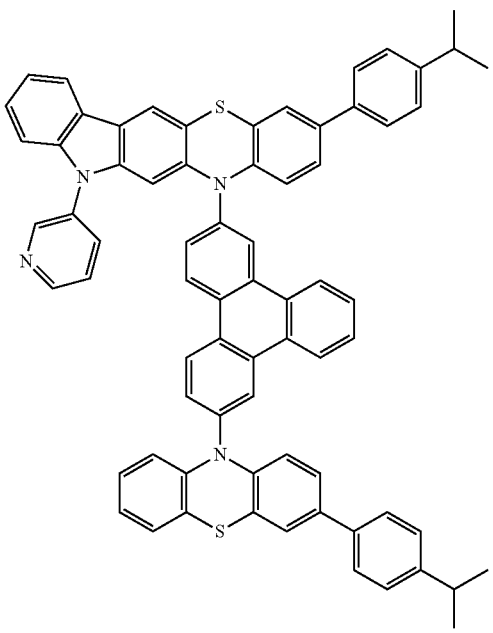
Compound 189
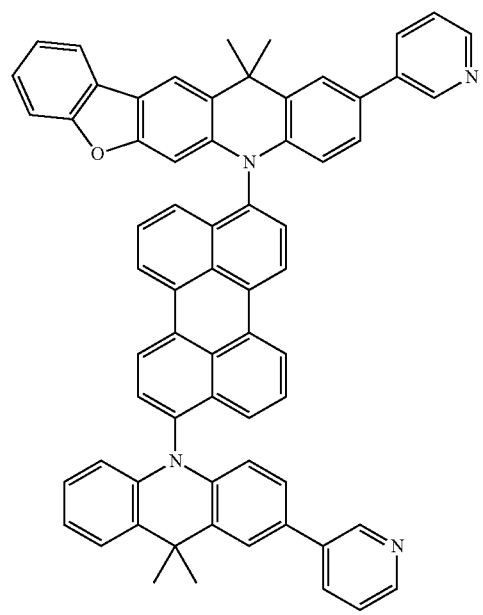
Compound 190
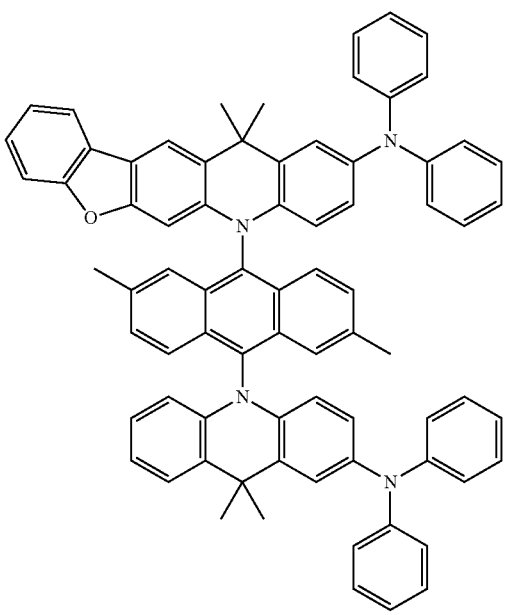

-continued
Compound 191
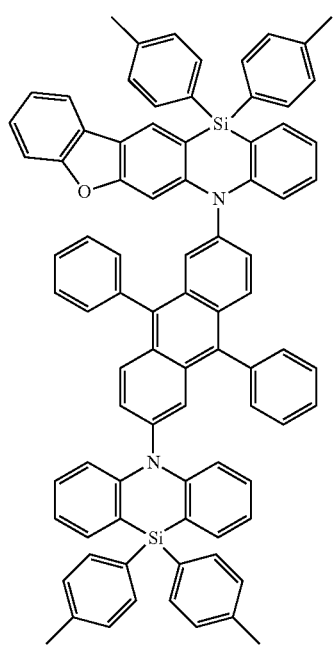
Compound 192
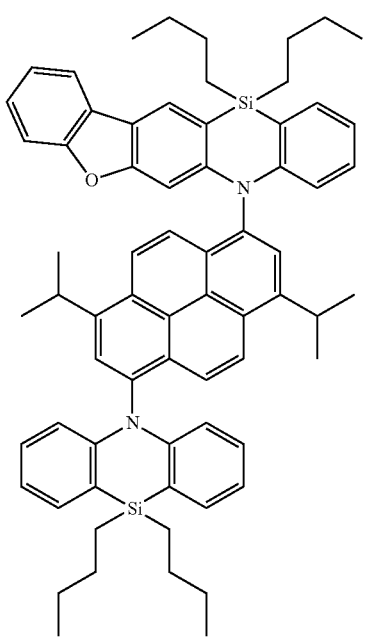
Compound 193
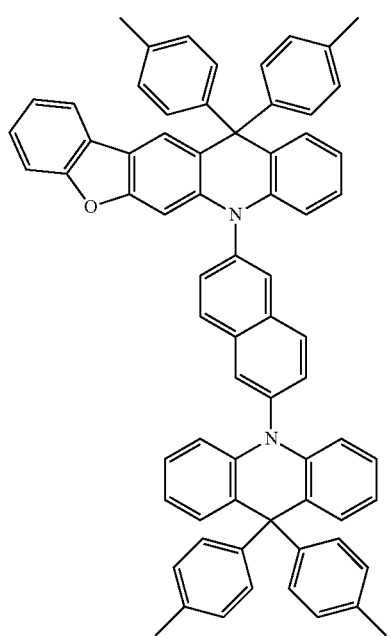
Compound 194
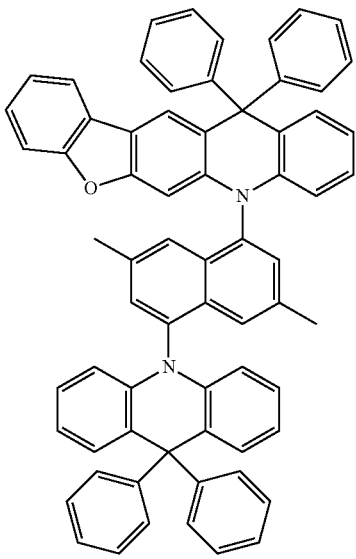

Compound 195
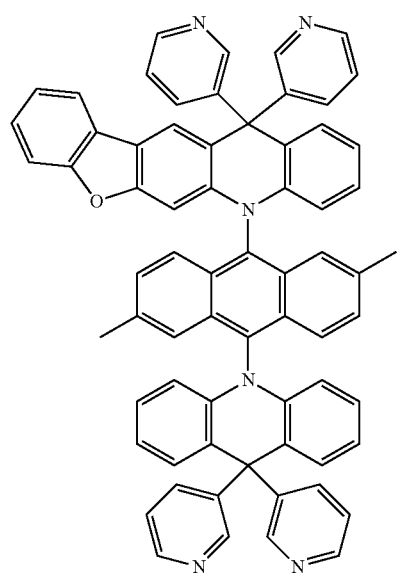
Compound 196
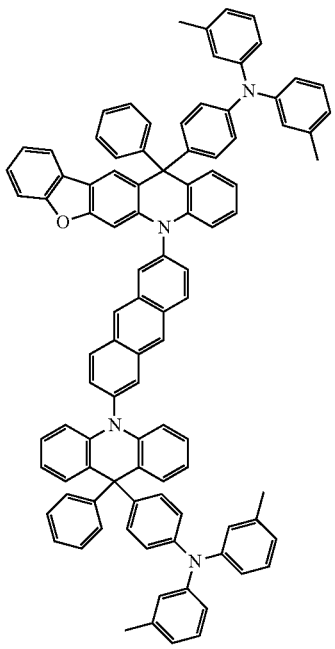
Compound 197
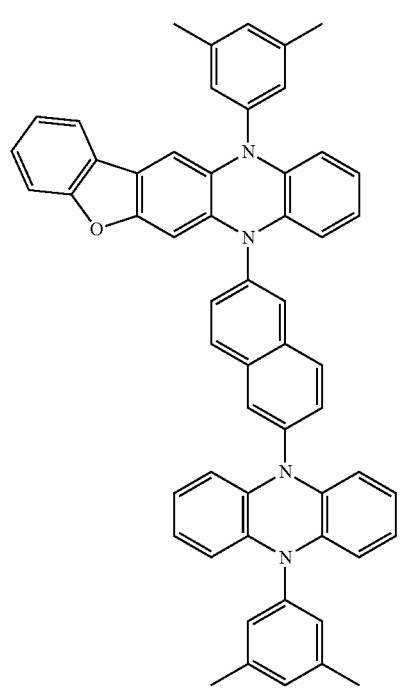
Compound 198
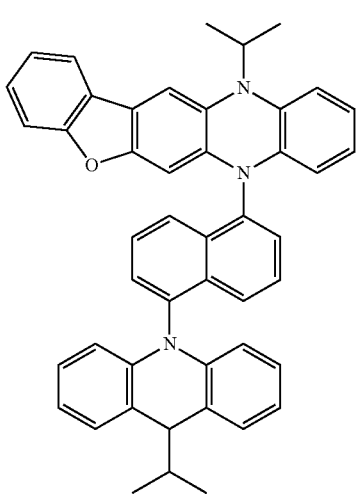

Compound 199
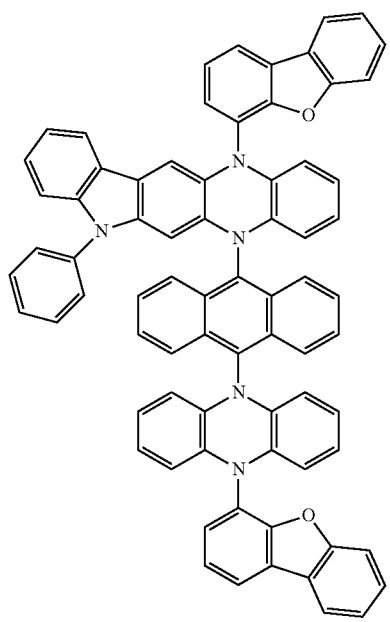
Compound 200
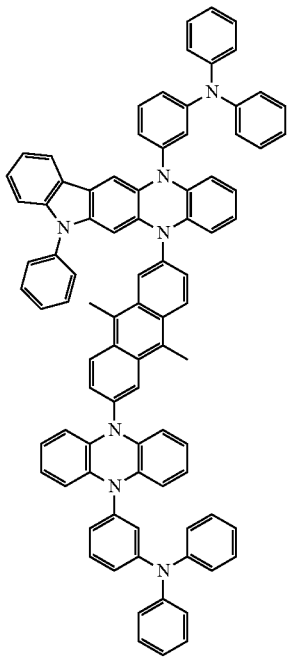
Compound 201
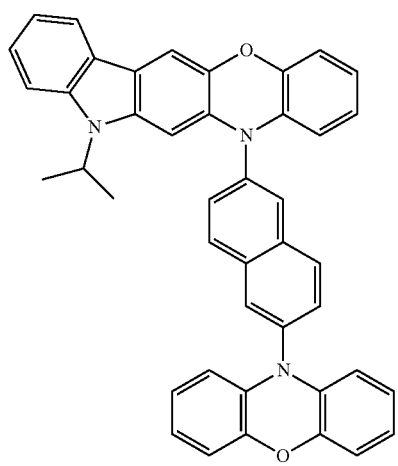
Compound 202
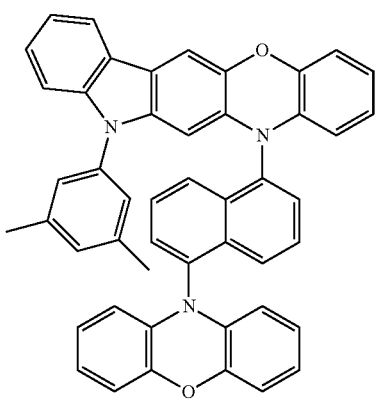
Compound 203
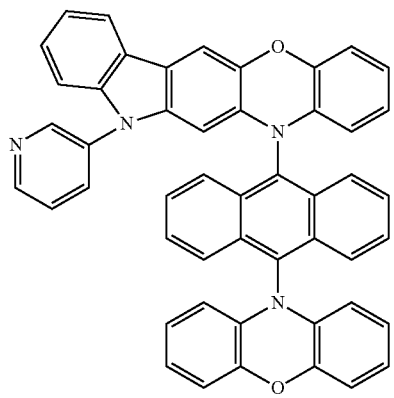
Compound 204
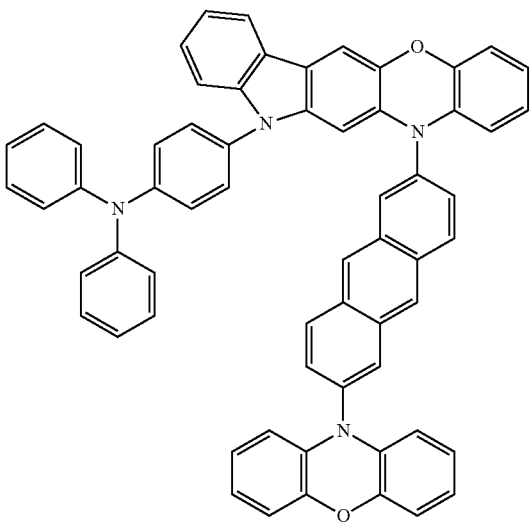

Compound 205
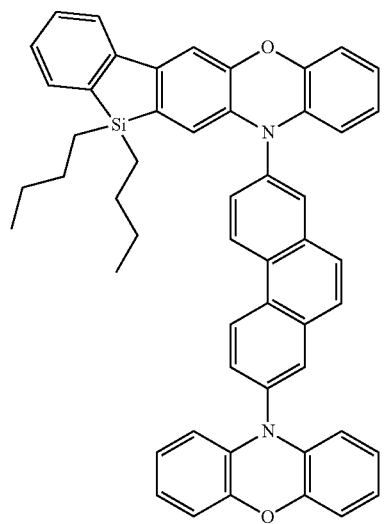
Compound 206
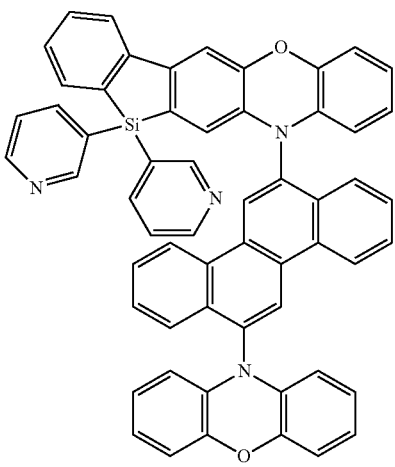
Compound 207
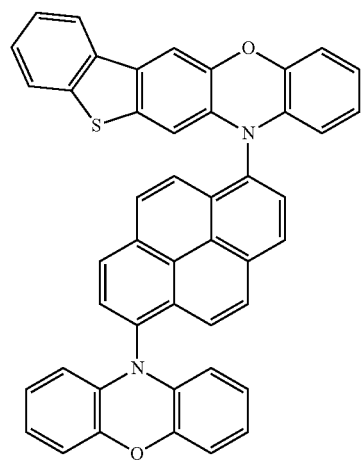
Compound 208
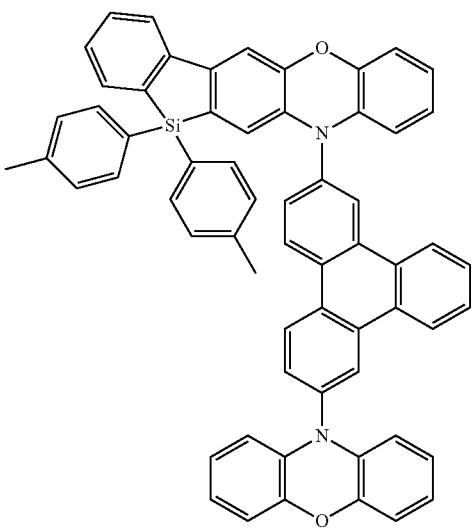
Compound 209
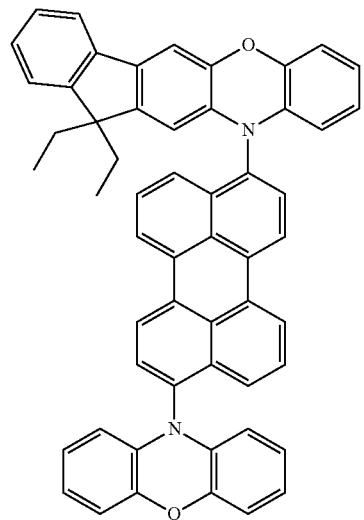
Compound 210
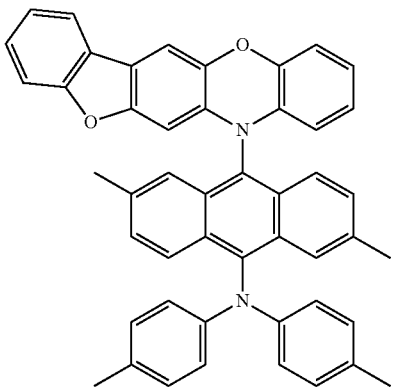

-continued
Compound 211
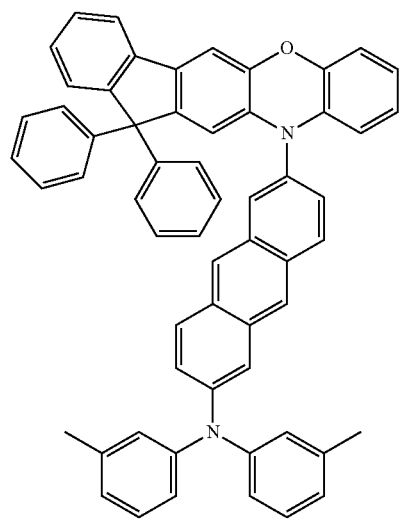
Compound 212
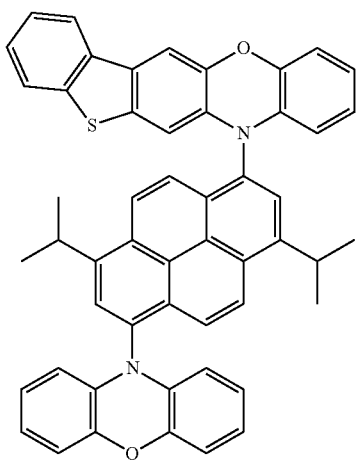
Compound 213
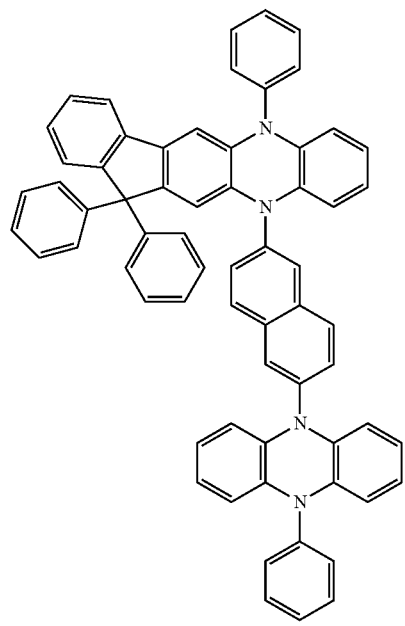
Compound 214
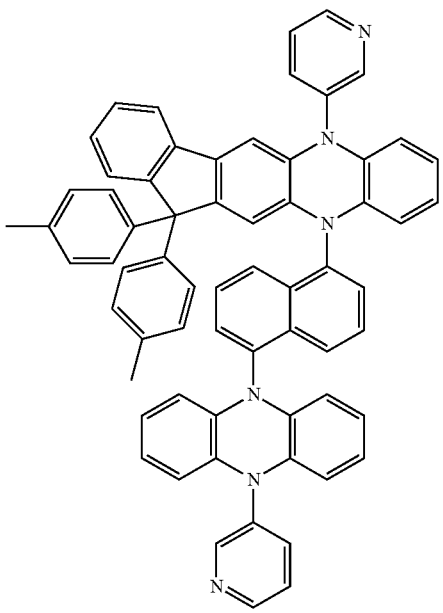

-continued
Compound 215
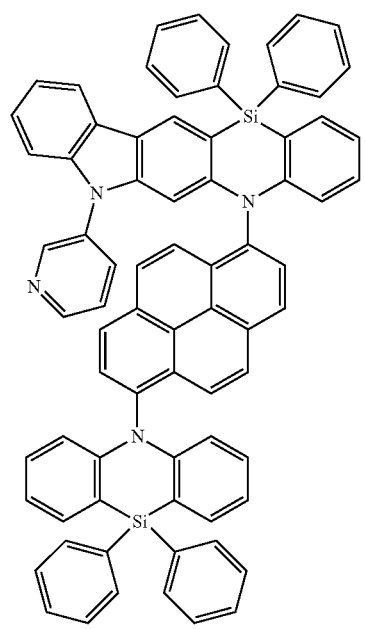
Compound 216
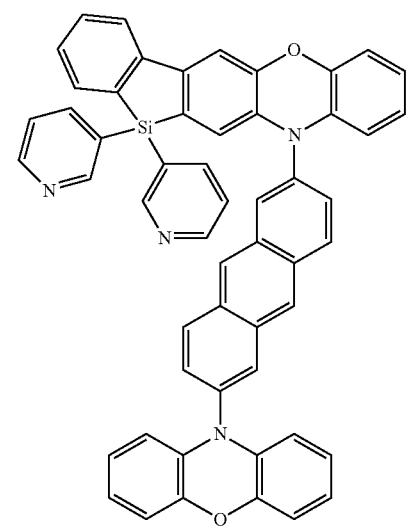
Compound 217
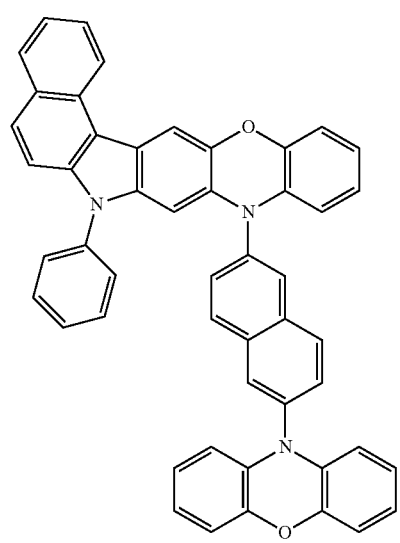
Compound 218
Compound 219
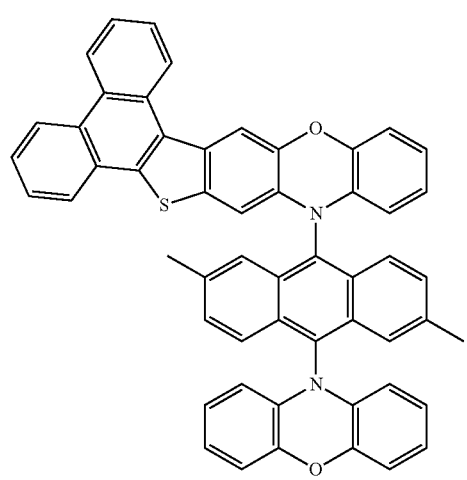
Compound 220
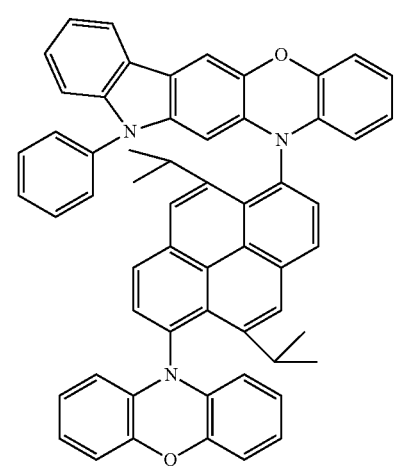

Compound 221
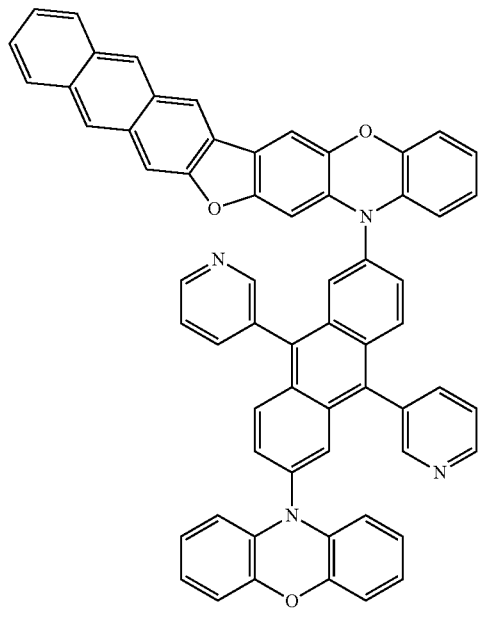
Compound 222
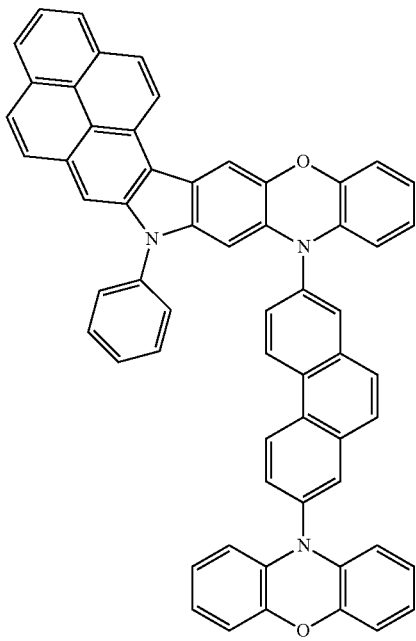
Compound 223
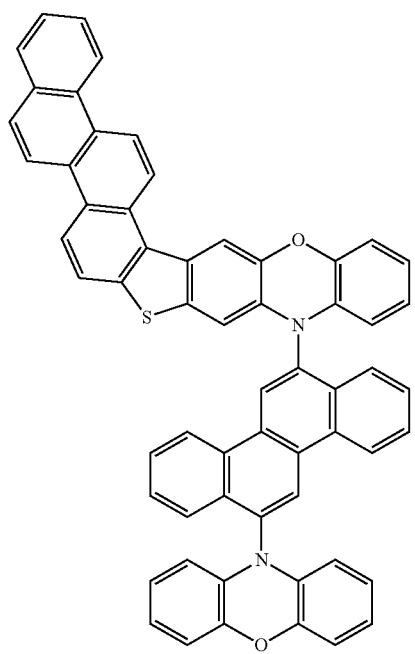
Compound 224
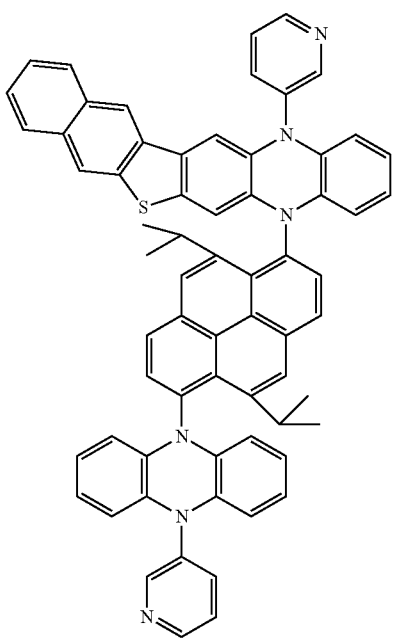

Compound 225
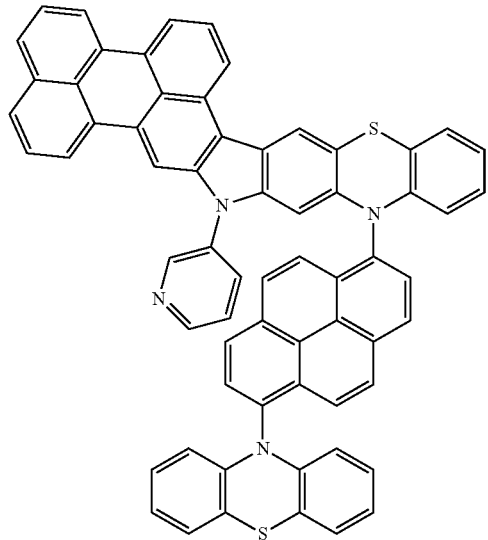
Compound 226
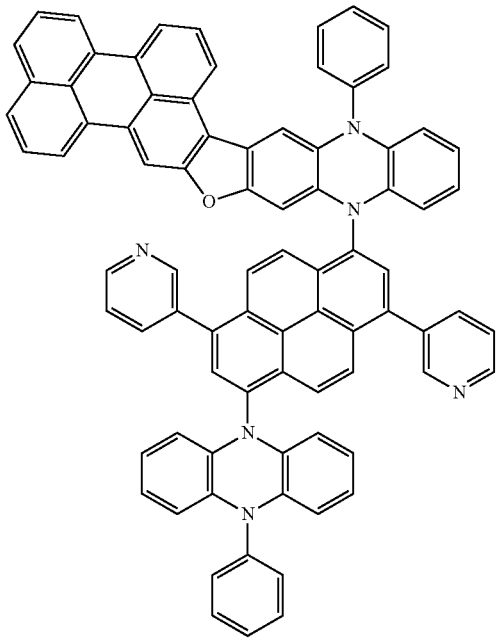
Compound 227
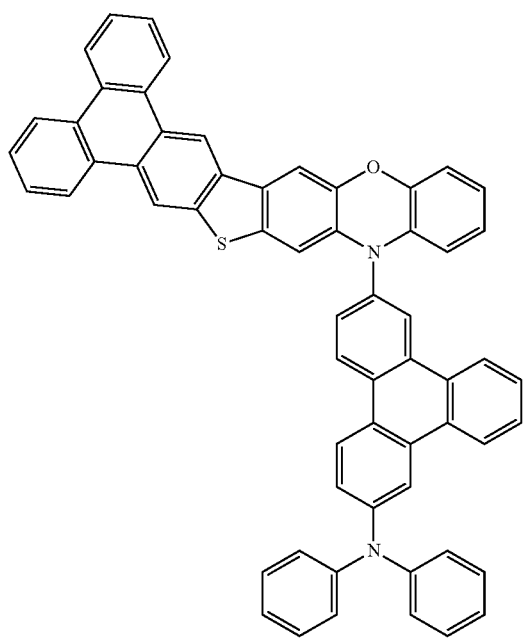
Compound 228
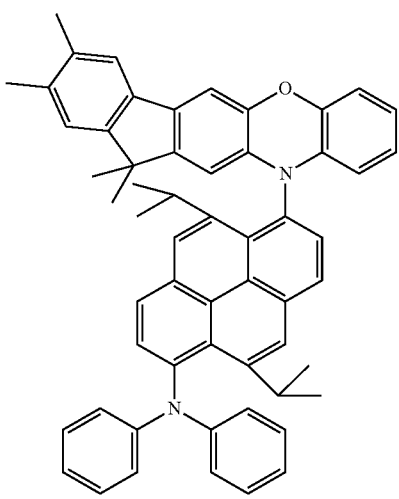

-continued
Compound 229
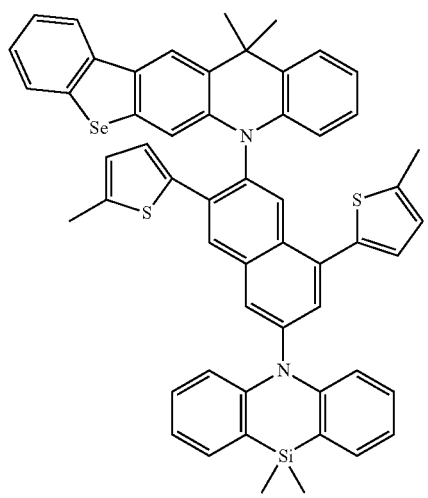
Compound 230
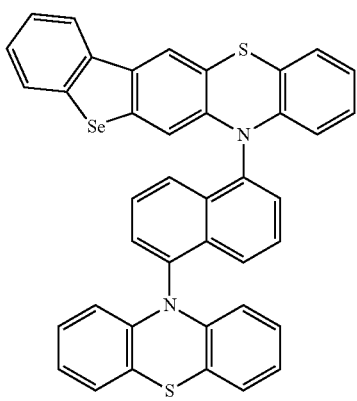
Compound 231
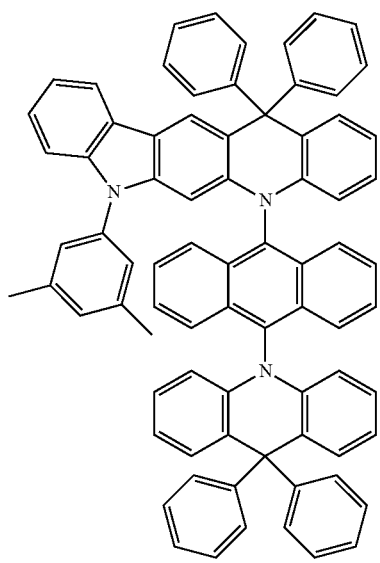
Compound 232
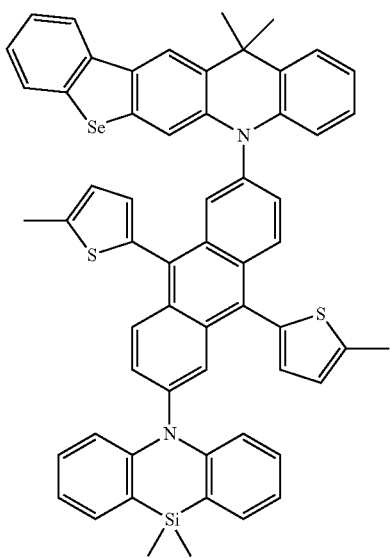
Compound 233
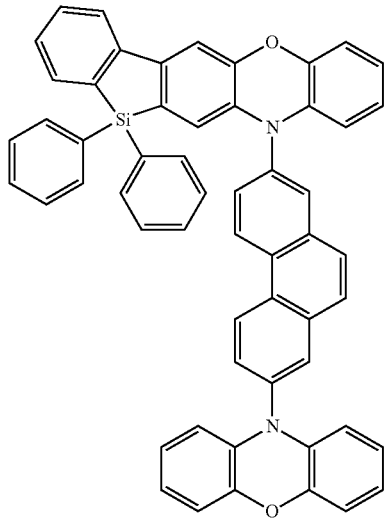
Compound 234
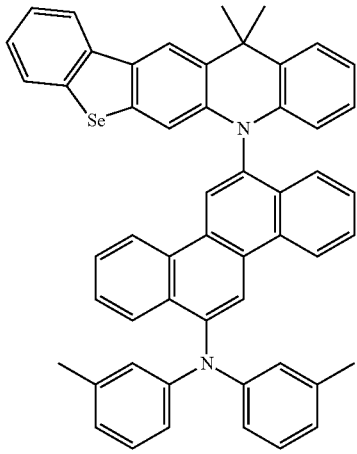

-continued
Compound 235
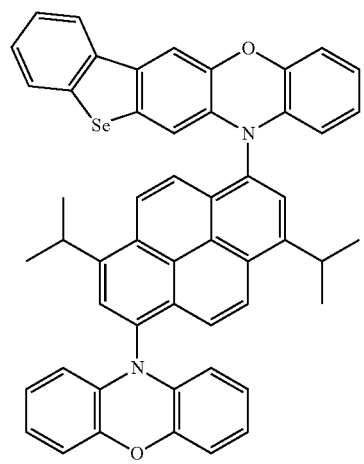
Compound 236
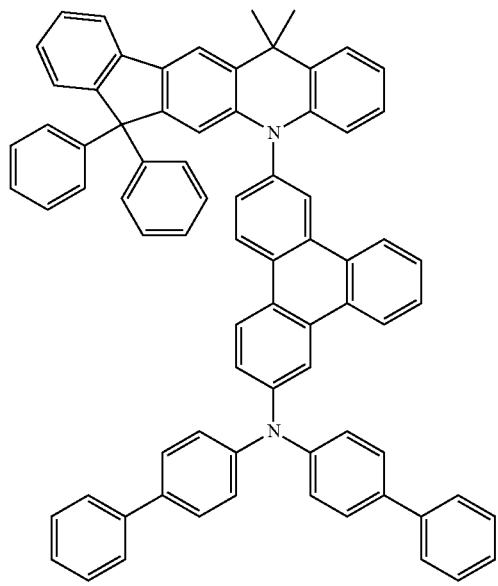
Compound 237
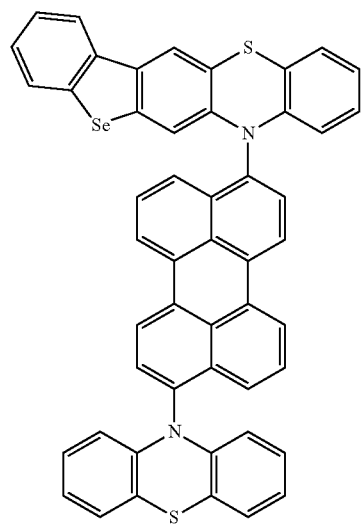
Compound 238
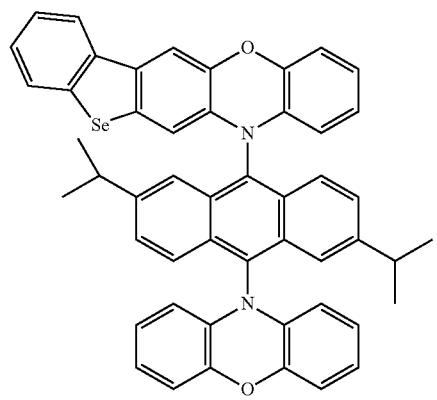

-continued
Compound 239
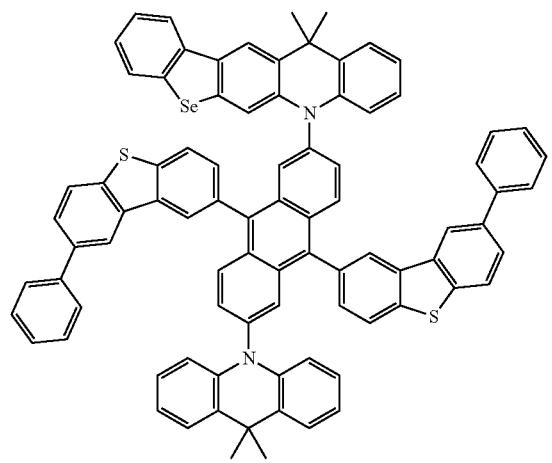
Compound 240
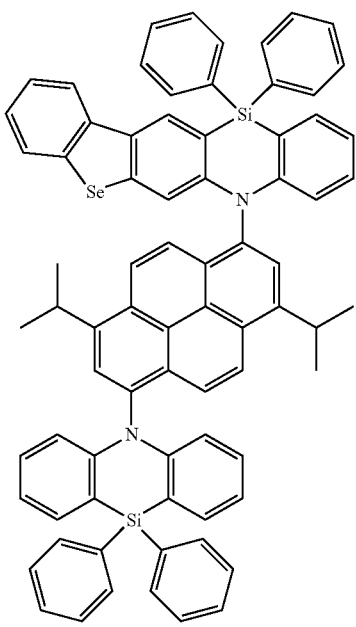
Compound 241
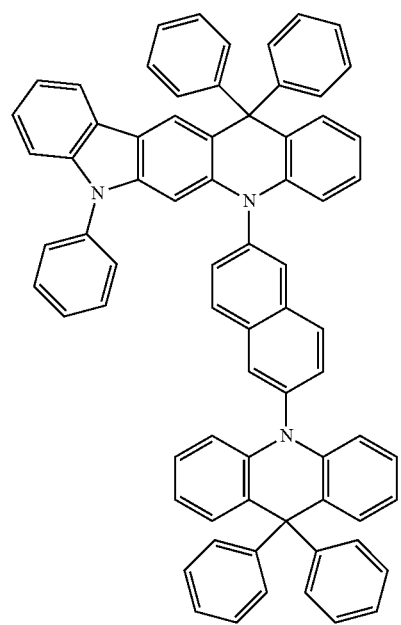
Compound 242
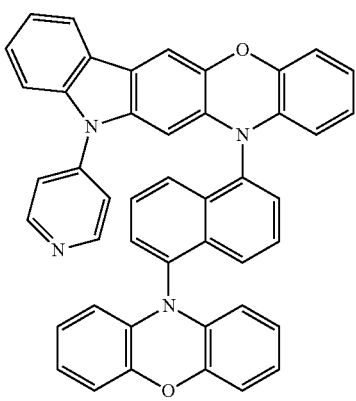

-continued
Compound 243
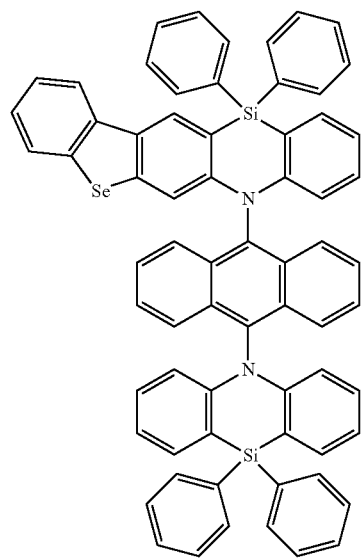
Compound 244
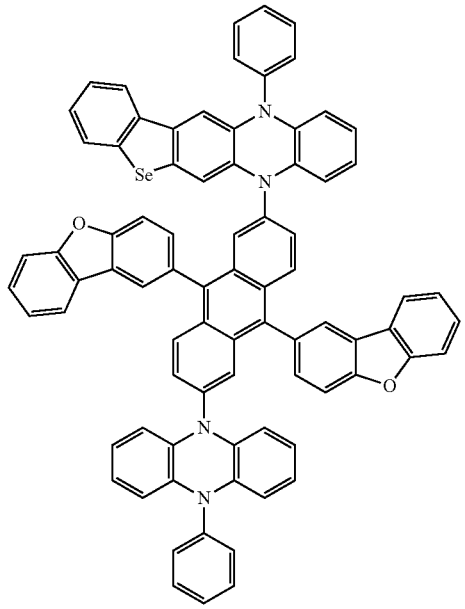
Compound 245
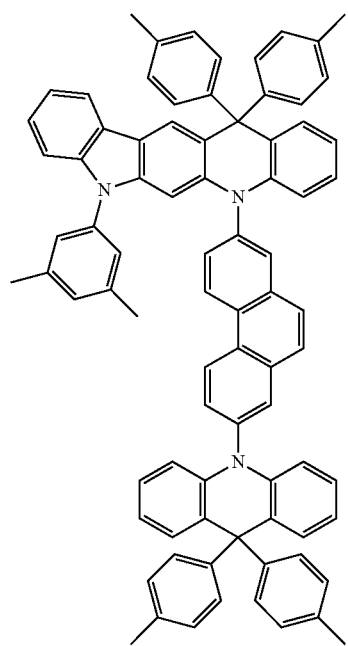
Compound 246
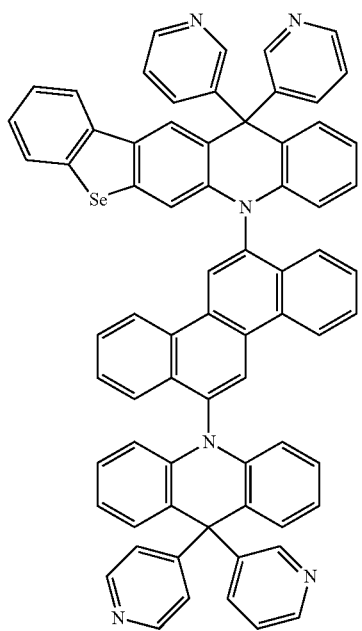

-continued
Compound 247
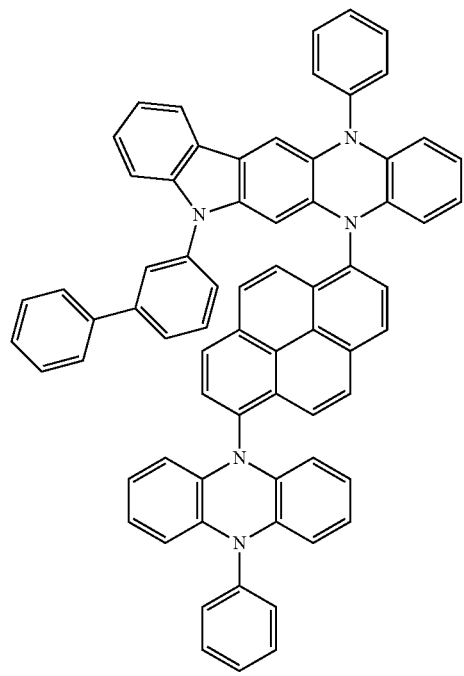
Compound 248
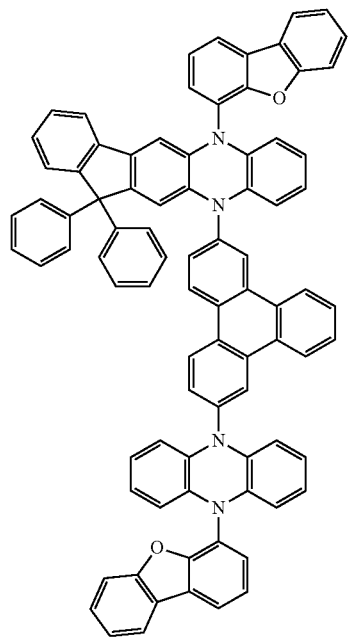
Compound 249
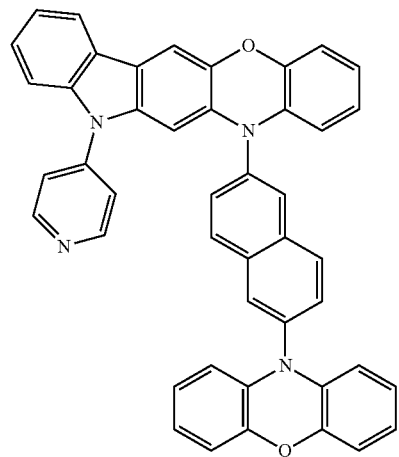
Compound 250
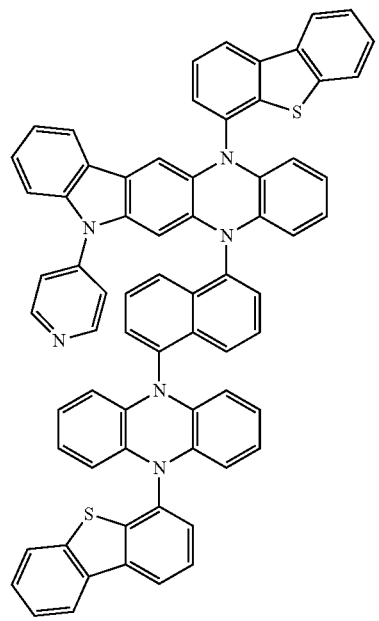

-continued
Compound 251
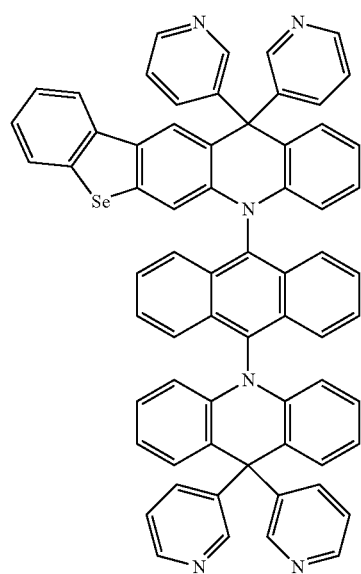
Compound 252
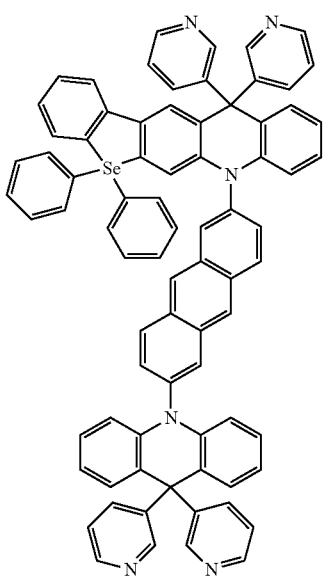
Compound 253
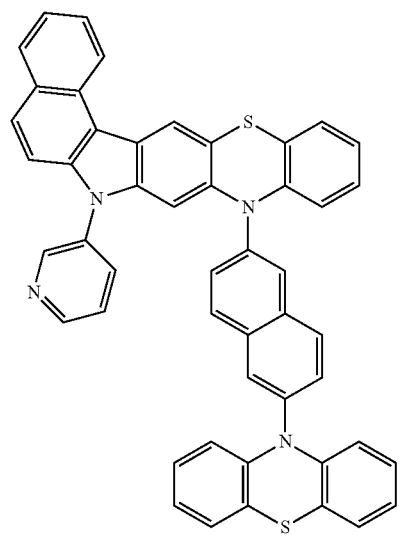
Compound 254
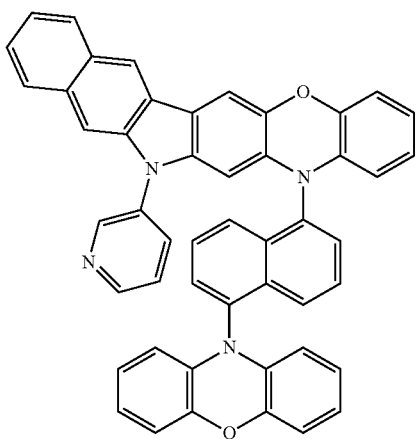

-continued
Compound 255
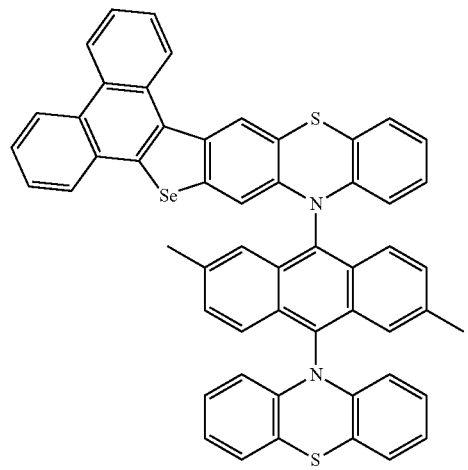
Compound 256
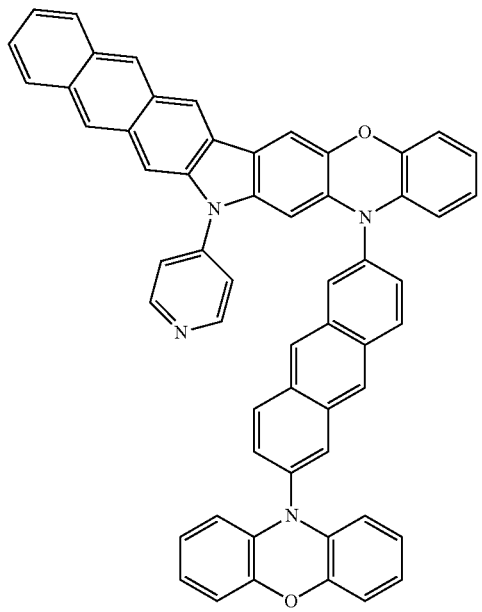
Compound 257
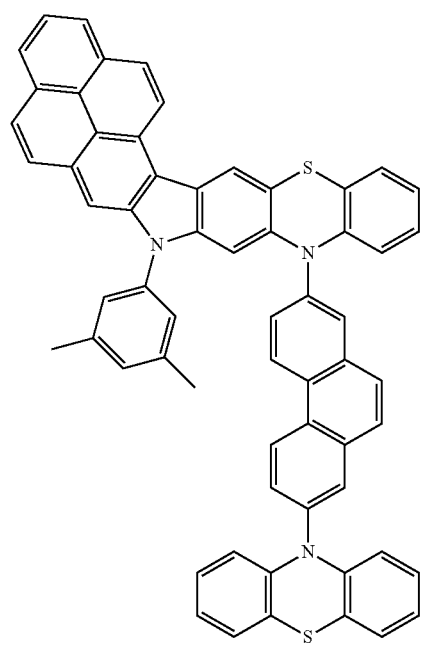
Compound 258
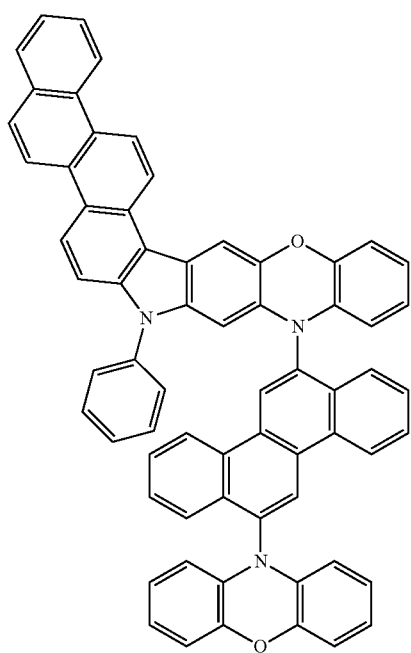

-continued
Compound 259
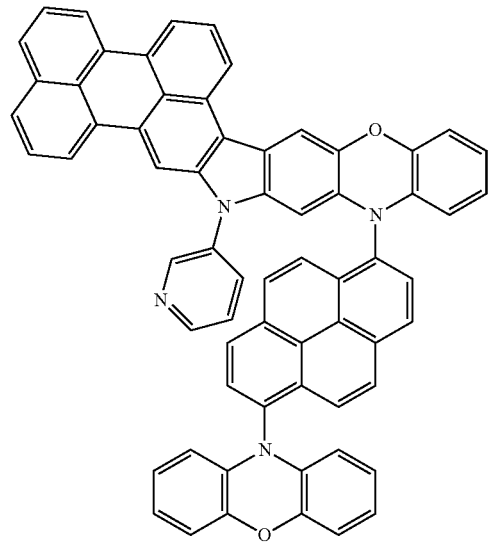
Compound 260
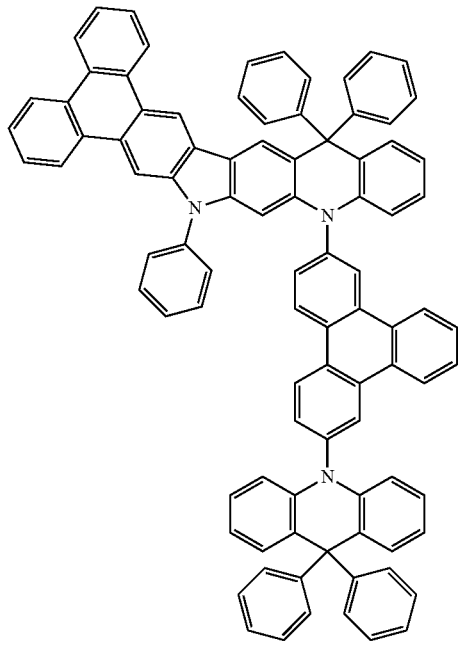
Compound 261
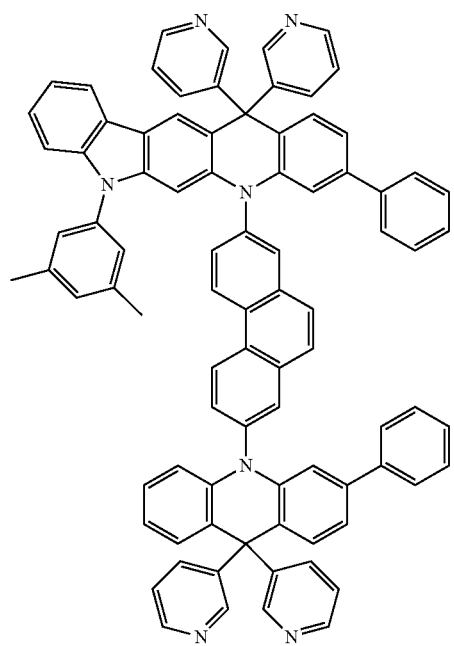
Compound 262
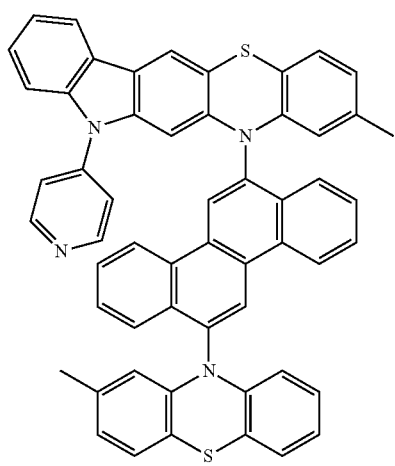

-continued
Compound 263
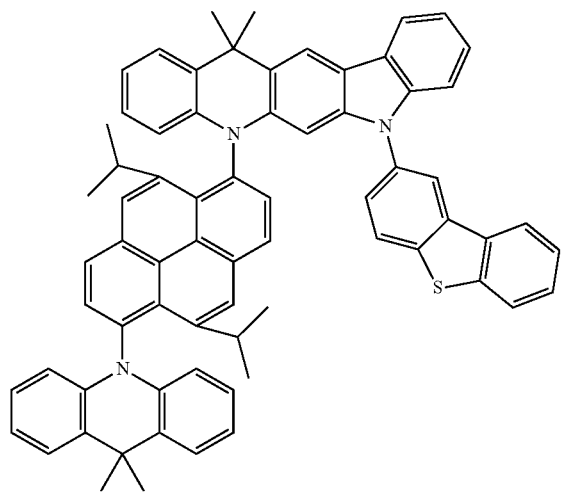
Compound 264
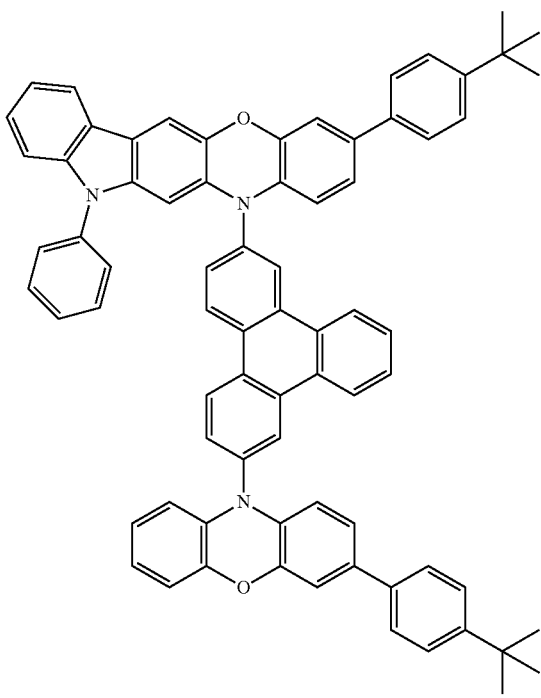
Compound 265
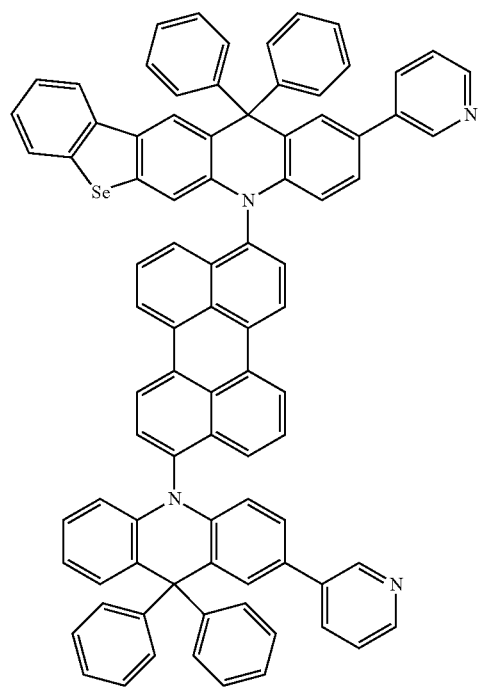
Compound 266
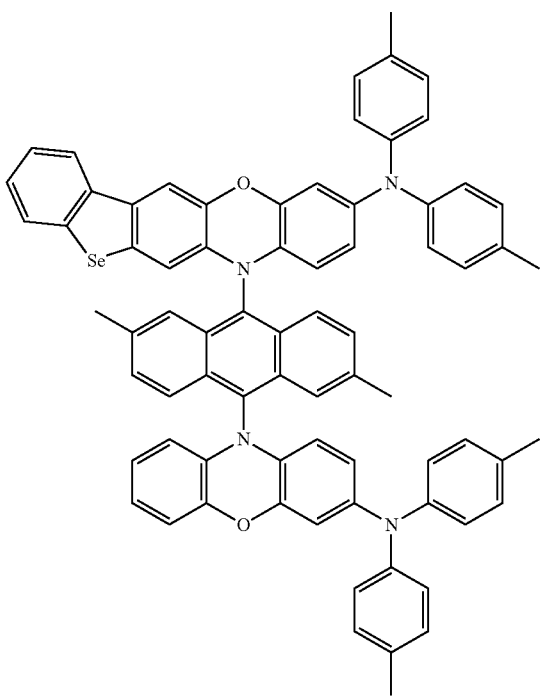

-continued
Compound 267
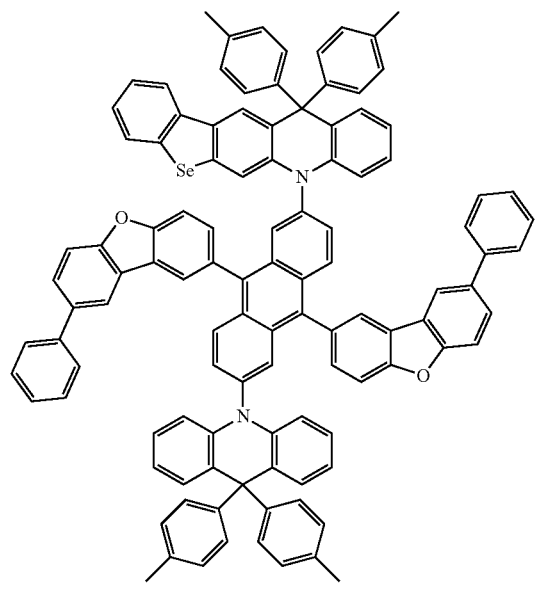
Compound 268
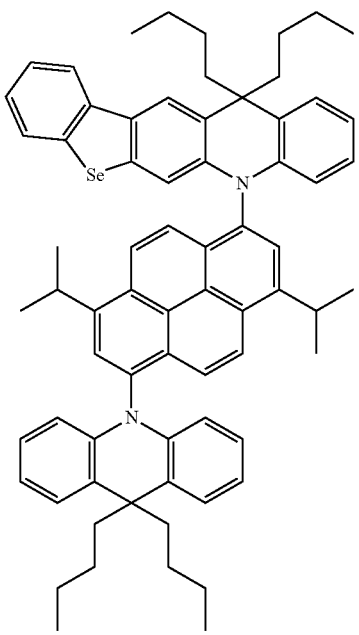
Compound 269
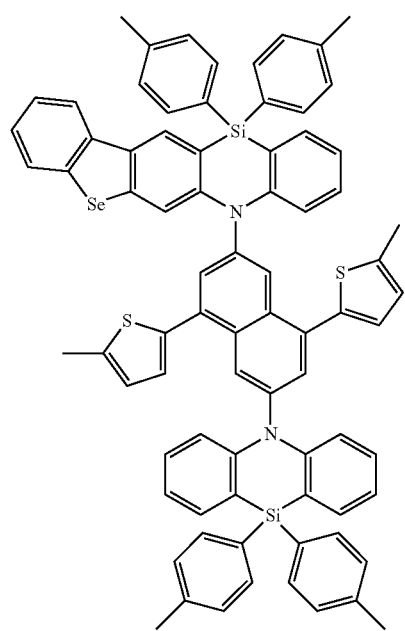
Compound 270
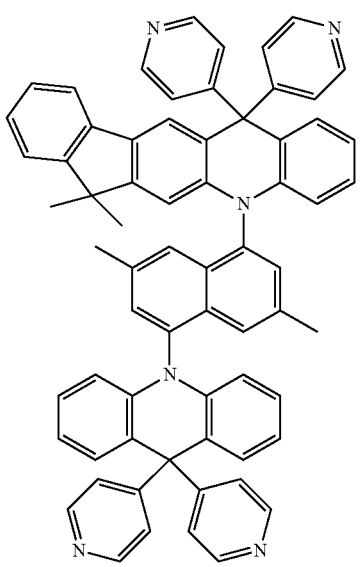

-continued
Compound 271
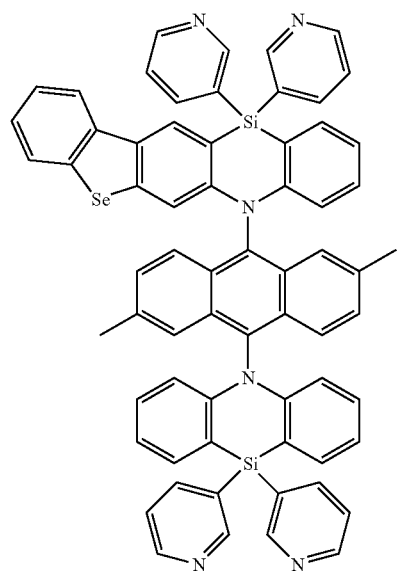
Compound 272
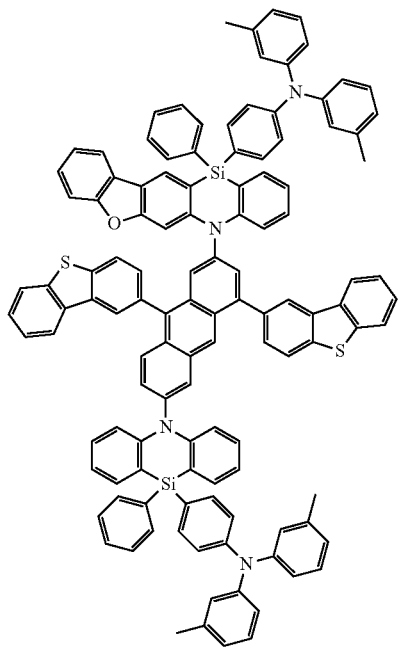
Compound 273
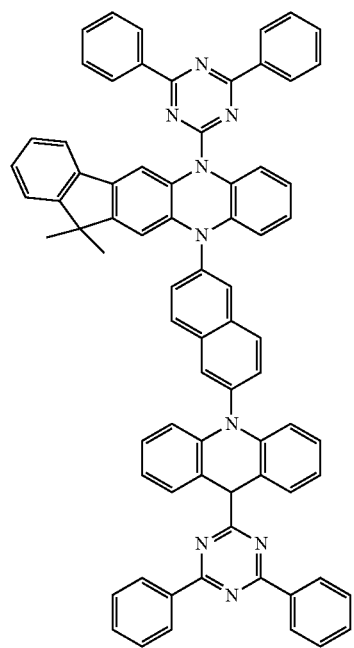
Compound 274
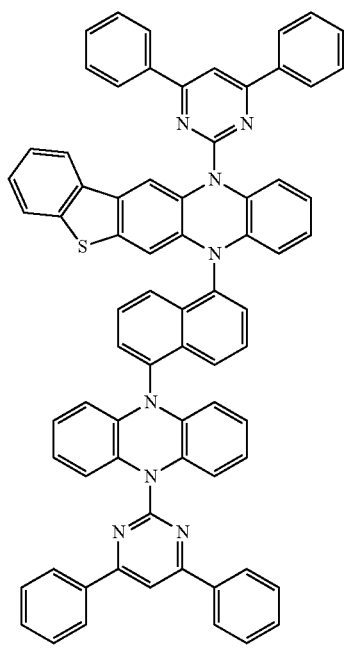

Compound 275
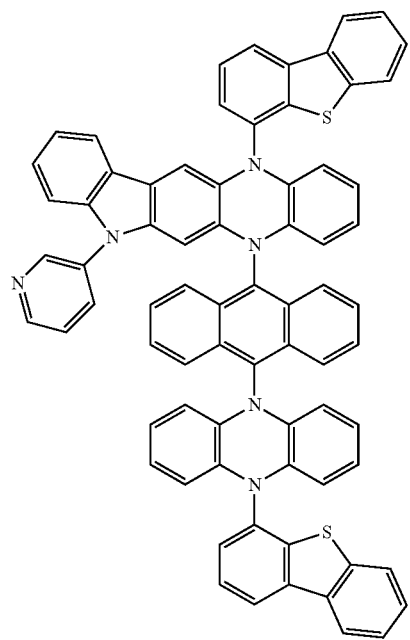
Compound 276
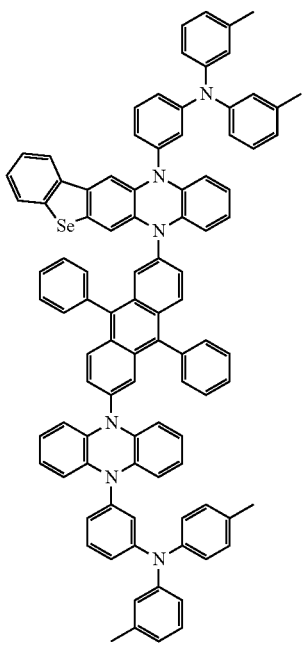
Compound 277
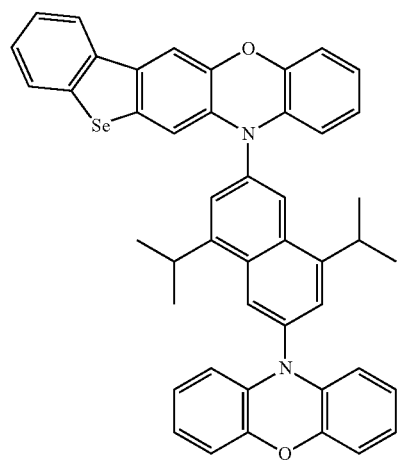
Compound 278
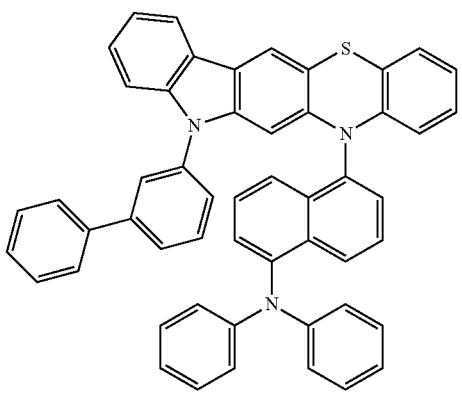

-continued
Compound 279
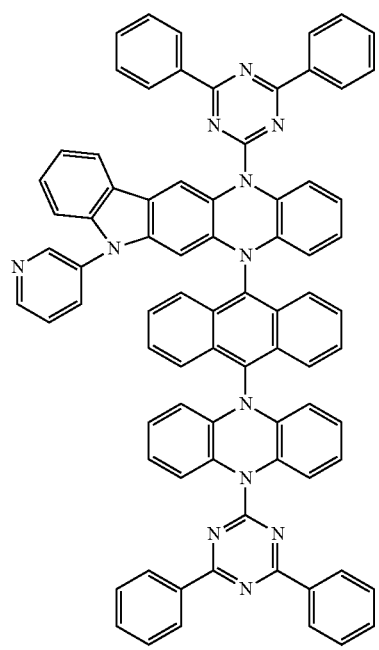
Compound 280
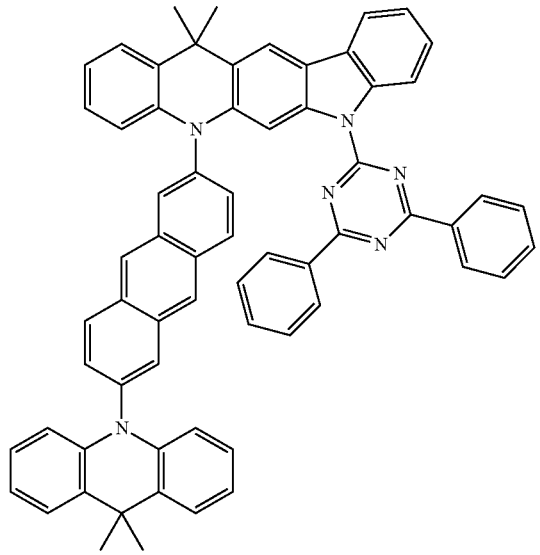
Compound 281
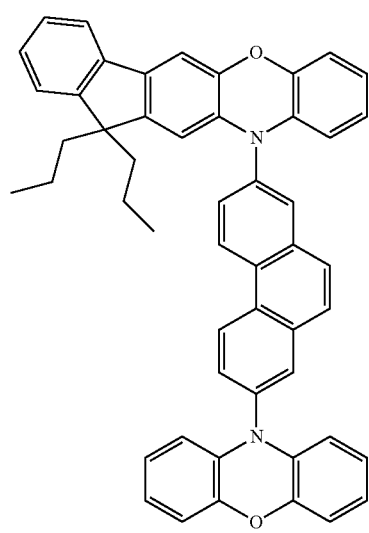
Compound 282
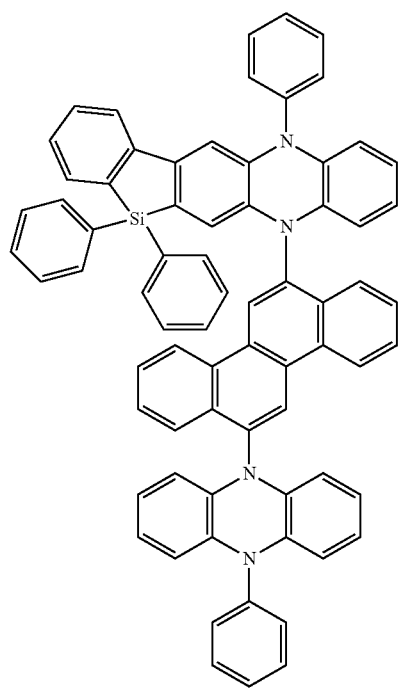

-continued
Compound 283
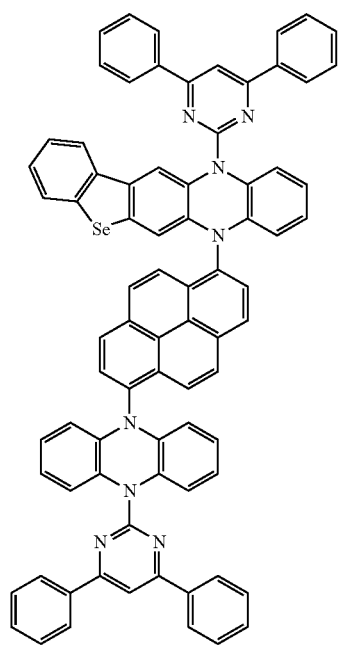
Compound 284
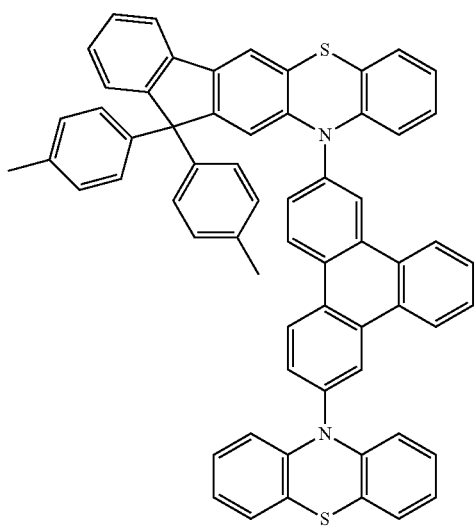
Compound 285
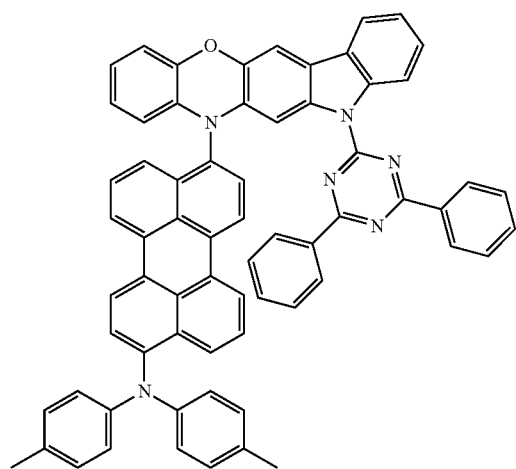
Compound 286
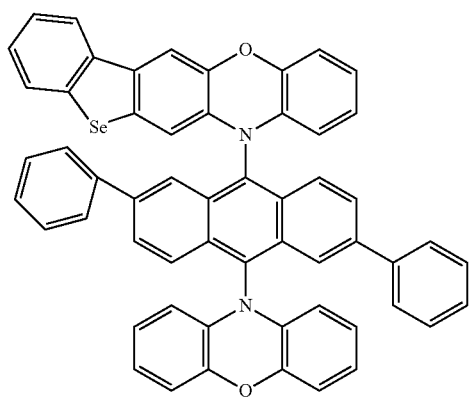
Compound 287
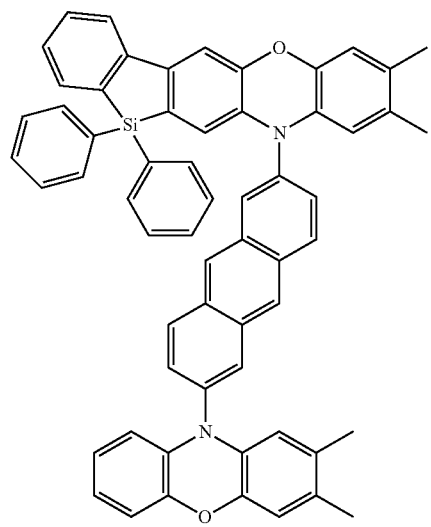
Compound 288
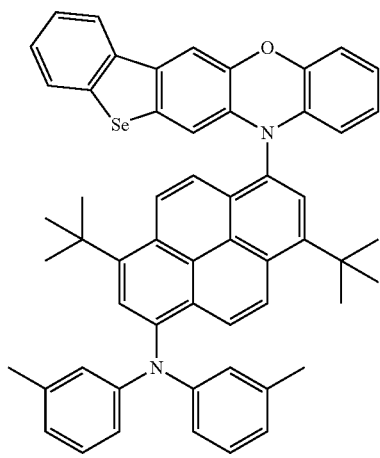

-continued
Compound 289
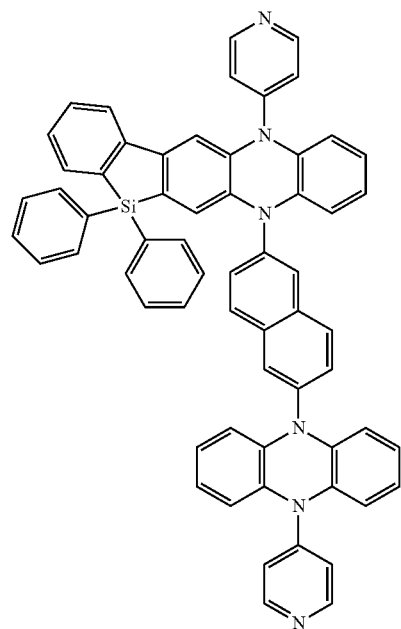
Compound 290
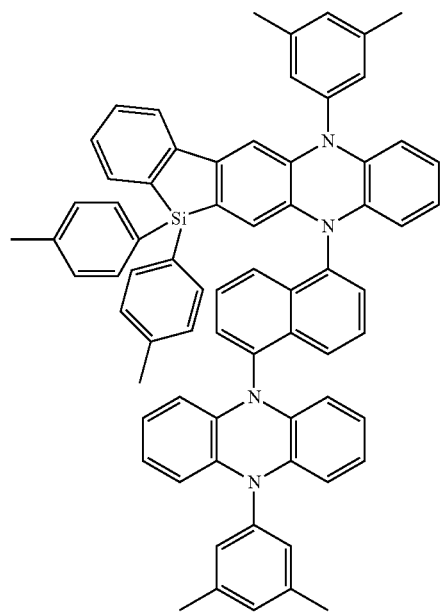
Compound 291
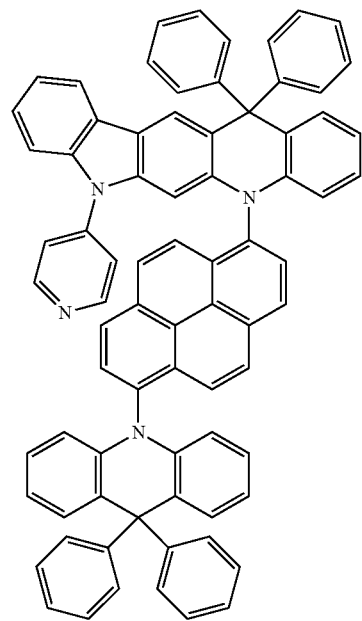
Compound 292
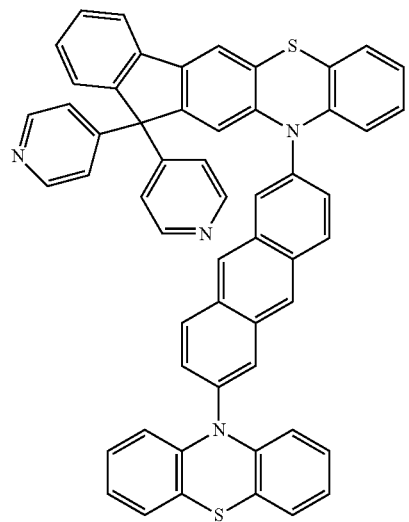

-continued
Compound 293
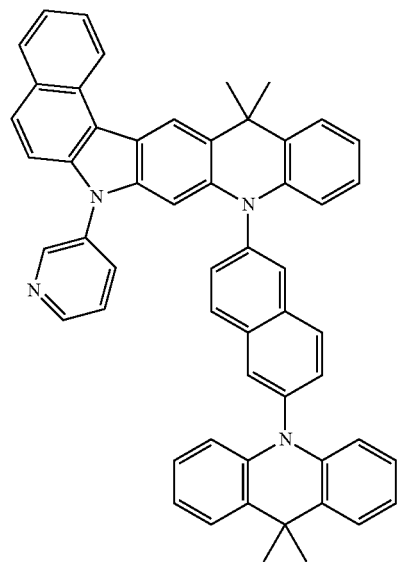
Compound 294
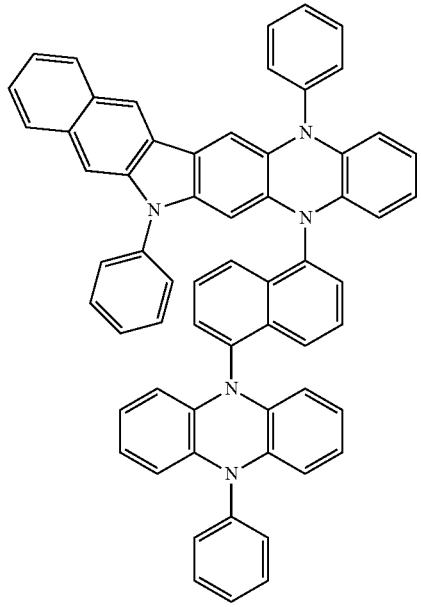
Compound 295
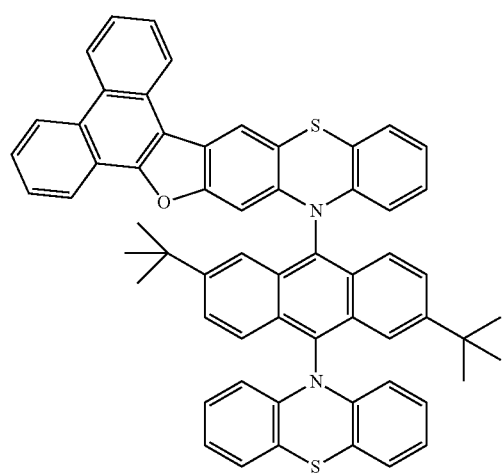
Compound 296
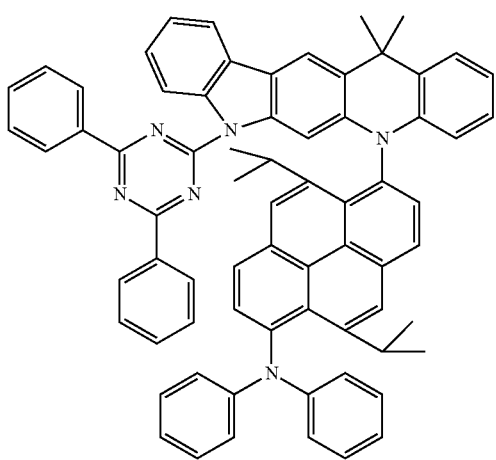

Compound 297
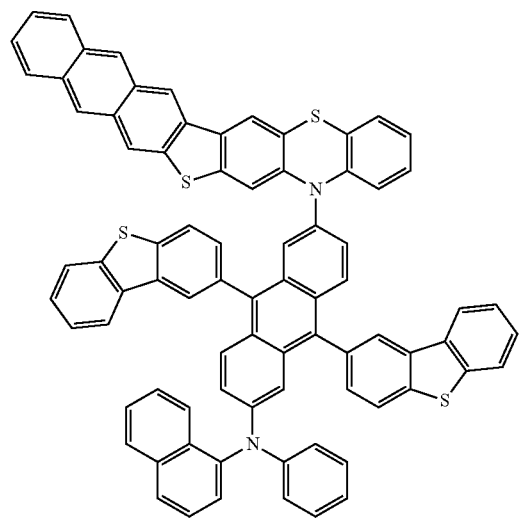
Compound 298
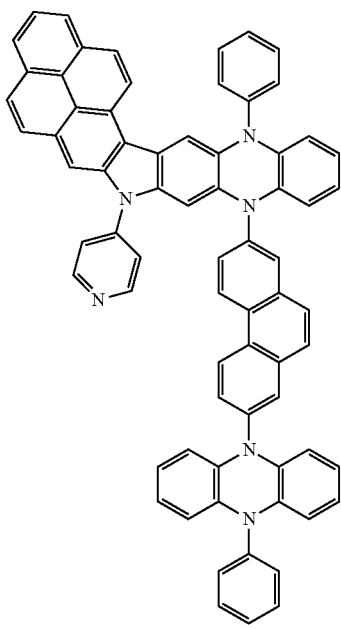
Compound 299
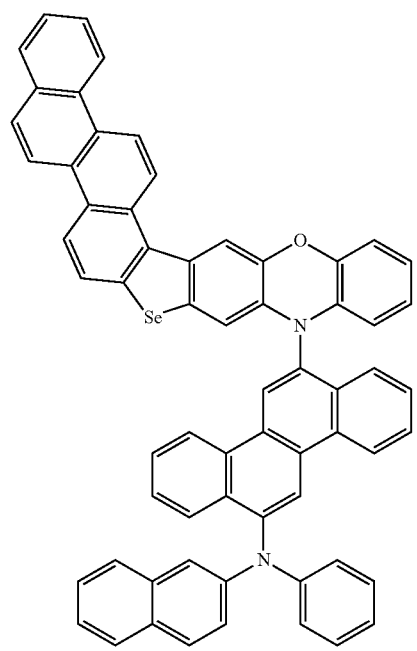
Compound 300
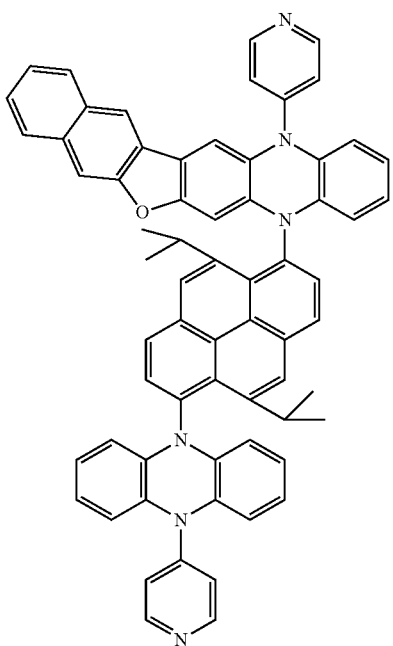

-continued
Compound 301
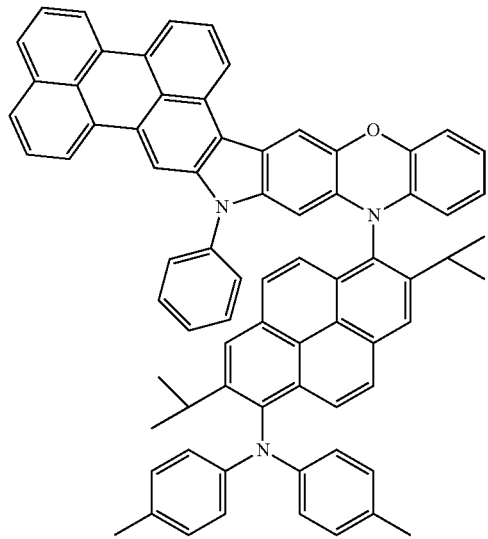
Compound 302
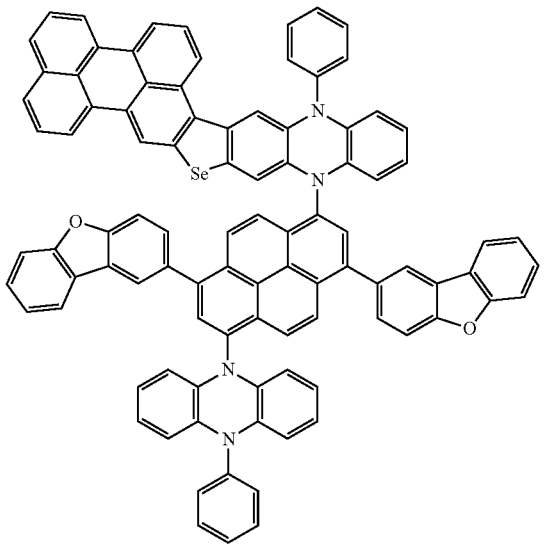
Compound 303
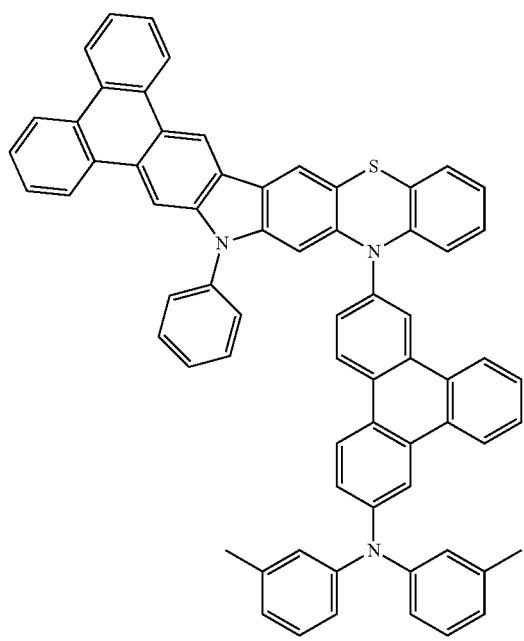
Compound 304
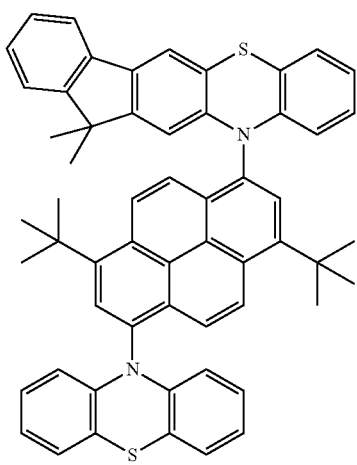

-continued
Compound 305
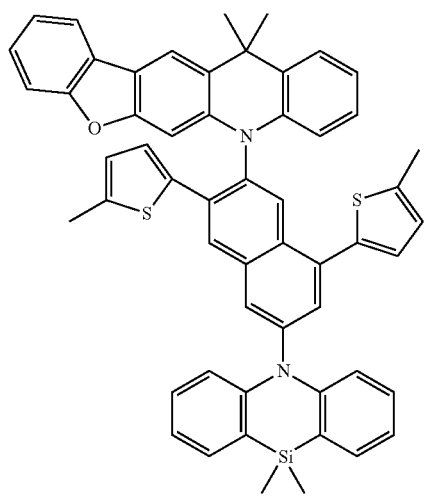
Compound 306
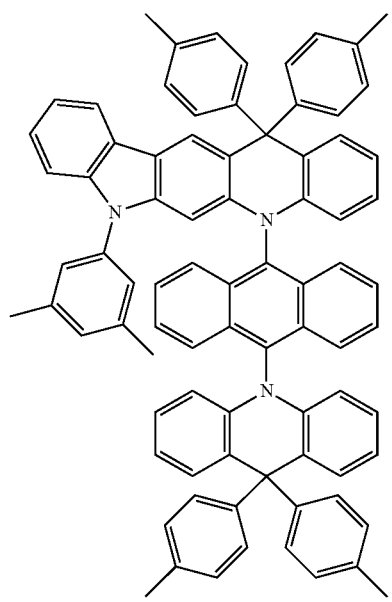
Compound 307
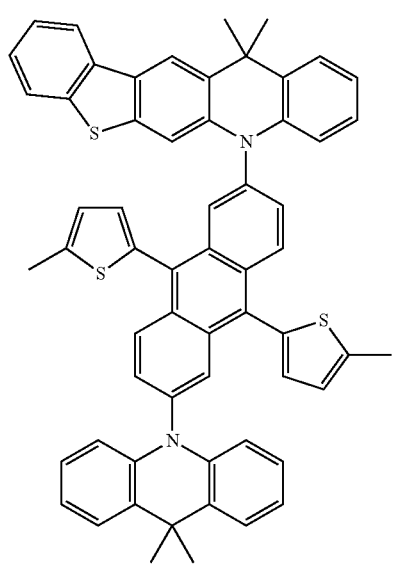
Compound 308
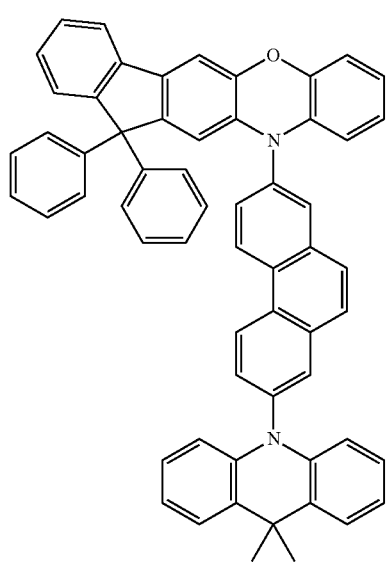

-continued
Compound 309
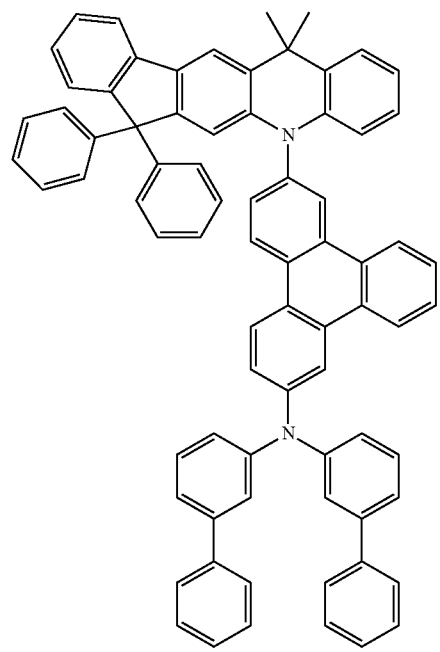
Compound 310
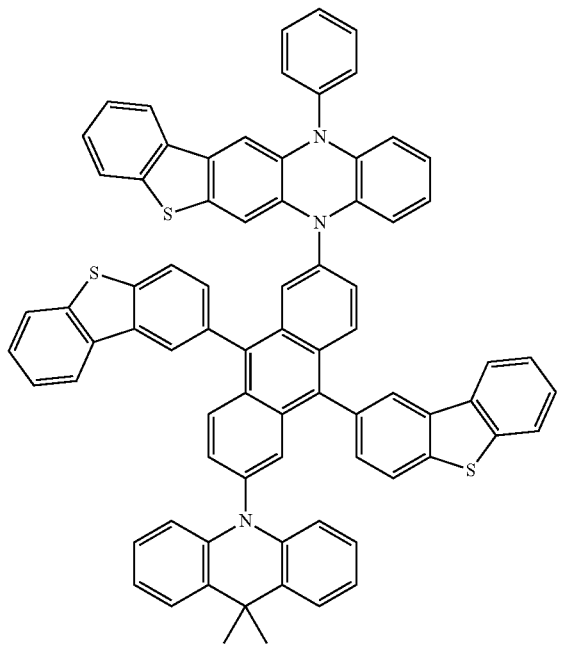
Compound 311
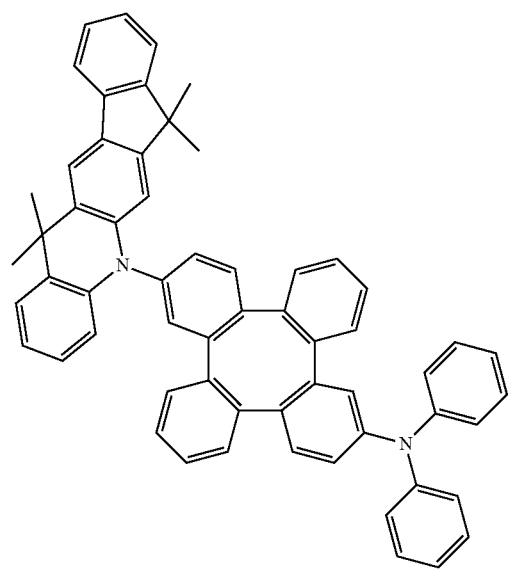
Compound 312
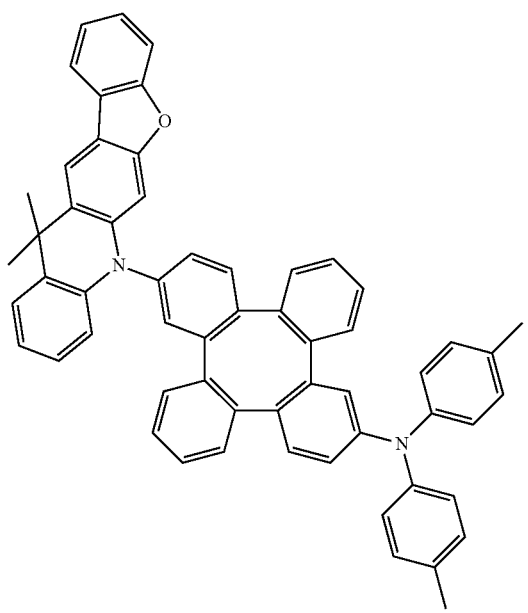

Compound 313
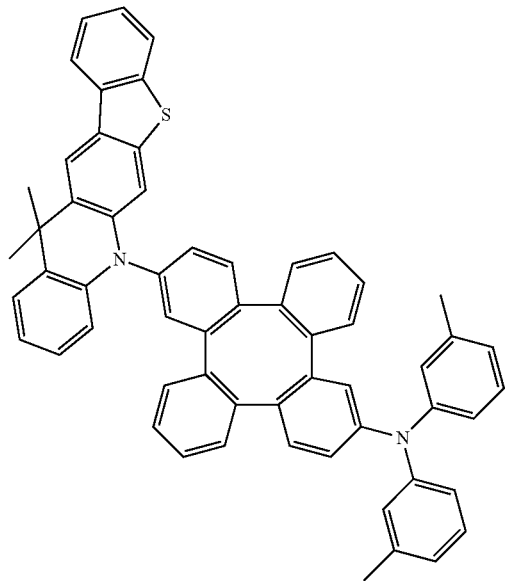
Compound 314
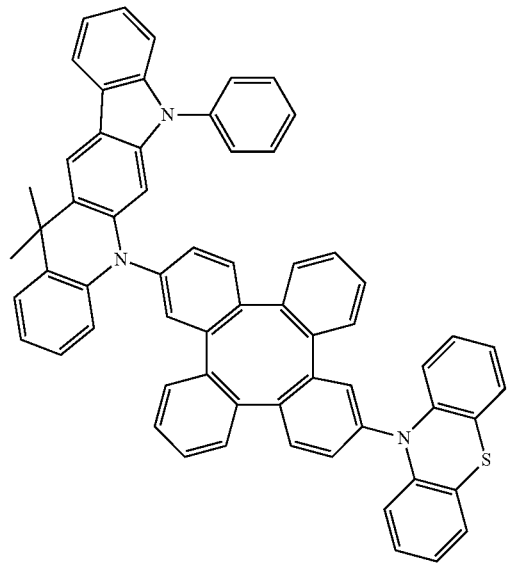
Compound 315
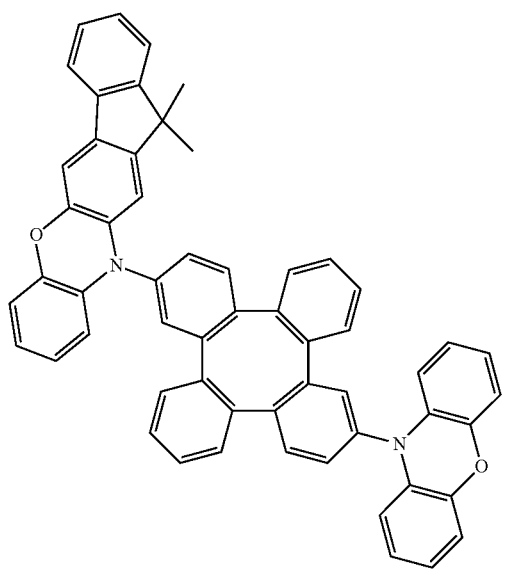
Compound 316
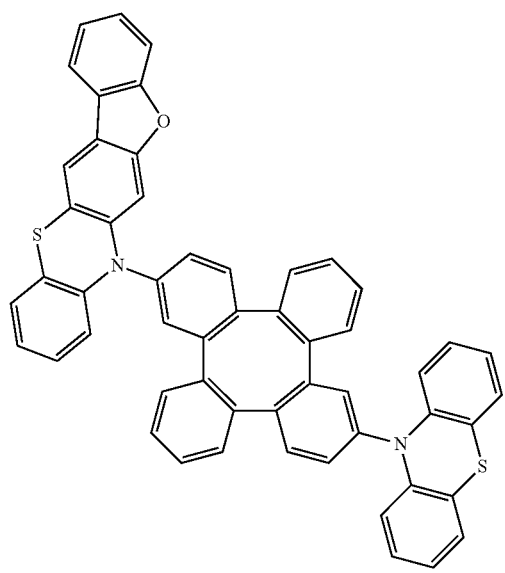

-continued
Compound 317
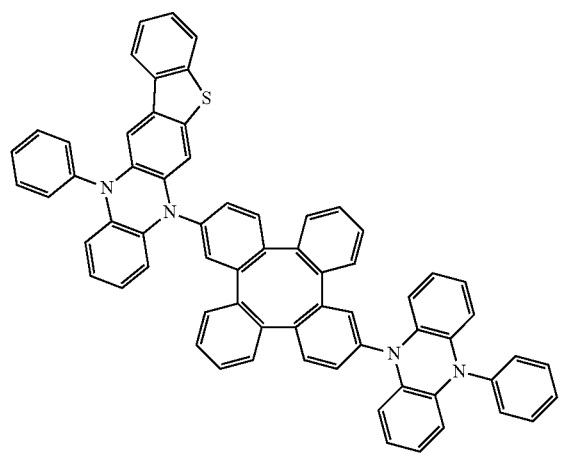
Compound 318
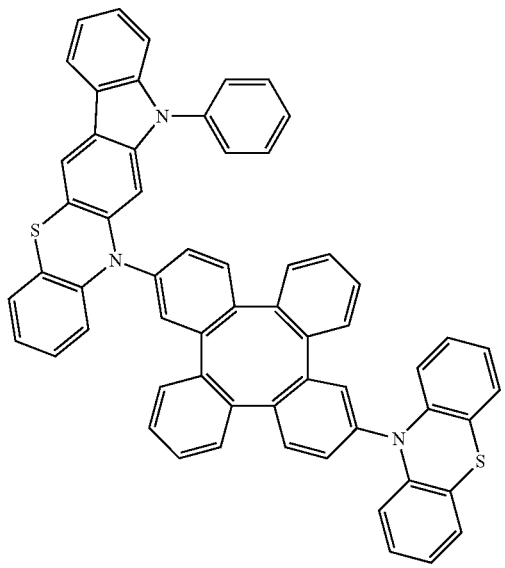
Compound 319
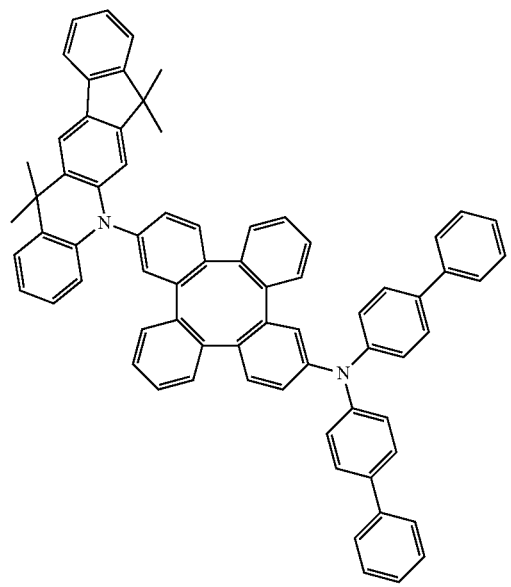
Compound 320
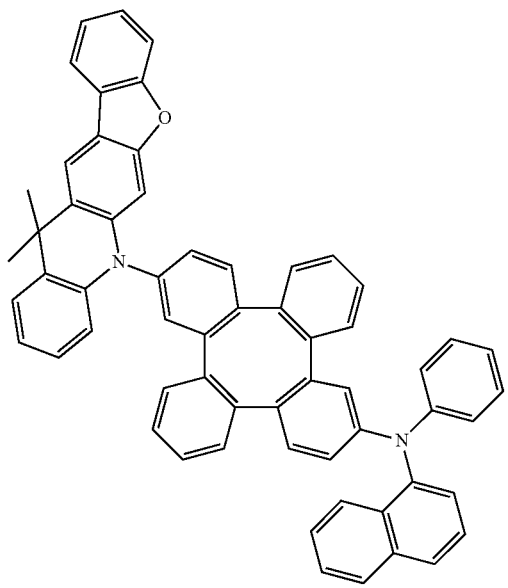

-continued
Compound 321
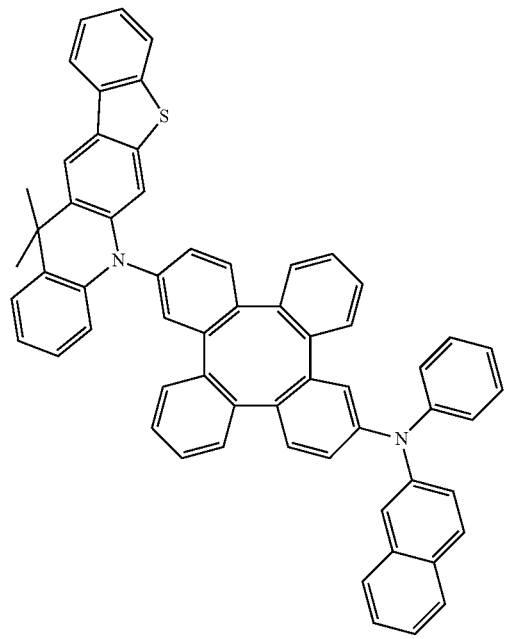
Compound 322
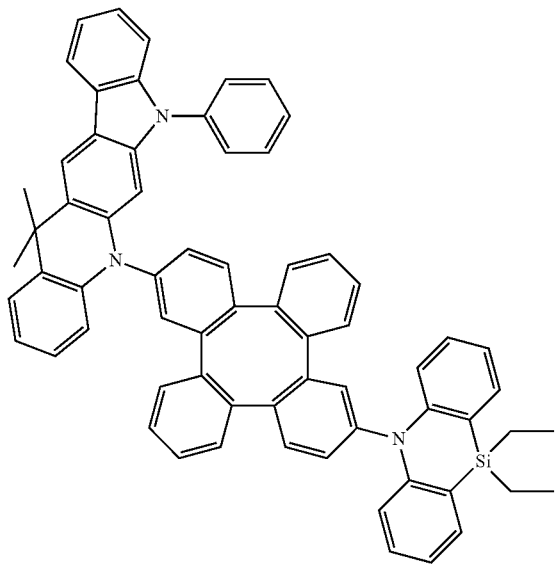
Compound 323
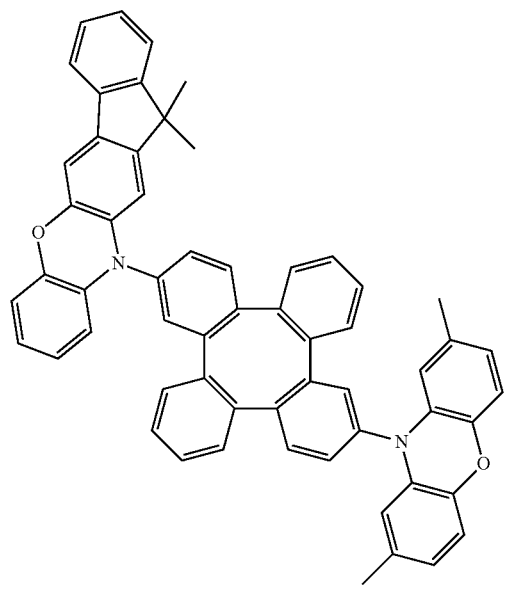
Compound 324
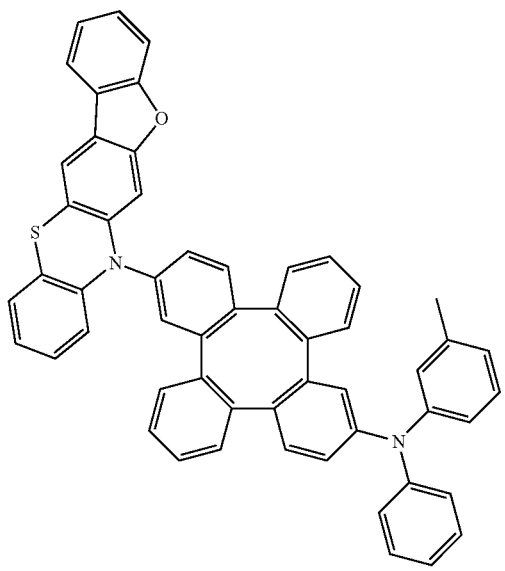

-continued
Compound 325
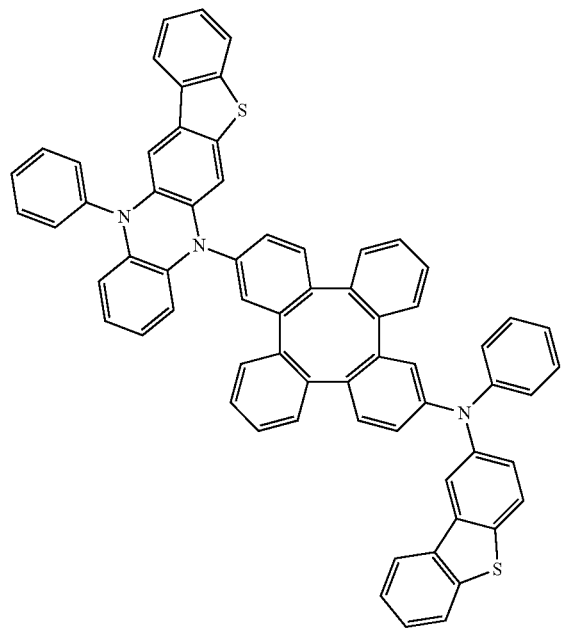
Compound 326
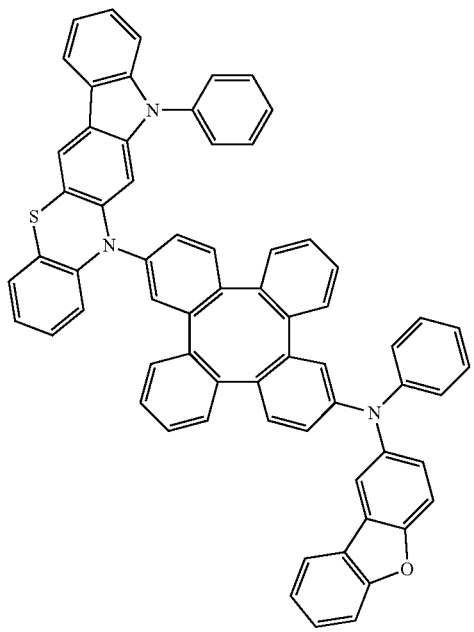
Compound 327
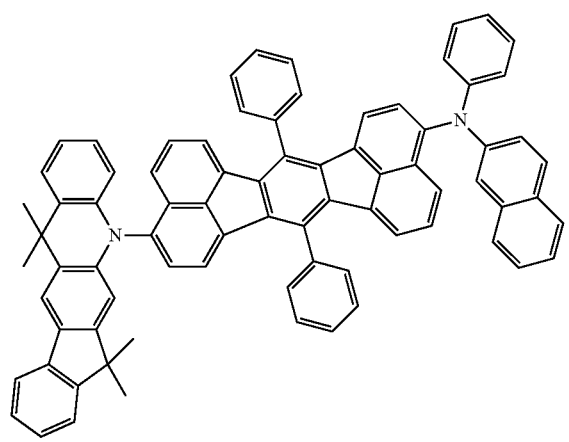
Compound 328
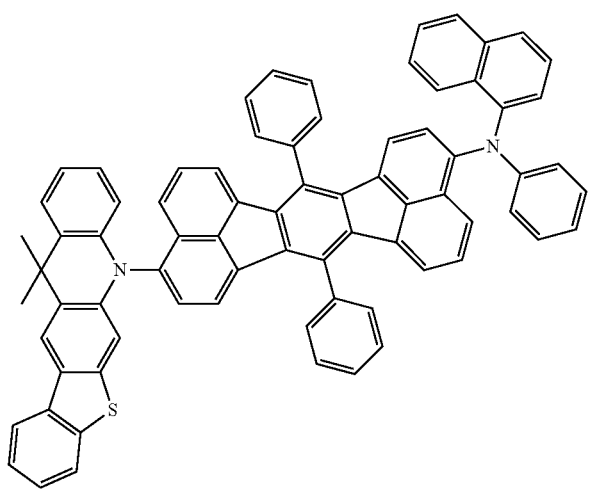
Compound 329
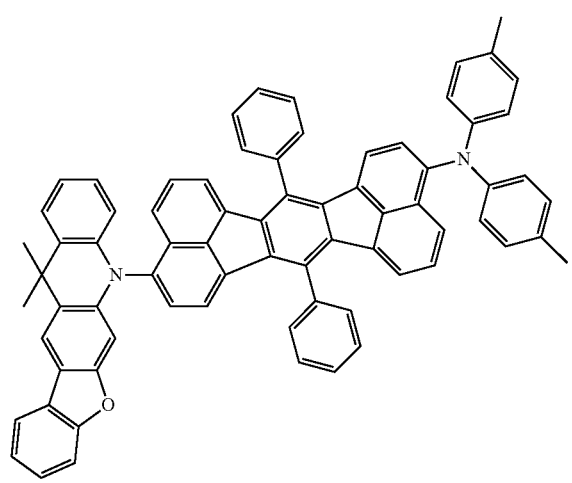
Compound 330
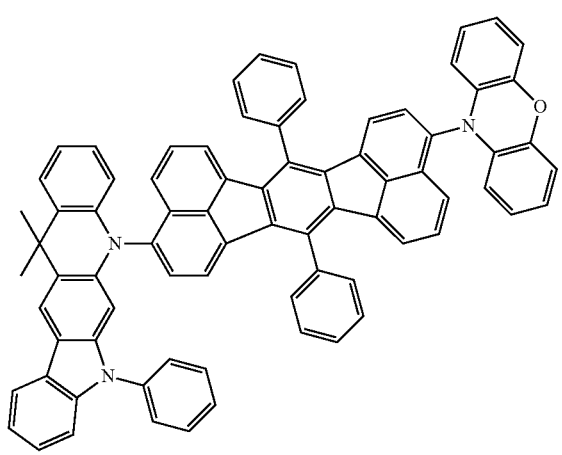

-continued
Compound 331
Compound 332
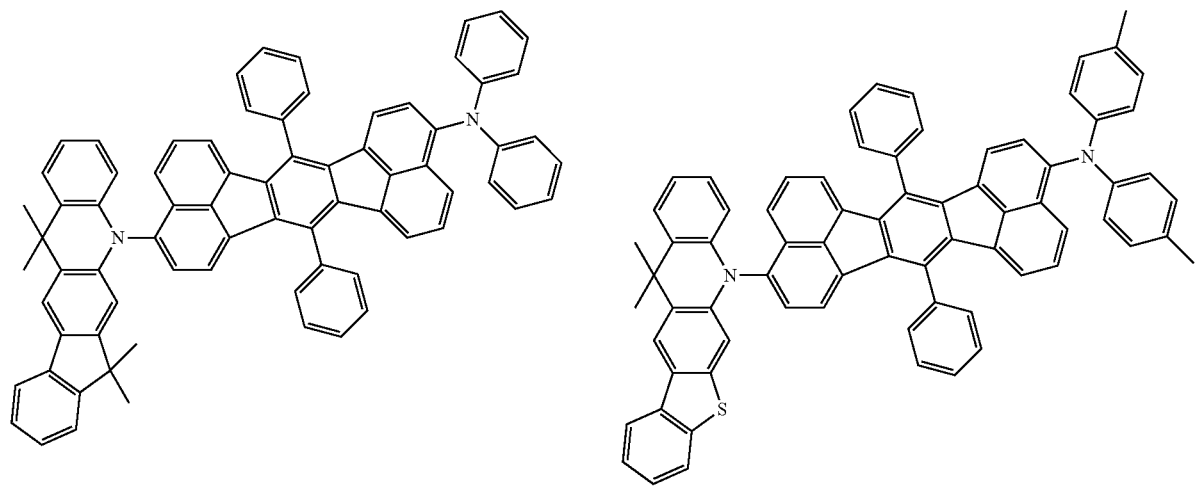
Compound 333
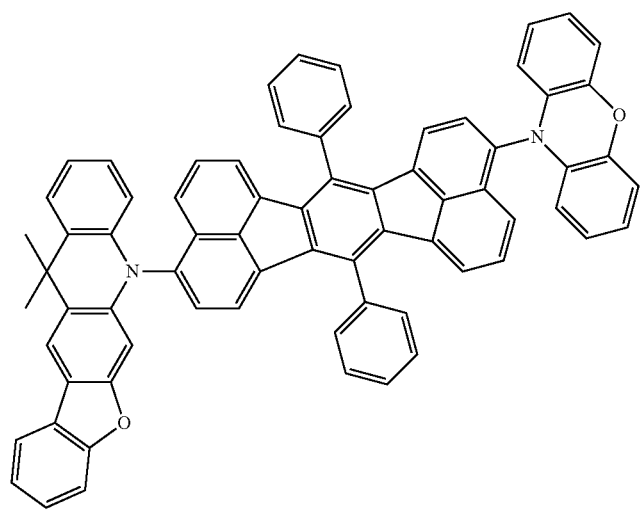
Compound 334
Compound 335
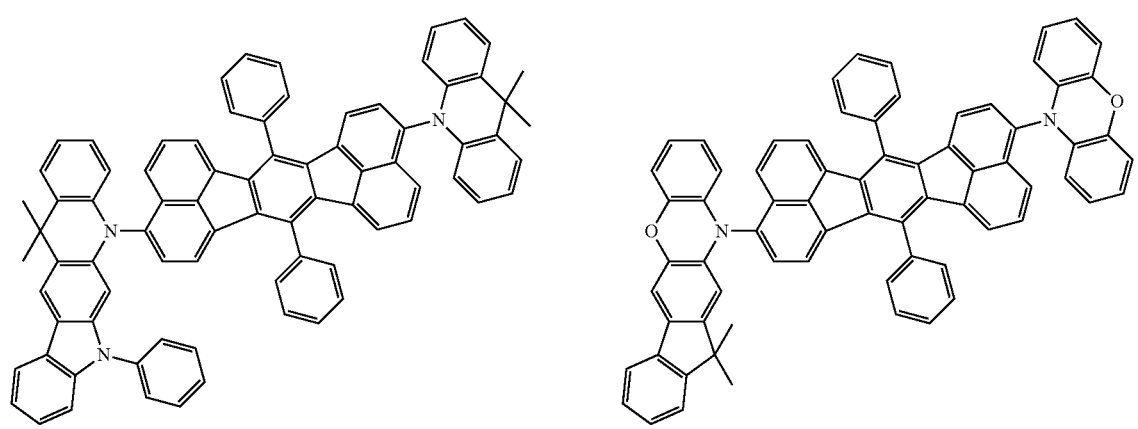

-continued
Compound 336
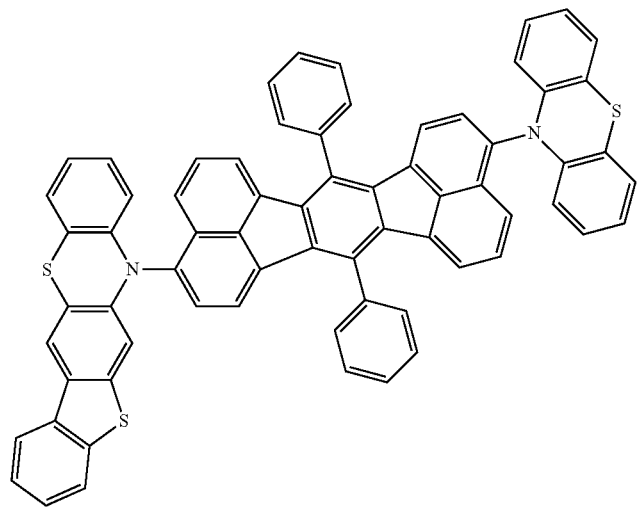
Compound 337
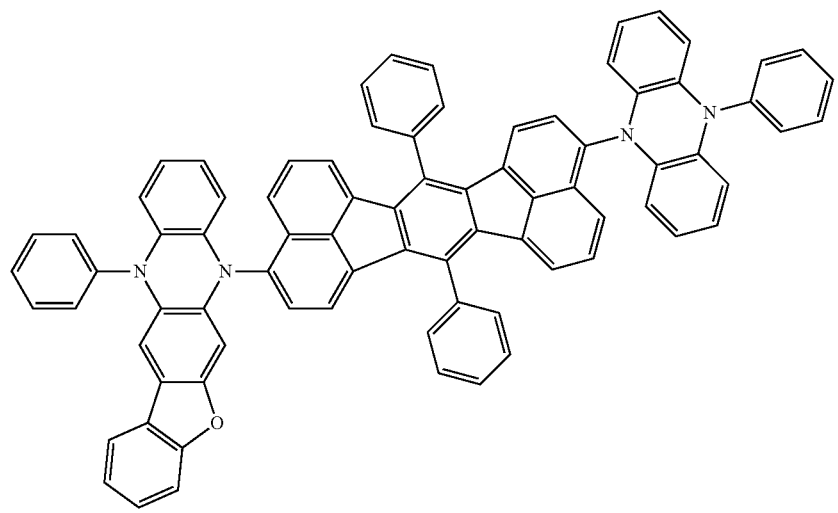
Compound 338
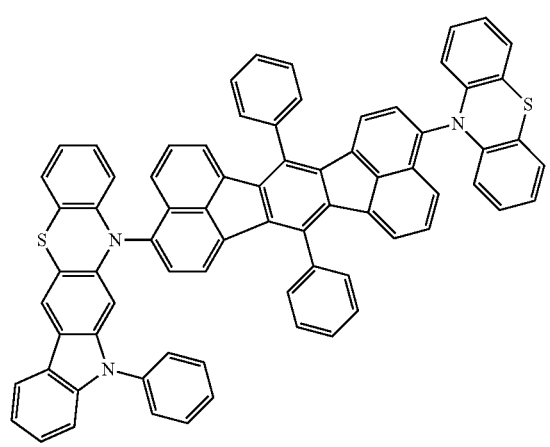
Compound 339
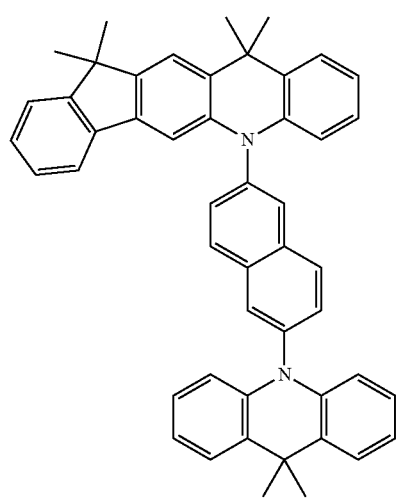

-continued
Compound 340
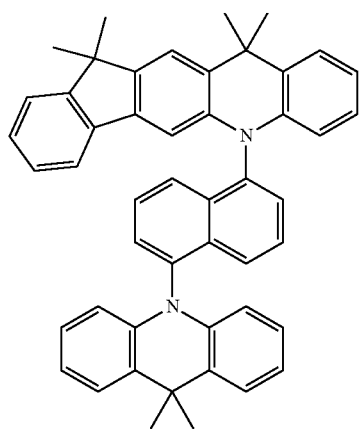
Compound 341
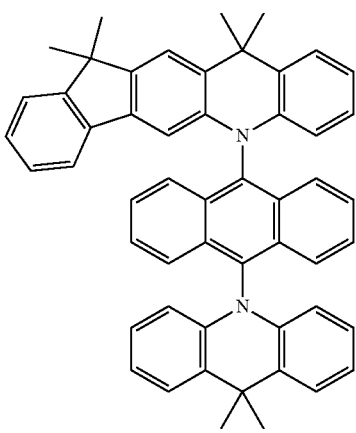
Compound 342
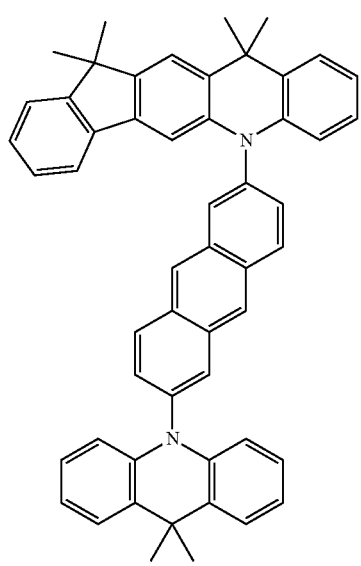
Compound 343
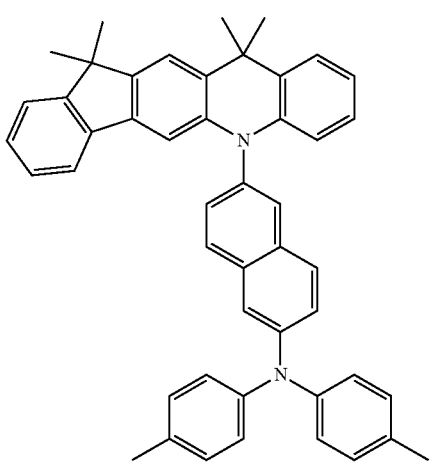
Compound 344
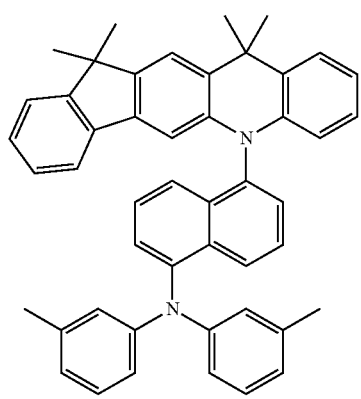
Compound 345
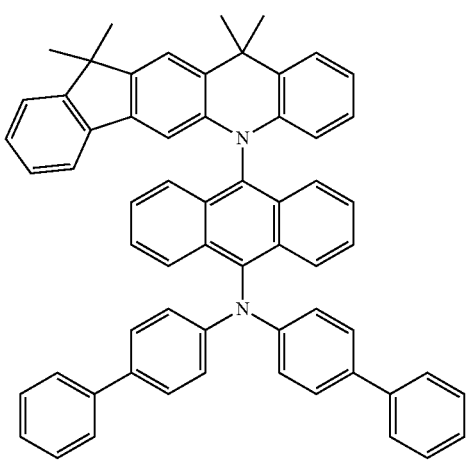

-continued
Compound 346
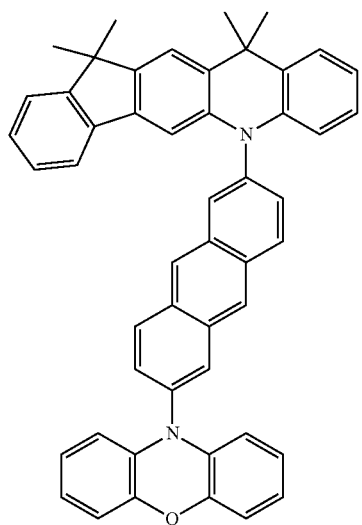
Compound 347
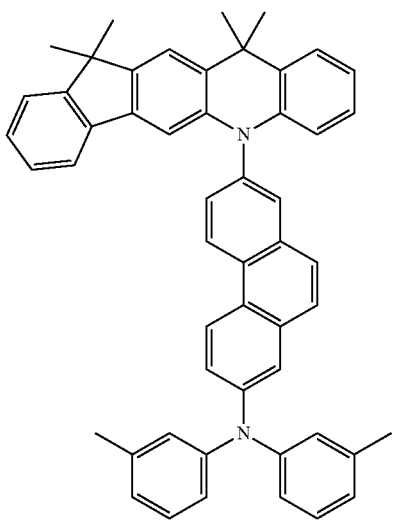
Compound 348
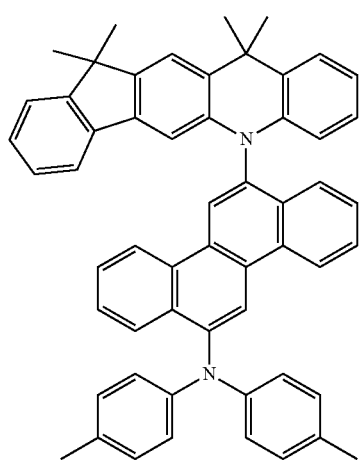
Compound 349
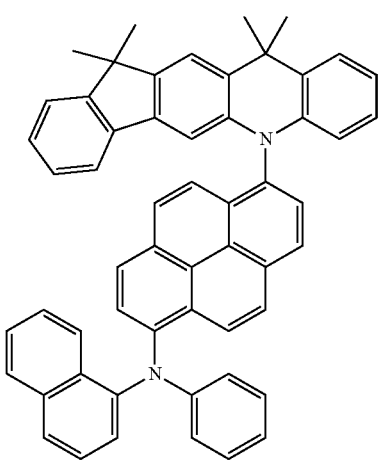
Compound 350
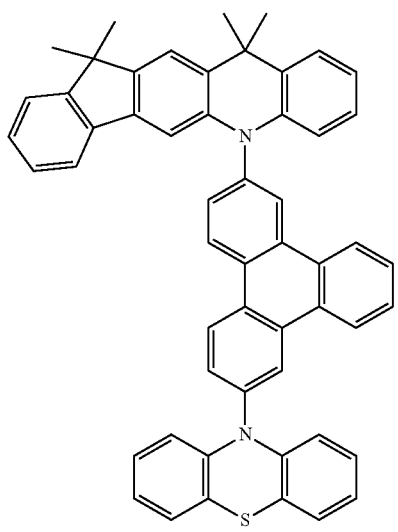
Compound 351
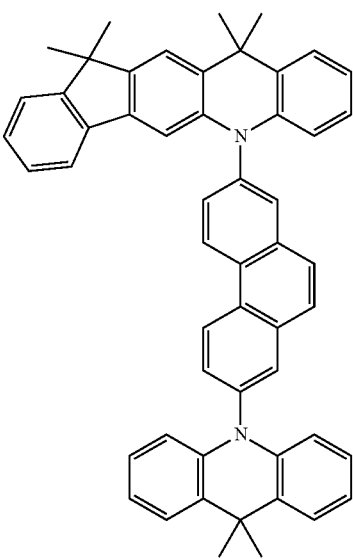

-continued
Compound 352
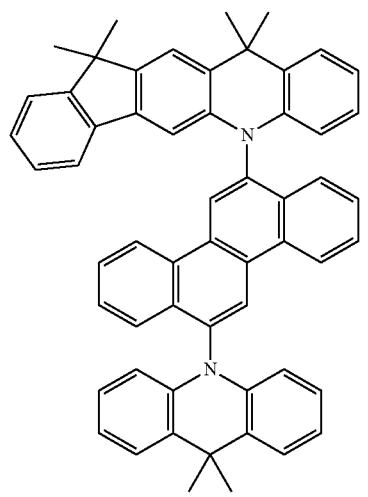
Compound 353
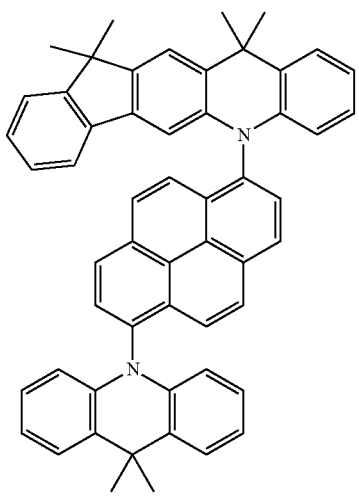
Compound 354
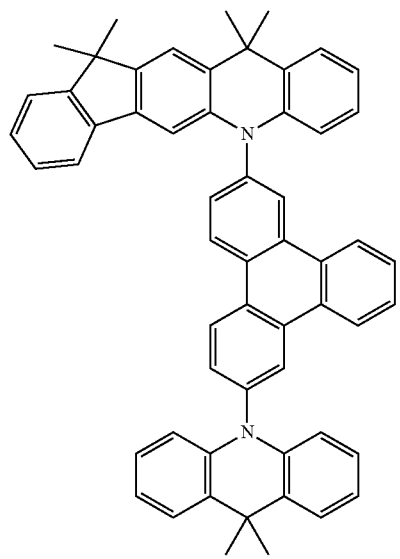
Compound 355
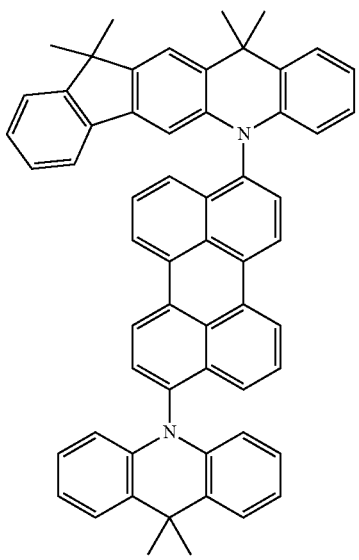
Compound 356
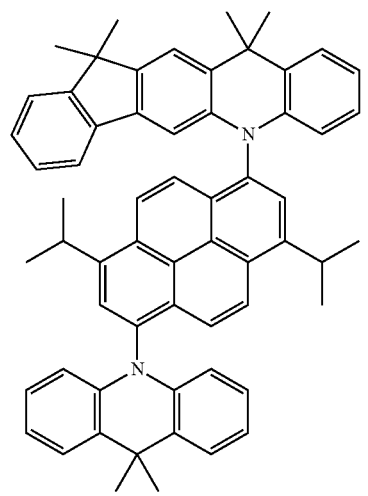
Compound 357
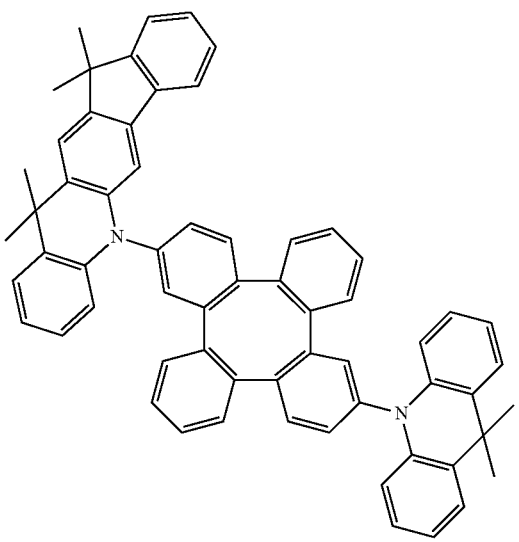

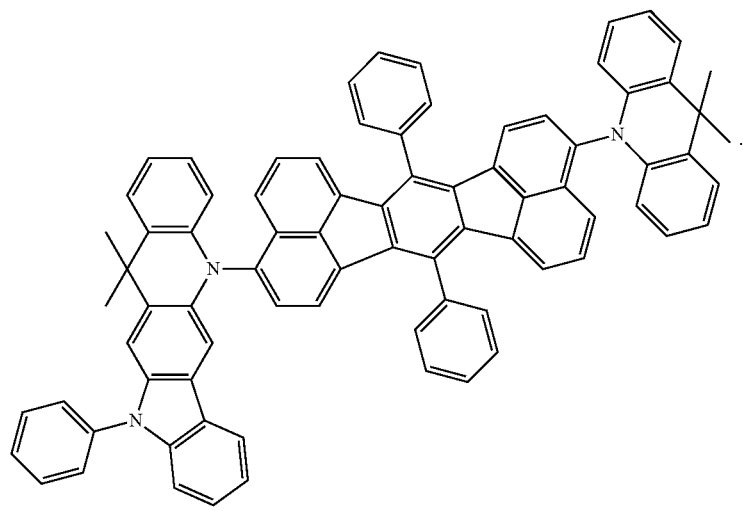

Compound 358

6. An organic electroluminescence device, comprising a pair of electrodes composed of a cathode and an anode, and a light emitting layer between the pair of electrodes, wherein the light emitting layer comprises the heteroaromatic compound according to claim 5.

7. The organic electroluminescence device according to claim 6, wherein the heteroaromatic compound is a fluorescent guest material.

8. The organic electroluminescence device according to claim 6, wherein the light emitting layer emits blue fluorescence.

9. The organic electroluminescence device according to claim 6, wherein the organic electroluminescence device is a lighting panel.

10. The organic electroluminescence device according to claim 6, wherein the organic electroluminescence device is a backlight panel.

* * * * *